(12) United States Patent
Riley et al.

(10) Patent No.: US 10,738,099 B2
(45) Date of Patent: Aug. 11, 2020

(54) METHOD OF REDIRECTING T CELLS TO TREAT HIV INFECTION

(71) Applicant: THE TRUSTEES OF THE UNIVERSITY OF PENNSYLVANIA, Philadelphia, PA (US)

(72) Inventors: James L. Riley, Downingtown, PA (US); Rachel Leibman, Philadelphia, PA (US); Aimee S. Payne, Merion Station, PA (US); Christoph T. Ellebrecht, Philadelphia, PA (US); Michael C. Milone, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 153 days.

(21) Appl. No.: 15/761,563

(22) PCT Filed: Sep. 22, 2016

(86) PCT No.: PCT/US2016/053097
§ 371 (c)(1),
(2) Date: Mar. 20, 2018

(87) PCT Pub. No.: WO2017/053556
PCT Pub. Date: Mar. 30, 2017

(65) Prior Publication Data
US 2018/0265565 A1 Sep. 20, 2018

Related U.S. Application Data

(60) Provisional application No. 62/222,132, filed on Sep. 22, 2015, provisional application No. 62/253,790, filed on Nov. 11, 2015.

(51) Int. Cl.
| | |
|---|---|
| C07K 14/73 | (2006.01) |
| C07K 14/725 | (2006.01) |
| C07K 14/705 | (2006.01) |
| A61P 31/18 | (2006.01) |
| A61K 35/17 | (2015.01) |
| A61K 38/17 | (2006.01) |
| A61K 39/42 | (2006.01) |
| A61K 45/06 | (2006.01) |
| C07K 16/10 | (2006.01) |
| A61K 39/00 | (2006.01) |

(52) U.S. Cl.
CPC ........ *C07K 14/70514* (2013.01); *A61K 35/17* (2013.01); *A61K 38/1774* (2013.01); *A61K 39/42* (2013.01); *A61K 45/06* (2013.01); *A61P 31/18* (2018.01); *C07K 14/7051* (2013.01); *C07K 14/70517* (2013.01); *C07K 14/70521* (2013.01); *C07K 14/70578* (2013.01); *C07K 16/1045* (2013.01); *A61K 2039/505* (2013.01); *A61K 2039/5158* (2013.01); *A61K 2039/572* (2013.01); *C07K 2317/21* (2013.01); *C07K 2317/24* (2013.01); *C07K 2317/622* (2013.01); *C07K 2317/76* (2013.01); *C07K 2319/00* (2013.01); *C07K 2319/02* (2013.01); *C07K 2319/03* (2013.01); *C07K 2319/30* (2013.01); *C07K 2319/33* (2013.01)

(58) Field of Classification Search
CPC .............................................. C07K 14/70514
See application file for complete search history.

(56) References Cited

U.S. PATENT DOCUMENTS

| | | | |
|---|---|---|---|
| 5,350,674 | A | 9/1994 | Boenisch et al. |
| 5,585,362 | A | 12/1996 | Wilson et al. |
| 6,326,193 | B1 | 12/2001 | Liu et al. |
| 7,049,136 | B2 | 5/2006 | Seed et al. |
| 2014/0271635 | A1 | 9/2014 | Brogdon et al. |
| 2014/0322212 | A1 | 10/2014 | Brogdon et al. |
| 2015/0099299 | A1 | 4/2015 | June et al. |
| 2015/0139943 | A1 | 5/2015 | Campana et al. |

FOREIGN PATENT DOCUMENTS

| | | |
|---|---|---|
| WO | 9521528 A1 | 8/1995 |
| WO | 0129058 A1 | 4/2001 |
| WO | 0196584 A2 | 12/2001 |
| WO | 2015017755 A1 | 2/2015 |
| WO | 2015077789 A2 | 5/2015 |
| WO | 2015123527 A1 | 8/2015 |

OTHER PUBLICATIONS

PCT/US2016/053097—International Search Report and Written Opinion dated Feb. 7, 2017.
Baca, et al., Antibody Humanization Using Monovalent Phage Display, 1997, J Biol Chem, 272(16):10678-10684.
Beatty, et al., Mesothelin-specific Chimeric Antigen Receptor mRNA-Engineered T cells Induce Anti-Tumor Activity in Solid Malignancies, Cancer Immunol Res. Feb. 1, 2014; 2(2): 112-120.
Bird, et al., Single-chain Antigen-Binding Proteins, 1988, Science 242:423-426.
Sims, et al., A humanized CD18 antibody can block function without cell destruction, J. Immunol., 151:2296-2308 (1993).
Bitton, et al., Characterization of T cell-expressed chimeric receptors with antibody-type specificity for the CD4 binding site of HIV-1 gp120., Eur. J. Immunol. 1998. 28: 4177-4187.
Brentjens, et al., Safety and persistence of adoptively transferred autologous CD19-targeted T cells in patients with relapsed or chemotherapy refractory B-cell leukemias., 2011, Blood 118:4817-4828.

(Continued)

*Primary Examiner* — Scott Long
(74) *Attorney, Agent, or Firm* — Saul Ewing Arnstein & Lehr LLP; Kathryn Doyle

(57) ABSTRACT

The present invention relates to compositions and methods for treating of a HIV infected mammal using a CD4 membrane-bound chimeric receptor or a HIV specific scFvs CARs. One aspect includes a modified T cell and pharmaceutical compositions comprising the modified cells for adoptive cell therapy and treating a disease or condition associated with HIV infection.

27 Claims, 53 Drawing Sheets

Specification includes a Sequence Listing.

(56) References Cited

OTHER PUBLICATIONS

Bruggerman, et al., Designer Mice: The Production of Human Antibody Repertoires in Transgenic Animals., 1993, Year in Immunol 7:33-40.
Caldas, et al., Design and synthesis of germline-based hemi-humanized single-chain Fv against the CD18 surface antigen, Protein Eng., 13(5):353-60 (2000).
Carter, et al., Humanization of an anti-p185HER2 antibody for human cancer therapy., 1992, Proc Natl Acad Sci USA 89:4285-4289.
Chothia, et al., Canonical Structures for the Hypervariable Regions of Immunoglobulins, J. Mol. Biol., vol. 196, pp. 901-917, 1987 ,1987 ,901-917.
Cillo, et al., Improved Single-Copy Assays for Quantification of Persistent HIV-1 Viremia in Patients on Suppressive Antiretroviral Therapy, J Clin Microbiol 52, 3944-3951 (2014).
Clackson, et al., Making antibody fragments using phage display libraries, Nature 352 ,1991 ,624-628.
Couto, et al., Anti-BA46 Monoclonal Antibody Mc3: Humanization Using a Novel Positional Consensus and in Vivo and in Vitro Characterization., Cancer Res., 55(8):1717-22 (1995).
Couto, et al., Designing Human Consensus Antibodies with Minimal Positional Templates, Cancer Res., 55 (23 Supp):5973s-5977s (1995).
Duchosal, et al., Immunization of hu-PBL-SCID mice and the rescue of human monoclonal Fab fragments through combinatorial libraries., 1992, Nature 355:258-262.
Griffith, et al., Human anti-self antibodies with high specificity from phage display libraries, EMBO J., 12:725-734 (1993).
Grupp, et al., Chimeric Antigen Receptor—Modified T Cells for Acute Lymphoid Leukemia, 2013, N Engl J Med 368 (16)1509-1518.
Hege, et al., Systemic T Cell-independent Tumor Immunity after Transplantation of Universal Receptor-modified Bone Marrow into SCID Mice, J Exp Med 184:2261-2269, 1996.
Hoogenboom, et al., By-passing immunisation. Human antibodies from synthetic repertoires of germline VH gene segments arranged in vitro., J Mol Biol Sep. 20, 1992;227(2):381-8. (Abstract).
Huston, et al.,"Protein engineering of antibody binding sites: Recovery of specific activity in an anti-digoxin single-chain Fv analogue produced in *Escherichia coli*.", 1988, Proc. Natl. Acad. Sci. USA 85:5879-5883.
Jakobovits, et al., Analysis of homozygous mutant chimeric mice: Deletion of the immunoglobulin heavy-chain joining region blocks B-cell development and antibody production, Proc. Natl. Acad. Sci. 90 ,1993 ,2551-2555.
Jakobovits, et al., Germ-line transmission and expression of a human-derived yeast artificial chromosome., 1993, Nature 362:255-258.
Johnson, et al., Human antibody engnieering., 1993, Current Opinion in Structural Biology 3:564-571.
Jones, et al., Replacing the complementarity-determining regions in a human antibody with those from a mouse, Nature, 321:522-525 (1986).
Liu, et al., Novel CD4-Based Bispecific Chimeric Antigen Receptor Designed for Enhanced Anti-HIV Potency and Absence of HIV Entry Receptor Activity., 2015, Journal of Virology 89(13):6685-6694—Jul. 2015.
Lonberg, et al., Human antibodies from transgenic mice., Int. Rev. Immunol., 13:65-93 (1995).
Marks, et al., By-passing immunization. Human antibodies from V-gene libraries displayed on phage, J. Mol. Biol. 222:581-597 (1991).
Maude, et al., Chimeric Antigen Receptor T Cells for Sustained Remissions in Leukemia., N Engl J Med. Oct. 16, 2014; 371(16): 1507-1517.
McCafferty, et al., Phage antibodies: filamentous phage displaying antibody variable domains, Nature, 348:552-553 (1990)93).
Migueles, et al., HLA B*5701 is highly associated with restriction of virus replication in a subgroup of HIV-infected long term nonprogressors, 2000, PNAS 97(6):2709-2714.
Milone, et al., Chimeric Receptors Containing C137 Signal Transduction Domains Mediate Enhanced Survival of T Cells and Increased Antileukemic Efficacy In Vivo., 2009, Mol Ther 17:1453-1464.
Morea, et al., Antibody modeling: implications for engineering and design, Methods, 20(3):267-79 (2000).
Padlan, et al., A possible procedure for reducing the immunogenicity of antibody variable domains while preserving their ligand-binding properties, 1991, Molecular Immunology, 28(4/5):489-498.
Pedersen, et al., Comparison of surface accessible residues in human and murine immunoglobulin Fv domains. Implication for humanization of murine antibodies., J. Mol. Biol., 235(3):959-73 (1994).
Porter, et al., Chimeric antigen receptor T cells persist and induce sustained remissions in relapsed refractory chronic lymphocytic leukemia, Sci Transl Med. Sep. 2, 2015; 7(303): 303ra139.
Porter, et al., Chimeric Antigen Receptor-Modified T Cels in Chronic Lymphoid Leukemia, 2011, N Engl J Med, 365:725-33.
Presta, et al., Antibody engineering., Current Opinion in Biotechnology 1992, 3:394-398.
Presta, et al., Humanization of an antibody directed against IgE, J. Immunol., 151:2623-32 (1993).
Richardson, et al., Stabilized Human TRIM5α Protects Human T Cells From HIV-1 Infection., Richardson et al., Mol Ther. Jun. 2014; 22(6): 1084-1095.
Riechmann, et al., Reshaping human antibodies for therapy, Nature, 332:323-327 (1988).
Roder, et al., The EBV-hybridoma technique, Methods Enzymol., 121:140-167 (1986).
Roguska, et al., A comparison of two murine monoclonal antibodies humanized by CDR-grafting and variable domain resurfacing, Protein Eng., 9(10):895-904 (1996).
Roguska, et al., Humanization of murine monoclonal antibodies through variable domain resurfacing, PNAS, 91:969-973 (1994).
Romeo, et al., Cellular immunity to HIV activated by CD4 fused to T cell or Fc receptor polypeptides, Cell 64: ,1991 ,1037-1046.
Rosenberg, et al., Use of Tumor-Infiltrating Lymphocytes and Interleukin-2 in the Immunotherapy of Patients with Metastatic Melanoma, New Eng. J. of Med. 319:1676-1680, 1988.
Saez-Cirion, et al., HIV controllers exhibit potent CD8 T cell capacity to suppress HIV infection ex vivo and peculiar cytotoxic T lymphocyte activation phenotype., 2007, PNAS 104(16):6776-6781.
Sandhu, et al., A rapid procedure for the humanization of monoclonal antibodies., Gene, 150(2):409-10(1994).
Scholler, et al., Decade-Long Safety and Function of Retroviral-Modified Chimeric Antigen Receptor T-cells., Sci Transl Med. May 2, 2012; 4(132): 132ra53.
Skerra, et al., Assembly of a Functional Immunoglobulin Fv Fragment in *Escherichia coli*, Science, 240 , 1988 ,1038-1041.
Studnicka, et al., Human-engineered monoclonal antibodies retain full specific binding activity by preserving non-CDR complementarity-modulating residues, Protein Engineering, 7(6):805-814 (1994).
Tan, et al.,"Superhumanized" Antibodies: Reduction of Immunogenic Potential by Complementarity-Determining Region Grafting with Human Germline Sequences: Application to an Anti-CD28, The Journal of Immunology 169 ,2002 ,1119-11125.
Van Der Stegen, et al., The pharmacology of second-generation chimeric antigen receptors., Nat Rev Drug Discov. Jul. 2015;14(7):499-509. (Abstract).
Varela-Rohena, et al., Control of HIV-1 immune escape by CD8 T-cells expressing enhanced T-cell receptor., Nat Med. Dec. 2008; 14(12): 1390-1395.
Vaughan, et al., Human antibodies with sub-nanomolar affinities isolated from a large non-immunized phage display library., Vaughan et al., 1996, Nature Biotech., 14:309-14 (Abstract).
Verhoeyen, et al., Reshaping human antibodies: grafting an antilysozyme activity, Science, 239:1534-1536 (1988).
Walker, et al., Unravelling the mechanisms of durable control of HIV-1., Nat Rev Immunol. Jul. 2013;13(7):487-98 (Abstract).

(56) References Cited

OTHER PUBLICATIONS

Ward, et al., "Binding activities of a repertoire of single immunoglobulin variable domains secreted from *Escherichia coli*." Nature 341:544-546 (1989).
Wu, et al., Humanization of a murine monoclonal antibody by simultaneous optimization of framework and CDR residues., J. Mol. Biol., 294:151-162 (1999).
Zhen, et al., HIV-specific Immunity Derived From Chimeric Antigen Receptor-engineered Stem Cells., Mol Ther. Aug. 2015;23(8):1358-1367.
Eurasian Patent Application No. 201890782—Office Action dated May 27, 2019.
European Patent Application No. 16849585.1—Office Action dated Jun. 18, 2019.
Singapore Patent Application No. 11201802168R—Search Report and Written Opinion dated Jul. 23, 2019.
Masiero, et al., "T-cell engineering by a chimeric T-cell receptor with antibody-type specificity for the HIV-1 gp120.", Gene Ther, Oct. 21, 2004, vol. 12, No. 4, pp. 299-310.
Sahu, et al., "Anti-HIV designer T cells progressively eradicate a latently infected cell line by sequentially inducing HIV reactivation then killing the newly gp120-positive cells.", Virology, Sep. 6, 2013, vol. 446, No. 1-2, pp. 268-275.
European Patent Application No. 16849585.1—Extended European Search Report dated Oct. 17, 2018.
Frigault, et al.,"Identification of Chimeric Antigen Receptors That Mediate Constitutive or Inducible Proliferation of T Cells.", 2015, Cancer Immunology Research 3(4):356-367.
Leibman, et al.,"Supraphysiologic control over HIV-1 replication mediated by CD8 T cells expressing a re-engineered CD4-based chimeric antigen receptor.", PLOS Pathogens 13(10:e1006613, Oct. 12, 2017.

EF1α promoter and CD8α TM improve control over HIV

A

B

D

E scFv could prevent susceptibility of engineered T cells to HIV-1

| ScFv | Epitope |
|---|---|
| VRC01 | CD4 binding site |
| PG9 | V1/V2 stem |
| 3BNC60 | CD4bs (VRC01 derivitive) |
| PGT128 | N332 glycan–V3 loop |
| PDGM1400 | trimer apex N160 glycan in V1/V2 |

ScFv CARs Kill Env targets as well as CD4 membrane-bound chimeric receptors

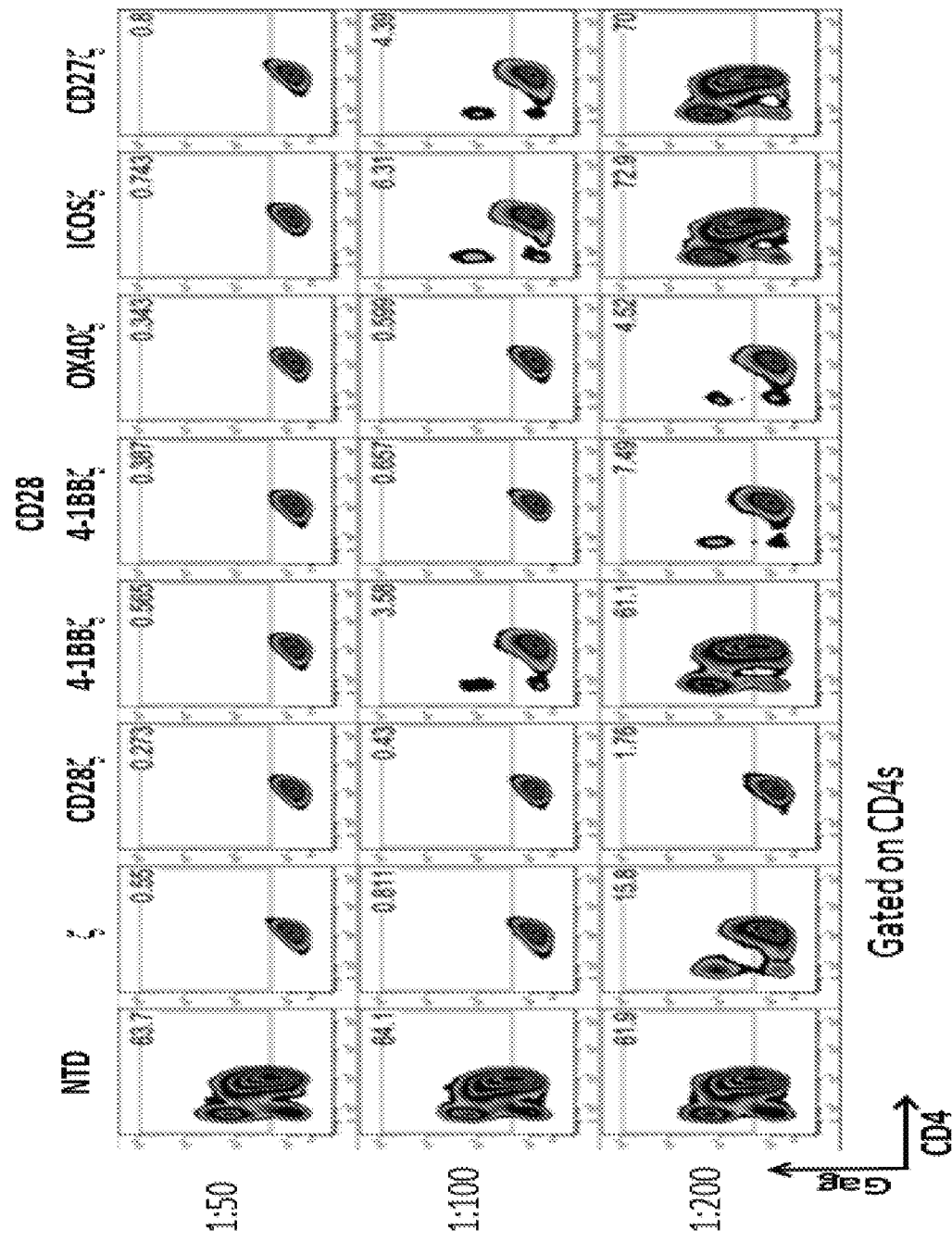

CD4 zeta annotated sequence (Whole Vector SEQ ID NO: 1)

Underline = EF1α promoter
Light Grey = CD4 extracellular domain
Dark Grey = CD8α extracellular hinge
Bold = CD8α transmembrane domain
Dotted line = CD3 zeta CGTGAGGCTCCGGTGCCCGTCAGTGGGCAGAGCGCACATCGCCCACAGTCCCCGAGAAGTTGGGGGGAGGGGTCGGCAATT
GAACCGGTGCCTAGAGAAGGTGGCGCGGGGTAAACTGGGAAAGTGATGTCGTGTACTGGCTCCGCCTTTTTCCCGAGGGTGG
GGGAGAACCGTATATAAGTGCAGTAGTCGCCGTGAACGTTCTTTTTCGCAACGGGTTTGCCGCCAGAACACAGGTAAGTGCCG
TGTGTGGTTCCCGCGGGCCTGGCCTCTTTACGGGTTATGGCCCTTGCGTGCCTTGAATTACTTCCACCTGGCTGCAGTACGTGA
TTCTTGATCCCGAGCTTCGGGTTGGAAGTGGGTGGGAGAGTTCGAGGCCTTGCGCTTAAGGAGCCCCTTCGCCTCGTGCTTGA
GTTGAGGCCTGGCCTGGGCGCTGGGGCCGCCGCGTGCGAATCTGGTGGCACCTTCGCGCCTGTCTCGCTGCTTTCGATAAGTC
TCTAGCCATTTAAAATTTTTGATGACCTGCTGCGACGCTTTTTTTCTGGCAAGATAGTCTTGTAAATGCGGGCCAAGATCTGCAC
ACTGGTATTTCGGTTTTTGGGGCCGCGGGCGGCGACGGGGCCCGTGCGTCCCAGCGCACATGTTCGGCGAGGCGGGGCCTGC
GAGCGCGGCCACCGAGAATCGGACGGGGGTAGTCTCAAGCTGGCCGGCCTGCTCTGGTGCCTGGCCTCGCGCCGCCGTGTAT
CGCCCCGCCCTGGGCGGCAAGGCTGGCCCGGTCGGCACCAGTTGCGTGAGCGGAAAGATGGCCGCTTCCCGGCCCTGCTGCA
GGGAGCTCAAAATGGAGGACGCGGCGCTCGGGAGAGCGGGCGGGTGAGTCACCCACACAAAGGAAAAGGGCCTTTCCGTCC
TCAGCCGTCGCTTCATGTGACTCCACTGAGTACCGGGCGCCGTCCAGGCACCTCGATTAGTTCTCGTGCTTTTGGAGTACGTCG
TCTTTAGGTTGGGGGGAGGGGTTTTATGCGATGGAGTTTCCCCACACTGAGTGGGTGGAGACTGAAGTTAGGCCAGCTTGGC
ACTTGATGTAATTCTCCTTGGAATTTGCCCTTTTTGAGTTTGGATCTTGGTTCATTCTCAAGCCTCAGACAGTGGTTCAAAGTTTT
TTTCTTCCATTTCAGGTGTCGTGAGCTAGCTCTAGAGCCACCATGGCCTTACCAGTGACCGCCTTGCTCCTGCCGCTGGCCTTGC
TGCTCCACGCCGCCAGGCCGGGATCCATGAACCGGGGAGTCCCTTTTAGGCACTTGCTTCTGGTGCTGCAACTGGCGCTCCTCC
CAGCAGCCACTCAGGGAAAGAAAGTGGTGCTGGGCAAAAAAGGGGATACAGTGGAACTGACCTGTACAGCTTCCCAGAAGA
AGAGCATACAATTCCACTGGAAAAACTCCAACCAGATAAAGATTCTGGGAAATCAGGGCTCCTTCTTAACTAAAGGTCCATCCA
AGCTGAATGATCGCGCTGACTCAAGAAGAAGCCTTTGGGACCAAGGAAACTTCCCCCTGATCATCAAGAATCTTAAGATAGAA
GACTCAGATACTTACATCTGTGAAGTGGAGGACCAGAAGGAGGAGGTGCAATTGCTAGTGTTCGGATTGACTGCCAACTCTG
ACACCCACCTGCTTCAGGGGCAGAGCCTGACCCTGACCTTGGAGAGCCCCCCTGGTAGTAGCCCCTCAGTGCAATGTAGGAGT
CCAAGGGGTAAAAACATACAGGGGGGGAAGACCCTCTCCGTGTCTCAGCTGGAGCTCCAGGATAGTGGCACCTGGACATGCA
CTGTCTTGCAGAACCAGAAGAAGGTGGAGTTCAAAATAGACATCGTGGTGCTAGCTTTCCAGAAGGCCTCCAGCATAGTCTAT
AAGAAAGAGGGGGAACAGGTGGAGTTCTCCTTCCCACTCGCCTTTACAGTTGAAAAGCTGACGGGCAGTGGCGAGCTGTGGT
GGCAGGCGGAGAGGGCTTCCTCCTCCAAGTCTTGGATCACCTTTGACCTGAAGAACAAGGAAGTGTCTGTAAAACGGGTTACC
CAGGACCCTAAGCTCCAGATGGGCAAGAAGCTCCCGCTCCACCTCACCCTGCCCCAGGCCTTGCCTCAGTATGCTGGCTCTGGA
AACCTCACCCTGGCCCTTGAAGCGAAAACAGGAAAGTTGCATCAGGAAGTGAACCTGGTGGTGATGAGAGCCACTCAGCTCC
AGAAAAATTTGACCTGTGAGGTGTGGGGACCCACCTCCCCTAAGCTGATGCTGAGCTTGAAACTGGAGAACAAGGAGGCAAA
GGTCTCGAAGCGGGAGAAGGCGGTGTGGGTGCTGAACCCTGAGGCGGGGATGTGGCAGTGTCTGCTGAGTGACTCGGGACA
GGTCCTGCTGGAATCCAACATCAAGGTTCTGCCCACATGGTCCACCCCGGTGCAGCCATCCGGAACCACGACGCCAGCGCCG
CGACCACCAACACCGGCGCCCACCATCGCGTCGCAGCCCCTGTCCCTGCGCCCAGAGGCGTGCCGGCCAGCGGCGGGGGGCGC
AGTGCACACGAGGGGGCTGGACTTCGCCTGTGA**TCTACATCTGGGCGCCCTTGGCCGGGACTTGTGGGGTCCTTCTCCTGT
CACTGGTTATCACCCCTTTACTGC**AGAGTGAAGTTCAGCAGGAGCGCAGACGCCCCCGCGTACCAGCAGGGCCAGAACCAGCT
CTATAACGAGCTCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCCTACAGTGAGAT
TGGGATGAAAGGCGAGCGCCGGAGGGGCAAGGGGCACGATGGCCTTTACCAGGGTCTCAGTACAGCCACCAAGGACACCTA
CGACGCCCTTCACATGCAGGCCCTGCCCCCTCGCTAA

FIG. 6 (Part 1/2)

EF1α promoter (SEQ ID NO: 2)
CGTGAGGCTCCGGTGCCCGTCAGTGGGCAGAGCGCACATCGCCCACAGTCCCCGAGAAGTTGGGGGGAGGGGTCGGCAATT
GAACCGGTGCCTAGAGAAGGTGGCGCGGGGTAAACTGGGAAAGTGATGTCGTGTACTGGCTCCGCCTTTTTCCCGAGGGTGG
GGGAGAACCGTATATAAGTGCAGTAGTCGCCGTGAACGTTCTTTTTCGCAACGGGTTTGCCGCCAGAACACAGGTAAGTGCCG
TGTGTGGTTCCCGCGGGCCTGGCCTCTTTACGGGTTATGGCCCTTGCGTGCCTTGAATTACTTCCACCTGGCTGCAGTACGTGA
TTCTTGATCCCGAGCTTCGGGTTGGAAGTGGGTGGGAGAGTTCGAGGCCTTGCGCTTAAGGAGCCCCTTCGCCTCGTGCTTGA
GTTGAGGCCTGGCCTGGGCGCTGGGGCCGCCGCGTGCGAATCTGGTGGCACCTTCGCGCCTGTCTCGCTGCTTTCGATAAGTC
TCTAGCCATTTAAAATTTTTGATGACCTGCTGCGACGCTTTTTTTCTGGCAAGATAGTCTTGTAAATGCGGGCCAAGATCTGCAC
ACTGGTATTTCGGTTTTTGGGGCCGCGGGCGGCGACGGGGCCCGTGCGTCCCAGCGCACATGTTCGGCGAGGCGGGGCCTGC
GAGCGCGGCCACCGAGAATCGGACGGGGGTAGTCTCAAGCTGGCCGGCCTGCTCTGGTGCCTGGCCTCGCGCCGCCGTGTAT
CGCCCCGCCCTGGGCGGCAAGGCTGGCCCGGTCGGCACCAGTTGCGTGAGCGGAAAGATGGCCGCTTCCCGGCCCTGCTGCA
GGGAGCTCAAAATGGAGGACGCGGCGCTCGGGAGAGCGGGCGGGTGAGTCACCCACACAAAGGAAAAGGGCCTTTCCGTCC
TCAGCCGTCGCTTCATGTGACTCCACTGAGTACCGGGCGCCGTCCAGGCACCTCGATTAGTTCTCGTGCTTTTGGAGTACGTCG
TCTTTAGGTTGGGGGGAGGGGTTTTATGCGATGGAGTTTCCCCACACTGAGTGGGTGGAGACTGAAGTTAGGCCAGCTTGGC
ACTTGATGTAATTCTCCTTGGAATTTGCCCTTTTTGAGTTTGGATCTTGGTTCATTCTCAAGCCTCAGACAGTGGTTCAAAGTTTT
TTTCTTCCATTTCAGGTGTCGTGA

CD4 extracellular domain (SEQ ID NO: 3)
ATGAACCGGGGAGTCCCTTTTAGGCACTTGCTTCTGGTGCTGCAACTGGCGCTCCTCCCAGCAGCCACTCAGGGAAAGAAAGT
GGTGCTGGGCAAAAAAGGGGATACAGTGGAACTGACCTGTACAGCTTCCCAGAAGAAGAGCATACAATTCCACTGGAAAAAC
TCCAACCAGATAAAGATTCTGGGAAATCAGGGCTCCTTCTTAACTAAAGGTCCATCCAAGCTGAATGATCGCGCTGACTCAAG
AAGAAGCCTTTGGGACCAAGGAAACTTCCCCCTGATCATCAAGAATCTTAAGATAGAAGACTCAGATACTTACATCTGTGAAGT
GGAGGACCAGAAGGAGGAGGTGCAATTGCTAGTGTTCGGATTGACTGCCAACTCTGACACCCACCTGCTTCAGGGGCAGAGC
CTGACCCTGACCTTGGAGAGCCCCCCTGGTAGTAGCCCCTCAGTGCAATGTAGGAGTCCAAGGGGTAAAAACATACAGGGGG
GGAAGACCCTCTCCGTGTCTCAGCTGGAGCTCCAGGATAGTGGCACCTGGACATGCACTGTCTTGCAGAACCAGAAGAAGGT
GGAGTTCAAAATAGACATCGTGGTGCTAGCTTTCCAGAAGGCCTCCAGCATAGTCTATAAGAAAGAGGGGGAACAGGTGGAG
TTCTCCTTCCCACTCGCCTTTACAGTTGAAAAGCTGACGGGCAGTGGCGAGCTGTGGTGGCAGGCGGAGAGGGCTTCCTCCTC
CAAGTCTTGGATCACCTTTGACCTGAAGAACAAGGAAGTGTCTGTAAAACGGGTTACCCAGGACCCTAAGCTCCAGATGGGCA
AGAAGCTCCCGCTCCACCTCACCCTGCCCCAGGCCTTGCCTCAGTATGCTGGCTCTGGAAACCTCACCCTGGCCCTTGAAGCGA
AAACAGGAAAGTTGCATCAGGAAGTGAACCTGGTGGTGATGAGAGCCACTCAGCTCCAGAAAAATTTGACCTGTGAGGTGTG
GGGACCCACCTCCCCTAAGCTGATGCTGAGCTTGAAACTGGAGAACAAGGAGGCAAAGGTCTCGAAGCGGGAGAAGGCGGT
GTGGGTGCTGAACCCTGAGGCGGGGATGTGGCAGTGTCTGCTGAGTGACTCGGGACAGGTCCTGCTGGAATCCAACATCAAG
GTTCTGCCCACATGGTCCACCCCGGTGCAGCCA

CD8α extracellular hinge (SEQ ID NO: 4)
ACCACGACGCCAGCGCCGCGACCACCAACACCGGCGCCCACCATCGCGTCGCAGCCCCTGTCCCTGCGCCCAGAGGCGTGCCG
GCCAGCGGCGGGGGGCGCAGTGCACACGAGGGGGCTGGACTTCGCCTGTGAT

CD8α transmembrane domain (SEQ ID NO: 5)
ATCTACATCTGGGCGCCCTTGGCCGGGACTTGTGGGGTCCTTCTCCTGTCACTGGTTATCACCCTTTACTGC

CD3 zeta (SEQ ID NO: 6)
AGAGTGAAGTTCAGCAGGAGCGCAGACGCCCCCGCGTACCAGCAGGGCCAGAACCAGCTCTATAACGAGCTCAATCTAGGAC
GAAGAGAGGAGTACGATGTTTTGGACAAGAGACGTGGCCGGGACCCTGAGATGGGGGGAAAGCCGAGAAGGAAGAACCCT
CAGGAAGGCCTGTACAATGAACTGCAGAAAGATAAGATGGCGGAGGCCTACAGTGAGATTGGGATGAAAGGCGAGCGCCGG
AGGGGCAAGGGGCACGATGGCCTTTACCAGGGTCTCAGTACAGCCACCAAGGACACCTACGACGCCCTTCACATGCAGGCCC
TGCCCCCTCGCTAA

FIG. 6 (Part 2/2)

CD4 CD28 zeta annotated sequences (Whole Vector SEQ ID NO: 7)

Underline = EF1α promoter
Light Grey = CD4 extracellular domain
Dark Grey = CD8α extracellular hinge
Bold = CD8α transmembrane domain
Wave line = DC28 costimulatory domain
Dotted line = CD3 zeta CGTGAGGCTCCGGTGCCCGTCAGTGGGCAGAGCGCACATCGCCCACAGTCCCCGAGAAGTTGGGGGGAGGGGTCGGCAATT
GAACCGGTGCCTAGAGAAGGTGGCGCGGGGTAAACTGGGAAAGTGATGTCGTGTACTGGCTCCGCCTTTTTCCCGAGGGTGG
GGGAGAACCGTATATAAGTGCAGTAGTCGCCGTGAACGTTCTTTTTCGCAACGGGTTTGCCGCCAGAACACAGGTAAGTGCCG
TGTGTGGTTCCCGCGGGCCTGGCCTCTTTACGGGTTATGGCCCTTGCGTGCCTTGAATTACTTCCACCTGGCTGCAGTACGTGA
TTCTTGATCCCGAGCTTCGGGTTGGAAGTGGGTGGGAGAGTTCGAGGCCTTGCGCTTAAGGAGCCCCTTCGCCTCGTGCTTGA
GTTGAGGCCTGGCCTGGGCGCTGGGGCCGCCGCGTGCGAATCTGGTGGCACCTTCGCGCCTGTCTCGCTGCTTTCGATAAGTC
TCTAGCCATTTAAAATTTTTGATGACCTGCTGCGACGCTTTTTTTCTGGCAAGATAGTCTTGTAAATGCGGGCCAAGATCTGCAC
ACTGGTATTTCGGTTTTTGGGGCCGCGGGCGGCGACGGGGCCCGTGCGTCCCAGCGCACATGTTCGGCGAGGCGGGGCCTGC
GAGCGCGGCCACCGAGAATCGGACGGGGGTAGTCTCAAGCTGGCCGGCCTGCTCTGGTGCCTGGCCTCGCGCCGCCGTGTAT
CGCCCCGCCCTGGGCGGCAAGGCTGGCCCGGTCGGCACCAGTTGCGTGAGCGGAAAGATGGCCGCTTCCCGGCCCTGCTGCA
GGGAGCTCAAAATGGAGGACGCGGCGCTCGGGAGAGCGGGCGGGTGAGTCACCCACACAAAGGAAAAGGGCCTTTCCGTCC
TCAGCCGTCGCTTCATGTGACTCCACTGAGTACCGGGCGCCGTCCAGGCACCTCGATTAGTTCTCGTGCTTTTGGAGTACGTCG
TCTTTAGGTTGGGGGGAGGGGTTTTATGCGATGGAGTTTCCCCACACTGAGTGGGTGGAGACTGAAGTTAGGCCAGCTTGGC
ACTTGATGTAATTCTCCTTGGAATTTGCCCTTTTTGAGTTTGGATCTTGGTTCATTCTCAAGCCTCAGACAGTGGTTCAAAGTTTT
TTTCTTCCATTTCAGGTGTCGTGAGCTAGCTCTAGAGCCACCATGGCCTTACCAGTGACCGCCTTGCTCCTGCCGCTGGCCTTGC
TGCTCCACGCCGCCAGGCCGGGATCCATGAACCGGGGAGTCCCTTTTAGGCACTTGCTTCTGGTGCTGCAACTGGCGCTCCTCC
CAGCAGCCACTCAGGGAAAGAAAGTGGTGCTGGGCAAAAAAGGGGATACAGTGGAACTGACCTGTACAGCTTCCCAGAAGA
AGAGCATACAATTCCACTGGAAAAACTCCAACCAGATAAAGATTCTGGGAAATCAGGGCTCCTTCTTAACTAAAGGTCCATCCA
AGCTGAATGATCGCGCTGACTCAAGAAGAAGCCTTTGGGACCAAGGAAACTTCCCCCTGATCATCAAGAATCTTAAGATAGAA
GACTCAGATACTTACATCTGTGAAGTGGAGGACCAGAAGGAGGAGGTGCAATTGCTAGTGTTCGGATTGACTGCCAACTCTG
ACACCCACCTGCTTCAGGGGCAGAGCCTGACCCTGACCTTGGAGAGCCCCCCTGGTAGTAGCCCCTCAGTGCAATGTAGGAGT
CCAAGGGGTAAAAACATACAGGGGGGAAGACCCTCTCCGTGTCTCAGCTGGAGCTCCAGGATAGTGGCACCTGGACATGCA
CTGTCTTGCAGAACCAGAAGAAGGTGGAGTTCAAAATAGACATCGTGGTGCTAGCTTTCCAGAAGGCCTCCAGCATAGTCTAT
AAGAAAGAGGGGGAACAGGTGGAGTTCTCCTTCCCACTCGCCTTTACAGTTGAAAAGCTGACGGGCAGTGGCGAGCTGTGGT
GGCAGGCGGAGAGGGCTTCCTCCTCCAAGTCTTGGATCACCTTTGACCTGAAGAACAAGGAAGTGTCTGTAAAACGGGTTACC
CAGGACCCTAAGCTCCAGATGGGCAAGAAGCTCCCGCTCCACCTCACCCTGCCCCAGGCCTTGCCTCAGTATGCTGGCTCTGGA
AACCTCACCCTGGCCCTTGAAGCGAAAACAGGAAAGTTGCATCAGGAAGTGAACCTGGTGGTGATGAGAGCCACTCAGCTCC
AGAAAAATTTGACCTGTGAGGTGTGGGGACCCACCTCCCCTAAGCTGATGCTGAGCTTGAAACTGGAGAACAAGGAGGCAAA
GGTCTCGAAGCGGGAGAAGGCGGTGTGGGTGCTGAACCCTGAGGCGGGGATGTGGCAGTGTCTGCTGAGTGACTCGGGACA
GGTCCTGCTGGAATCCAACATCAAGGTTCTGCCCACATGGTCCACCCGGTGCAGCCATCCGGAACCACGACGCCAGCGCCGG
GACCACCAACACCGGCGCCCACCATCGCGTCGCAGCCCCTGTCCCTGCGCCCAGAGGCGTGCCGGCCAGCGGCGGGGGGCGC
AGTGCACACGAGGGGGCTGGACTTCGCCTGTGA**TTTTGGGTGCTGGTGGTGGTTGGTGGAGTCCTGGCTTGCTATAGCTTG
CTAGTAACAGTGGCCTTTATTATTTTCTGGGTG**AGGAGTAAGAGGAGCAGGCTCCTGCACAGTGACTACATGAACATGACTCC
CCGCCGCCCCGGGCCCACCCGCAAGCATTACCAGCCCTATGCCCCACCACGCGACTTCGCAGCCTATCGCTCCATCGATAGAGT
GAAGTTCAGCAGGAGCGCAGACGCCCCCGCGTACCAGCAGGGCCAGAACCAGCTCTATAACGAGCTCAATCTAGGACGAAGA
GAGGAGTACGATGTTTTGGACAAGAGACGTGGCCGGGACCCTGAGATGGGGGGAAAGCCGAGAAGGAAGAACCCTCAGGA
AGGCCTGTACAATGAACTGCAGAAAGATAAGATGGCGGAGGCCTACAGTGAGATTGGGATGAAAGGCGAGCGCCGGAGGG
GCAAGGGGCACGATGGCCTTTACCAGGGTCTCAGTACAGCCACCAAGGACACCTACGACGCCCTTCACATGCAGGCCCTGCCC
CCTCGCTAA

FIG. 7 (Part 1/2)

CD28 transmembrane domain (SEQ ID NO: 8)
TTTTGGGTGCTGGTGGTGGTTGGTGGAGTCCTGGCTTGCTATAGCTTGCTAGTAACAGTGGCCTTTATTATTTTCTG
GGTG

CD28 costimulatory domain (SEQ ID NO: 9)
AGGAGTAAGAGGAGCAGGCTCCTGCACAGTGACTACATGAACATGACTCCCCGCCGCCCCGGGCCCACCCGCAAG
CATTACCAGCCCTATGCCCCACCACGCGACTTCGCAGCCTATCGCTCC

FIG. 7 (Part 2/2)

ScFvs CARs sequences

PGDM1400 KIR nucleotide sequence (SEQ ID NO: 10)
ATGGGGGGACTTGAACCCTGCAGCAGGTTCCTGCTCCTGCCTCTCCTGCTGGCTGTAAGTGGTCTCCGTCCTGTCCAGGTCCAG
GCCCAGAGCGATTGCAGTTGCTCTACGGTGAGCCCGGGCGTGCTGGCAGGGATCGTGATGGGAGACCTGGTGCTGACAGTG
CTCATTGCCCTGGCCGTGTACTTCCTGGGCCGGCTGGTCCCTCGGGGGCGAGGGGCTGCGGAGGCAGCGACCCGGAAACAGC
GTATCACTGAGACCGAGTCGCCTTATCAGGAGCTCCAGGGTCAGAGGTCGGATGTCTACAGCGACCTCAACACACAGAGGCC
GTATTACAAAGTCGAGGGCGGCGGAGAGGGCAGAGGAAGTCTTCTAACATGCGGTGACGTGGAGGAGAATCCCGGCCCTAG
GATGGCTCTGCCTGTGACAGCTCTGCTGCTGCCTCTGGCCCTGCTGCTGCATGCTGCCAGACCTGGATCCGACTTCGTGCTGAC
CCAGAGCCCTCACAGCCTGAGCGTGACACCTGGCGAGAGCGCCAGCATCAGCTGCAAGAGCAGCCACTCCCTGATCCACGGC
GACCGGAACAACTACCTGGCTTGGTACGTGCAGAAGCCCGGCAGATCCCCCCAGCTGCTGATCTACCTGGCCAGCAGCAGAG
CCAGCGGCGTGCCCGATAGATTTTCTGGCAGCGGCAGCGACAAGGACTTCACCCTGAAGATCAGCCGGGTGGAAACCGAGGA
CGTGGGCACCTACTACTGTATGCAGGGCAGAGAGAGCCCCTGGACCTTTGGCCAGGGCACCAAGGTGGACATCAAGGGCGG
CAGCTCCAGAAGCAGCTCTAGCGGAGGCGGAGGATCTGGCGGCGGAGGACAGGCTCAGCTGGTGCAGTCTGGACCCGAAGT
GCGGAAGCCTGGCACCAGCGTGAAGGTGTCCTGTAAAGCCCCTGGCAACACCCTGAAAACCTACGACCTGCACTGGGTGCGC
AGCGTGCCAGGACAGGGACTGCAGTGGATGGGCTGGATCAGCCACGAGGGCGACAAGAAAGTGATCGTGGAACGGTTCAA
GGCCAAAGTGACCATCGACTGGGACAGAAGCACCAACACCGCCTACCTGCAGCTGAGCGGCCTGACCTCTGGCGATACCGCC
GTGTACTACTGCGCCAAGGGCAGCAAGCACCGGCTGAGAGACTACGCCCTGTACGACGATGACGGCGCCCTGAACTGGGCCG
TGGATGTGGACTACCTGAGCAACCTGGAATTCTGGGGCCAGGGAACCGCCGTGACCGTGTCATCTGCTAGCGGCGGAGGGG
GATCTGGAGGTGGGGGTTCCTCACCCACTGAACCAAGCTCCAAAACCGGTAACCCCAGACACCTGCATGTTCTGATTGGGACC
TCAGTGGTCAAAATCCCTTTCACCATCCTCCTCTTCTTTCTCCTTCATCGCTGGTGCTCCAACAAAAAAAATGCTGCTGTAATGGA
CCAAGAGCCTGCAGGGAACAGAACAGTGAACAGCGAGGATTCTGATGAACAAGACCATCAGGAGGTGTCATACGCATAA PGDM1400KIR aa sequence (SEQ ID NO: 11)
MGGLEPCSRFLLLPLLLAVSGLRPVQVQAQSDCSCSTVSPGVLAGIVMGDLVLTVLIALAVYFLGRLVPRGRGAAEEAATRKQRITETES
PYQELQGQRSDVYSDLNTQRPYYKVEGGGEGRGSLLTCGDVEENPGPRMALPVTALLLPLALLLHAARPGSDFVLTQSPHSLSVTPG
ESASISCKSSHSLIHGDRNNYLAWYVQKPGRSPQLLIYLASSRASGVPDRFSGSGSDKDFTLKISRVETEDVGTYYCMQGRESPWTFG
QGTKVDIKGGSSRSSSSGGGGSGGGGQAQLVQSGPEVRKPGTSVKVSCKAPGNTLKTYDLHWVRSVPGQGLQWMGWISHEGDK
KVIVERFKAKVTIDWDRSTNTAYLQLSGLTSGDTAVYYCAKGSKHRLRDYALYDDDGALNWAVDVDYLSNLEFWGQGTAVTVSSAS
GGGGSGGGGSSPTEPSSKTGNPRHLHVLIGTSVVKIPFTILLFFLLHRWCSNKKNAAVMDQEPAGNRTVNSEDSDEQDHQEVSYAZ

FIG. 8 (Part 1/9)

PGDM1400 scFv nucleotide sequence (SEQ ID NO: 12):
ATGGCTCTGCCTGTGACAGCTCTGCTGCTGCCTCTGGCCCTGCTGCTGCATGCTGCCAGACCTGGATCCGACTTCGTGCTGACC
CAGAGCCCTCACAGCCTGAGCGTGACACCTGGCGAGAGCGCCAGCATCAGCTGCAAGAGCAGCCACTCCCTGATCCACGGCG
ACCGGAACAACTACCTGGCTTGGTACGTGCAGAAGCCCGGCAGATCCCCCCAGCTGCTGATCTACCTGGCCAGCAGCAGAGCC
AGCGGCGTGCCCGATAGATTTTCTGGCAGCGGCAGCGACAAGGACTTCACCCTGAAGATCAGCCGGGTGGAAACCGAGGAC
GTGGGCACCTACTACTGTATGCAGGGCAGAGAGAGCCCCTGGACCTTTGGCCAGGGCACCAAGGTGGACATCAAGGGCGGC
AGCTCCAGAAGCAGCTCTAGCGGAGGCGGAGGATCTGGCGGCGGAGGACAGGCTCAGCTGGTGCAGTCTGGACCCGAAGTG
CGGAAGCCTGGCACCAGCGTGAAGGTGTCCTGTAAAGCCCCTGGCAACACCCTGAAAACCTACGACCTGCACTGGGTGCGCA
GCGTGCCAGGACAGGGACTGCAGTGGATGGGCTGGATCAGCCACGAGGGCGACAAGAAAGTGATCGTGGAACGGTTCAAG
GCCAAAGTGACCATCGACTGGGACAGAAGCACCAACACCGCCTACCTGCAGCTGAGCGGCCTGACCTCTGGCGATACCGCCG
TGTACTACTGCGCCAAGGGCAGCAAGCACCGGCTGAGAGACTACGCCCTGTACGACGATGACGGCGCCCTGAACTGGGCCGT
GGATGTGGACTACCTGAGCAACCTGGAATTCTGGGGCCAGGGAACCGCCGTGACCGTGTCATCT PGDM1400 scFv amino acid (aa) sequence (SEQ ID NO: 13):
MALPVTALLLPLALLLHAARPGSDFVLTQSPHSLSVTPGESASISCKSSHSLIHGDRNNYLAWYVQKPGRSPQLLIYLASSRASGVPDR
FSGSGSDKDFTLKISRVETEDVGTYYCMQGRESPWTFGQGTKVDIKGGSSRSSSSGGGGSGGGGQAQLVQSGPEVRKPGTSVKVS
CKAPGNTLKTYDLHWVRSVPGQGLQWMGWISHEGDKKVIVERFKAKVTIDWDRSTNTAYLQLSGLTSGDTAVYYCAKGSKHRLR
DYALYDDDGALNWAVDVDYLSNLEFWGQGTAVTVSS PGT128-KIR nucleotide sequence (SEQ ID NO: 14)
ATGGGGGGACTTGAACCCTGCAGCAGGTTCCTGCTCCTGCCTCTCCTGCTGGCTGTAAGTGGTCTCCGTCCTGTCCAGGTCCAG
GCCCAGAGCGATTGCAGTTGCTCTACGGTGAGCCCGGGCGTGCTGGCAGGGATCGTGATGGGAGACCTGGTGCTGACAGTG
CTCATTGCCCTGGCCGTGTACTTCCTGGGCCGGCTGGTCCCTCGGGGGCGAGGGGCTGCGGAGGCAGCGACCCGGAAACAGC
GTATCACTGAGACCGAGTCGCCTTATCAGGAGCTCCAGGGTCAGAGGTCGGATGTCTACAGCGACCTCAACACACAGAGGCC
GTATTACAAAGTCGAGGGCGGCGGAGAGGGCAGAGGAAGTCTTCTAACATGCGGTGACGTGGAGGAGAATCCCGGCCCTAG
GATGGCTCTGCCTGTGACAGCTCTGCTGCTGCCTCTGGCCCTGCTGCTGCATGCTGCCAGACCTGGATCCCAGTCTGCCCTGAC
TCAGCCTCCCTCCGCGTCCGGGTCTCCTGGACAGTCAATCACCATCTCCTGCACTGGAACCAGCAATAACTTTGTCTCCTGGTAC
CAGCAACACGCAGGCAAGGCCCCCAAGCTCGTCATTTATGACGTCAATAAGCGCCCCTCAGGTGTCCCTGATCGTTTCTCTGGC
TCCAAGTCTGGCAACACGGCCTCCCTGACCGTCTCTGGACTCCAGACTGACGATGAGGCTGTCTATTACTGCGGCTCACTTGTA
GGCAACTGGGATGTGATTTTCGGCGGAGGGACCAAGTTGACCGTCCTAGGCGGAAGCAGCAGAAGCAGCTCTAGCGGCGGA
GGCGGATCTGGCGGAGGGGGACAGATGCAGTTACAGGAGTCGGGCCCCGGACTGGTGAAGCCTTCGGAAACCCTGTCCCTC
ACGTGCAGTGTGTCTGGTGCCTCCATAAGTGACAGTTACTGGAGCTGGATCCGGCGGTCCCCAGGGAAGGGACTTGAGTGGA
TTGGGTATGTCCACAAAAGCGGCGACACAAATTACAGCCCCTCCCTCAAGAGTCGAGTCAACTTGTCGTTAGACACGTCCAAA
AATCAGGTGTCCCTGAGCCTTGTGGCCGCGACCGCTGCGGACTCGGGCAAATATTATTGCGCGAGAACACTGCACGGGAGGA
GAATTTATGGAATCGTTGCCTTCAATGAGTGGTTCACCTACTTCTACATGGACGTCTGGGGCAATGGGACTCAGGTCACCGTCT
CCTCAGCTAGCGGCGGAGGGGGATCTGGAGGTGGGGGTTCCTCACCCACTGAACCAAGCTCCAAAACCGGTAACCCCAGACA
CCTGCATGTTCTGATTGGGACCTCAGTGGTCAAAATCCCTTTCACCATCCTCCTCTTCTTTCTCCTTCATCGCTGGTGCTCCAACA
AAAAAAATGCTGCTGTAATGGACCAAGAGCCTGCAGGGAACAGAACAGTGAACAGCGAGGATTCTGATGAACAAGACCATCA
GGAGGTGTCATACGCATAA

FIG. 8 (Part 2/9)

PGT128-KIR aa sequence (SEQ ID NO: 15)
MGGLEPCSRFLLLPLLLAVSGLRPVQVQAQSDCSCSTVSPGVLAGIVMGDLVLTVLIALAVYFLGRLVPRGRGAAEEAATRKQRITETES
PYQELQGQRSDVYSDLNTQRPYYKVEGGGEGRGSLLTCGDVEENPGPRMALPVTALLLPLALLLHAARPGSQSALTQPPSASGSPG
QSITISCTGTSNNFVSWYQQHAGKAPKLVIYDVNKRPSGVPDRFSGSKSGNTASLTVSGLQTDDEAVYYCGSLVGNWDVIFGGGTK
LTVLGGSSRSSSSGGGGSGGGGQMQLQESGPGLVKPSETLSLTCSVSGASISDSYWSWIRRSPGKGLEWIGYVHKSGDTNYSPSLKS
RVNLSLDTSKNQVSLSLVAATAADSGKYYCARTLHGRRIYGIVAFNEWFTYFYMDVWGNGTQVTVSSASGGGGSGGGGSSPTEPS
SKTGNPRHLHVLIGTSVVKIPFTILLFFLLHRWCSNKKNAAVMDQEPAGNRTVNSEDSDEQDHQEVSYAZ

PGT128 scFv nucleotide sequence (SEQ ID NO: 16):
ATGGCTCTGCCTGTGACAGCTCTGCTGCTGCCTCTGGCCCTGCTGCTGCATGCTGCCAGACCTGGATCCCAGTCTGCCCTGACT
CAGCCTCCCTCCGCGTCCGGGTCTCCTGGACAGTCAATCACCATCTCCTGCACTGGAACCAGCAATAACTTTGTCTCCTGGTACC
AGCAACACGCAGGCAAGGCCCCCAAGCTCGTCATTTATGACGTCAATAAGCGCCCCTCAGGTGTCCCTGATCGTTTCTCTGGCT
CCAAGTCTGGCAACACGGCCTCCCTGACCGTCTCTGGACTCCAGACTGACGATGAGGCTGTCTATTACTGCGGCTCACTTGTAG
GCAACTGGGATGTGATTTTCGGCGGAGGGACCAAGTTGACCGTCCTAGGCGGAAGCAGCAGAAGCAGCTCTAGCGGCGGAG
GCGGATCTGGCGGAGGGGGACAGATGCAGTTACAGGAGTCGGGCCCCGGACTGGTGAAGCCTTCGGAAACCCTGTCCCTCAC
GTGCAGTGTGTCTGGTGCCTCCATAAGTGACAGTTACTGGAGCTGGATCCGGCGGTCCCCAGGGAAGGGACTTGAGTGGATT
GGGTATGTCCACAAAAGCGGCGACACAAATTACAGCCCCTCCCTCAAGAGTCGAGTCAACTTGTCGTTAGACACGTCCAAAAA
TCAGGTGTCCCTGAGCCTTGTGGCCGCGACCGCTGCGGACTCGGGCAAATATTATTGCGCGAGAACACTGCACGGGAGGAGA
ATTTATGGAATCGTTGCCTTCAATGAGTGGTTCACCTACTTCTACATGGACGTCTGGGGCAATGGGACTCAGGTCACCGTCTCC
TCA

PGT128 scFv aa sequence (SEQ ID NO: 17):
MALPVTALLLPLALLLHAARPGSQSALTQPPSASGSPGQSITISCTGTSNNFVSWYQQHAGKAPKLVIYDVNKRPSGVPDRFSGSKSG
NTASLTVSGLQTDDEAVYYCGSLVGNWDVIFGGGTKLTVLGGSSRSSSSGGGGSGGGGQMQLQESGPGLVKPSETLSLTCSVSGAS
ISDSYWSWIRRSPGKGLEWIGYVHKSGDTNYSPSLKSRVNLSLDTSKNQVSLSLVAATAADSGKYYCARTLHGRRIYGIVAFNEWFTY
FYMDVWGNGTQVTVSS

FIG. 8 (Part 3/9)

VRC01-KIR nucleotide sequence (SEQ ID NO: 18)
ATGGGGGGACTTGAACCCTGCAGCAGGTTCCTGCTCCTGCCTCTCCTGCTGGCTGTAAGTGGTCTCCGTCCTGTCCAGGTCCAG
GCCCAGAGCGATTGCAGTTGCTCTACGGTGAGCCCGGGCGTGCTGGCAGGGATCGTGATGGGAGACCTGGTGCTGACAGTG
CTCATTGCCCTGGCCGTGTACTTCCTGGGCCGGCTGGTCCCTCGGGGGCGAGGGGCTGCGGAGGCAGCGACCCGGAAACAGC
GTATCACTGAGACCGAGTCGCCTTATCAGGAGCTCCAGGGTCAGAGGTCGGATGTCTACAGCGACCTCAACACACAGAGGCC
GTATTACAAAGTCGAGGGCGGCGGAGAGGGCAGAGGAAGTCTTCTAACATGCGGTGACGTGGAGGAGAATCCCGGCCCTAG
GATGGCTCTGCCTGTGACAGCTCTGCTGCTGCCTCTGGCCCTGCTGCTGCATGCTGCCAGACCTGGATCCGAGATCGTGCTGAC
ACAGAGCCCTGGCACCCTGAGCCTGTCTCCAGGCGAGACAGCCATCATCAGCTGCCGGACAAGCCAGTACGGCAGCCTGGCC
TGGTATCAGCAGAGGCCTGGACAGGCCCCCAGACTCGTGATCTACAGCGGCAGCACAAGAGCCGCCGGAATCCCCGATAGAT
TCAGCGGCTCTAGATGGGGCCCTGACTACAACCTGACCATCAGCAACCTGGAAAGCGGCGACTTCGGCGTGTACTACTGCCAG
CAGTACGAGTTCTTCGGCCAGGGCACCAAGGTGCAGGTGGACATCAAGAGAGGCGGCAGCTCCAGAAGCTCCAGCTCTGGCG
GCGGAGGATCTGGCGGAGGCGGACAGGTGCAGCTGGTGCAGTCTGGCGGCCAGATGAAGAAACCCGGCGAGAGCATGCGG
ATCAGCTGCAGAGCCTCCGGCTACGAGTTCATCGACTGCACCCTGAACTGGATTCGGCTGGCCCCTGGCAAAAGACCCGAGTG
GATGGGCTGGCTGAAGCCCAGAGGCGGAGCCGTGAATTACGCCAGACCTCTGCAGGGCAGAGTGACCATGACCCGGGACGT
GTACAGCGATACCGCCTTCCTGGAACTGCGGAGCCTGACCGTGGATGATACCGCCGTGTACTTCTGCACCCGGGGCAAGAACT
GCGACTACAACTGGGACTTCGAGCACTGGGGCAGAGGCACCCCTGTGATCGTGTCTAGCGCTAGCGGCGGAGGGGGATCTG
GAGGTGGGGGTTCCTCACCCACTGAACCAAGCTCCAAAACCGGTAACCCCAGACACCTGCATGTTCTGATTGGGACCTCAGTG
GTCAAAATCCCTTTCACCATCCTCCTCTTCTTTCTCCTTCATCGCTGGTGCTCCAACAAAAAAAATGCTGCTGTAATGGACCAAG
AGCCTGCAGGGAACAGAACAGTGAACAGCGAGGATTCTGATGAACAAGACCATCAGGAGGTGTCATACGCATAA VRC01 aa sequence (SEQ ID NO: 19)
MGGLEPCSRFLLLPLLLAVSGLRPVQVQAQSDCSCSTVSPGVLAGIVMGDLVLTVLIALAVYFLGRLVPRGRGAAEAATRKQRITETES
PYQELQGQRSDVYSDLNTQRPYYKVEGGGEGRGSLLTCGDVEENPGPRMALPVTALLLPLALLLHAARPGSEIVLTQSPGTLSLSPGE
TAIISCRTSQYGSLAWYQQRPGQAPRLVIYSGSTRAAGIPDRFSGSRWGPDYNLTISNLESGDFGVYYCQQYEFFGQGTKVQVDIKR
GGSSRSSSSGGGGSGGGGQVQLVQSGGQMKKPGESMRISCRASGYEFIDCTLNWIRLAPGKRPEWMGWLKPRGGAVNYARPLQ
GRVTMTRDVYSDTAFLELRSLTVDDTAVYFCTRGKNCDYNWDFEHWGRGTPVIVSSASGGGGSGGGGSSPTEPSSKTGNPRHLHV
LIGTSVVKIPFTILLFFLLHRWCSNKKNAAVMDQEPAGNRTVNSEDSDEQDHQEVSYAZ VRC01 scFv nucleotide sequence (SEQ ID NO: 20):
ATGGCCCTGCCTGTGACAGCCCTGCTGCTGCCTCTGGCTCTGCTGCTGCACGCCGCTAGACCTGGATCCGAGATCGTGCTGACA
CAGAGCCCTGGCACCCTGAGCCTGTCTCCAGGCGAGACAGCCATCATCAGCTGCCGGACAAGCCAGTACGGCAGCCTGGCCT
GGTATCAGCAGAGGCCTGGACAGGCCCCCAGACTCGTGATCTACAGCGGCAGCACAAGAGCCGCCGGAATCCCCGATAGATT
CAGCGGCTCTAGATGGGGCCCTGACTACAACCTGACCATCAGCAACCTGGAAAGCGGCGACTTCGGCGTGTACTACTGCCAGC
AGTACGAGTTCTTCGGCCAGGGCACCAAGGTGCAGGTGGACATCAAGAGAGGCGGCAGCTCCAGAAGCTCCAGCTCTGGCG
GCGGAGGATCTGGCGGAGGCGGACAGGTGCAGCTGGTGCAGTCTGGCGGCCAGATGAAGAAACCCGGCGAGAGCATGCGG
ATCAGCTGCAGAGCCTCCGGCTACGAGTTCATCGACTGCACCCTGAACTGGATTCGGCTGGCCCCTGGCAAAAGACCCGAGTG
GATGGGCTGGCTGAAGCCCAGAGGCGGAGCCGTGAATTACGCCAGACCTCTGCAGGGCAGAGTGACCATGACCCGGGACGT
GTACAGCGATACCGCCTTCCTGGAACTGCGGAGCCTGACCGTGGATGATACCGCCGTGTACTTCTGCACCCGGGGCAAGAACT
GCGACTACAACTGGGACTTCGAGCACTGGGGCAGAGGCACCCCTGTGATCGTGTCTAGC

FIG. 8 (Part 4/9)

VRC01 scFv aa sequence (SEQ ID NO: 21):
MALPVTALLLPLALLLHAARPGSEIVLTQSPGTLSLSPGETAIISCRTSQYGSLAWYQQRPGQAPRLVIYSGSTRAAGIPDRFSGSRWG
PDYNLTISNLESGDFGVYYCQQYEFFGQGTKVQVDIKRGGSSRSSSSGGGGSGGGGQVQLVQSGGQMKKPGESMRISCRASGYEFI
DCTLNWIRLAPGKRPEWMGWLKPRGGAVNYARPLQGRVTMTRDVYSDTAFLELRSLTVDDTAVYFCTRGKNCDYNWDFEHWG
RGTPVIVSS

3BNC60 KIR nucleotide sequence (SEQ ID NO: 22)
ATGGGGGGACTTGAACCCTGCAGCAGGTTCCTGCTCCTGCCTCTCCTGCTGGCTGTAAGTGGTCTCCGTCCTGTCCAGGTCCAG
GCCCAGAGCGATTGCAGTTGCTCTACGGTGAGCCCGGGCGTGCTGGCAGGGATCGTGATGGGAGACCTGGTGCTGACAGTG
CTCATTGCCCTGGCCGTGTACTTCCTGGGCCGGCTGGTCCCTCGGGGGCGAGGGGCTGCGGAGGCAGCGACCCGGAAACAGC
GTATCACTGAGACCGAGTCGCCTTATCAGGAGCTCCAGGGTCAGAGGTCGGATGTCTACAGCGACCTCAACACACAGAGGCC
GTATTACAAAGTCGAGGGCGGCGGAGAGGGCAGAGGAAGTCTTCTAACATGCGGTGACGTGGAGGAGAATCCCGGCCCTAG
GATGGCTCTGCCTGTGACAGCTCTGCTGCTGCCTCTGGCCCTGCTGCTGCATGCTGCCAGACCTGGATCCGACATCCAGATGAC
CCAGAGCCCCAGCAGCCTGTCTGCCAGAGTGGGCGACACCGTGACCATCACCTGTCAGGCCAACGGCTACCTGAACTGGTATC
AGCAGCGGAGAGGCAAGGCCCCCAAGCTGCTGATCTACGACGGCAGCAAGCTGGAAAGAGGCGTGCCCGCCAGATTCAGCG
GCAGAAGATGGGGCCAGGAGTACAACCTGACCATCAACAACCTGCAGCCCGAGGACGTGGCCACATACTTTTGCCAGGTGTA
CGAGTTCATCGTGCCCGGCACCCGGCTGGATCTGAAGGGCGGAAGCAGCAGAAGCAGCTCTAGCGGCGGAGGCGGATCTGG
CGGAGGGGACAGGTGCACCTGAGTCAGTCTGGCGCCGCTGTGACAAAGCCAGGCGCTTCTGTGCGGGTGTCCTGTGAAGCC
AGCGGCTACAAGATCAGCGACCACTTCATCCACTGGTGGCGGCAGGCTCCAGGACAGGGACTGCAGTGGGTGGGATGGATC
AACCCCAAGACCGGCCAGCCCAACAACCCCAGACAGTTCCAGGGCAGAGTGTCCCTGACCAGACAGGCCAGCTGGGACTTCG
ACACCTACAGCTTCTACATGGACCTGAAGGCCGTGCGGAGCGACGACACCGCCATCTACTTTTGCGCCAGACAGAGAAGCGAC
TTCTGGGATTTCGACGTGTGGGGCAGCGGCACCCAAGTGACCGTGTCATCTGCTAGCGGCGGAGGGGGATCTGGAGGTGGG
GGTTCCTCACCCACTGAACCAAGCTCCAAAACCGGTAACCCCAGACACCTGCATGTTCTGATTGGGACCTCAGTGGTCAAAATC
CCTTTCACCATCCTCCTCTTCTTTCTCCTTCATCGCTGGTGCTCCAACAAAAAAAATGCTGCTGTAATGGACCAAGAGCCTGCAG
GGAACAGAACAGTGAACAGCGAGGATTCTGATGAACAAGACCATCAGGAGGTGTCATACGCATAA

3BNC60 KIR aa sequence (SEQ ID NO: 23)
MGGLEPCSRFLLLPLLLAVSGLRPVQVQAQSDCSCSTVSPGVLAGIVMGDLVLTVLIALAVYFLGRLVPRGRGAAEAATRKQRITETES
PYQELQGQRSDVYSDLNTQRPYYKVEGGGEGRGSLLTCGDVEENPGPRMALPVTALLLPLALLLHAARPGSDIQMTQSPSSLSARV
GDTVTITCQANGYLNWYQQRRGKAPKLLIYDGSKLERGVPARFSGRRWGQEYNLTINNLQPEDVATYFCQVYEFIVPGTRLDLKGG
SSRSSSSGGGGSGGGGQVHLSQSGAAVTKPGASVRVSCEASGYKISDHFIHWWRQAPGQGLQWVGWINPKTGQPNNPRQFQG
RVSLTRQASWDFDTYSFYMDLKAVRSDDTAIYFCARQRSDFWDFDVWGSGTQVTVSSASGGGGSGGGGSSPTEPSSKTGNPRHL
HVLIGTSVVKIPFTILLFFLLHRWCSNKKNAAVMDQEPAGNRTVNSEDSDEQDHQEVSYAZ

3BNC60 scFv nucleotide sequence (SEQ ID NO: 24):
GACATCCAGATGACCCAGAGCCCCAGCAGCCTGTCTGCCAGAGTGGGCGACACCGTGACCATCACCTGTCAGGCCAACGGCT
ACCTGAACTGGTATCAGCAGCGGAGAGGCAAGGCCCCCAAGCTGCTGATCTACGACGGCAGCAAGCTGGAAAGAGGCGTGC
CCGCCAGATTCAGCGGCAGAAGATGGGGCCAGGAGTACAACCTGACCATCAACAACCTGCAGCCCGAGGACGTGGCCACATA
CTTTTGCCAGGTGTACGAGTTCATCGTGCCCGGCACCCGGCTGGATCTGAAGGGCGGAAGCAGCAGAAGCAGCTCTAGCGGC
GGAGGCGGATCTGGCGGAGGGGGACAGGTGCACCTGAGTCAGTCTGGCGCCGCTGTGACAAAGCCAGGCGCTTCTGTGCGG
GTGTCCTGTGAAGCCAGCGGCTACAAGATCAGCGACCACTTCATCCACTGGTGGCGGCAGGCTCCAGGACAGGGACTGCAGT
GGGTGGGATGGATCAACCCCAAGACCGGCCAGCCCAACAACCCCAGACAGTTCCAGGGCAGAGTGTCCCTGACCAGACAGGC
CAGCTGGGACTTCGACACCTACAGCTTCTACATGGACCTGAAGGCCGTGCGGAGCGACGACACCGCCATCTACTTTTGCGCCA
GACAGAGAAGCGACTTCTGGGATTTCGACGTGTGGGGCAGCGGCACCCAAGTGACCGTGTCATCT

FIG. 8 (Part 5/9)

3BNC60 scFv aa sequence (SEQ ID NO: 25):
MALPVTALLLPLALLLHAARPGSDIQMTQSPSSLSARVGDTVTITCQANGYLNWYQQRRGKAPKLLIYDGSKLERGVPARFSGRRW
GQEYNLTINNLQPEDVATYFCQVYEFIVPGTRLDLKGGSSRSSSSGGGGSGGGGQVHLSQSGAAVTKPGASVRVSCEASGYKISDHF
IHWWRQAPGQGLQWVGWINPKTGQPNNPRQFQGRVSLTRQASWDFDTYSFYMDLKAVRSDDTAIYFCARQRSDFWDFDVW
GSGTQVTVSS VRC01c-KIR nucleotide sequence (SEQ ID NO: 26)
ATGGGGGGACTTGAACCCTGCAGCAGGTTCCTGCTCCTGCCTCTCCTGCTGGCTGTAAGTGGTCTCCGTCCTGTCCAGGTCCAG
GCCCAGAGCGATTGCAGTTGCTCTACGGTGAGCCCGGGCGTGCTGGCAGGGATCGTGATGGGAGACCTGGTGCTGACAGTG
CTCATTGCCCTGGCCGTGTACTTCCTGGGCCGGCTGGTCCCTCGGGGGCGAGGGGCTGCGGAGGCAGCGACCCGGAAACAGC
GTATCACTGAGACCGAGTCGCCTTATCAGGAGCTCCAGGGTCAGAGGTCGGATGTCTACAGCGACCTCAACACACAGAGGCC
GTATTACAAAGTCGAGGGCGGCGGAGAGGGCAGAGGAAGTCTTCTAACATGCGGTGACGTGGAGGAGAATCCCGGCCCTAG
GATGGCTCTGCCTGTGACAGCTCTGCTGCTGCCTCTGGCCCTGCTGCTGCATGCTGCCAGACCTGGATCCGAGATCGTGCTGAC
ACAGAGCCCTGGCACCCTGAGCCTGTCTCCAGGCGAGACAGCCATCATCAGCTGCCGGACAAGCCAGTACGGCAGCCTGGCC
TGGTATCAGCAGAGGCCTGGACAGGCCCCCAGACTCGTGATCTACAGCGGCAGCACAAGAGCCGCCGGAATCCCCGATAGAT
TCAGCGGCTCTAGATGGGGCCCTGACTACAACCTGACCATCAGCAACCTGGAAAGCGGCGACTTCGGCGTGTACTACTGCCAG
CAGTACGAGTTCTTCGGCCAGGGCACCAAGGTGCAGGTGGACATCAAGAGAGGTGGTTCCTCTAGATCTTCCTCCTCTGGTGG
CGGTGGCTCGGGCGGTGGTGGGCAGGTGCAGCTGGTGCAGTCTGGCGGCCAGATGAAGAAACCCGGCGAGAGCATGCGGA
TCAGCTGCAGAGCCTCCGGCTACGAGTTCATCGACGCCACCCTGAACTGGATTCGGCTGGCCCCTGGCAAAAGACCCGAGTGG
ATGGGCTGGCTGAAGCCCAGAGGCGGAGCCGTGAATTACGCCAGACCTCTGCAGGGCAGAGTGACCATGACCCGGGACGTG
TACAGCGATACCGCCTTCCTGGAACTGCGGAGCCTGACCGTGGATGATACCGCCGTGTACTTCTGCACCCGGGGCAAGAACAG
CGACTACAACTGGGACTTCGAGCACTGGGGCAGAGGCACCCCTGTGATCGTGTCTAGCGCTAGCGGCGGAGGGGGATCTGG
AGGTGGGGGTTCCTCACCCACTGAACCAAGCTCCAAAACCGGTAACCCCAGACACCTGCATGTTCTGATTGGGACCTCAGTGG
TCAAAATCCCTTTCACCATCCTCCTCTTCTTTCTCCTTCATCGCTGGTGCTCCAACAAAAAAATGCTGCTGTAATGGACCAAGA
GCCTGCAGGGAACAGAACAGTGAACAGCGAGGATTCTGATGAACAAGACCATCAGGAGGTGTCATACGCATAA VRC01c-KIR aa sequence (SEQ ID NO: 27)
MGGLEPCSRFLLLPLLLAVSGLRPVQVQAQSDCSCSTVSPGVLAGIVMGDLVLTVLIALAVYFLGRLVPRGRGAAEAATRKQRITETES
PYQELQGQRSDVYSDLNTQRPYYKVEGGGEGRGSLLTCGDVEENPGPRMALPVTALLLPLALLLHAARPGSEIVLTQSPGTLSLSPGE
TAIISCRTSQYGSLAWYQQRPGQAPRLVIYSGSTRAAGIPDRFSGSRWGPDYNLTISNLESGDFGVYYCQQYEFFGQGTKVQVDIKR
GGSSRSSSSGGGGSGGGGQVQLVQSGGQMKKPGESMRISCRASGYEFIDATLNWIRLAPGKRPEWMGWLKPRGGAVNYARPLQ
GRVTMTRDVYSDTAFLELRSLTVDDTAVYFCTRGKNSDYNWDFEHWGRGTPVIVSSASGGGGSGGGGSSPTEPSSKTGNPRHLHV
LIGTSVVKIPFTILLFFLLHRWCSNKKNAAVMDQEPAGNRTVNSEDSDEQDHQEVSYAZ

FIG. 8 (Part 6/9)

VRC01 c-scFv nucleotide sequence (SEQ ID NO: 28):
GAGATCGTGCTGACACAGAGCCCTGGCACCCTGAGCCTGTCTCCAGGCGAGACAGCCATCATCAGCTGCCGGACAAGCCAGT
ACGGCAGCCTGGCCTGGTATCAGCAGAGGCCTGGACAGGCCCCCAGACTCGTGATCTACAGCGGCAGCACAAGAGCCGCCGG
AATCCCCGATAGATTCAGCGGCTCTAGATGGGGCCCTGACTACAACCTGACCATCAGCAACCTGGAAAGCGGCGACTTCGGCG
TGTACTACTGCCAGCAGTACGAGTTCTTCGGCCAGGGCACCAAGGTGCAGGTGGACATCAAGAGAGGCGGCAGCTCCAGAAG
CTCCAGCTCTGGCGGCGGAGGATCTGGCGGAGGCGGACAGGTGCAGCTGGTGCAGTCTGGCGGCCAGATGAAGAAACCCGG
CGAGAGCATGCGGATCAGCTGCAGAGCCTCCGGCTACGAGTTCATCGACAGCACCCTGAACTGGATTCGGCTGGCCCCTGGC
AAAAGACCCGAGTGGATGGGCTGGCTGAAGCCCAGAGGCGGAGCCGTGAATTACGCCAGACCTCTGCAGGGCAGAGTGACC
ATGACCCGGGACGTGTACAGCGATACCGCCTTCCTGGAACTGCGGAGCCTGACCGTGGATGATACCGCCGTGTACTTCTGCAC
CCGGGGCAAGAACGCCGACTACAACTGGGACTTCGAGCACTGGGGCAGAGGCACCCCTGTGATCGTGTCTAGC VRC01 c-scFv aa sequence (SEQ ID NO: 29):
MALPVTALLLPLALLLHAARPGSEIVLTQSPGTLSLSPGETAIISCRTSQYGSLAWYQQRPGQAPRLVIYSGSTRAAGIPDRFSGSRWG
PDYNLTISNLESGDFGVYYCQQYEFFGQGTKVQVDIKRGGSSRSSSSGGGGSGGGGQVQLVQSGGQMKKPGESMRISCRASGYEFI
DSTLNWIRLAPGKRPEWMGWLKPRGGAVNYARPLQGRVTMTRDVYSDTAFLELRSLTVDDTAVYFCTRGKNADYNWDFEHWG
RGTPVIVSS CD4 Dap12-KIRS2 nucleotide sequence (SEQ ID NO: 30):
ATGGGGGGACTTGAACCCTGCAGCAGGTTCCTGCTCCTGCCTCTCCTGCTGGCTGTAAGTGGTCTCCGTCCTGTCCAGGTCCAG
GCCCAGAGCGATTGCAGTTGCTCTACGGTGAGCCCGGGCGTGCTGGCAGGGATCGTGATGGGAGACCTGGTGCTGACAGTG
CTCATTGCCCTGGCCGTGTACTTCCTGGGCCGGCTGGTCCCTCGGGGGCGAGGGGCTGCGGAGGCAGCGACCCGGAAACAGC
GTATCACTGAGACCGAGTCGCCTTATCAGGAGCTCCAGGGTCAGAGGTCGGATGTCTACAGCGACCTCAACACACAGAGGCC
GTATTACAAAGTCGAGGGCGGCGGAGAGGGCAGAGGAAGTCTTCTAACATGCGGTGACGTGGAGGAGAATCCCGGCCCTAG
GATGGCTCTGCCTGTGACAGCTCTGCTGCTGCCTCTGGCCCTGCTGCTGCATGCTGCCAGACCTGGATCCAAGAAAGTGGTGC
TTGGCAAGAAGGGCGACACCGTGGAACTGACCTGCACCGCCAGCCAGAAGAAGTCCATCCAGTTCCACTGGAAGAACAGCAA
CCAGATCAAGATCCTGGGCAACCAGGGCAGCTTCCTGACCAAGGGCCCCAGCAAGCTGAACGACAGAGCCGACTCTCGGCGG
AGCCTGTGGGACCAGGGCAATTTCCCCACTGATCATCAAGAACCTGAAGATCGAGGACAGCGACACCTACATCTGCGAGGTGG
AAGATCAGAAAGAAGAGGTGCAGCTGCTGGTGTTCGGCCTGACCGCCAACTCCGACACCCATCTGCTGCAGGGCCAGAGCCT
GACCCTGACACTGGAAAGCCCTCCAGGCAGCAGCCCGAGCGTGCAGTGTAGAAGCCCCAGAGGCAAGAACATCCAGGGCGG
CAAGACCCTGAGCGTGTCCCAGCTTGAACTGCAGGATAGCGGCACCTGGACCTGTACCGTGCTGCAGAACCAGAAGAAAGTG
GAATTCAAGATCGACATCGTCGTGCTCGCCTTCCAGAAAGCCAGCTCCATCGTGTACAAGAAGGAGGGCGAACAGGTGGAAT
TTTCCTTCCCCCTGGCCTTCACTGTGGAAAAGCTGACCGGCAGCGGCGAGCTGTGGTGGCAGGCTGAAAGAGCCAGCTCCAGC
AAGTCCTGGATCACCTTCGACCTGAAGAACAAAGAGGTGTCCGTGAAGAGAGTGACCCAGGACCCCAAGCTGCAGATGGGCA
AGAAGCTGCCCCTGCATCTGACACTGCCACAGGCCCTTCCACAGTATGCCGGCTCTGGCAATCTCACTCTTGCTCTTGAAGCCA
AGACCGGCAAGCTGCACCAGGAAGTGAACCTGGTCGTGATGCGGGCCACCCAGCTGCAGAAGAATCTGACCTGCGAAGTGTG
GGGCCCTACCAGCCCTAAGCTGATGCTGAGCCTGAAGCTGGAAAACAAAGAAGCCAAGGTGTCCAAGCGCGAGAAGGCCGT
GTGGGTGCTGAATCCTGAGGCCGGCATGTGGCAGTGTCTGCTGAGCGATTCTGGCCAGGTGCTGCTCGAAAGCAACATCAAG
GTGCTGCCCACCTGGTCCACTCCAGTGCAGCCTGCTAGCGGCGGAGGGGGATCTGGAGGTGGGGTTCCTCACCCACTGAAC
CAAGCTCCAAAACCGGTAACCCCAGACACCTGCATGTTCTGATTGGGACCTCAGTGGTCAAAATCCCTTTCACCATCCTCCTCTT
CTTTCTCCTTCATCGCTGGTGCTCCAACAAAAAAAATGCTGCTGTAATGGACCAAGAGCCTGCAGGGAACAGAACAGTGAACA
GCGAGGATTCTGATGAACAAGACCATCAGGAGGTGTCATACGCATAA

FIG. 8 (Part 7/9)

CD4 Dap12-KIRS2 aa sequence (SEQ ID NO: 31):
MGGLEPCSRFLLLPLLLAVSGLRPVQVQAQSDCSCSTVSPGVLAGIVMGDLVLTVLIALAVYFLGRLVPRGRGAAEAATRKQRITETES
PYQELQGGQRSDVYSDLNTQRPYYKVEGGGEGRGSLLTCGDVEENPGPRMALPVTALLLPLALLLHAARPGSKKVVLGKKGDTVELTC
TASQKKSIQFHWKNSNQIKILGNQGSFLTKGPSKLNDRADSRRSLWDQGNFPLIIKNLKIEDSDTYICEVEDQKEEVQLLVFGLTANSD
THLLQGQSLTLTLESPPGSSPSVQCRSPRGKNIQGGKTLSVSQLELQDSGTWTCTVLQNQKKVEFKIDIVVLAFQKASSIVYKKEGEQV
EFSFPLAFTVEKLTGSGELWWQAERASSSKSWITFDLKNKEVSVKRVTQDPKLQMGKKLPLHLTLPQALPQYAGSGNLTLALEAKTG
KLHQEVNLVVMRATQLQKNLTCEVWGPTSPKLMLSLKLENKEAKVSKREKAVWVLNPEAGMWQCLLSDSGQVLLESNIKVLPTW
STPVQPASGGGGSGGGGSSPTEPSSKTGNPRHLHVLIGTSVVKIPFTILLFFLLHRWCSNKKNAAVMDQEPAGNRTVNSEDSDEQD
HQEVSYAZ CD4KIR nucleotide sequence (SEQ ID NO: 32)
ATGGGGGGACTTGAACCCTGCAGCAGGTTCCTGCTCCTGCCTCTCCTGCTGGCTGTAAGTGGTCTCCGTCCTGTCCAGGTCCAG
GCCCAGAGCGATTGCAGTTGCTCTACGGTGAGCCCGGGCGTGCTGGCAGGGATCGTGATGGGAGACCTGGTGCTGACAGTG
CTCATTGCCCTGGCCGTGTACTTCCTGGGCCGGCTGGTCCCTCGGGGGCGAGGGGCTGCGGAGGCAGCGACCCGGAAACAGC
GTATCACTGAGACCGAGTCGCCTTATCAGGAGCTCCAGGGTCAGAGGTCGGATGTCTACAGCGACCTCAACACACAGAGGCC
GTATTACAAAGTCGAGGGCGGCGGAGAGGGCAGAGGAAGTCTTCTAACATGCGGTGACGTGGAGGAGAATCCCGGCCCTAG
GATGGCTCTGCCTGTGACAGCTCTGCTGCTGCCTCTGGCCCTGCTGCTGCATGCTGCCAGACCTGGATCCAAGAAAGTGGTGC
TTGGCAAGAAGGGCGACACCGTGGAACTGACCTGCACCGCCAGCCAGAAGAAGTCCATCCAGTTCCACTGGAAGAACAGCAA
CCAGATCAAGATCCTGGGCAACCAGGGCAGCTTCCTGACCAAGGGCCCCAGCAAGCTGAACGACAGAGCCGACTCTCGGCGG
AGCCTGTGGGACCAGGGCAATTTCCCACTGATCATCAAGAACCTGAAGATCGAGGACAGCGACACCTACATCTGCGAGGTGG
AAGATCAGAAAGAAGAGGTGCAGCTGCTGGTGTTCGGCCTGACCGCCAACTCCGACACCCATCTGCTGCAGGGCCAGAGCCT
GACCCTGACACTGGAAAGCCCTCCAGGCAGCAGCCCGAGCGTGCAGTGTAGAAGCCCCAGAGGCAAGAACATCCAGGGCGG
CAAGACCCTGAGCGTGTCCCAGCTTGAACTGCAGGATAGCGGCACCTGGACCTGTACCGTGCTGCAGAACCAGAAGAAAGTG
GAATTCAAGATCGACATCGTCGTGCTCGCCTTCCAGAAAGCCAGCTCCATCGTGTACAAGAAGGAGGGCGAACAGGTGGAAT
TTTCCTTCCCCCTGGCCTTCACTGTGGAAAAGCTGACCGGCAGCGGCGAGCTGTGGTGGCAGGCTGAAAGAGCCAGCTCCAGC
AAGTCCTGGATCACCTTCGACCTGAAGAACAAAGAGGTGTCCGTGAAGAGAGTGACCCAGGACCCCAAGCTGCAGATGGGCA
AGAAGCTGCCCCTGCATCTGACACTGCCACAGGCCCTTCCACAGTATGCCGGCTCTGGCAATCTCACTCTTGCTCTTGAAGCCA
AGACCGGCAAGCTGCACCAGGAAGTGAACCTGGTCGTGATGCGGGCCACCCAGCTGCAGAAGAATCTGACCTGCGAAGTGTG
GGGCCCTACCAGCCCTAAGCTGATGCTGAGCCTGAAGCTGGAAAACAAAGAAGCCAAGGTGTCCAAGCGCGAGAAGGCCGT
GTGGGTGCTGAATCCTGAGGCCGGCATGTGGCAGTGTCTGCTGAGCGATTCTGGCCAGGTGCTGCTCGAAAGCAACATCAAG
GTGCTGCCCACCTGGTCCACTCCAGTGCAGCCTGCTAGCGGCGGAGGGGGATCGGAGGTGGGGGTTCCTCACCCACTGAAC
CAAGCTCCAAAACCGGTAACCCCAGACACCTGCATGTTCTGATTGGGACCTCAGTGGTCAAAATCCCTTTCACCATCCTCCTCTT
CTTTCTCCTTCATCGCTGGTGCTCCAACAAAAAAAATGCTGCTGTAATGGACCAAGAGCCTGCAGGGAACAGAACAGTGAACA
GCGAGGATTCTGATGAACAAGACCATCAGGAGGTGTCATACGCATAA CD4KIR aa sequence (SEQ ID NO: 33)
MGGLEPCSRFLLLPLLLAVSGLRPVQVQAQSDCSCSTVSPGVLAGIVMGDLVLTVLIALAVYFLGRLVPRGRGAAEAATRKQRITETES
PYQELQGGQRSDVYSDLNTQRPYYKVEGGGEGRGSLLTCGDVEENPGPRMALPVTALLLPLALLLHAARPGSKKVVLGKKGDTVELTC
TASQKKSIQFHWKNSNQIKILGNQGSFLTKGPSKLNDRADSRRSLWDQGNFPLIIKNLKIEDSDTYICEVEDQKEEVQLLVFGLTANSD
THLLQGQSLTLTLESPPGSSPSVQCRSPRGKNIQGGKTLSVSQLELQDSGTWTCTVLQNQKKVEFKIDIVVLAFQKASSIVYKKEGEQV
EFSFPLAFTVEKLTGSGELWWQAERASSSKSWITFDLKNKEVSVKRVTQDPKLQMGKKLPLHLTLPQALPQYAGSGNLTLALEAKTG
KLHQEVNLVVMRATQLQKNLTCEVWGPTSPKLMLSLKLENKEAKVSKREKAVWVLNPEAGMWQCLLSDSGQVLLESNIKVLPTW
STPVQPASGGGGSGGGGSSPTEPSSKTGNPRHLHVLIGTSVVKIPFTILLFFLLHRWCSNKKNAAVMDQEPAGNRTVNSEDSDEQD
HQEVSYAZ

FIG. 8 (Part 8/9)

VRC01 – IgG4 hinge-bbz nucleotide sequence (SEQ ID NO:34)
ATGGCTCTGCCTGTGACAGCTCTGCTGCTGCCTCTGGCCCTGCTGCTGCATGCTGCCAGACCTGGATCCGAGATCG
TGCTGACACAGAGCCCTGGCACCCTGAGCCTGTCTCCAGGCGAGACAGCCATCATCAGCTGCCGGACAAGCCAGT
ACGGCAGCCTGGCCTGGTATCAGCAGAGGCCTGGACAGGCCCCCAGACTCGTGATCTACAGCGGCAGCACAAGA
GCCGCCGGAATCCCCGATAGATTCAGCGGCTCTAGATGGGGCCCTGACTACAACCTGACCATCAGCAACCTGGAA
AGCGGCGACTTCGGCGTGTACTACTGCCAGCAGTACGAGTTCTTCGGCCAGGGCACCAAGGTGCAGGTGGACATC
AAGAGAGGCGGCAGCTCCAGAAGCTCCAGCTCTGGCGGCGGAGGATCTGGCGGAGGCGGACAGGTGCAGCTG
GTGCAGTCTGGCGGCCAGATGAAGAAACCCGGCGAGAGCATGCGGATCAGCTGCAGAGCCTCCGGCTACGAGTT
CATCGACTGCACCCTGAACTGGATTCGGCTGGCCCCTGGCAAAAGACCCGAGTGGATGGGCTGGCTGAAGCCCAG
AGGCGGAGCCGTGAATTACGCCAGACCTCTGCAGGGCAGAGTGACCATGACCCGGGACGTGTACAGCGATACCG
CCTTCCTGGAACTGCGGAGCCTGACCGTGGATGATACCGCCGTGTACTTCTGCACCCGGGGCAAGAACTGCGAC
ACAACTGGGACTTCGAGCACTGGGGCAGAGGCACCCCTGTGATCGTGTCTAGCGCTAGCGAGAGCAAGTACGGC
CCTCCCTGCCCCCCTTGCCCTGCCCCCGAGTTCCTGGGCGGACCCAGCGTGTTCCTGTTCCCCCCCAAGCCCAAGGA
CACCCTGATGATCAGCCGGACCCCCGAGGTGACCTGTGTGGTGGTGGACGTGTCCCAGGAGGACCCCGAGGTCC
AGTTCAACTGGTACGTGGACGGCGTGGAGGTGCACAACGCCAAGACCAAGCCCCGGGAGGAGCAGTTCAATAGC
ACCTACCGGGTGGTGTCCGTGCTGACCGTGCTGCACCAGGACTGGCTGAACGGCAAGGAATACAAGTGTAAGGT
GTCCAACAAGGGCCTGCCCAGCAGCATCGAGAAAACCATCAGCAAGGCCAAGGGCCAGCCTCGGGAGCCCCAGG
TGTACACCCTGCCCCCTAGCCAAGAGGAGATGACCAAGAACCAGGTGTCCCTGACCTGCCTGGTGAAGGGCTTCT
ACCCCAGCGACATCGCCGTGGAGTGGGAGAGCAACGGCCAGCCCGAGAACAACTACAAGACCACCCCCCCTGTG
CTGGACAGCGACGGCAGCTTCTTCCTGTACAGCCGGCTGACCGTGGACAAGAGCCGGTGGCAGGAGGGCAACGT
CTTTAGCTGCTCCGTGATGCACGAGGCCCTGCACAACCACTACACCCAGAAGAGCCTGAGCCTGTCCCTGGGCAA
GATGTCCGGA*ATCTACATCTGGGCGCCCTTGGCCGGGACTTGTGGGGTCCTTCTCCTGTCACTGGTTATCACCCTTT*
*ACTGCAAACGGGGCAGAAAGAAACTCCTGTATATATTCAAACAACCATTTATGAGACCAGTACAAACTACTCAAGA*
*GGAAGATGGCTGTAGCTGCCGATTTCCAGAAGAAGAAGAAGGAGGATGTGAACTGCGTGGCCGGGACCCTGAGA*
*TGGGGGGAAAGCCGAGAAGGAAGAACCCTCAGGAAGGCCTGTACAATGAACTGCAGAAAGATAAGATGGCGGA*
*GGCCTACAGTGAGATTGGGATGAAAGGCGAGCGCCGGAGGGGCAAGGGGCACGATGGCCTTTACCAGGGTCTCA*
*GTACAGCCACCAAGGACACCTACGACGCCCTTCACATGCAGGCCCTGCCCCCTCGCTAA*

VRC01 – IgG4 hinge-bbz aa sequence (SEQ ID NO:35)
MALPVTALLLPLALLLHAARPGSEIVLTQSPGTLSLSPGETAIISCRTSQYGSLAWYQQRPGQAPRLVIYSGSTRAAGIPDR
FSGSRWGPDYNLTISNLESGDFGVYYCQQYEFFGQGTKVQVDIKRGGSSRSSSSGGGGSGGGGQVQLVQSGGQMKK
PGESMRISCRASGYEFIDCTLNWIRLAPGKRPEWMGWLKPRGGAVNYARPLQGRVTMTRDVYSDTAFLELRSLTVDD
TAVYFCTRGKNCDYNWDFEHWGRGTPVIVSSASESKYGPPCPPCPAPEFLGGPSVFLFPPKPKDTLMISRTPEVTCVVV
DVSQEDPEVQFNWYVDGVEVHNAKTKPREEQFNSTYRVVSVLTVLHQDWLNGKEYKCKVSNKGLPSSIEKTISKAKGQ
PREPQVYTLPPSQEEMTKNQVSLTCLVKGFYPSDIAVEWESNGQPENNYKTTPPVLDSDGSFFLYSRLTVDKSRWQEG
NVFSCSVMHEALHNHYTQKSLSLSLGKMSG*IYIWAPLAGTCGVLLLSLVITLYCKRGRKKLLYIFKQPFMRPVQTTQEED*
*GCSCRFPEEEEGGCELRVKFSRSADAPAYKQGQNQLYNELNLGRREEYDVLDKRRGRDPEMGGKPRRKNPQEGLYNEL*
*QKDKMAEAYSEIGMKGERRRGKGHDGLYQGLSTATKDTYDALHMQALPPRZ*

Underline = CD8 signal peptide
Light Grey = V light chain
Dark Grey = V heavy chain
Bold = GS-linker between V light and V heavy chain
Dotted line = IgG4 hinge (CH2/CH3)
*Inclined = CD8 transmembrane and 4-1BB/CD3z intracellular domains*

FIG. 8 (Part 9/9)

B

C

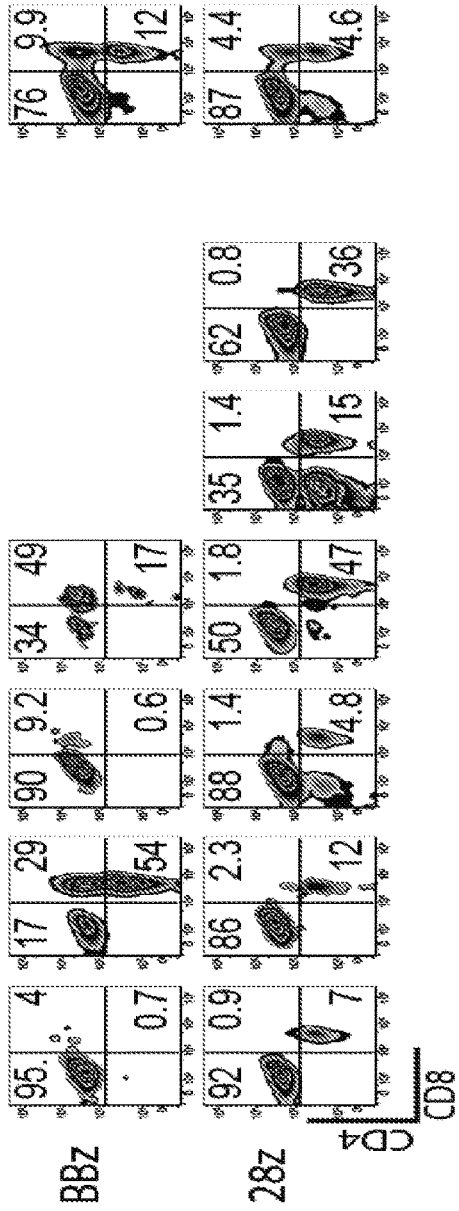
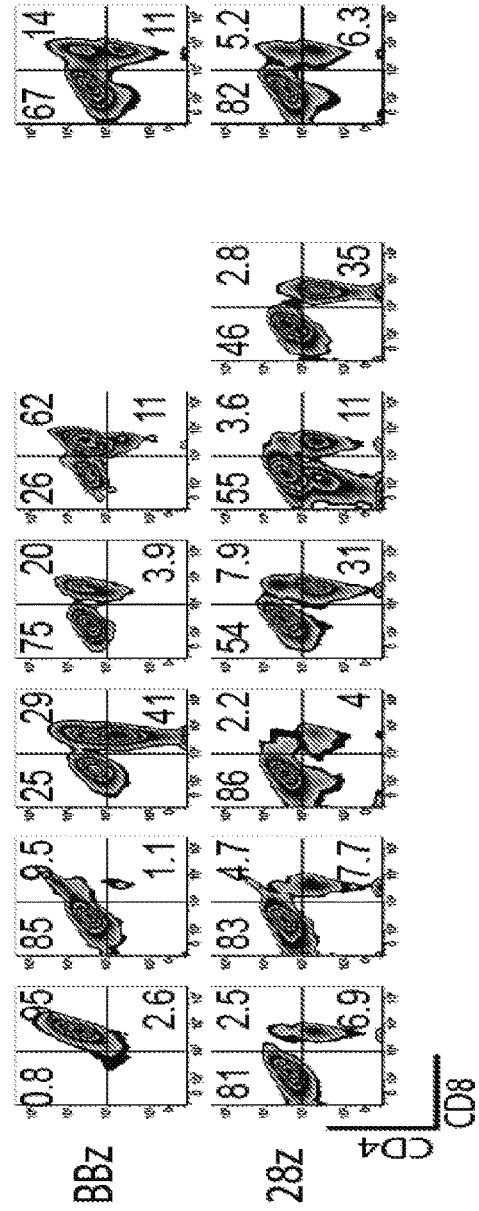
FIG. 15

A

B

| Component | Clinical Trial Construct | Optimized Constructs | Functional Impact |
|---|---|---|---|
| Viral Vector | murine γ retrovirus (MMLV based) | lentivirus (HIV based) | safety, sustained expression, transduction efficiency |
| Promoter | PGK | EF1 α | sustained expression, higher expression (MFI) |
| Hinge | none | CD8 α | flexibility |
| Transmebrane Domain | CD4 | CD8 α or CD28 | prevent infection, block degradation, dimerization |
| Costimulatory Domains | CD3 ζ | CD28-CD3 ζ 4-1BB-CD3 ζ | survival, proliferation, and effector function |
| Extracellular Domain | CD4 | CD4 or ScFv | epitope targeted, prevent infection |

 Clinical Trial CAR

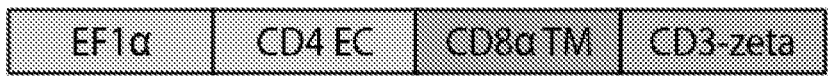 Optimized CAR

FIG. 17A

Amino acid sequences of optimized CD4 CARs:

1) CD4 CD28 CD3-zeta sequence (SEQ ID NO: 44):

MNRGVPFRHLLLVLQLALLPAATQGKKVVLGKKGDTVELTCTASQKKSIQFHWKNSNQ
IKILGNQGSFLTKGPSKLNDRADSRRSLWDQGNFPLIIKNLKIEDSDTYICEVEDQKEEVQ
LLVFGLTANSDTHLLQGQSLTLTLESPPGSSPSVQCRSPRGKNIQGGKTLSVSQLELQDS
GTWTCTVLQNQKKVEFKIDIVVLAFQKASSIVYKKEGEQVEFSFPLAFTVEKLTGSGEL
WWQAERASSSKSWITFDLKNKEVSVKRVTQDPKLQMGKKLPLHLTLPQALPQYAGSG
NLTLALEAKTGKLHQEVNLVVMRATQLQKNLTCEVWGPTSPKLMLSLKLENKEAKVS
KREKAVWVLNPEAGMWQCLLSDSGQVLLESNIKVLPTWSTPVQPSGTTTPAPRPPTPAP
TIASQPLSLRPEACRPAAGGAVHTRGLDFACD**FWVLVVVGGVLACYSLLVTVAFIIFW
VRSKRSRLLHSDYMNMTPRRPGPTRKHYQPYAPPRDFAAYRS**IDRVKFSRSADAPA
YQQGQNQLYNELNLGRREEYDVLDKRRGRDPEMGGKPRRKNPQEGLYNELQKDKMA
EAYSEIGMKGERRRGKGHDGLYQGLSTATKDTYDALHMQALPPR

Light Grey = CD4 extracellular domain
Dark Grey = CD8α extracellular hinge
Bold  = CD28 transmembrane domain and intracellular domain
Dotted line = CD3 zeta

2) CD4 4-1BB CD3-zeta sequence (SEQ ID NO: 45):

MNRGVPFRHLLLVLQLALLPAATQGKKVVLGKKGDTVELTCTASQKKSIQFHWKNSNQ
IKILGNQGSFLTKGPSKLNDRADSRRSLWDQGNFPLIIKNLKIEDSDTYICEVEDQKEEVQ
LLVFGLTANSDTHLLQGQSLTLTLESPPGSSPSVQCRSPRGKNIQGGKTLSVSQLELQDS
GTWTCTVLQNQKKVEFKIDIVVLAFQKASSIVYKKEGEQVEFSFPLAFTVEKLTGSGEL
WWQAERASSSKSWITFDLKNKEVSVKRVTQDPKLQMGKKLPLHLTLPQALPQYAGSG
NLTLALEAKTGKLHQEVNLVVMRATQLQKNLTCEVWGPTSPKLMLSLKLENKEAKVS
KREKAVWVLNPEAGMWQCLLSDSGQVLLESNIKVLPTWSTPVQPSGTTTPAPRPPTPAP
TIASQPLSLRPEACRPAAGGAVHTRGLDFACDIYIWAPLAGTCGVLLLSLVITLYCKRG
RKKLLYIFKQPFMRPVQTTQEEDGCSCRFPEEEEGGCELRVKFSRSADAPAYQQGQNQL
YNELNLGRREEYDVLDKRRGRDPEMGGKPRRKNPQEGLYNELQKDKMAEAYSEIGMK
GERRRGKGHDGLYQGLSTATKDTYDALHMQALPPR

Light Grey = CD4 extracellular domain
Dark Grey = CD8α extracellular hinge
Bold  = CD8α transmembrane domain
Wave line = 4-1BB costimulatory domain
Dotted line = CD3 zeta

FIG. 18 (Part 1/5)

3) CD4 extracellular domain (SEQ ID NO: 46):
MNRGVPFRHLLLVLQLALLPAATQGKKVVLGKKGDTVELTCTASQKKSIQFHWKNSNQ
IKILGNQGSFLTKGPSKLNDRADSRRSLWDQGNFPLIIKNLKIEDSDTYICEVEDQKEEVQ
LLVFGLTANSDTHLLQGQSLTLTLESPPGSSPSVQCRSPRGKNIQGGKTLSVSQLELQDS
GTWTCTVLQNQKKVEFKIDIVVLAFQKASSIVYKKEGEQVEFSFPLAFTVEKLTGSGEL
WWQAERASSSKSWITFDLKNKEVSVKRVTQDPKLQMGKKLPLHLTLPQALPQYAGSG
NLTLALEAKTGKLHQEVNLVVMRATQLQKNLTCEVWGPTSPKLMLSLKLENKEAKVS
KREKAVWVLNPEAGMWQCLLSDSGQVLLESNIKVLPTWSTPVQP 4) CD8α extracellular hinge (SEQ ID NO: 47):
TTTPAPRPPTPAPTIASQPLSLRPEACRPAAGGAVHTRGLDFACD 6) CD8α transmembrane domain (SEQ ID NO: 48):
IYIWAPLAGTCGVLLLSLVITLYC 5) CD28 transmembrane domain and intracellular domain (SEQ ID NO: 49):
FWVLVVVGGVLACYSLLVTVAFIIFWVRSKRSRLLHSDYMNMTPRRPGPTRKHYQPYA
PPRDFAAYRS 7) 4-1BB costimulatory domain (SEQ ID NO: 50):
KRGRKKLLYIFKQPFMRPVQTTQEEDGCSCRFPEEEEGGCEL 8) CD3 zeta (SEQ ID NO: 51):
RVKFSRSADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR

FIG. 18 (Part 2/5)

Amino acid sequences of optimized antibody based CARs

1) PG9 CD3-zeta sequence (SEQ ID NO: 52):
QRLVESGGGVVQPGSSLRLSCAASGFDFSRQGMHWVRQAPGQGLEWVAFIKYDGSEK
YHADSVWGRLSISRDNSKDTLYLQMNSLRVEDTATYFCVREAGGPDYRNGYNYYDFY
DGYYNYHYMDVWGKGTTVTVSSGGGGSGGGGSGGGGSQSALTQPASVSGSPGQSITIS
CNGTSNDVGGYESVSWYQQHPGKAPKVVIYDVSKRPSGVSNRFSGSKSGNTASLTISGL
QAEDEGDYYCKSLTSTRRRVFGTGTKLTVLSGTTTPAPRPPTPAPTIASQPLSLRPEACRP
AAGGAVHTRGLDFACDIYIWAPLAGTCGVLLLSLVITLYCRVKFSRSADAPAYQQGQ
NQLYNELNLGRREEYDVLDKRRGRDPEMGGKPRRKNPQEGLYNELQKDKMAEAYSEI
GMKGERRRGKGHDGLYQGLSTATKDTYDALHMQALPPR 2) PGT128 CD3-zeta sequence (SEQ ID NO: 53):
QSALTQPPSASGSPGQSITISCTGTSNNFVSWYQQHAGKAPKLVIYDVNKRPSGVPDRFS
GSKSGNTASLTVSGLQTDDEAVYYCGSLVGNWDVIFGGGTKLTVLGGSSRSSSSGGGGS
GGGGQPQLQESGPTLVEASETLSLTCAVSGDSTAACNSFWGWVRQPPGKGLEWVGSLS
HCASYWNRGWTYHNPSLKSRLTLALDTPKNLVFLKLNSVTAADTATYYCARFGGEVLR
YTDWPKPAWVDLWGRGTLVTVSSSGTTTPAPRPPTPAPTIASQPLSLRPEACRPAAGGA
VHTRGLDFACDIYIWAPLAGTCGVLLLSLVITLYCRVKFSRSADAPAYQQGQNQLYN
ELNLGRREEYDVLDKRRGRDPEMGGKPRRKNPQEGLYNELQKDKMAEAYSEIGMKGE
RRRGKGHDGLYQGLSTATKDTYDALHMQALPPRR 3) VRC01 CD3-zeta sequence (SEQ ID NO: 54):
EIVLTQSPGTLSLSPGETAIISCRTSQYGSLAWYQQRPGQAPRLVIYSGSTRAAGIPDRFSG
SRWGPDYNLTISNLESGDFGVYYCQQYEFFGQGTKVQVDIKRGGSSRSSSSGGGGSGGG
GQVQLVQSGGQMKKPGESMRISCRASGYEFIDCTLNWIRLAPGKRPEWMGWLKPRGG
AVNYARPLQGRVTMTRDVYSDTAFLELRSLTVDDTAVYFCTRGKNCDYNWDFEHWG
RGTPVIVSSSGTTTPAPRPPTPAPTIASQPLSLRPEACRPAAGGAVHTRGLDFACDIYIWA
PLAGTCGVLLLSLVITLYCRVKFSRSADAPAYQQGQNQLYNELNLGRREEYDVLDKR
RGRDPEMGGKPRRKNPQEGLYNELQKDKMAEAYSEIGMKGERRRGKGHDGLYQGLST
ATKDTYDALHMQALPPR Light Grey = ScFv extracellular domain
Dark Grey = CD8α extracellular hinge
Bold = CD8α transmembrane domain
Dotted line = CD3 zeta

FIG. 18 (Part 3/5)

4) 3BNC60 CD3-zeta sequence (SEQ ID NO: 55):
DIQMTQSPSSLSARVGDTVTITCQANGYLNWYQQRRGKAPKLLIYDGSKLERGVPARFS
GRRWGQEYNLTINNLQPEDVATYFCQVYEFIVPGTRLDLKGGSSRSSSSGGGGSGGGGQ
VHLSQSGAAVTKPGASVRVSCEASGYKISDHFIHWWRQAPGQGLQWVGWINPKTGQP
NNPRQFQGRVSLTRQASWDFDTYSFYMDLKAVRSDDTAIYFCARQRSDFWDFDVWGS
GTQVTVSSSGTTTPAPRPPTPAPTIASQPLSLRPEACRPAAGGAVHTRGLDFACDIYIWA
PLAGTCGVLLLSLVITLYCRVKFSRSADAPAYQQGQNQLYNELNLGRREEYDVLDKR
RGRDPEMGGKPRRKNPQEGLYNELQKDKMAEAYSEIGMKGERRRGKGHDGLYQGLST
ATKDTYDALHMQALPPR 5) PGDM1400 CD3-zeta sequence (SEQ ID NO: 56):
DFVLTQSPHSLSVTPGESASISCKSSHSLIHGDRNNYLAWYVQKPGRSPQLLIYLASSRAS
GVPDRFSGSGSDKDFTLKISRVETEDVGTYYCMQGRESPWTFGQGTKVDIKGGSSRSSS
SGGGGSGGGGQAQLVQSGPEVRKPGTSVKVSCKAPGNTLKTYDLHWVRSVPGQGLQW
MGWISHEGDKKVIVERFKAKVTIDWDRSTNTAYLQLSGLTSGDTAVYYCAKGSKHRLR
DYALYDDDGALNWAVDVDYLSNLEFWGQGTAVTVSSSGTTTPAPRPPTPAPTIASQPLS
LRPEACRPAAGGAVHTRGLDFACDIYIWAPLAGTCGVLLLSLVITLYCRVKFSRSADA
PAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR Light Grey = ScFv extracellular domain
Dark Grey = CD8α extracellular hinge
Bold = CD8α transmembrane domain
Dotted line = CD3 zeta

FIG. 18 (Part 4/5)

6) PG9 CD3-zeta ScFv extracellular domain sequence (SEQ ID NO: 57):
QRLVESGGGVVQPGSSLRLSCAASGFDFSRQGMHWVRQAPGQGLEWVAFIKYDGSEK
YHADSVWGRLSISRDNSKDTLYLQMNSLRVEDTATYFCVREAGGPDYRNGYNYYDFY
DGYYNYHYMDVWGKGTTVTVSSGGGGSGGGGSGGGGSQSALTQPASVSGSPGQSITIS
CNGTSNDVGGYESVSWYQQHPGKAPKVVIYDVSKRPSGVSNRFSGSKSGNTASLTISGL
QAEDEGDYYCKSLTSTRRRVFGTGTKLTVL 7) PGT128 CD3-zeta ScFv extracellular domain sequence (SEQ ID NO: 58):
QSALTQPPSASGSPGQSITISCTGTSNNFVSWYQQHAGKAPKLVIYDVNKRPSGVPDRFS
GSKSGNTASLTVSGLQTDDEAVYYCGSLVGNWDVIFGGGTKLTVLGGSSRSSSSGGGGS
GGGGQPQLQESGPTLVEASETLSLTCAVSGDSTAACNSFWGWVRQPPGKGLEWVGSLS
HCASYWNRGWTYHNPSLKSRLTLALDTPKNLVFLKLNSVTAADTATYYCARFGGEVLR
YTDWPKPAWVDLWGRGTLVTVSS 8) VRC01 CD3-zeta ScFv extracellular domain sequence (SEQ ID NO: 59):
EIVLTQSPGTLSLSPGETAIISCRTSQYGSLAWYQQRPGQAPRLVIYSGSTRAAGIPDRFSG
SRWGPDYNLTISNLESGDFGVYYCQQYEFFGQGTKVQVDIKRGGSSRSSSSGGGGSGGG
GQVQLVQSGGQMKKPGESMRISCRASGYEFIDCTLNWIRLAPGKRPEWMGWLKPRGG
AVNYARPLQGRVTMTRDVYSDTAFLELRSLTVDDTAVYFCTRGKNCDYNWDFEHWG
RGTPVIVSS 9) 3BNC60 CD3-zeta sequence (SEQ ID NO: 60):
DIQMTQSPSSLSARVGDTVTITCQANGYLNWYQQRRGKAPKLLIYDGSKLERGVPARFS
GRRWGQEYNLTINNLQPEDVATYFCQVYEFIVPGTRLDLKGGSSRSSSSGGGGSGGGGQ
VHLSQSGAAVTKPGASVRVSCEASGYKISDHFIHWWRQAPGQGLQWVGWINPKTGQP
NNPRQFQGRVSLTRQASWDFDTYSFYMDLKAVRSDDTAIYFCARQRSDFWDFDVWGS
GTQVTVSS 10) PGDM1400 CD3-zeta sequence (SEQ ID NO: 61):
DFVLTQSPHSLSVTPGESASISCKSSHSLIHGDRNNYLAWYVQKPGRSPQLLIYLASSRAS
GVPDRFSGSGSDKDFTLKISRVETEDVGTYYCMQGRESPWTFGQGTKVDIKGGSSRSSS
SGGGGSGGGGQAQLVQSGPEVRKPGTSVKVSCKAPGNTLKTYDLHWVRSVPGQGLQW
MGWISHEGDKKVIVERFKAKVTIDWDRSTNTAYLQLSGLTSGDTAVYYCAKGSKHRLR
DYALYDDDGALNWAVDVDYLSNLEFWGQGTAVTVSS

FIG. 18 (Part 5/5)

Nucleic acid sequences of optimized CD4 CARs

1) CD4 CD28 CD3-zeta sequence (SEQ ID NO: 62):

ATGAACCGGGGAGTCCCTTTTAGGCACTTGCTTCTGGTGCTGCAACTGGCGCTCCTCCCAGCAGCCACT
CAGGGAAAGAAAGTGGTGCTGGGCAAAAAAGGGGATACAGTGGAACTGACCTGTACAGCTTCCCAGA
AGAAGAGCATACAATTCCACTGGAAAAAACTCCAACCAGATAAAGATTCTGGGAAATCAGGGCTCCTTC
TTAACTAAAGGTCCATCCAAGCTGAATGATCGCGCTGACTCAAGAAGAAGCCTTTGGGACCAAGGAA
ACTTCCCCCTGATCATCAAGAATCTTAAGATAGAAGACTCAGATACTTACATCTGTGAAGTGGAGGAC
CAGAAGGAGGAGGTGCAATTGCTAGTGTTCGGATTGACTGCCAACTCTGACACCCACCTGCTTCAGGG
GCAGAGCCTGACCCTGACCTTGGAGAGCCCCCCTGGTAGTAGCCCCTCAGTGCAATGTAGGAGTCCAA
GGGGTAAAAACATACAGGGGGGGAAGACCCTCTCCGTGTCTCAGCTGGAGCTCCAGGATAGTGGCAC
CTGGACATGCACTGTCTTGCAGAACCAGAAGAAGGTGGAGTTCAAAATAGACATCGTGGTGCTAGCTT
TCCAGAAGGCCTCCAGCATAGTCTATAAGAAAGAGGGGGAACAGGTGGAGTTCTCCTTCCCACTCGCC
TTTACAGTTGAAAAGCTGACGGGCAGTGGCGAGCTGTGGTGGCAGGCGGAGAGGGCTTCCTCCTCCAA
GTCTTGGATCACCTTTGACCTGAAGAACAAGGAAGTGTCTGTAAAACGGGTTACCCAGGACCCTAAGC
TCCAGATGGGCAAGAAGCTCCCGCTCCACCTCACCCTGCCCCAGGCCTTGCCTCAGTATGCTGGCTCTG
GAAACCCTCACCCTGGCCCTTGAAGCGAAAACAGGAAAGTTGCATCAGGAAGTGAACCTGGTGGTGAT
GAGAGCCACTCAGCTCCAGAAAAATTTGACCTGTGAGGTGTGGGGACCCACCTCCCCTAAGCTGATGC
TGAGCTTGAAACTGGAGAACAAGGAGGCAAAGGTCTCGAAGCGGGAGAAGGCGGTGTGGGTGCTGAA
CCCTGAGGCGGGGATGTGGCAGTGTCTGCTGAGTGACTCGGGACAGGTCCTGCTGGAATCCAACATCA
AGGTTCTGCCCACATGGTCCACCCCGGTGCAGCCAACCACGACGCCAGCGCCGCGACCACCAACACCG
GCGCCCACCATCGCGTCGCAGCCCCTGTCCCTGCGCCCAGAGGCGTGCCGGCCAGCGGCGGGGGGCGC
AGTGCACACGAGGGGGCTGGACTTCGCCTGTGATTTTTGGGTGCTGGTGGTGGTTGGTGGAGTCCT
GGCTTGCTATAGCTTGCTAGTAACAGTGGCCTTTATTATTTTCTGGGTGAGGAGTAAGAGGAGC
AGGCTCCTGCACAGTGACTACATGAACATGACTCCCCGCCGCCCCGGGCCCACCCGCAAGCATT
ACCAGCCCTATGCCCCACCACGCGACTTCGCAGCCTATCGCTCCAGAGTGAAGTTCAGCAGGAGC
GCAGACGCCCCCGCGTACCAGCAGGGCCAGAACCAGCTCTATAACGAGCTCAATCTAGGACGAAGAG
AGGAGTACGATGTTTTGGACAAGAGACGTGGCCGGGACCCTGAGATGGGGGGAAAGCCGAGAAGGA
AGAACCCTCAGGAAGGCCTGTACAATGAACTGCAGAAAGATAAGATGGCGGAGGCCTACAGTGAGAT
TGGGATGAAAGGCGAGCGCCGGAGGGGCAAGGGGCACGATGGCCTTTACCAGGGTCTCAGTACAGCC
ACCAAGGACACCTACGACGCCCTTCACATGCAGGCCCTGCCCCCTCGC

Light Grey = CD4 extracellular domain
Dark Grey = CD8α extracellular hinge
Bold = CD28 transmembrane domain and intracellular domain
Dotted line = CD3 zeta

FIG. 19 (Part 1/8)

2) CD4 4-1BB CD3-zeta sequence (SEQ ID NO: 63):
ATGAACCGGGGAGTCCCTTTTAGGCACTTGCTTCTGGTGCTGCAACTGGCGCTCCTCCCAGCAGCCACT
CAGGGAAAGAAAGTGGTGCTGGGCAAAAAAGGGGATACAGTGGAACTGACCTGTACAGCTTCCCAGA
AGAAGAGCATACAATTCCACTGGAAAAACTCCAACCAGATAAAGATTCTGGGAAATCAGGGCTCCTTC
TTAACTAAAGGTCCATCCAAGCTGAATGATCGCGCTGACTCAAGAAGAAGCCTTTGGGACCAAGGAA
ACTTCCCCCTGATCATCAAGAATCTTAAGATAGAAGACTCAGATACTTACATCTGTGAAGTGGAGGAC
CAGAAGGAGGAGGTGCAATTGCTAGTGTTCGGATTGACTGCCAACTCTGACACCCACCTGCTTCAGGG
GCAGAGCCTGACCCTGACCTTGGAGAGCCCCCCTGGTAGTAGCCCCTCAGTGCAATGTAGGAGTCCAA
GGGGTAAAAACATACAGGGGGGGAAGACCCTCTCCGTGTCTCAGCTGGAGCTCCAGGATAGTGGCAC
CTGGACATGCACTGTCTTGCAGAACCAGAAGAAGGTGGAGTTCAAAATAGACATCGTGGTGCTAGCTT
TCCAGAAGGCCTCCAGCATAGTCTATAAGAAAGAGGGGGAACAGGTGGAGTTCTCCTTCCCACTCGCC
TTTACAGTTGAAAAGCTGACGGGCAGTGGCGAGCTGTGGTGGCAGGCGGAGAGGGCTTCCTCCTCCAA
GTCTTGGATCACCTTTGACCTGAAGAACAAGGAAGTGTCTGTAAAACGGGTTACCCAGGACCCTAAGC
TCCAGATGGGCAAGAAGCTCCCGCTCCACCTCACCCTGCCCCAGGCCTTGCCTCAGTATGCTGGCTCTG
GAAACCTCACCCTGGCCCTTGAAGCGAAAACAGGAAAGTTGCATCAGGAAGTGAACCTGGTGGTGAT
GAGAGCCACTCAGCTCCAGAAAAATTTGACCTGTGAGGTGTGGGGACCCACCTCCCCTAAGCTGATGC
TGAGCTTGAAACTGGAGAACAAGGAGGCAAAGGTCTCGAAGCGGGAGAAGGCGGTGTGGGTGCTGAA
CCCTGAGGCGGGGATGTGGCAGTGTCTGCTGAGTGACTCGGGACAGGTCCTGCTGGAATCCAACATCA
AGGTTCTGCCCACATGGTCCACCCCGGTGCAGCCAACCACGACGCCAGCGCCGCGACCACCAACACCG
GCGCCCACCATCGCGTCGCAGCCCCTGTCCCTGCGCCCAGAGGCGTGCCGGCCAGCGGCGGGGGGCGC
AGTGCACACGAGGGGGCTGGACTTCGCCTGTGAT<u>ATCTACATCTGGGCGCCCTTGGCCGGGACTTG</u>
TGGGGTCCTTCTCCTGTCACTGGTTATCACCCTTTACTGC<u>AAACGGGGCAGAAAGAAACTCCTGTA
TATATTCAAACAACCATTTATGAGACCAGTACAAACTACTCAAGAGGAAGATGGCTGTAGCTGCCGAT
TTCCAGAAGAAGAAGAAGGAGGATGTGAACTGAGAGTGAAGTTCAGCAGGAGCGCAGACGCCCCCGC</u>
GTACCAGCAGGGCCAGAACCAGCTCTATAACGAGCTCAATCTAGGACGAAGAGAGGAGTACGATGTT
TTGGACAAGAGACGTGGCCGGGACCCTGAGATGGGGGGAAAGCCGAGAAGGAAGAACCCTCAGGAA
GGCCTGTACAATGAACTGCAGAAAGATAAGATGGCGGAGGCCTACAGTGAGATTGGGATGAAAGGCG
AGCGCCGGAGGGGCAAGGGGCACGATGGCCTTTACCAGGGTCTCAGTACAGCCACCAAGGACACCTA
CGACGCCCTTCACATGCAGGCCCTGCCCCCTCGC Light Grey = CD4 extracellular domain
Dark Grey = CD8α extracellular hinge
Bold = CD8α transmembrane domain
Wave line = 4-1BB costimulatory domain
Dotted line = CD3 zeta

FIG. 19 (Part 2/8)

3) CD4 extracellular domain (SEQ ID NO: 64):
ATGAACCGGGGAGTCCCTTTTAGGCACTTGCTTCTGGTGCTGCAACTGGCGCTCCTCCCAGCAGCCACT
CAGGGAAAGAAAGTGGTGCTGGGCAAAAAAGGGGATACAGTGGAACTGACCTGTACAGCTTCCCAGA
AGAAGAGCATACAATTCCACTGGAAAAACTCCAACCAGATAAAGATTCTGGGAAATCAGGGCTCCTTC
TTAACTAAAGGTCCATCCAAGCTGAATGATCGCGCTGACTCAAGAAGAAGCCTTTGGGACCAAGGAA
ACTTCCCCCTGATCATCAAGAATCTTAAGATAGAAGACTCAGATACTTACATCTGTGAAGTGGAGGAC
CAGAAGGAGGAGGTGCAATTGCTAGTGTTCGGATTGACTGCCAACTCTGACACCCACCTGCTTCAGGG
GCAGAGCCTGACCCTGACCTTGGAGAGCCCCCCTGGTAGTAGCCCCTCAGTGCAATGTAGGAGTCCAA
GGGGTAAAAACATACAGGGGGGGAAGACCCTCTCCGTGTCTCAGCTGGAGCTCCAGGATAGTGGCAC
CTGGACATGCACTGTCTTGCAGAACCAGAAGAAGGTGGAGTTCAAAATAGACATCGTGGTGCTAGCTT
TCCAGAAGGCCTCCAGCATAGTCTATAAGAAAGAGGGGGAACAGGTGGAGTTCTCCTTCCCACTCGCC
TTTACAGTTGAAAAGCTGACGGGCAGTGGCGAGCTGTGGTGGCAGGCGGAGAGGGCTTCCTCCTCCAA
GTCTTGGATCACCTTTGACCTGAAGAACAAGGAAGTGTCTGTAAAACGGGTTACCCAGGACCCTAAGC
TCCAGATGGGCAAGAAGCTCCCGCTCCACCTCACCCTGCCCCAGGCCTTGCCTCAGTATGCTGGCTCTG
GAAACCTCACCCTGGCCCTTGAAGCGAAAACAGGAAAGTTGCATCAGGAAGTGAACCTGGTGGTGAT
GAGAGCCACTCAGCTCCAGAAAAATTTGACCTGTGAGGTGTGGGGACCCACCTCCCCTAAGCTGATGC
TGAGCTTGAAACTGGAGAACAAGGAGGCAAAGGTCTCGAAGCGGGAGAAGGCGGTGTGGGTGCTGAA
CCCTGAGGCGGGGATGTGGCAGTGTCTGCTGAGTGACTCGGGACAGGTCCTGCTGGAATCCAACATCA
AGGTTCTGCCCACATGGTCCACCCCGGTGCAGCCA

4) CD8α extracellular hinge (SEQ ID NO: 65):
ACCACGACGCCAGCGCCGCGACCACCAACACCGGCGCCCACCATCGCGTCGCAGCCCCTGTCCCTGCG
CCCAGAGGCGTGCCGGCCAGCGGCGGGGGCGCAGTGCACACGAGGGGGCTGGACTTCGCCTGTGAT

6) CD8α transmembrane domain (SEQ ID NO: 66):
ATCTACATCTGGGCGCCCTTGGCCGGGACTTGTGGGGTCCTTCTCCTGTCACTGGTTATCACCCTTTACT
GC

5) CD28 transmembrane domain and intracellular domain (SEQ ID NO: 67):
TTTTGGGTGCTGGTGGTGGTTGGTGGAGTCCTGGCTTGCTATAGCTTGCTAGTAACAGTGGCCTTTATT
ATTTTCTGGGTGAGGAGTAAGAGGAGCAGGCTCCTGCACAGTGACTACATGAACATGACTCCCCGCCG
CCCCGGGCCCACCCGCAAGCATTACCAGCCCTATGCCCCACCACGCGACTTCGCAGCCTATCGCTCC

7) 4-1BB costimulatory domain (SEQ ID NO: 68):
AAACGGGGCAGAAAGAAACTCCTGTATATATTCAAACAACCATTTATGAGACCAGTACAAACTACTCA
AGAGGAAGATGGCTGTAGCTGCCGATTTCCAGAAGAAGAAGAAGGAGGATGTGAACTG

8) CD3 zeta (SEQ ID NO: 69):
AGAGTGAAGTTCAGCAGGAGCGCAGACGCCCCCGCGTACCAGCAGGGCCAGAACCAGCTCTATAACG
AGCTCAATCTAGGACGAAGAGAGGAGTACGATGTTTTGGACAAGAGACGTGGCCGGGACCCTGAGAT
GGGGGGAAAGCCGAGAAGGAAGAACCCTCAGGAAGGCCTGTACAATGAACTGCAGAAAGATAAGAT
GGCGGAGGCCTACAGTGAGATTGGGATGAAAGGCGAGCGCCGGAGGGGCAAGGGGCACGATGGCCTT
TACCAGGGTCTCAGTACAGCCACCAAGGACACCTACGACGCCCTTCACATGCAGGCCCTGCCCCCTCG
C

FIG. 19 (Part 3/8)

Nucleic acid sequences of optimized antibody based CARs

1) PG9 CD3-zeta sequence (SEQ ID NO: 70):
CAGAGACTGGTGGAAAGCGGTGGAGGCGTGGTGCAGCCTGGCAGCAGCCTGAGACTGAGCTGCGCCG
CTTCCGGCTTCGACTTCAGCCGGCAGGGCATGCATTGGGTGCGCCAGGCTCCAGGACAGGGACTGGAA
TGGGTGGCCTTCATCAAGTACGACGGCAGCGAGAAGTACCACGCCGACAGCGTGTGGGGTAGACTGT
CTATCAGCCGGGACAACAGCAAGGACACCCTGTACCTGCAGATGAACAGCCTGCGGGTGGAGGACAC
CGCCACATACTTTTGCGTGCGGGAGGCTGGTGGACCTGACTACCGGAACGGCTACAACTACTACGACT
TCTACGACGGCTACTACAACTACCACTACATGGATGTGTGGGGCAAGGGCACCACCGTGACCGTGTCT
AGCGGAGGCGGAGGATCTGGCGGCGGAGGAAGTGGAGGCGGCGGAAGCCAGTCTGCCCTGACCCAGC
CTGCCTCTGTGTCTGGCAGCCCTGGCCAGAGCATCACCATCAGCTGCAACGGCACCAGCAACGACGTG
GGCGGCTACGAGAGCGTGTCCTGGTATCAGCAGCACCCCGGCAAGGCCCCCAAGGTGGTGATCTACG
ACGTGTCCAAGAGGCCCAGCGGCGTGAGCAACCGGTTCAGCGGCAGCAAGAGCGGCAATACCGCCAG
CCTGACCATCTCTGGGCTGCAGGCCGAGGACGAGGGCGACTACTACTGCAAGAGCCTGACCAGCACC
AGGCGGAGAGTGTTCGGCACCGGCACCAAGCTGACCGTGCTGA[illegible]ATCTACATCTGGGCGCCCTTGGCC
GGGACTTGTGGGGTCCTTCTCCTGTCACTGGTTATCACCCTTTACTGCGAGTGAAGTTCAGCAGG
AGCGCAGACGCCCCCGCGTACAAGCAGGGCCAGAACCAGCTCTATAACGAGCTCAATCTAGGACGAA
GAGAGGAGTACGATGTTTTGGACAAGAGACGTGGCCGGGACCCTGAGATGGGGGGAAAGCCGAGAA
GGAAGAACCCTCAGGAAGGCCTGTACAATGAACTGCAGAAAGATAAGATGGCGGAGGCCTACAGTGA
GATTGGGATGAAAGGCGAGCGCCGGAGGGGCAAGGGGCACGATGGCCTTTACCAGGGTCTCAGTACA
GCCACCAAGGACACCTACGACGCCCTTCACATGCAGGCCCTGCCCCCTCGC

2) PGT128 CD3-zeta sequence (SEQ ID NO: 71):
GGATCCCAGAGCGCCCTGACACAGCCTCCTAGCGCCTCTGGATCTCCCGGCCAGAGCATCACCATCAG
CTGTACCGGCACCAGCAACAACTTCGTGTCCTGGTATCAGCAGCACGCCGGCAAGGCCCCCAAGCTCG
TGATCTACGACGTGAACAAGCGGCCCAGCGGCGTGCCCGATAGATTCAGCGGCAGCAAGAGCGGCAA
CACCGCCAGCCTGACAGTGTCTGGCCTGCAGACCGATGACGAGGCCGTGTACTACTGCGGCAGCCTCG
TGGGCAACTGGGACGTGATCTTTGGCGGAGGCACCAAGCTGACCGTGCTGGGCGGAAGCAGCAGAAG
CTCTAGTTCTGGCGGCGGAGGAAGCGGAGGCGGAGGACAGCCTCAGCTGCAGGAATCTGGCCCCACA
CTGGTGGAAGCCAGCGAGACACTGAGCCTGACCTGTGCCGTGTCCGGCGATTCTACCGCCGCCTGCAA
TAGCTTCTGGGGCTGGGTGCGCCAGCCTCCTGGAAAGGGACTGGAATGGGTGGGAAGCCTGAGCCACT
GCGCCAGCTATTGGAACCGGGGCTGGACCTACCACAACCCCAGCCTGAAGTCCAGACTGACCCTGGCC
CTGGACACCCCCAAGAACCTGGTGTTCCTGAAGCTGAACAGCGTGACAGCCGCCGACACCGCCACCTA
CTACTGTGCCAGATTTGGCGGCGAGGTGCTGCGGTACACCGACTGGCCTAAACCTGCCTGGGTGGACC
TGTGGGGCAGAGGAACACTCGTGACCGTGTCTAGCTCCGGA[illegible]ATCTACATCTGGGCGCCCTTGGCCG
GGACTTGTGGGGTCCTTCTCCTGTCACTGGTTATCACCCTTTACTGCGAGTGAAGTTCAGCAGGA
GCGCAGACGCCCCCGCGTACAAGCAGGGCCAGAACCAGCTCTATAACGAGCTCAATCTAGGACGAAG
AGAGGAGTACGATGTTTTGGACAAGAGACGTGGCCGGGACCCTGAGATGGGGGGAAAGCCGAGAAG
GAAGAACCCTCAGGAAGGCCTGTACAATGAACTGCAGAAAGATAAGATGGCGGAGGCCTACAGTGAG
ATTGGGATGAAAGGCGAGCGCCGGAGGGGCAAGGGGCACGATGGCCTTTACCAGGGTCTCAGTACAG
CCACCAAGGACACCTACGACGCCCTTCACATGCAGGCCCTGCCCCCTCGC

FIG. 19 (Part 4/8)

3) VRC01 CD3-zeta sequence (SEQ ID NO: 72):
GGATCCGAGATCGTGCTGACACAGAGCCCTGGCACCCTGAGCCTGTCTCCAGGCGAGACAGCCATCAT
CAGCTGCCGGACAAGCCAGTACGGCAGCCTGGCCTGGTATCAGCAGAGGCCTGGACAGGCCCCCAGA
CTCGTGATCTACAGCGGCAGCACAAGAGCCGCCGGAATCCCCGATAGATTCAGCGGCTCTAGATGGGG
CCCTGACTACAACCTGACCATCAGCAACCTGGAAAGCGGCGACTTCGGCGTGTACTACTGCCAGCAGT
ACGAGTTCTTCGGCCAGGGCACCAAGGTGCAGGTGGACATCAAGAGAGGCGGCAGCTCCAGAAGCTC
CAGCTCTGGCGGCGGAGGATCTGGCGGAGGCGGACAGGTGCAGCTGGTGCAGTCTGGCGGCCAGATG
AAGAAACCCGGCGAGAGCATGCGGATCAGCTGCAGAGCCTCCGGCTACGAGTTCATCGACTGCACCCT
GAACTGGATTCGGCTGGCCCCTGGCAAAAGACCCGAGTGGATGGGCTGGCTGAAGCCCAGAGGCGGA
GCCGTGAATTACGCCAGACCTCTGCAGGGCAGAGTGACCATGACCCGGGACGTGTACAGCGATACCG
CCTTCCTGGAACTGCGGAGCCTGACCGTGGATGATACCGCCGTGTACTTCTGCACCCGGGGCAAGAAC
TGCGACTACAACTGGGACTTCGAGCACTGGGGCAGAGGCACCCCTGTGATCGTGTCTAGCTCCGGAA
ACGACGCCAGCGCCGACCACCAACACCGGCGCCACCATCGCGTGCAGCCCTGTCCTGCGCC
AGAGGCGTGCCGGCAGCGGCGGGGGCGCAGTGCACACGAGGGGGCTGGACTTCGCCTGTGATAT
CTACATCTGGGCGCCCTTGGCCGGGACTTGTGGGGTCCTTCTCCTGTCACTGGTTATCACCCTTT
ACTGCGAGTGAAGTTCAGCAGGAGCGCAGACGCCCCCGCGTACAAGCAGGGCCAGAACCAGCTCTAT
AACGAGCTCAATCTAGGACGAAGAGAGGAGTACGATGTTTTGGACAAGAGACGTGGCCGGGACCCTG
AGATGGGGGGAAAGCCGAGAAGGAAGAACCCTCAGGAAGGCCTGTACAATGAACTGCAGAAAGATA
AGATGGCGGAGGCCTACAGTGAGATTGGGATGAAAGGCGAGCGCCGGAGGGGCAAGGGGCACGATG
GCCTTTACCAGGGTCTCAGTACAGCCACCAAGGACACCTACGACGCCCTTCACATGCAGGCCCTGCCC
CCTCGC 4) 3BNC60 CD3-zeta sequence (SEQ ID NO: 73):
GACATCCAGATGACCCAGAGCCCCAGCAGCCTGTCTGCCAGAGTGGGCGACACCGTGACCATCACCTG
TCAGGCCAACGGCTACCTGAACTGGTATCAGCAGCGGAGAGGCAAGGCCCCCAAGCTGCTGATCTAC
GACGGCAGCAAGCTGGAAAGAGGCGTGCCCGCCAGATTCAGCGGCAGAAGATGGGGCCAGGAGTAC
AACCTGACCATCAACAACCTGCAGCCCGAGGACGTGGCCACATACTTTTGCCAGGTGTACGAGTTCAT
CGTGCCCGGCACCCGGCTGGATCTGAAGGGCGGAAGCAGCAGAAGCAGCTCTAGCGGCGGAGGCGGA
TCTGGCGGAGGGGGACAGGTGCACCTGAGTCAGTCTGGCGCCGCTGTGACAAAGCCAGGCGCTTCTGT
GCGGGTGTCCTGTGAAGCCAGCGGCTACAAGATCAGCGACCACTTCATCCACTGGTGCGGCAGGCTC
CAGGACAGGGACTGCAGTGGGTGGGATGGATCAACCCCAAGACCGGCCAGCCCAACAACCCCAGACA
GTTCCAGGGCAGAGTGTCCCTGACCAGACAGGCCAGCTGGGACTTCGACACCTACAGCTTCTACATGG
ACCTGAAGGCCGTGCGGAGCGACGACACCGCCATCTACTTTTGCGCCAGACAGAGAAGCGACTTCTGG
GATTTCGACGTGTGGGGCAGCGGCACCCAAGTGACCGTGTCATCTACCACGACGCCAGCGCCGACC
ACCAACACCGGCGCCACCATCGCCGTGCAGCCCTGTCCTGCGCCAGAGGCGTGCCGGCAGCGG
CGGGGGCGCAGTGCACACGAGGGGGCTGGACTTCGCCTGTGATCTACATCTGGGCGCCCTTGG
CCGGGACTTGTGGGGTCCTTCTCCTGTCACTGGTTATCACCCTTTACTGCGAGTGAAGTTCAGCA
GGAGCGCAGACGCCCCCGCGTACAAGCAGGGCCAGAACCAGCTCTATAACGAGCTCAATCTAGGACG
AAGAGAGGAGTACGATGTTTTGGACAAGAGACGTGGCCGGGACCCTGAGATGGGGGGAAAGCCGAG
AAGGAAGAACCCTCAGGAAGGCCTGTACAATGAACTGCAGAAAGATAAGATGGCGGAGGCCTACAGT
GAGATTGGGATGAAAGGCGAGCGCCGGAGGGGCAAGGGGCACGATGGCCTTTACCAGGGTCTCAGTA
CAGCCACCAAGGACACCTACGACGCCCTTCACATGCAGGCCCTGCCCCCTCGC

FIG. 19 (Part 5/8)

5) PGDM1400 CD3-zeta sequence (SEQ ID NO: 74):
GACTTCGTGCTGACCCAGAGCCCTCACAGCCTGAGCGTGACACCTGGCGAGAGCGCCAGCATCAGCTG
CAAGAGCAGCCACTCCCTGATCCACGGCGACCGGAACAACTACCTGGCTTGGTACGTGCAGAAGCCCG
GCAGATCCCCCCAGCTGCTGATCTACCTGGCCAGCAGCAGAGCCAGCGGCGTGCCCGATAGATTTTCT
GGCAGCGGCAGCGACAAGGACTTCACCCTGAAGATCAGCCGGGTGGAAACCGAGGACGTGGGCACCT
ACTACTGTATGCAGGGCAGAGAGAGCCCCTGGACCTTTGGCCAGGGCACCAAGGTGGACATCAAGGG
CGGCAGCTCCAGAAGCAGCTCTAGCGGAGGCGGAGGATCTGGCGGCGGAGGACAGGCTCAGCTGGTG
CAGTCTGGACCCGAAGTGCGGAAGCCTGGCACCAGCGTGAAGGTGTCCTGTAAAGCCCCTGGCAACA
CCCTGAAAAACCTACGACCTGCACTGGGTGCGCAGCGTGCCAGGACAGGGACTGCAGTGGATGGGCTG
GATCAGCCACGAGGGCGACAAGAAAGTGATCGTGGAACGGTTCAAGGCCAAAGTGACCATCGACTGG
GACAGAAGCACCAACACCGCCTACCTGCAGCTGAGCGGCCTGACCTCTGGCGATACCGCCGTGTACTA
CTGCGCCAAGGGCAGCAAGCACCGGCTGAGAGACTACGCCCTGTACGACGATGACGGCGCCCTGAAC
TGGGCCGTGGATGTGGACTACCTGAGCAACCTGGAATTCTGGGGCCAGGGAACCGCCGTGACCGTGTC
ATCTACCACGACGCCAGCGCCGCGACCACCAACACCGGCGCCACCATCGCGTCGCAGCCCCTGTCCC
TGCGCCCAGAGGCGTGCCGGCCAGCGGCGGGGGCGCAGTGCACACGAGGGGCTGGACTTCGCCTG
TGAATCTACATCTGGGCGCCCTTGGCCGGGACTTGTGGGGTCCTTCTCCTGTCACTGGTTATCA
CCCTTTACTGCGAGTGAAGTTCAGCAGGAGCGCAGACGCCCCGCGTACAAGCAGGGCCAGAACCA
GCTCTATAACGAGCTCAATCTAGGACGAAGAGAGGAGTACGATGTTTTGGACAAGAGACGTGGCCGG
GACCCTGAGATGGGGGGAAAGCCGAGAAGGAAGAACCCTCAGGAAGGCCTGTACAATGAACTGCAG
AAAGATAAGATGGCGGAGGCCTACAGTGAGATTGGGATGAAAGGCGAGCGCCGGAGGGGCAAGGGG
CACGATGGCCTTTACCAGGGTCTCAGTACAGCCACCAAGGACACCTACGACGCCCTTCACATGCAGGC
CCTGCCCCCTCGC Light Grey = ScFv EC domain
Dark Grey = CD8α extracellular hinge
Bold = CD8α transmembrane domain
Dotted line = CD3 zeta

FIG. 19 (Part 6/8)

6) PG9 CD3-zeta ScFv extracellular domain sequence (SEQ ID NO: 75):
CAGAGACTGGTGGAAAGCGGTGGAGGCGTGGTGCAGCCTGGCAGCAGCCTGAGACTGAGCTGCGCCG
CTTCCGGCTTCGACTTCAGCCGGCAGGGCATGCATTGGGTGCGCCAGGCTCCAGGACAGGGACTGGAA
TGGGTGGCCTTCATCAAGTACGACGGCAGCGAGAAGTACCACGCCGACAGCGTGTGGGGTAGACTGT
CTATCAGCCGGGACAACAGCAAGGACACCCTGTACCTGCAGATGAACAGCCTGCGGGTGGAGGACAC
CGCCACATACTTTTGCGTGCGGGAGGCTGGTGGACCTGACTACCGGAACGGCTACAACTACTACGACT
TCTACGACGGCTACTACAACTACCACTACATGGATGTGTGGGGCAAGGGCACCACCGTGACCGTGTCT
AGCGGAGGCGGAGGATCTGGCGGCGGAGGAAGTGGAGGCGGCGGAAGCCAGTCTGCCCTGACCCAGC
CTGCCTCTGTGTCTGGCAGCCCTGGCCAGAGCATCACCATCAGCTGCAACGGCACCAGCAACGACGTG
GGCGGCTACGAGAGCGTGTCCTGGTATCAGCAGCACCCCGGCAAGGCCCCCAAGGTGGTGATCTACG
ACGTGTCCAAGAGGCCCAGCGGCGTGAGCAACCGGTTCAGCGGCAGCAAGAGCGGCAATACCGCCAG
CCTGACCATCTCTGGGCTGCAGGCCGAGGACGAGGGCGACTACTACTGCAAGAGCCTGACCAGCACC
AGGCGGAGAGTGTTCGGCACCGGCACCAAGCTGACCGTGCTG

7) PGT128 CD3-zeta ScFv extracellular domain sequence (SEQ ID NO: 76):
GGATCCCAGAGCGCCCTGACACAGCCTCCTAGCGCCTCTGGATCTCCCGGCCAGAGCATCACCATCAG
CTGTACCGGCACCAGCAACAACTTCGTGTCCTGGTATCAGCAGCACGCCGGCAAGGCCCCCAAGCTCG
TGATCTACGACGTGAACAAGCGGCCCAGCGGCGTGCCCGATAGATTCAGCGGCAGCAAGAGCGGCAA
CACCGCCAGCCTGACAGTGTCTGGCCTGCAGACCGATGACGAGGCCGTGTACTACTGCGGCAGCCTCG
TGGGCAACTGGGACGTGATCTTTGGCGGAGGCACCAAGCTGACCGTGCTGGGCGGAAGCAGCAGAAG
CTCTAGTTCTGGCGGCGGAGGAAGCGGAGGCGGAGGACAGCCTCAGCTGCAGGAATCTGGCCCCACA
CTGGTGGAAGCCAGCGAGACACTGAGCCTGACCTGTGCCGTGTCCGGCGATTCTACCGCCGCCTGCAA
TAGCTTCTGGGGCTGGGTGCGCCAGCCTCCTGGAAAGGGACTGGAATGGGTGGGAAGCCTGAGCCACT
GCGCCAGCTATTGGAACCGGGGCTGGACCTACCACAACCCCAGCCTGAAGTCCAGACTGACCCTGGCC
CTGGACACCCCCAAGAACCTGGTGTTCCTGAAGCTGAACAGCGTGACAGCCGCCGACACCGCCACCTA
CTACTGTGCCAGATTTGGCGGCGAGGTGCTGCGGTACACCGACTGGCCTAAACCTGCCTGGGTGGACC
TGTGGGGCAGAGGAACACTCGTGACCGTGTCTAGCTCCGGA

8) VRC01 CD3-zeta ScFv extracellular domain sequence (SEQ ID NO: 77):
GGATCCGAGATCGTGCTGACACAGAGCCCTGGCACCCTGAGCCTGTCTCCAGGCGAGACAGCCATCAT
CAGCTGCCGGACAAGCCAGTACGGCAGCCTGGCCTGGTATCAGCAGAGGCCTGGACAGGCCCCCAGA
CTCGTGATCTACAGCGGCAGCACAAGAGCCGCCGGAATCCCCGATAGATTCAGCGGCTCTAGATGGGG
CCCTGACTACAACCTGACCATCAGCAACCTGGAAAGCGGCGACTTCGGCGTGTACTACTGCCAGCAGT
ACGAGTTCTTCGGCCAGGGCACCAAGGTGCAGGTGGACATCAAGAGAGGCGGCAGCTCCAGAAGCTC
CAGCTCTGGCGGCGGAGGATCTGGCGGAGGCGGACAGGTGCAGCTGGTGCAGTCTGGCGGCCAGATG
AAGAAACCCGGCGAGAGCATGCGGATCAGCTGCAGAGCCTCCGGCTACGAGTTCATCGACTGCACCCT
GAACTGGATTCGGCTGGCCCCTGGCAAAAGACCCGAGTGGATGGGCTGGCTGAAGCCCAGAGGCGGA
GCCGTGAATTACGCCAGACCTCTGCAGGGCAGAGTGACCATGACCCGGGACGTGTACAGCGATACCG
CCTTCCTGGAACTGCGGAGCCTGACCGTGGATGATACCGCCGTGTACTTCTGCACCCGGGGCAAGAAC
TGCGACTACAACTGGGACTTCGAGCACTGGGGCAGAGGCACCCCTGTGATCGTGTCTAGCTCCGGA

FIG. 19 (Part 7/8)

9) 3BNC60 CD3-zeta sequence (SEQ ID NO: 78):
GACATCCAGATGACCCAGAGCCCCAGCAGCCTGTCTGCCAGAGTGGGCGACACCGTGACCATCACCTG
TCAGGCCAACGGCTACCTGAACTGGTATCAGCAGCGGAGAGGCAAGGCCCCCAAGCTGCTGATCTAC
GACGGCAGCAAGCTGGAAAGAGGCGTGCCCGCCAGATTCAGCGGCAGAAGATGGGGCCAGGAGTAC
AACCTGACCATCAACAACCTGCAGCCCGAGGACGTGGCCACATACTTTTGCCAGGTGTACGAGTTCAT
CGTGCCCGGCACCCGGCTGGATCTGAAGGGCGGAAGCAGCAGAAGCAGCTCTAGCGGCGGAGGCGGA
TCTGGCGGAGGGGGACAGGTGCACCTGAGTCAGTCTGGCGCCGCTGTGACAAAGCCAGGCGCTTCTGT
GCGGGTGTCCTGTGAAGCCAGCGGCTACAAGATCAGCGACCACTTCATCCACTGGTGGCGGCAGGCTC
CAGGACAGGGACTGCAGTGGGTGGGATGGATCAACCCCAAGACCGGCCAGCCCAACAACCCCAGACA
GTTCCAGGGCAGAGTGTCCCTGACCAGACAGGCCAGCTGGGACTTCGACACCTACAGCTTCTACATGG
ACCTGAAGGCCGTGCGGAGCGACGACACCGCCATCTACTTTGCGCCAGACAGAGAAGCGACTTCTGG
GATTTCGACGTGTGGGGCAGCGGCACCCAAGTGACCGTGTCATCT

10) PGDM1400 CD3-zeta sequence (SEQ ID NO: 79):
GACTTCGTGCTGACCCAGAGCCCTCACAGCCTGAGCGTGACACCTGGCGAGAGCGCCAGCATCAGCTG
CAAGAGCAGCCACTCCCTGATCCACGGCGACCGGAACAACTACCTGGCTTGGTACGTGCAGAAGCCCG
GCAGATCCCCCCAGCTGCTGATCTACCTGGCCAGCAGCAGAGCCAGCGGCGTGCCCGATAGATTTTCT
GGCAGCGGCAGCGACAAGGACTTCACCCTGAAGATCAGCCGGGTGGAAACCGAGGACGTGGGCACCT
ACTACTGTATGCAGGGCAGAGAGAGCCCCTGGACCTTTGGCCAGGGCACCAAGGTGGACATCAAGGG
CGGCAGCTCCAGAAGCAGCTCTAGCGGAGGCGGAGGATCTGGCGGCGGAGGACAGGCTCAGCTGGTG
CAGTCTGGACCCGAAGTGCGGAAGCCTGGCACCAGCGTGAAGGTGTCCTGTAAAGCCCCTGGCAACA
CCCTGAAAAACCTACGACCTGCACTGGGTGCGCAGCGTGCCAGGACAGGGACTGCAGTGGATGGGCTG
GATCAGCCACGAGGGCGACAAGAAAGTGATCGTGGAACGGTTCAAGGCCAAAGTGACCATCGACTGG
GACAGAAGCACCAACACCGCCTACCTGCAGCTGAGCGGCCTGACCTCTGGCGATACCGCCGTGTACTA
CTGCGCCAAGGGCAGCAAGCACCGGCTGAGAGACTACGCCCTGTACGACGATGACGGCGCCCTGAAC
TGGGCCGTGGATGTGGACTACCTGAGCAACCTGGAATTCTGGGGCCAGGGAACCGCCGTGACCGTGTC
ATCT

FIG. 19 (Part 8/8)

SEQUENCE LISTING

<160> NUMBER OF SEQ ID NOS: 83

<210> SEQ ID NO 1
<211> LENGTH: 3011
<212> TYPE: DNA
<213> ORGANISM: Artificial Sequence
<220> FEATURE:
<223> OTHER INFORMATION: Artificially Synthesized

<400> SEQUENCE: 1

| | | | | | |
|---|---|---|---|---|---|
| cgtgaggctc | cggtgcccgt | cagtgggcag | agcgcacatc | gcccacagtc | cccgagaagt | 60 |
| tgggggagg | ggtcggcaat | tgaaccggtg | cctagagaag | gtggcgcggg | gtaaactggg | 120 |
| aaagtgatgt | cgtgtactgg | ctccgccttt | ttcccgaggg | tggggagaa | ccgtatataa | 180 |
| gtgcagtagt | cgccgtgaac | gttcttttc | gcaacgggtt | tgccgccaga | acacaggtaa | 240 |
| gtgccgtgtg | tggttcccgc | gggcctggcc | tctttacggg | ttatggccct | tgcgtgcctt | 300 |
| gaattacttc | cacctggctg | cagtacgtga | ttcttgatcc | cgagcttcgg | gttggaagtg | 360 |
| ggtgggagag | ttcgaggcct | tgcgcttaag | gagccccttc | gcctcgtgct | tgagttgagg | 420 |
| cctggcctgg | gcgctgggc | cgccgcgtgc | gaatctggtg | gcaccttcgc | gcctgtctcg | 480 |
| ctgctttcga | taagtctcta | gccatttaaa | atttttgatg | acctgctgcg | acgcttttt | 540 |
| tctggcaaga | tagtccttgta | aatgcgggcc | aagatctgca | cactggtatt | tcggttttg | 600 |
| gggccgcggg | cggcgacggg | gcccgtgcgt | cccagcgcac | atgttcggcg | aggcggggcc | 660 |
| tgcgagcgcg | gccaccgaga | tcggacggg | ggtagtctca | agctggccgg | cctgctctgg | 720 |
| tgcctggcct | cgcgccgccg | tgtatcgccc | cgccctgggc | ggcaaggctg | gccgggtcgg | 780 |
| caccagttgc | gtgagcggaa | agatggccgc | ttccgggccc | tgctgcaggg | agctcaaaat | 840 |
| ggaggacgcg | gcgctcggga | gagcgggcgg | gtgagtcacc | cacacaaagg | aaaagggcct | 900 |
| ttccgtcctc | agccgtcgct | tcatgtgact | ccactgagta | ccgggcgccg | tccaggcacc | 960 |
| tcgattagtt | ctcgtgcttt | tggagtacgt | cgtctttagg | ttgggggag | gggttttatg | 1020 |
| cgatggagtt | tccccacact | gagtgggtgg | agactgaagt | taggccagct | tggcacttga | 1080 |
| tgtaattctc | cttggaattt | gccctttttg | agtttggatc | ttggttcatt | ctcaagcctc | 1140 |
| agacagtggt | tcaaagtttt | tttcttccat | ttcaggtgtc | gtgagctagc | tctagagcca | 1200 |
| ccatggcctt | accagtgacc | gccttgctcc | tgcctctggc | cttgctgctc | cacgccgcca | 1260 |
| ggccgggatc | catgaaccgg | ggagtcccctt | ttaggcactt | gcttctggtg | ctgcaactgg | 1320 |
| cgctcctccc | agcagccact | cagggaaaga | agtggtgct | gggcaaaaaa | ggggatacag | 1380 |
| tggaactgac | ctgtacagct | tcccagaaga | agagcataca | attccactgg | aaaaactcca | 1440 |
| accagataaa | gattctggga | aatcagggct | ccttcttaac | taaaggtcca | tccaagctga | 1500 |
| atgatcgcgc | tgactcaaga | agaagccttt | gggaccaagg | aaacttcccc | ctgatcatca | 1560 |
| agaatcttaa | gatagaagac | tcagatactt | acatctgtga | agtggaggac | cagaaggagg | 1620 |
| aggtgcaatt | gctagtgttc | ggattgactg | ccaactctga | cacccacctg | cttcaggggc | 1680 |
| agagcctgac | cctgaccttg | gagagccccc | ctggtagtag | cccctcagtg | caatgtagga | 1740 |
| gtccaagggg | taaaacata | caggggggga | agaccctctc | cgtgtctcag | ctggagctcc | 1800 |
| aggatagtgg | cacctggaca | tgcactgtct | tgcagaacca | gaagaaggtg | gagttcaaaa | 1860 |
| tagacatcgt | ggtgctagct | ttccagaagg | cctccagcat | agtctataag | aaagagggg | 1920 |
| aacaggtgga | gttctcctc | ccactcgcct | ttacagttga | aaagctgacg | ggcagtggcg | 1980 |
| agctgtggtg | gcaggcggag | agggcttcct | cctccaagtc | ttggatcacc | tttgacctga | 2040 |

```
agaacaagga agtgtctgta aaacgggtta cccaggaccc taagctccag atgggcaaga    2100
agctcccgct ccacctcacc ctgccccagg ccttgcctca gtatgctggc tctggaaacc    2160
tcaccctggc ccttgaagcg aaaacaggaa agttgcatca ggaagtgaac ctggtggtga    2220
tgagagccac tcagctccag aaaaatttga cctgtgaggt gtggggaccc acctccccta    2280
agctgatgct gagcttgaaa ctggagaaca aggaggcaaa ggtctcgaag cgggagaagg    2340
cggtgtgggt gctgaaccct gaggcgggga tgtggcagtg tctgctgagt gactcgggac    2400
aggtcctgct ggaatccaac atcaaggttc tgcccacatg gtccaccccg gtgcagccat    2460
ccggaaccac gacgccagcg ccgcgaccac caacaccggc gcccaccatc gcgtcgcagc    2520
ccctgtccct gcgcccagag gcgtgccggc cagcggcggg gggcgcagtg cacacgaggg    2580
ggctggactt cgcctgtgat atctacatct gggcgccctt ggccgggact tgtgggtcc    2640 ttctcctgtc actggttatc ccctttact gcagagtgaa gttcagcagg agcgcagacg    2700 ccccgcgta ccagcagggc cagaaccagc tctataacga gctcaatcta ggacgaagag    2760
aggagtacga tgttttggac aagagacgtg gccgggaccc tgagatgggg ggaaagccga    2820
gaaggaagaa ccctcaggaa ggcctgtaca atgaactgca gaaagataag atggcggagg    2880
cctacagtga gattgggatg aaaggcgagc gccgagggg caaggggcac gatggccttt    2940
accagggtct cagtacagcc accaaggaca cctacgacgc ccttcacatg caggccctgc    3000
cccctcgcta a                                                         3011

<210> SEQ ID NO 2
<211> LENGTH: 1184
<212> TYPE: DNA
<213> ORGANISM: Artificial Sequence
<220> FEATURE:
<223> OTHER INFORMATION: Artificially Synthesized

<400> SEQUENCE: 2
cgtgaggctc cggtgcccgt cagtgggcag agcgcacatc gcccacagtc cccgagaagt      60
tggggggagg ggtcggcaat tgaaccggtg cctagagaag gtggcgcggg gtaaactggg     120
aaagtgatgt cgtgtactgg ctccgccttt ttcccgaggg tgggggagaa ccgtatataa     180
gtgcagtagt cgccgtgaac gttctttttc gcaacgggtt tgccgccaga acacaggtaa     240
gtgccgtgtg tggttcccgc gggcctggcc tctttacggg ttatggccct tgcgtgcctt     300
gaattacttc cacctggctg cagtacgtga ttcttgatcc cgagcttcgg gttggaagtg     360
ggtgggagag ttcgaggcct tgcgcttaag gagcccttc gcctcgtgct tgagttgagg     420
cctggcctgg gcgctggggc cgccgcgtgc gaatctggtg gcaccttcgc gcctgtctcg     480
ctgctttcga taagtctcta gccatttaaa attttttgatg acctgctgcg acgcttttt     540 tctggcaaga tagtcttgta aatgcgggcc aagatctgca cactggtatt tcggtttttg     600
gggccgcggg cggcgacggg gcccgtgcgt cccagcgcac atgttcggcg aggcggggcc     660
tgcgagcgcg gccaccgaga tcggacgggg gtagtctca gctggccgg cctgctctgg      720 tgcctggcct cgcgccgccg tgtatcgccc cgccctgggc ggcaaggctg gcccggtcgg     780
caccagttgc gtgagcggaa agatggccgc ttccgccc tgctgcaggg agctcaaaat      840
ggaggacgcg gcgctcggga gagcgggcgg gtgagtcacc cacacaaagg aaaagggcct     900
ttccgtcctc agccgtcgct tcatgtgact ccactgagta ccgggcgccg tccaggcacc     960
tcgattagtt ctcgtgcttt tggagtacgt cgtctttagg ttgggggag gggttttatg    1020 cgatggagtt tccccacact gagtgggtgg agactgaagt taggccagct tggcacttga    1080
```
tgtaattctc cttggaattt gccctttttg agtttggatc ttggttcatt ctcaagcctc    1140
agacagtggt tcaaagtttt tttcttccat ttcaggtgtc gtga    1184

<210> SEQ ID NO 3
<211> LENGTH: 1188
<212> TYPE: DNA
<213> ORGANISM: Artificial Sequence
<220> FEATURE:
<223> OTHER INFORMATION: Artificially Synthesized

<400> SEQUENCE: 3
atgaaccggg gagtcccttt taggcacttg cttctggtgc tgcaactggc gctcctccca      60
gcagccactc agggaaagaa agtggtgctg ggcaaaaaag gggatacagt ggaactgacc     120
tgtacagctt cccagaagaa gagcatacaa ttccactgga aaaactccaa ccagataaag     180
attctgggaa atcagggctc cttcttaact aaaggtccat ccaagctgaa tgatcgcgct     240
gactcaagaa gaagcctttg ggaccaagga aacttccccc tgatcatcaa gaatcttaag     300
atagaagact cagatactta catctgtgaa gtggaggacc agaaggagga ggtgcaattg     360
ctagtgttcg gattgactgc caactctgac acccacctgc ttcaggggca gagcctgacc     420
ctgacccttg gagaccccccc tggtagtagc ccctcagtgc aatgtaggag tccaaggggt     480
aaaaacatac aggggggaa gaccctctcc gtgtctcagc tggagctcca ggatagtggc     540
acctggacat gcactgtctt gcagaaccag aagaaggtgg agttcaaaat agacatcgtg     600
gtgctagctt tccagaaggc ctccagcata gtctataaga agagggggga acaggtggag     660
ttctccttcc cactcgcctt tacagttgaa aagctgacgg gcagtggcga gctgtggtgg     720
caggcggaga gggcttcctc ctccaagtct tggatcacct ttgacctgaa gaacaaggaa     780
gtgtctgtaa acgggttac ccaggaccct aagctccaga tgggcaagaa gctcccgctc     840 caccctcaccc tgccccaggc cttgcctcag tatgctggct ctggaaacct caccctggcc     900
cttgaagcga aaacaggaaa gttgcatcag gaagtgaacc tggtggtgat gagagccact     960
cagctccaga aaatttgac ctgtgaggtg tggggaccca cctcccctaa gctgatgctg    1020
agcttgaaac tggagaacaa ggaggcaaag gtctcgaagc gggagaaggc ggtgtgggtg    1080
ctgaaccctg aggcggggat gtggcagtgt ctgctgagtg actcgggaca ggtcctgctg    1140
gaatccaaca tcaaggttct gcccacatgg tccaccccgg tgcagcca    1188

<210> SEQ ID NO 4
<211> LENGTH: 135
<212> TYPE: DNA
<213> ORGANISM: Artificial Sequence
<220> FEATURE:
<223> OTHER INFORMATION: Artificially Synthesized

<400> SEQUENCE: 4
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgat    135

<210> SEQ ID NO 5
<211> LENGTH: 72
<212> TYPE: DNA
<213> ORGANISM: Artificial Sequence
<220> FEATURE:
<223> OTHER INFORMATION: Artificially Synthesized

<400> SEQUENCE: 5

```
atctacatct gggcgcccct tggccgggact tgtggggtcc ttctcctgtc actggttatc    60 acccttact gc                                                          72
```

<210> SEQ ID NO 6
<211> LENGTH: 339
<212> TYPE: DNA
<213> ORGANISM: Artificial Sequence
<220> FEATURE:
<223> OTHER INFORMATION: Artificially Synthesized

<400> SEQUENCE: 6

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga agataagat ggcggaggcc tacagtgaga ttgggatgaa aggcgagcgc   240 cggagggggca aggggcacga tggccttac cagggtctca gtacagccac caaggacacc   300
tacgacgccc ttcacatgca ggccctgccc cctcgctaa                          339
```

<210> SEQ ID NO 7
<211> LENGTH: 3149
<212> TYPE: DNA
<213> ORGANISM: Artificial Sequence
<220> FEATURE:
<223> OTHER INFORMATION: Artificially Synthesized

<400> SEQUENCE: 7

```
cgtgaggctc cggtgcccgt cagtgggcag agcgcacatc gcccacagtc cccgagaagt    60
tggggggagg ggtcggcaat tgaaccggtg cctagaaag gtggcgcggg gtaaactggg    120
aaagtgatgt cgtgtactgg ctccgccttt ttcccgaggg tgggggagaa ccgtatataa   180
gtgcagtagt cgccgtgaac gttctttttc gcaacgggtt tgccgccaga acacaggtaa   240
gtgccgtgtg tggttcccgc gggcctggcc tctttacggg ttatggccct tgcgtgcctt   300
gaattacttc cacctggctg cagtacgtga ttcttgatcc cgagcttcgg gttggaagtg   360
ggtgggagag ttcgaggcct tgcgcttaag gagccccttc gcctcgtgct tgagttgagg   420
cctggcctgg gcgctgggc cgccgcgtgc gaatctggtg gcaccttcgc gcctgtctcg   480
ctgctttcga taagtctcta gccatttaaa attttttgatg acctgctgcg acgcttttttt   540 tctggcaaga tagtcttgta aatgcgggcc aagatctgca cactggtatt tcggtttttg   600
gggccgcggg cggcgacggg gcccgtgcgt cccagcgcac atgttcggcg aggcggggcc   660
tgcgagcgcg gccaccgaga tcggacgggg ggtagtctca agctggccgg cctgctctgg   720
tgcctggcct cgcgccgccg tgtatcgccc cgccctgggc ggcaaggctg gcccggtcgg   780
caccagttgc gtgagcggaa agatggccgc ttcccggccc tgctgcaggg agctcaaaat   840
ggaggacgcg gcgctcggga gagcgggcgg gtgagtcacc cacacaaagg aaaagggcct   900
ttccgtcctc agccgtcgct tcatgtgact ccactgagta ccgggcgccg tccaggcacc   960
tcgattagtt ctcgtgcttt tggagtacgt cgtctttagg ttgggggggag gggttttatg  1020 cgatggagtt tccccacact gagtgggtgg agactgaagt taggccagct tggcacttga  1080
tgtaattctc cttggaattt gcccttttttg agtttggatc ttggttcatt ctcaagcctc  1140
agacagtggt tcaaagtttt tttcttccat ttcaggtgtc gtgagctagc tctagagcca  1200
ccatggcctt accagtgacc gccttgctcc tgccgctggc cttgctgctc cacgccgcca  1260
```

| | |
|---|---:|
| ggccgggatc catgaaccgg ggagtccctt ttaggcactt gcttctggtg ctgcaactgg | 1320 |
| cgctcctccc agcagccact cagggaaaga aagtggtgct gggcaaaaaa ggggatacag | 1380 |
| tggaactgac ctgtacagct tcccagaaga agagcataca attccactgg aaaaactcca | 1440 |
| accagataaa gattctggga aatcagggct ccttcttaac taaaggtcca tccaagctga | 1500 |
| atgatcgcgc tgactcaaga agaagccttt gggaccaagg aaacttcccc ctgatcatca | 1560 |
| agaatcttaa gatagaagac tcagatactt acatctgtga agtggaggac cagaaggagg | 1620 |
| aggtgcaatt gctagtgttc ggattgactg ccaactctga cacccacctg cttcaggggc | 1680 |
| agagcctgac cctgaccttg gagagccccc ctggtagtag ccctcagtg caatgtagga | 1740 |
| gtccaagggg taaaaacata cagggggga agaccctctc cgtgtctcag ctggagctcc | 1800 |
| aggatagtgg cacctggaca tgcactgtct tgcagaacca aagaaggtg gagttcaaaa | 1860 |
| tagacatcgt ggtgctagct ttccagaagg cctccagcat agtctataag aaagagggg | 1920 |
| aacaggtgga gttctccttc ccactcgcct ttacagttga aaagctgacg ggcagtggcg | 1980 |
| agctgtggtg gcaggcggag agggcttcct cctccaagtc ttggatcacc tttgacctga | 2040 |
| agaacaagga agtgtctgta aaacgggtta cccaggaccc taagctccag atgggcaaga | 2100 |
| agctcccgct ccacctcacc ctgccccagg ccttgcctca gtatgctggc tctggaaacc | 2160 |
| tcaccctggc ccttgaagcg aaaacaggaa agttgcatca ggaagtgaac ctggtggtga | 2220 |
| tgagagccac tcagctccag aaaaatttga cctgtgaggt gtggggaccc acctcccta | 2280 |
| agctgatgct gagcttgaaa ctggagaaca aggaggcaaa ggtctcgaag cgggagaagg | 2340 |
| cggtgtgggt gctgaaccct gaggcgggga tgtggcagtg tctgctgagt gactcgggac | 2400 |
| aggtcctgct ggaatccaac atcaaggttc tgcccacatg gtccaccccg gtgcagccat | 2460 |
| ccggaaccac gacgccagcg ccgcgaccac caacaccggc gcccaccatc gcgtcgcagc | 2520 |
| ccctgtccct gcgcccagag gcgtgccggc cagcggcggg gggcgcagtg cacacgaggg | 2580 |
| ggctggactt cgcctgtgat ttttgggtgc tggtggtggt tggtggagtc ctggcttgct | 2640 |
| atagcttgct agtaacagtg gcctttatta ttttctgggt gaggagtaag aggagcaggc | 2700 |
| tcctgcacag tgactacatg aacatgactc cccgccgccc cgggcccacc cgcaagcatt | 2760 |
| accagcccta tgccccacca cgcgacttcg cagcctatcg ctccatcgat agagtgaagt | 2820 |
| tcagcaggag cgcagacgcc cccgcgtacc agcagggcca gaaccagctc tataacgagc | 2880 |
| tcaatctagg acgaagagag gagtacgatg ttttggacaa gagacgtggc cgggaccctg | 2940 |
| agatgggggg aaagccgaga aggaagaacc ctcaggaagg cctgtacaat gaactgcaga | 3000 |
| aagataagat ggcggaggcc tacagtgaga ttgggatgaa aggcgagcgc cggagggca | 3060 |
| aggggcacga tggcctttac cagggtctca gtacagccac caaggacacc tacgacgccc | 3120 |
| ttcacatgca ggccctgccc cctcgctaa | 3149 |

<210> SEQ ID NO 8
<211> LENGTH: 81
<212> TYPE: DNA
<213> ORGANISM: Artificial Sequence
<220> FEATURE:
<223> OTHER INFORMATION: Artificially Synthesized

<400> SEQUENCE: 8

| | |
|---|---:|
| ttttgggtgc tggtggtggt tggtggagtc ctggcttgct atagcttgct agtaacagtg | 60 |
| gcctttatta ttttctgggt g | 81 |

```
<210> SEQ ID NO 9
<211> LENGTH: 123
<212> TYPE: DNA
<213> ORGANISM: Artificial Sequence
<220> FEATURE:
<223> OTHER INFORMATION: Artificially Synthesized

<400> SEQUENCE: 9
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 10
<211> LENGTH: 1557
<212> TYPE: DNA
<213> ORGANISM: Artificial Sequence
<220> FEATURE:
<223> OTHER INFORMATION: Artificially Synthesized

<400> SEQUENCE: 10 atgggggac ttgaaccctg cagcaggttc ctgctcctgc ctctcctgct ggctgtaagt     60
ggtctccgtc ctgtccaggt ccaggcccag agcgattgca gttgctctac ggtgagcccg   120
ggcgtgctgg cagggatcgt gatgggagac ctggtgctga cagtgctcat tgccctggcc   180
gtgtacttcc tgggccggct ggtccctcgg ggcgagggg ctgcggaggc agcgacccgg    240
aaacagcgta tcactgagac cgagtcgcct tatcaggagc tccagggtca gaggtcggat   300
gtctacagcg acctcaacac acagaggcca tattacaaag tcgaggggcgg cggagagggc   360 agaggaagtc ttctaacatg cggtgacgtg gaggagaatc ccggccctag gatggctctg   420
cctgtgacag ctctgctgct gcctctggcc ctgctgctgc atgctgccag acctggatcc   480
gacttcgtgc tgacccagag ccctcacagc ctgagcgtga cacctggcga gagcgccagc   540
atcagctgca agagcagcca ctccctgatc cacggcgacc ggaacaacta cctggcttgg   600
tacgtgcaga gcccggcag atccccccag ctgctgatct acctggccag cagcagagcc   660
agcggcgtgc ccgatagatt ttctggcagc ggcagcgaca ggacttcac cctgaagatc    720 agccgggtgg aaaccgagga cgtgggcacc tactactgta tgcagggcag agagagcccc   780
tggacctttg gccagggcac caaggtggac atcaagggcg cagctccag aagcagctct    840 agcggaggcg gaggatctgg cggcggagga caggctcagc tggtgcagtc tggacccgaa   900
gtgcggaagc ctggcaccag cgtgaaggtg tcctgtaaag ccctggcaa cacctgaaa    960 acctacgacc tgcactgggt gcgcagcgtg ccaggacagg gactgcagtg gatgggctgg   1020
atcagccacg agggcgacaa gaaagtgatc gtggaacggt tcaaggccaa agtgaccatc   1080
gactgggaca gaagcaccaa caccgcctac ctgcagctga gcggcctgac ctctggcgat   1140
accgccgtgt actactgcgc caaggcagc aagcaccggt gagagacta cgccctgtac    1200 gacgatgacg gcgccctgaa ctgggccgtg gatgtggact acctgagcaa cctggaattc   1260
tggggccagg gaaccgccgt gaccgtgtca tctgctagcg gcgagggggg atctggaggt   1320
gggggttcct cacccactga accaagctcc aaaaccggta accccagaca cctgcatgtt   1380
ctgattggga cctcagtggt caaaatccct tcaccatcc tcctcttctt tctccttcat    1440
cgctggtgct ccaacaaaaa aaatgctgct gtaatggacc aagagcctgc agggaacaga   1500
acagtgaaca gcgaggattc tgatgaacaa gaccatcagg aggtgtcata cgcataa      1557
```

<210> SEQ ID NO 11
<211> LENGTH: 519
<212> TYPE: PRT
<213> ORGANISM: Artificial Sequence
<220> FEATURE:
<223> OTHER INFORMATION: Artificially Synthesized

<400> SEQUENCE: 11

```
Met Gly Gly Leu Glu Pro Cys Ser Arg Phe Leu Leu Leu Pro Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys Val Glu Gly Gly Glu Gly Arg Gly Ser Leu Leu Thr Cys Gly
            115                 120                 125

Asp Val Glu Glu Asn Pro Gly Pro Arg Met Ala Leu Pro Val Thr Ala
        130                 135                 140

Leu Leu Leu Pro Leu Ala Leu Leu His Ala Ala Arg Pro Gly Ser
145                 150                 155                 160

Asp Phe Val Leu Thr Gln Ser Pro His Ser Leu Ser Val Thr Pro Gly
                165                 170                 175

Glu Ser Ala Ser Ile Ser Cys Lys Ser Ser His Ser Leu Ile His Gly
            180                 185                 190

Asp Arg Asn Asn Tyr Leu Ala Trp Tyr Val Gln Lys Pro Gly Arg Ser
        195                 200                 205

Pro Gln Leu Leu Ile Tyr Leu Ala Ser Ser Arg Ala Ser Gly Val Pro
    210                 215                 220

Asp Arg Phe Ser Gly Ser Gly Ser Asp Lys Asp Phe Thr Leu Lys Ile
225                 230                 235                 240

Ser Arg Val Glu Thr Glu Asp Val Gly Thr Tyr Tyr Cys Met Gln Gly
                245                 250                 255

Arg Glu Ser Pro Trp Thr Phe Gly Gln Gly Thr Lys Val Asp Ile Lys
            260                 265                 270

Gly Gly Ser Ser Arg Ser Ser Ser Gly Gly Gly Ser Gly Gly
        275                 280                 285

Gly Gly Gln Ala Gln Leu Val Gln Ser Gly Pro Glu Val Arg Lys Pro
    290                 295                 300

Gly Thr Ser Val Lys Val Ser Cys Lys Ala Pro Gly Asn Thr Leu Lys
305                 310                 315                 320

Thr Tyr Asp Leu His Trp Val Arg Ser Val Pro Gly Gln Gly Leu Gln
                325                 330                 335

Trp Met Gly Trp Ile Ser His Glu Gly Asp Lys Lys Val Ile Val Glu
            340                 345                 350

Arg Phe Lys Ala Lys Val Thr Ile Asp Trp Asp Arg Ser Thr Asn Thr
        355                 360                 365
```

-continued

```
Ala Tyr Leu Gln Leu Ser Gly Leu Thr Ser Gly Asp Thr Ala Val Tyr
        370             375                 380

Tyr Cys Ala Lys Gly Ser Lys His Arg Leu Arg Asp Tyr Ala Leu Tyr
385                 390                 395                 400

Asp Asp Asp Gly Ala Leu Asn Trp Ala Val Asp Val Asp Tyr Leu Ser
                405                 410                 415

Asn Leu Glu Phe Trp Gly Gln Gly Thr Ala Val Thr Val Ser Ser Ala
            420                 425                 430

Ser Gly Gly Gly Gly Ser Gly Gly Gly Ser Pro Thr Glu Pro
        435                 440                 445

Ser Ser Lys Thr Gly Asn Pro Arg His Leu His Val Leu Ile Gly Thr
    450                 455                 460

Ser Val Val Lys Ile Pro Phe Thr Ile Leu Leu Phe Phe Leu Leu His
465                 470                 475                 480

Arg Trp Cys Ser Asn Lys Lys Asn Ala Ala Val Met Asp Gln Glu Pro
                485                 490                 495

Ala Gly Asn Arg Thr Val Asn Ser Glu Asp Ser Asp Glu Gln Asp His
                500                 505                 510

Gln Glu Val Ser Tyr Ala Glx
        515
```

```
<210> SEQ ID NO 12
<211> LENGTH: 882
<212> TYPE: DNA
<213> ORGANISM: Artificial Sequence
<220> FEATURE:
<223> OTHER INFORMATION: Artificially Synthesized

<400> SEQUENCE: 12
atggctctgc ctgtgacagc tctgctgctg cctctggccc tgctgctgca tgctgccaga      60
cctggatccg acttcgtgct gacccagagc cctcacagcc tgagcgtgac acctggcgag     120
agcgccagca tcagctgcaa gagcagccac tccctgatcc acggcgaccg gaacaactac     180
ctggcttggt acgtgcagaa gcccggcaga tcccccccagc tgctgatcta cctggccagc     240
agcagagcca gcggcgtgcc cgatagattt tctggcagcg gcagcgacaa ggacttcacc     300
ctgaagatca gccgggtgga aaccgaggac gtgggcacct actactgtat gcagggcaga     360
gagagcccct ggaccttggg ccagggcacc aaggtggaca tcaagggcgg cagctccaga     420
agcagctcta gcggaggcgg aggatctggc ggcggaggac aggctcagct ggtgcagtct     480
ggacccgaag tgcggaagcc tggcaccagc gtgaaggtgt cctgtaaagc ccctggcaac     540
accctgaaaa cctacgacct gcactgggtg cgcagcgtgc aggacagggg actgcagtgg     600
atgggctgga tcagccacga gggcgacaag aaagtgatcg tggaacggtt caaggccaaa     660
gtgaccatcg actgggacag aagcaccaac accgcctacc tgcagctgag cggcctgacc     720
tctggcgata ccgccgtgta ctactgcgcc aagggcagca gcaccggct gagagactac     780 gccctgtacg acgatgacgg cgccctgaac tgggccgtgg atgtggacta cctgagcaac     840
ctggaattct ggggccaggg aaccgccgtg accgtgtcat ct                        882
```

```
<210> SEQ ID NO 13
<211> LENGTH: 294
<212> TYPE: PRT
<213> ORGANISM: Artificial Sequence
<220> FEATURE:
<223> OTHER INFORMATION: Artificially Synthesized
```

<400> SEQUENCE: 13

Met Ala Leu Pro Val Thr Ala Leu Leu Leu Pro Leu Ala Leu Leu Leu
1               5                   10                  15

His Ala Ala Arg Pro Gly Ser Asp Phe Val Leu Thr Gln Ser Pro His
            20                  25                  30

Ser Leu Ser Val Thr Pro Gly Glu Ser Ala Ser Ile Ser Cys Lys Ser
        35                  40                  45

Ser His Ser Leu Ile His Gly Asp Arg Asn Asn Tyr Leu Ala Trp Tyr
    50                  55                  60

Val Gln Lys Pro Gly Arg Ser Pro Gln Leu Leu Ile Tyr Leu Ala Ser
65                  70                  75                  80

Ser Arg Ala Ser Gly Val Pro Asp Arg Phe Ser Gly Ser Gly Ser Asp
                85                  90                  95

Lys Asp Phe Thr Leu Lys Ile Ser Arg Val Glu Thr Glu Asp Val Gly
            100                 105                 110

Thr Tyr Tyr Cys Met Gln Gly Arg Glu Ser Pro Trp Thr Phe Gly Gln
        115                 120                 125

Gly Thr Lys Val Asp Ile Lys Gly Gly Ser Ser Arg Ser Ser Ser Ser
    130                 135                 140

Gly Gly Gly Gly Ser Gly Gly Gly Gln Ala Gln Leu Val Gln Ser
145                 150                 155                 160

Gly Pro Glu Val Arg Lys Pro Gly Thr Ser Val Lys Val Ser Cys Lys
                165                 170                 175

Ala Pro Gly Asn Thr Leu Lys Thr Tyr Asp Leu His Trp Val Arg Ser
            180                 185                 190

Val Pro Gly Gln Gly Leu Gln Trp Met Gly Trp Ile Ser His Glu Gly
        195                 200                 205

Asp Lys Lys Val Ile Val Glu Arg Phe Lys Ala Lys Val Thr Ile Asp
    210                 215                 220

Trp Asp Arg Ser Thr Asn Thr Ala Tyr Leu Gln Leu Ser Gly Leu Thr
225                 230                 235                 240

Ser Gly Asp Thr Ala Val Tyr Tyr Cys Ala Lys Gly Ser Lys His Arg
                245                 250                 255

Leu Arg Asp Tyr Ala Leu Tyr Asp Asp Gly Ala Leu Asn Trp Ala
            260                 265                 270

Val Asp Val Asp Tyr Leu Ser Asn Leu Glu Phe Trp Gly Gln Gly Thr
        275                 280                 285

Ala Val Thr Val Ser Ser
    290

<210> SEQ ID NO 14
<211> LENGTH: 1509
<212> TYPE: DNA
<213> ORGANISM: Artificial Sequence
<220> FEATURE:
<223> OTHER INFORMATION: Artificially Synthesized

<400> SEQUENCE: 14 atgggggac ttgaaccctg cagcaggttc ctgctcctgc ctctcctgct ggctgtaagt      60
ggtctccgtc ctgtccaggt ccaggcccag agcgattgca gttgctctac ggtgagcccg     120
ggcgtgctgg cagggatcgt gatgggagac ctggtgctga cagtgctcat tgccctggcc    180
gtgtacttcc tgggccggct ggtccctcgg gggcagggg ctgcggaggc agcgaccccg     240
aaacagcgta tcactgagac cgagtcgcct tatcaggagc tccagggtca gaggtcggat    300

-continued

```
gtctacagcg acctcaacac acagaggccg tattacaaag tcgagggcgg cggagagggc    360
agaggaagtc ttctaacatg cggtgacgtg gaggagaatc ccggcccctag gatggctctg   420
cctgtgacag ctctgctgct gcctctggcc ctgctgctgc atgctgccag acctggatcc   480
cagtctgccc tgactcagcc tcctcctcgcg tccgggtctc ctggacagtc aatcaccatc   540
tcctgcactg gaaccagcaa taactttgtc tcctggtacc agcaacacgc aggcaaggcc   600
cccaagctcg tcatttatga cgtcaataag cgccctcag gtgtccctga tcgtttctct    660
ggctccaagt ctggcaacac ggcctccctg accgtctctg gactccagac tgacgatgag   720
gctgtctatt actgcggctc acttgtaggc aactgggatg tgattttcgg cggagggacc   780
aagttgaccg tcctaggcgg aagcagcaga agcagctcta gcggcggagg cggatctggc   840
ggagggggac agatgcagtt acaggagtcg ggcccccggac tggtgaagcc ttcggaaacc   900
ctgtccctca cgtgcagtgt gtctggtgcc tccataagtg acagttactg gagctggatc   960
cggcggtccc cagggaaggg acttgagtgg attgggtatg tccacaaaag cggcgacaca   1020
aattacagcc cctccctcaa gagtcgagtc aacttgtcgt tagacacgtc caaaatcag    1080
gtgtccctga gccttgtggc cgcgaccgct gcggactcgg caaatatta ttgcgcgaga    1140
acactgcacg ggaggagaat ttatggaatc gttgccttca atgagtggtt cacctacttc   1200
tacatggacg tctggggcaa tgggactcag gtcaccgtct cctcagctag cggcggaggg   1260
ggatctggag gtgggggttc ctcaccccact gaaccaagct ccaaaaccgg taaccccaga  1320
cacctgcatg ttctgattgg gacctcagtg gtcaaaatcc ctttcaccat cctcctcttc   1380
tttctccttc atcgctggtg ctccaacaaa aaaaatgctg ctgtaatgga ccaagagcct   1440
gcagggaaca gaacagtgaa cagcgaggat tctgatgaac aagaccatca ggaggtgtca   1500
tacgcataa                                                           1509
```

<210> SEQ ID NO 15
<211> LENGTH: 503
<212> TYPE: PRT
<213> ORGANISM: Artificial Sequence
<220> FEATURE:
<223> OTHER INFORMATION: Artificially Synthesized

<400> SEQUENCE: 15

```
Met Gly Gly Leu Glu Pro Cys Ser Arg Phe Leu Leu Leu Pro Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys Val Glu Gly Gly Gly Glu Gly Arg Gly Ser Leu Leu Thr Cys Gly
        115                 120                 125

Asp Val Glu Glu Asn Pro Gly Pro Arg Met Ala Leu Pro Val Thr Ala
    130                 135                 140
```

```
Leu Leu Leu Pro Leu Ala Leu Leu Leu His Ala Ala Arg Pro Gly Ser
145                 150                 155                 160

Gln Ser Ala Leu Thr Gln Pro Pro Ser Ala Ser Gly Ser Pro Gly Gln
            165                 170                 175

Ser Ile Thr Ile Ser Cys Thr Gly Thr Ser Asn Asn Phe Val Ser Trp
        180                 185                 190

Tyr Gln Gln His Ala Gly Lys Ala Pro Lys Leu Val Ile Tyr Asp Val
    195                 200                 205

Asn Lys Arg Pro Ser Gly Val Pro Asp Arg Phe Ser Gly Ser Lys Ser
210                 215                 220

Gly Asn Thr Ala Ser Leu Thr Val Ser Gly Leu Gln Thr Asp Asp Glu
225                 230                 235                 240

Ala Val Tyr Tyr Cys Gly Ser Leu Val Gly Asn Trp Asp Val Ile Phe
            245                 250                 255

Gly Gly Gly Thr Lys Leu Thr Val Leu Gly Gly Ser Ser Arg Ser Ser
        260                 265                 270

Ser Ser Gly Gly Gly Gly Ser Gly Gly Gly Gly Gln Met Gln Leu Gln
        275                 280                 285

Glu Ser Gly Pro Gly Leu Val Lys Pro Ser Glu Thr Leu Ser Leu Thr
290                 295                 300

Cys Ser Val Ser Gly Ala Ser Ile Ser Asp Ser Tyr Trp Ser Trp Ile
305                 310                 315                 320

Arg Arg Ser Pro Gly Lys Gly Leu Glu Trp Ile Gly Tyr Val His Lys
            325                 330                 335

Ser Gly Asp Thr Asn Tyr Ser Pro Ser Leu Lys Ser Arg Val Asn Leu
        340                 345                 350

Ser Leu Asp Thr Ser Lys Asn Gln Val Ser Leu Ser Leu Val Ala Ala
    355                 360                 365

Thr Ala Ala Asp Ser Gly Lys Tyr Tyr Cys Ala Arg Thr Leu His Gly
370                 375                 380

Arg Arg Ile Tyr Gly Ile Val Ala Phe Asn Glu Trp Phe Thr Tyr Phe
385                 390                 395                 400

Tyr Met Asp Val Trp Gly Asn Gly Thr Gln Val Thr Val Ser Ser Ala
            405                 410                 415

Ser Gly Gly Gly Gly Ser Gly Gly Gly Gly Ser Ser Pro Thr Glu Pro
        420                 425                 430

Ser Ser Lys Thr Gly Asn Pro Arg His Leu His Val Leu Ile Gly Thr
    435                 440                 445

Ser Val Val Lys Ile Pro Phe Thr Ile Leu Leu Phe Phe Leu Leu His
450                 455                 460

Arg Trp Cys Ser Asn Lys Lys Asn Ala Ala Val Met Asp Gln Glu Pro
465                 470                 475                 480

Ala Gly Asn Arg Thr Val Asn Ser Glu Asp Ser Asp Glu Gln Asp His
            485                 490                 495

Gln Glu Val Ser Tyr Ala Glx
            500
```

<210> SEQ ID NO 16
<211> LENGTH: 834
<212> TYPE: DNA
<213> ORGANISM: Artificial Sequence
<220> FEATURE:
<223> OTHER INFORMATION: Artificially Synthesized

<400> SEQUENCE: 16

```
atggctctgc ctgtgacagc tctgctgctg cctctggccc tgctgctgca tgctgccaga      60
cctggatccc agtctgccct gactcagcct ccctccgcgt ccgggtctcc tggacagtca     120
atcaccatct cctgcactgg aaccagcaat aactttgtct cctggtacca gcaacacgca     180
ggcaaggccc ccaagctcgt catttatgac gtcaataagc gcccctcagg tgtccctgat     240
cgtttctctg gctccaagtc tggcaacacg gcctccctga ccgtctctgg actccagact     300
gacgatgagg ctgtctatta ctgcggctca cttgtaggca actgggatgt gattttcggc     360
ggagggacca gttgaccgt cctaggcgga agcagcagaa gcagctctag cggcggaggc      420
ggatctggcg aggggggaca gatgcagtta caggagtcgg gccccggact ggtgaagcct     480
tcggaaaccc tgtccctcac gtgcagtgtg tctggtgcct ccataagtga cagttactgg     540
agctggatcc ggcggtcccc agggaaggga cttgagtgga ttgggtatgt ccacaaaagc     600
ggcgacacaa attacagccc ctccctcaag agtcgagtca acttgtcgtt agacacgtcc     660
aaaaatcagg tgtccctgag ccttgtggcc gcgaccgctg cggactcggg caaatattat     720
tgcgcgagaa cactgcacgg aggagaatt  tatggaatcg ttgccttcaa tgagtggttc     780
acctacttct acatggacgt ctggggcaat gggactcagg tcaccgtctc ctca           834
```

<210> SEQ ID NO 17
<211> LENGTH: 278
<212> TYPE: PRT
<213> ORGANISM: Artificial Sequence
<220> FEATURE:
<223> OTHER INFORMATION: Artificially Synthesized

<400> SEQUENCE: 17

```
Met Ala Leu Pro Val Thr Ala Leu Leu Pro Leu Ala Leu Leu
1               5                   10                  15

His Ala Ala Arg Pro Gly Ser Gln Ser Ala Leu Thr Gln Pro Pro Ser
                20                  25                  30

Ala Ser Gly Ser Pro Gly Gln Ser Ile Thr Ile Ser Cys Thr Gly Thr
            35                  40                  45

Ser Asn Asn Phe Val Ser Trp Tyr Gln Gln His Ala Gly Lys Ala Pro
        50                  55                  60

Lys Leu Val Ile Tyr Asp Val Asn Lys Arg Pro Ser Gly Val Pro Asp
65                  70                  75                  80

Arg Phe Ser Gly Ser Lys Ser Gly Asn Thr Ala Ser Leu Thr Val Ser
                85                  90                  95

Gly Leu Gln Thr Asp Asp Glu Ala Val Tyr Tyr Cys Gly Ser Leu Val
                100                 105                 110

Gly Asn Trp Asp Val Ile Phe Gly Gly Gly Thr Lys Leu Thr Val Leu
            115                 120                 125

Gly Gly Ser Ser Arg Ser Ser Ser Gly Gly Gly Ser Gly Gly
        130                 135                 140

Gly Gly Gln Met Gln Leu Gln Glu Ser Gly Pro Gly Leu Val Lys Pro
145                 150                 155                 160

Ser Glu Thr Leu Ser Leu Thr Cys Ser Val Ser Gly Ala Ser Ile Ser
                165                 170                 175

Asp Ser Tyr Trp Ser Trp Ile Arg Arg Ser Pro Gly Lys Gly Leu Glu
            180                 185                 190
```

```
Trp Ile Gly Tyr Val His Lys Ser Gly Asp Thr Asn Tyr Ser Pro Ser
            195                 200                 205

Leu Lys Ser Arg Val Asn Leu Ser Leu Asp Thr Ser Lys Asn Gln Val
    210                 215                 220

Ser Leu Ser Leu Val Ala Ala Thr Ala Ala Asp Ser Gly Lys Tyr Tyr
225                 230                 235                 240

Cys Ala Arg Thr Leu His Gly Arg Arg Ile Tyr Gly Ile Val Ala Phe
            245                 250                 255

Asn Glu Trp Phe Thr Tyr Phe Tyr Met Asp Val Trp Gly Asn Gly Thr
            260                 265                 270

Gln Val Thr Val Ser Ser
            275

<210> SEQ ID NO 18
<211> LENGTH: 1473
<212> TYPE: DNA
<213> ORGANISM: Artificial Sequence
<220> FEATURE:
<223> OTHER INFORMATION: Artificially Synthesized

<400> SEQUENCE: 18
```

| | | | | | |
|---|---|---|---|---|---|
| atgggggac | ttgaaccctg | cagcaggttc | ctgctcctgc | tctcctgct | ggctgtaagt | 60 |
| ggtctccgtc | ctgtccaggt | ccaggcccag | agcgattgca | gttgctctac | ggtgagcccg | 120 |
| ggcgtgctgg | cagggatcgt | gatgggagac | ctggtgctga | cagtgctcat | tgccctggcc | 180 |
| gtgtacttcc | tgggccggct | ggtccctcgg | gggcgagggg | ctgcggaggc | agcgacccgg | 240 |
| aaacagcgta | tcactgagac | cgagtcgcct | atcaggagc | tccagggtca | gaggtcggat | 300 |
| gtctacagcg | acctcaacac | acagaggccg | tattacaaag | tcgagggcgg | cggagagggc | 360 |
| agaggaagtc | ttctaacatg | cggtgacgtg | gaggagaatc | ccggccctag | gatggctctg | 420 |
| cctgtgacag | ctctgctgct | gcctctggcc | ctgctgctgc | atgctgccag | acctggatcc | 480 |
| gagatcgtgc | tgacacagag | ccctggcacc | ctgagcctgt | ctccaggcga | cagccatc | 540 |
| atcagctgcc | ggacaagcca | gtacggcagc | ctggcctggt | atcagcagag | gcctggacag | 600 |
| gccccagac | tcgtgatcta | cagcggcagc | acaagccg | ccggaatccc | cgatagattc | 660 |
| agcggctcta | gatggggccc | tgactacaac | ctgaccatca | gcaacctgga | aagcggcgac | 720 |
| ttcggcgtgt | actactgcca | gcagtacgag | ttcttcggcc | agggcaccaa | ggtgcaggtg | 780 |
| gacatcaaga | gaggcggcag | ctccagaagc | tccagctctg | gcggcggagg | atctggcgga | 840 |
| ggcggacagg | tgcagctggt | gcagtctggc | ggccagatga | agaaacccgg | cgagagcatg | 900 |
| cggatcagct | gcagagcctc | cggctacgag | ttcatcgact | gcaccctgaa | ctggattcgg | 960 |
| ctggccctg | caaaagacc | cgagtggatg | ggctggctga | agcccagagg | cggagccgtg | 1020 |
| aattacgcca | gacctctgca | gggcagagtg | accatgaccc | gggacgtgta | cagcgatacc | 1080 |
| gccttcctgg | aactgcggag | cctgaccgtg | gatgataccg | ccgtgtactt | ctgcacccgg | 1140 |
| ggcaagaact | gcgactacaa | ctgggacttc | gagcactggg | gcagaggcac | ccctgtgatc | 1200 |
| gtgtctagcg | ctagcggcgg | agggggatct | ggaggtgggg | gttcctcacc | cactgaacca | 1260 |
| agctccaaaa | ccggtaaccc | cagacacctg | catgttctga | ttgggacctc | agtggtcaaa | 1320 |
| atccctttca | ccatcctcct | cttctttctc | cttcatcgct | ggtgctccaa | caaaaaaaat | 1380 |
| gctgctgtaa | tggaccaaga | gcctgcaggg | aacagaacag | tgaacagcga | ggattctgat | 1440 |
| gaacaagacc | atcaggaggt | gtcatacgca | taa | | | 1473 |

```
<210> SEQ ID NO 19
<211> LENGTH: 491
<212> TYPE: PRT
<213> ORGANISM: Artificial Sequence
<220> FEATURE:
<223> OTHER INFORMATION: Artificially Synthesized

<400> SEQUENCE: 19

Met Gly Gly Leu Glu Pro Cys Ser Arg Phe Leu Leu Leu Pro Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys Val Glu Gly Gly Glu Gly Arg Gly Ser Leu Leu Thr Cys Gly
            115                 120                 125

Asp Val Glu Glu Asn Pro Gly Pro Arg Met Ala Leu Pro Val Thr Ala
        130                 135                 140

Leu Leu Leu Pro Leu Ala Leu Leu His Ala Ala Arg Pro Gly Ser
145                 150                 155                 160

Glu Ile Val Leu Thr Gln Ser Pro Gly Thr Leu Ser Leu Ser Pro Gly
                165                 170                 175

Glu Thr Ala Ile Ile Ser Cys Arg Thr Ser Gln Tyr Gly Ser Leu Ala
            180                 185                 190

Trp Tyr Gln Gln Arg Pro Gly Gln Ala Pro Arg Leu Val Ile Tyr Ser
        195                 200                 205

Gly Ser Thr Arg Ala Ala Gly Ile Pro Asp Arg Phe Ser Gly Ser Arg
    210                 215                 220

Trp Gly Pro Asp Tyr Asn Leu Thr Ile Ser Asn Leu Glu Ser Gly Asp
225                 230                 235                 240

Phe Gly Val Tyr Tyr Cys Gln Gln Tyr Glu Phe Phe Gly Gln Gly Thr
                245                 250                 255

Lys Val Gln Val Asp Ile Lys Arg Gly Gly Ser Ser Arg Ser Ser Ser
            260                 265                 270

Ser Gly Gly Gly Gly Ser Gly Gly Gly Gln Val Gln Leu Val Gln
        275                 280                 285

Ser Gly Gly Gln Met Lys Lys Pro Gly Glu Ser Met Arg Ile Ser Cys
    290                 295                 300

Arg Ala Ser Gly Tyr Glu Phe Ile Asp Cys Thr Leu Asn Trp Ile Arg
305                 310                 315                 320

Leu Ala Pro Gly Lys Arg Pro Glu Trp Met Gly Trp Leu Lys Pro Arg
                325                 330                 335

Gly Gly Ala Val Asn Tyr Ala Arg Pro Leu Gln Gly Arg Val Thr Met
            340                 345                 350

Thr Arg Asp Val Tyr Ser Asp Thr Ala Phe Leu Glu Leu Arg Ser Leu
        355                 360                 365
```

Thr Val Asp Asp Thr Ala Val Tyr Phe Cys Thr Arg Gly Lys Asn Cys
        370                 375                 380

Asp Tyr Asn Trp Asp Phe Glu His Trp Gly Arg Gly Thr Pro Val Ile
385                 390                 395                 400

Val Ser Ser Ala Ser Gly Gly Gly Ser Gly Gly Gly Ser Ser
                405                 410                 415

Pro Thr Glu Pro Ser Ser Lys Thr Gly Asn Pro Arg His Leu His Val
            420                 425                 430

Leu Ile Gly Thr Ser Val Val Lys Ile Pro Phe Thr Ile Leu Leu Phe
        435                 440                 445

Phe Leu Leu His Arg Trp Cys Ser Asn Lys Lys Asn Ala Ala Val Met
    450                 455                 460

Asp Gln Glu Pro Ala Gly Asn Arg Thr Val Asn Ser Glu Asp Ser Asp
465                 470                 475                 480

Glu Gln Asp His Gln Glu Val Ser Tyr Ala Glx
                485                 490

<210> SEQ ID NO 20
<211> LENGTH: 798
<212> TYPE: DNA
<213> ORGANISM: Artificial Sequence
<220> FEATURE:
<223> OTHER INFORMATION: Artificially Synthesized

<400> SEQUENCE: 20

```
atggccctgc ctgtgacagc cctgctgctg cctctggctc tgctgctgca cgccgctaga      60
cctggatccg agatcgtgct gacacagagc cctggcaccc tgagcctgtc tccaggcgag     120
acagccatca tcagctgccg gacaagccag tacggcagcc tggcctggta tcagcagagg     180
cctggacagg cccccagact cgtgatctac agcggcagca agagccgcc ggaatcccc       240 gatagattca gcggctctag atggggccct gactacaacc tgaccatcag caacctggaa     300
agcggcgact cggcgtgta ctactgccag cagtacgagt tcttcggcca gggcaccaag      360
gtgcaggtgg acatcaagag aggcggcagc tccagaagct ccagctctgg cggcggagga     420
tctggcggag gcgacaggt gcagctggtg cagtctggcg ccagatgaa gaaacccggc       480 gagagcatgc ggatcagctg cagagcctcc ggctacgagt tcatcgactg caccctgaac     540
tggattcggc tggcccctgg caaaagaccc gagtggatgg gctggctgaa gcccagaggc     600
ggagccgtga attacgccag acctctgcag ggcagagtga ccatgacccg ggacgtgtac     660
agcgataccg ccttcctgga actgcggagc ctgaccgtgg atgataccgc cgtgtacttc     720
tgcacccggg gcaagaactg cgactacaac tgggacttcg agcactgggg cagaggcacc     780
cctgtgatcg tgtctagc                                                   798
```

<210> SEQ ID NO 21
<211> LENGTH: 266
<212> TYPE: PRT
<213> ORGANISM: Artificial Sequence
<220> FEATURE:
<223> OTHER INFORMATION: Artificially Synthesized

<400> SEQUENCE: 21

Met Ala Leu Pro Val Thr Ala Leu Leu Leu Pro Leu Ala Leu Leu Leu
1               5                   10                  15

His Ala Ala Arg Pro Gly Ser Glu Ile Val Leu Thr Gln Ser Pro Gly
            20                  25                  30

Thr Leu Ser Leu Ser Pro Gly Glu Thr Ala Ile Ile Ser Cys Arg Thr
            35                  40                  45
Ser Gln Tyr Gly Ser Leu Ala Trp Tyr Gln Gln Arg Pro Gly Gln Ala
    50                  55                  60
Pro Arg Leu Val Ile Tyr Ser Gly Ser Thr Arg Ala Ala Gly Ile Pro
65                  70                  75                  80
Asp Arg Phe Ser Gly Ser Arg Trp Gly Pro Asp Tyr Asn Leu Thr Ile
                85                  90                  95
Ser Asn Leu Glu Ser Gly Asp Phe Gly Val Tyr Cys Gln Gln Tyr
            100                 105                 110
Glu Phe Phe Gly Gln Gly Thr Lys Val Gln Val Asp Ile Lys Arg Gly
        115                 120                 125
Gly Ser Ser Arg Ser Ser Ser Gly Gly Gly Ser Gly Gly Gly
    130                 135                 140
Gly Gln Val Gln Leu Val Gln Ser Gly Gly Gln Met Lys Lys Pro Gly
145                 150                 155                 160
Glu Ser Met Arg Ile Ser Cys Arg Ala Ser Gly Tyr Glu Phe Ile Asp
                165                 170                 175
Cys Thr Leu Asn Trp Ile Arg Leu Ala Pro Gly Lys Arg Pro Glu Trp
            180                 185                 190
Met Gly Trp Leu Lys Pro Arg Gly Gly Ala Val Asn Tyr Ala Arg Pro
        195                 200                 205
Leu Gln Gly Arg Val Thr Met Thr Arg Asp Val Tyr Ser Asp Thr Ala
    210                 215                 220
Phe Leu Glu Leu Arg Ser Leu Thr Val Asp Asp Thr Ala Val Tyr Phe
225                 230                 235                 240
Cys Thr Arg Gly Lys Asn Cys Asp Tyr Asn Trp Asp Phe Glu His Trp
                245                 250                 255
Gly Arg Gly Thr Pro Val Ile Val Ser Ser
            260                 265

<210> SEQ ID NO 22
<211> LENGTH: 1464
<212> TYPE: DNA
<213> ORGANISM: Artificial Sequence
<220> FEATURE:
<223> OTHER INFORMATION: Artificially Synthesized

<400> SEQUENCE: 22 atgggggac ttgaaccctg cagcaggttc ctgctcctgc ctctcctgct ggctgtaagt     60
ggtctccgtc ctgtccaggt ccaggcccag agcgattgca gttgctctac ggtgagcccg    120
ggcgtgctgg cagggatcgt gatgggagac tggtgctga cagtgctcat tgccctggcc    180
gtgtacttcc tgggccggct ggtccctcgg gggcgagggg ctgcggaggc agcgacccgg    240
aaacagcgta tcactgagac cgagtcgcct tatcaggagc tccagggtca gaggtcggat    300
gtctacagcg acctcaacac acagaggccg tattacaaag tcgagggcgg cggagagggc    360
agaggaagtc ttctaacatg cggtgacgtg aggagaatc ccggccctag gatggctctg    420
cctgtgacag ctctgctgct gcctctggcc ctgctgctgc atgctgccag acctggatcc    480
gacatccaga tgacccagag ccccagcagc ctgtctgcca gagtgggcga caccgtgacc    540
atcacctgtc aggccaacgg ctacctgaac tggtatcagc agcggagagg caaggccccc    600
aagctgctga tctacgacgg cagcaagctg gaaagaggcg tgcccgccag attcagcggc    660
agaagatggg gccaggagta caacctgacc atcaacaacc tgcagcccga ggacgtggcc    720

```
acatactttt gccaggtgta cgagttcatc gtgcccggca cccggctgga tctgaagggc    780
ggaagcagca gaagcagctc tagcggcgga ggcggatctg gcggaggggg acaggtgcac    840
ctgagtcagt ctggcgccgc tgtgacaaag ccaggcgctt ctgtgcgggt gtcctgtgaa    900
gccagcggct acaagatcag cgaccacttc atccactggt ggcggcaggc tccaggacag    960
ggactgcagt gggtgggatg gatcaacccc aagaccggcc agcccaacaa ccccagacag   1020
ttccagggca gagtgtccct gaccagacag gccagctggg acttcgacac ctacagcttc   1080
tacatggacc tgaaggccgt gcggagcgac gacaccgcca tctactttg cgccagacag    1140 agaagcgact ctgggatttt cgacgtgtgg ggcagcggca cccaagtgac cgtgtcatct   1200
gctagcggcg agggggatc tggaggtggg ggttcctcac ccactgaacc aagctccaaa    1260
accggtaacc ccagacacct gcatgttctg attgggacct cagtggtcaa aatcccttc    1320 accatcctcc tcttctttct ccttcatcgc tggtgctcca acaaaaaaaa tgctgctgta   1380
atggaccaag agcctgcagg gaacagaaca gtgaacagcg aggattctga tgaacaagac   1440
catcaggagg tgtcatacgc ataa                                           1464
```

<210> SEQ ID NO 23
<211> LENGTH: 488
<212> TYPE: PRT
<213> ORGANISM: Artificial Sequence
<220> FEATURE:
<223> OTHER INFORMATION: Artificially Synthesized

<400> SEQUENCE: 23

```
Met Gly Gly Leu Glu Pro Cys Ser Arg Phe Leu Leu Leu Pro Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys Val Glu Gly Gly Gly Glu Gly Arg Gly Ser Leu Leu Thr Cys Gly
        115                 120                 125

Asp Val Glu Glu Asn Pro Gly Pro Arg Met Ala Leu Pro Val Thr Ala
    130                 135                 140

Leu Leu Leu Pro Leu Ala Leu Leu His Ala Ala Arg Pro Gly Ser
145                 150                 155                 160

Asp Ile Gln Met Thr Gln Ser Pro Ser Ser Leu Ser Ala Arg Val Gly
                165                 170                 175

Asp Thr Val Thr Ile Thr Cys Gln Ala Asn Gly Tyr Leu Asn Trp Tyr
            180                 185                 190

Gln Gln Arg Arg Gly Lys Ala Pro Lys Leu Leu Ile Tyr Asp Gly Ser
        195                 200                 205

Lys Leu Glu Arg Gly Val Pro Ala Arg Phe Ser Gly Arg Trp Gly
    210                 215                 220
```

Gln Glu Tyr Asn Leu Thr Ile Asn Asn Leu Gln Pro Glu Asp Val Ala
225                 230                 235                 240

Thr Tyr Phe Cys Gln Val Tyr Glu Phe Ile Val Pro Gly Thr Arg Leu
            245                 250                 255

Asp Leu Lys Gly Gly Ser Ser Arg Ser Ser Ser Gly Gly Gly Gly
        260                 265                 270

Ser Gly Gly Gly Gly Gln Val His Leu Ser Gln Ser Gly Ala Ala Val
    275                 280                 285

Thr Lys Pro Gly Ala Ser Val Arg Val Ser Cys Glu Ala Ser Gly Tyr
    290                 295                 300

Lys Ile Ser Asp His Phe Ile His Trp Trp Arg Gln Ala Pro Gly Gln
305                 310                 315                 320

Gly Leu Gln Trp Val Gly Trp Ile Asn Pro Lys Thr Gly Gln Pro Asn
                325                 330                 335

Asn Pro Arg Gln Phe Gln Gly Arg Val Ser Leu Thr Arg Gln Ala Ser
            340                 345                 350

Trp Asp Phe Asp Thr Tyr Ser Phe Tyr Met Asp Leu Lys Ala Val Arg
        355                 360                 365

Ser Asp Asp Thr Ala Ile Tyr Phe Cys Ala Arg Gln Arg Ser Asp Phe
370                 375                 380

Trp Asp Phe Asp Val Trp Gly Ser Gly Thr Gln Val Thr Val Ser Ser
385                 390                 395                 400

Ala Ser Gly Gly Gly Gly Ser Gly Gly Gly Gly Ser Ser Pro Thr Glu
                405                 410                 415

Pro Ser Ser Lys Thr Gly Asn Pro Arg His Leu His Val Leu Ile Gly
            420                 425                 430

Thr Ser Val Val Lys Ile Pro Phe Thr Ile Leu Leu Phe Phe Leu Leu
        435                 440                 445

His Arg Trp Cys Ser Asn Lys Lys Asn Ala Ala Val Met Asp Gln Glu
    450                 455                 460

Pro Ala Gly Asn Arg Thr Val Asn Ser Glu Asp Ser Asp Glu Gln Asp
465                 470                 475                 480

His Gln Glu Val Ser Tyr Ala Glx
                485

<210> SEQ ID NO 24
<211> LENGTH: 720
<212> TYPE: DNA
<213> ORGANISM: Artificial Sequence
<220> FEATURE:
<223> OTHER INFORMATION: Artificially Synthesized

<400> SEQUENCE: 24
gacatccaga tgacccagag ccccagcagc ctgtctgcca gagtgggcga caccgtgacc      60
atcacctgtc aggccaacgg ctacctgaac tggtatcagc agcggagagg caaggccccc     120
aagctgctga tctacgacgg cagcaagctg aaagaggcg tgcccgccag attcagcggc     180
agaagatggg gccaggagta caacctgacc atcaacaacc tgcagcccga ggacgtggcc     240
acatactttt gccaggtgta cgagttcatc gtgcccggca cccggctgga tctgaagggc     300
ggaagcagca gaagcagctc tagcggcgga ggcggatctg gcggaggggg acaggtgcac     360
ctgagtcagt ctggcgccgc tgtgacaaag ccaggcgctt ctgtgcgggt gtcctgtgaa     420
gccagcggct acaagatcag cgaccacttc atccactggt ggcggcaggc tccaggacag     480

```
ggactgcagt gggtgggatg gatcaacccc aagaccggcc agcccaacaa ccccagacag    540
ttccagggca gagtgtccct gaccagacag gccagctggg acttcgacac ctacagcttc    600
tacatggacc tgaaggccgt gcggagcgac gacaccgcca tctactttg cgccagacag    660 agaagcgact ctgggattt cgacgtgtgg ggcagcggca cccaagtgac cgtgtcatct    720
```

<210> SEQ ID NO 25
<211> LENGTH: 263
<212> TYPE: PRT
<213> ORGANISM: Artificial Sequence
<220> FEATURE:
<223> OTHER INFORMATION: Artificially Synthesized

<400> SEQUENCE: 25

```
Met Ala Leu Pro Val Thr Ala Leu Leu Leu Pro Leu Ala Leu Leu Leu
1               5                   10                  15

His Ala Ala Arg Pro Gly Ser Asp Ile Gln Met Thr Gln Ser Pro Ser
            20                  25                  30

Ser Leu Ser Ala Arg Val Gly Asp Thr Val Thr Ile Thr Cys Gln Ala
        35                  40                  45

Asn Gly Tyr Leu Asn Trp Tyr Gln Gln Arg Arg Gly Lys Ala Pro Lys
    50                  55                  60

Leu Leu Ile Tyr Asp Gly Ser Lys Leu Glu Arg Gly Val Pro Ala Arg
65                  70                  75                  80

Phe Ser Gly Arg Arg Trp Gly Gln Glu Tyr Asn Leu Thr Ile Asn Asn
                85                  90                  95

Leu Gln Pro Glu Asp Val Ala Thr Tyr Phe Cys Gln Val Tyr Glu Phe
            100                 105                 110

Ile Val Pro Gly Thr Arg Leu Asp Leu Lys Gly Gly Ser Ser Arg Ser
        115                 120                 125

Ser Ser Ser Gly Gly Gly Ser Gly Gly Gly Gln Val His Leu
    130                 135                 140

Ser Gln Ser Gly Ala Ala Val Thr Lys Pro Gly Ala Ser Val Arg Val
145                 150                 155                 160

Ser Cys Glu Ala Ser Gly Tyr Lys Ile Ser Asp His Phe Ile His Trp
                165                 170                 175

Trp Arg Gln Ala Pro Gly Gln Gly Leu Gln Trp Val Gly Trp Ile Asn
            180                 185                 190

Pro Lys Thr Gly Gln Pro Asn Asn Pro Arg Gln Phe Gln Gly Arg Val
        195                 200                 205

Ser Leu Thr Arg Gln Ala Ser Trp Asp Phe Asp Thr Tyr Ser Phe Tyr
    210                 215                 220

Met Asp Leu Lys Ala Val Arg Ser Asp Asp Thr Ala Ile Tyr Phe Cys
225                 230                 235                 240

Ala Arg Gln Arg Ser Asp Phe Trp Asp Phe Asp Val Trp Gly Ser Gly
                245                 250                 255

Thr Gln Val Thr Val Ser Ser
            260
```

<210> SEQ ID NO 26
<211> LENGTH: 1473
<212> TYPE: DNA
<213> ORGANISM: Artificial Sequence
<220> FEATURE:
<223> OTHER INFORMATION: Artificially Synthesized

<400> SEQUENCE: 26

```
atgggggac ttgaaccctg cagcaggttc ctgctcctgc ctctcctgct ggctgtaagt      60
ggtctccgtc ctgtccaggt ccaggcccag agcgattgca gttgctctac ggtgagcccg     120
ggcgtgctgg cagggatcgt gatgggagac ctggtgctga cagtgctcat tgccctggcc     180
gtgtacttcc tgggccggct ggtccctcgg gggcgagggg ctgcggaggc agcgacccgg     240
aaacagcgta tcactgagac cgagtcgcct tatcaggagc tccagggtca gaggtcggat     300
gtctacagcg acctcaacac acagaggccg tattacaaag tcgagggcgg cggagagggc     360
agaggaagtc ttctaacatg cggtgacgtg gaggagaatc ccggccctag gatggctctg     420
cctgtgacag ctctgctgct gcctctggcc ctgctgctgc atgctgccag acctggatcc     480
gagatcgtgc tgacacagag ccctggcacc ctgagcctgt ctccaggcga cagccatc      540
atcagctgcc ggacaagcca gtacggcagc tggcctggt atcagcagag gcctggacag     600
gccccagac tcgtgatcta cagcggcagc acaagagccg ccggaatccc cgatagattc     660
agcggctcta gatggggccc tgactacaac ctgaccatca gcaacctgga agcggcgac    720
ttcgcgtgt actactgcca gcagtacgag ttcttcggcc agggcaccaa ggtgcaggtg     780
gacatcaaga gaggtggttc ctctagatct tcctcctctg gtggcggtgg ctcgggcggt     840
ggtgggcagg tgcagctggt gcagtctggc ggccagatga agaaacccgg cgagagcatg     900
cggatcagct gcagagcctc cggctacgag ttcatcgacg ccaccctgaa ctggattcgg     960
ctggccctg gcaaaagacc cgagtggatg ggctggctga gcccagagg cggagccgtg    1020
aattacgcca gacctctgca gggcagagtg accatgaccc gggacgtgta cagcgatacc    1080
gccttcctgg aactgcggag cctgaccgtg gatgataccg ccgtgtactt ctgcacccgg    1140
ggcaagaaca gcgactacaa ctgggacttc gagcactggg gcagaggcac ccctgtgatc    1200
gtgtctagcg ctagcggcgg aggggatct ggaggtgggg ttcctcacc cactgaacca    1260
agctccaaaa ccggtaaccc cagacacctg catgttctga ttgggaccctc agtggtcaaa    1320
atccctttca ccatcctcct cttctttctc cttcatcgct ggtgctccaa caaaaaat    1380
gctgctgtaa tggaccaaga gcctgcaggg aacagaacag tgaacagcga ggattctgat    1440
gaacaagacc atcaggaggt gtcatacgca taa                                1473
```

<210> SEQ ID NO 27
<211> LENGTH: 491
<212> TYPE: PRT
<213> ORGANISM: Artificial Sequence
<220> FEATURE:
<223> OTHER INFORMATION: Artificially Synthesized

<400> SEQUENCE: 27

```
Met Gly Gly Leu Glu Pro Cys Ser Arg Phe Leu Leu Leu Pro Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80
```

```
Lys Gln Arg Ile Thr Glu Thr Glu Ser Pro Tyr Gln Glu Leu Gln Gly
                85                  90                  95
Gln Arg Ser Asp Val Tyr Ser Asp Leu Asn Thr Gln Arg Pro Tyr Tyr
            100                 105                 110
Lys Val Glu Gly Gly Glu Gly Arg Gly Ser Leu Leu Thr Cys Gly
        115                 120                 125
Asp Val Glu Asn Pro Gly Pro Arg Met Ala Leu Pro Val Thr Ala
    130                 135                 140
Leu Leu Leu Pro Leu Ala Leu Leu Leu His Ala Ala Arg Pro Gly Ser
145                 150                 155                 160
Glu Ile Val Leu Thr Gln Ser Pro Gly Thr Leu Ser Leu Ser Pro Gly
                165                 170                 175
Glu Thr Ala Ile Ile Ser Cys Arg Thr Ser Gln Tyr Gly Ser Leu Ala
                180                 185                 190
Trp Tyr Gln Gln Arg Pro Gly Gln Ala Pro Arg Leu Val Ile Tyr Ser
                195                 200                 205
Gly Ser Thr Arg Ala Ala Gly Ile Pro Asp Arg Phe Ser Gly Ser Arg
            210                 215                 220
Trp Gly Pro Asp Tyr Asn Leu Thr Ile Ser Asn Leu Glu Ser Gly Asp
225                 230                 235                 240
Phe Gly Val Tyr Tyr Cys Gln Gln Tyr Glu Phe Phe Gly Gln Gly Thr
                245                 250                 255
Lys Val Gln Val Asp Ile Lys Arg Gly Gly Ser Ser Arg Ser Ser Ser
            260                 265                 270
Ser Gly Gly Gly Gly Ser Gly Gly Gly Gly Gln Val Gln Leu Val Gln
        275                 280                 285
Ser Gly Gly Gln Met Lys Lys Pro Gly Glu Ser Met Arg Ile Ser Cys
    290                 295                 300
Arg Ala Ser Gly Tyr Glu Phe Ile Asp Ala Thr Leu Asn Trp Ile Arg
305                 310                 315                 320
Leu Ala Pro Gly Lys Arg Pro Glu Trp Met Gly Trp Leu Lys Pro Arg
                325                 330                 335
Gly Gly Ala Val Asn Tyr Ala Arg Pro Leu Gln Gly Arg Val Thr Met
                340                 345                 350
Thr Arg Asp Val Tyr Ser Asp Thr Ala Phe Leu Glu Leu Arg Ser Leu
            355                 360                 365
Thr Val Asp Asp Thr Ala Val Tyr Phe Cys Thr Arg Gly Lys Asn Ser
        370                 375                 380
Asp Tyr Asn Trp Asp Phe Glu His Trp Gly Arg Gly Thr Pro Val Ile
385                 390                 395                 400
Val Ser Ser Ala Ser Gly Gly Gly Gly Ser Gly Gly Gly Gly Ser Ser
                405                 410                 415
Pro Thr Glu Pro Ser Ser Lys Thr Gly Asn Pro Arg His Leu His Val
            420                 425                 430
Leu Ile Gly Thr Ser Val Val Lys Ile Pro Phe Thr Ile Leu Leu Phe
        435                 440                 445
Phe Leu Leu His Arg Trp Cys Ser Asn Lys Lys Asn Ala Ala Val Met
    450                 455                 460
Asp Gln Glu Pro Ala Gly Asn Arg Thr Val Asn Ser Glu Asp Ser Asp
465                 470                 475                 480
Glu Gln Asp His Gln Glu Val Ser Tyr Ala Glx
                485                 490
```

<210> SEQ ID NO 28
<211> LENGTH: 729
<212> TYPE: DNA
<213> ORGANISM: Artificial Sequence
<220> FEATURE:
<223> OTHER INFORMATION: Artificially Synthesized

<400> SEQUENCE: 28

```
gagatcgtgc tgacacagag ccctggcacc ctgagcctgt ctccaggcga gacagccatc      60
atcagctgcc ggacaagcca gtacggcagc ctggcctggt atcagcagag gcctggacag     120
gcccccagac tcgtgatcta cagcggcagc acaagagccg ccggaatccc cgatagattc     180
agcggctcta gatggggccc tgactacaac ctgaccatca gcaacctgga aagcggcgac     240
ttcggcgtgt actactgcca gcagtacgag ttcttcggcc agggcaccaa ggtgcaggtg     300
gacatcaaga gaggcggcag ctccagaagc tccagctctg gcggcggagg atctggcgga     360
ggcggacagg tgcagctggt gcagtctggc ggccagatga agaaacccgg cgagagcatg     420
cggatcagct gcagagcctc cggctacgag ttcatcgaca gcaccctgaa ctggattcgg     480
ctggcccctg gcaaaagacc cgagtggatg ggctggctga gcccagagg cggagccgtg     540
aattacgcca gacctctgca gggcagagtg accatgaccc gggacgtgta cagcgatacc     600
gccttcctgg aactgcggag cctgaccgtg gatgataccg ccgtgtactt ctgcacccgg     660
ggcaagaacg ccgactacaa ctgggacttc gagcactggg gcagaggcac ccctgtgatc     720
gtgtctagc                                                             729
```

<210> SEQ ID NO 29
<211> LENGTH: 266
<212> TYPE: PRT
<213> ORGANISM: Artificial Sequence
<220> FEATURE:
<223> OTHER INFORMATION: Artificially Synthesized

<400> SEQUENCE: 29

```
Met Ala Leu Pro Val Thr Ala Leu Leu Leu Pro Leu Ala Leu Leu Leu
1               5                   10                  15

His Ala Ala Arg Pro Gly Ser Glu Ile Val Leu Thr Gln Ser Pro Gly
            20                  25                  30

Thr Leu Ser Leu Ser Pro Gly Glu Thr Ala Ile Ile Ser Cys Arg Thr
        35                  40                  45

Ser Gln Tyr Gly Ser Leu Ala Trp Tyr Gln Gln Arg Pro Gly Gln Ala
    50                  55                  60

Pro Arg Leu Val Ile Tyr Ser Gly Ser Thr Arg Ala Ala Gly Ile Pro
65                  70                  75                  80

Asp Arg Phe Ser Gly Ser Arg Trp Gly Pro Asp Tyr Asn Leu Thr Ile
                85                  90                  95

Ser Asn Leu Glu Ser Gly Asp Phe Gly Val Tyr Tyr Cys Gln Gln Tyr
            100                 105                 110

Glu Phe Phe Gly Gln Gly Thr Lys Val Gln Val Asp Ile Lys Arg Gly
        115                 120                 125

Gly Ser Ser Arg Ser Ser Ser Gly Gly Gly Ser Gly Gly Gly
    130                 135                 140

Gly Gln Val Gln Leu Val Gln Ser Gly Gly Gln Met Lys Lys Pro Gly
145                 150                 155                 160

Glu Ser Met Arg Ile Ser Cys Arg Ala Ser Gly Tyr Glu Phe Ile Asp
                165                 170                 175
```

```
Ser Thr Leu Asn Trp Ile Arg Leu Ala Pro Gly Lys Arg Pro Glu Trp
            180                 185                 190

Met Gly Trp Leu Lys Pro Arg Gly Gly Ala Val Asn Tyr Ala Arg Pro
            195                 200                 205

Leu Gln Gly Arg Val Thr Met Thr Arg Asp Val Tyr Ser Asp Thr Ala
            210                 215                 220

Phe Leu Glu Leu Arg Ser Leu Thr Val Asp Asp Thr Ala Val Tyr Phe
225                 230                 235                 240

Cys Thr Arg Gly Lys Asn Ala Asp Tyr Asn Trp Asp Phe Glu His Trp
                245                 250                 255

Gly Arg Gly Thr Pro Val Ile Val Ser Ser
            260                 265

<210> SEQ ID NO 30
<211> LENGTH: 1857
<212> TYPE: DNA
<213> ORGANISM: Artificial Sequence
<220> FEATURE:
<223> OTHER INFORMATION: Artificially Synthesized

<400> SEQUENCE: 30 atgggggac ttgaaccctg cagcaggttc ctgctcctgc ctctcctgct ggctgtaagt      60
ggtctccgtc ctgtccaggt ccaggcccag agcgattgca gttgctctac ggtgagcccg    120
ggcgtgctgg cagggatcgt gatgggagac ctggtgctga cagtgctcat tgccctggcc    180
gtgtacttcc tgggccggct ggtccctcgg gggcgagggg ctgcggaggc agcgacccgg    240
aaacagcgta tcactgagac cgagtcgcct tatcaggagc tccagggtca gaggtcggat    300
gtctacagcg acctcaacac acagaggccg tattacaaag tcgagggcgg cggagagggc    360
agaggaagtc ttctaacatg cggtgacgtg aggagaatc ccggcctag gatggctctg    420 cctgtgacag ctctgctgct gcctctggcc ctgctgctgc atgctgccag acctggatcc    480
aagaaagtgg tgcttggcaa gaagggcgac accgtgaac tgacctgcac cgccagccag    540
aagaagtcca tccagttcca ctggaagaac agcaaccaga tcaagatcct gggcaaccag    600
ggcagcttcc tgaccaaggg ccccagcaag ctgaacgaca gagccgactc tcggcggagc    660
ctgtgggacc agggcaattt cccactgatc atcaagaacc tgaagatcga ggacagcgac    720
acctacatct gcgaggtgga agatcagaaa gaagaggtgc agctgctggt gttcggcctg    780
accgccaact ccgacaccca tctgctgcag gccagagcc tgaccctgac actggaaagc    840
cctccaggca gcagcccgag cgtgcagtgt agaagcccca gaggcaagaa catccagggc    900
ggcaagaccc tgagcgtgtc ccagcttgaa ctgcaggata gcggcacctg gacctgtacc    960
gtgctgcaga accagaagaa agtggaattc aagatcgaca tcgtcgtgct cgccttccag   1020
aaagccagct ccatcgtgta caagaaggag ggcgaacagg tggaattttc cttcccctg    1080 gccttcactg tggaaaagct gaccggcagc ggcgagctgt ggtggcaggc tgaaagagcc   1140
agctccagca agtcctggat caccttcgac ctgaagaaca agaggtgtc cgtgaagaga   1200 gtgacccagg accccaagct gcagatgggc aagaagctgc ccctgcatct gacactgcca   1260
caggcccttc cacagtatgc cggctctggc aatctcactc ttgctcttga agccaagacc   1320
ggcaagctgc accaggaagt gaacctggtc gtgatgcggg ccacccagct gcagaagaat   1380
ctgacctgcg aagtgtgggg ccctaccagc cctaagctga tgctgagcct gaagctggaa   1440
aacaaagaag ccaaggtgtc caagcgcgag aaggccgtgt gggtgctgaa tcctgaggcc   1500
ggcatgtggc agtgtctgct gagcgattct ggccaggtgc tgctcgaaag caacatcaag   1560
```

-continued

```
gtgctgccca cctggtccac tccagtgcag cctgctagcg gcggaggggg atctggaggt    1620
gggggttcct cacccactga accaagctcc aaaaccggta accccagaca cctgcatgtt    1680
ctgattggga cctcagtggt caaaatccct ttcaccatcc tcctcttctt tctccttcat    1740
cgctggtgct ccaacaaaaa aaatgctgct gtaatggacc aagagcctgc agggaacaga    1800
acagtgaaca gcgaggattc tgatgaacaa gaccatcagg aggtgtcata cgcataa      1857
```

<210> SEQ ID NO 31
<211> LENGTH: 619
<212> TYPE: PRT
<213> ORGANISM: Artificial Sequence
<220> FEATURE:
<223> OTHER INFORMATION: Artificially Synthesized

<400> SEQUENCE: 31

```
Met Gly Gly Leu Glu Pro Cys Ser Arg Phe Leu Leu Pro Leu Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys Val Glu Gly Gly Gly Glu Gly Arg Gly Ser Leu Leu Thr Cys Gly
        115                 120                 125

Asp Val Glu Glu Asn Pro Gly Pro Arg Met Ala Leu Pro Val Thr Ala
    130                 135                 140

Leu Leu Leu Pro Leu Ala Leu Leu His Ala Ala Arg Pro Gly Ser
145                 150                 155                 160

Lys Lys Val Val Leu Gly Lys Lys Gly Asp Thr Val Glu Leu Thr Cys
                165                 170                 175

Thr Ala Ser Gln Lys Lys Ser Ile Gln Phe His Trp Lys Asn Ser Asn
            180                 185                 190

Gln Ile Lys Ile Leu Gly Asn Gln Gly Ser Phe Leu Thr Lys Gly Pro
        195                 200                 205

Ser Lys Leu Asn Asp Arg Ala Asp Ser Arg Arg Ser Leu Trp Asp Gln
    210                 215                 220

Gly Asn Phe Pro Leu Ile Ile Lys Asn Leu Lys Ile Glu Asp Ser Asp
225                 230                 235                 240

Thr Tyr Ile Cys Glu Val Glu Asp Gln Lys Glu Glu Val Gln Leu Leu
                245                 250                 255

Val Phe Gly Leu Thr Ala Asn Ser Asp Thr His Leu Leu Gln Gly Gln
            260                 265                 270

Ser Leu Thr Leu Thr Leu Glu Ser Pro Pro Gly Ser Ser Pro Ser Val
        275                 280                 285

Gln Cys Arg Ser Pro Arg Gly Lys Asn Ile Gln Gly Gly Lys Thr Leu
    290                 295                 300

Ser Val Ser Gln Leu Glu Leu Gln Asp Ser Gly Thr Trp Thr Cys Thr
305                 310                 315                 320
```

Val Leu Gln Asn Gln Lys Lys Val Glu Phe Lys Ile Asp Ile Val Val
            325                 330                 335

Leu Ala Phe Gln Lys Ala Ser Ser Ile Val Tyr Lys Lys Glu Gly Glu
            340                 345                 350

Gln Val Glu Phe Ser Phe Pro Leu Ala Phe Thr Val Glu Lys Leu Thr
            355                 360                 365

Gly Ser Gly Glu Leu Trp Trp Gln Ala Glu Arg Ala Ser Ser Ser Lys
        370                 375                 380

Ser Trp Ile Thr Phe Asp Leu Lys Asn Lys Glu Val Ser Val Lys Arg
385                 390                 395                 400

Val Thr Gln Asp Pro Lys Leu Gln Met Gly Lys Lys Leu Pro Leu His
                405                 410                 415

Leu Thr Leu Pro Gln Ala Leu Pro Gln Tyr Ala Gly Ser Gly Asn Leu
            420                 425                 430

Thr Leu Ala Leu Glu Ala Lys Thr Gly Lys Leu His Gln Glu Val Asn
        435                 440                 445

Leu Val Val Met Arg Ala Thr Gln Leu Gln Lys Asn Leu Thr Cys Glu
        450                 455                 460

Val Trp Gly Pro Thr Ser Pro Lys Leu Met Leu Ser Leu Lys Leu Glu
465                 470                 475                 480

Asn Lys Glu Ala Lys Val Ser Lys Arg Glu Lys Ala Val Trp Val Leu
                485                 490                 495

Asn Pro Glu Ala Gly Met Trp Gln Cys Leu Leu Ser Asp Ser Gly Gln
            500                 505                 510

Val Leu Leu Glu Ser Asn Ile Lys Val Leu Pro Thr Trp Ser Thr Pro
        515                 520                 525

Val Gln Pro Ala Ser Gly Gly Gly Ser Gly Gly Gly Ser Ser
        530                 535                 540

Pro Thr Glu Pro Ser Ser Lys Thr Gly Asn Pro Arg His Leu His Val
545                 550                 555                 560

Leu Ile Gly Thr Ser Val Val Lys Ile Pro Phe Thr Ile Leu Leu Phe
                565                 570                 575

Phe Leu Leu His Arg Trp Cys Ser Asn Lys Lys Asn Ala Ala Val Met
            580                 585                 590

Asp Gln Glu Pro Ala Gly Asn Arg Thr Val Asn Ser Glu Asp Ser Asp
        595                 600                 605

Glu Gln Asp His Gln Glu Val Ser Tyr Ala Glx
    610                 615

<210> SEQ ID NO 32
<211> LENGTH: 1857
<212> TYPE: DNA
<213> ORGANISM: Artificial Sequence
<220> FEATURE:
<223> OTHER INFORMATION: Artificially Synthesized

<400> SEQUENCE: 32 atgggggac ttgaaccctg cagcaggttc ctgctcctgc ctctcctgct ggctgtaagt      60
ggtctccgtc ctgtccaggt ccaggcccag agcgattgca gttgctctac ggtgagcccg     120
ggcgtgctgg cagggatcgt gatgggagac ctggtgctga cagtgctcat tgccctggcc    180
gtgtacttcc tgggccggct ggtccctcgg gggcgagggg ctgcggaggc agcgacccgg    240
aaacagcgta tcactgagac cgagtcgcct tatcaggagc tccagggtca gaggtcggat    300
gtctacagcg acctcaacac acagaggccg tattacaaag tcgagggcgg cggagagggc    360

-continued

```
agaggaagtc ttctaacatg cggtgacgtg gaggagaatc ccggccctag gatggctctg    420
cctgtgacag ctctgctgct gcctctggcc ctgctgctgc atgctgccag acctggatcc    480
aagaaagtgg tgcttggcaa gaagggcgac accgtggaac tgacctgcac cgccagccag    540
aagaagtcca tccagttcca ctggaagaac agcaaccaga tcaagatcct gggcaaccag    600
ggcagcttcc tgaccaaggg ccccagcaag ctgaacgaca gagccgactc tcggcggagc    660
ctgtgggacc agggcaattt cccactgatc atcaagaacc tgaagatcga ggacagcgac    720
acctacatct gcgaggtgga agatcagaaa gaagaggtgc agctgctggt gttcggcctg    780
accgccaact ccgacaccca tctgctgcag ggccagagcc tgaccctgac actggaaagc    840
cctccaggca gcagcccgag cgtgcagtgt agaagcccca gaggcaagaa catccagggc    900
ggcaagaccc tgagcgtgtc ccagcttgaa ctgcaggata gcggcacctg gacctgtacc    960
gtgctgcaga accagaagaa agtggaattc aagatcgaca tcgtcgtgct cgccttccag   1020
aaagccagct ccatcgtgta caagaaggag ggcgaacagg tggaattttc cttccccctg   1080
gccttcactg tggaaaagct gaccggcagc ggcgagctgt ggtggcaggc tgaaagagcc   1140
agctccagca gtcctggat caccttcgac ctgaagaaca agaggtgtc cgtgaagaga   1200
gtgacccagg accccaagct gcagatgggc aagaagctgc ccctgcatct gacactgcca   1260
caggcccttc acagtatgc cggctctggc aatctcactc ttgctcttga agccaagacc   1320
ggcaagctgc accaggaagt gaacctggtc gtgatgcggg ccacccagct gcagaagaat   1380
ctgacctgcg aagtgtgggg ccctaccagc cctaagctga tgctgagcct gaagctggaa   1440
aacaaagaag ccaaggtgtc caagcgcgag aaggccgtgt gggtgctgaa tcctgaggcc   1500
ggcatgtggc agtgtctgct gagcgattct ggccaggtgt gctcgaaag caacatcaag   1560
gtgctgccca cctggtccac tccagtgcag cctgctagcg gcggaggggg atctggaggt   1620
gggggttcct cacccactga accaagctcc aaaaccggta accccagaca cctgcatgtt   1680
ctgattggga cctcagtggt caaaatccct ttcaccatcc tcctcttctt tctccttcat   1740
cgctggtgct ccaacaaaaa aaatgctgct gtaatggacc aagagcctgc agggaacaga   1800
acagtgaaca gcgaggattc tgatgaacaa gaccatcagg aggtgtcata cgcataa      1857
```

<210> SEQ ID NO 33
<211> LENGTH: 619
<212> TYPE: PRT
<213> ORGANISM: Artificial Sequence
<220> FEATURE:
<223> OTHER INFORMATION: Artificially Synthesized

<400> SEQUENCE: 33

```
Met Gly Gly Leu Glu Pro Cys Ser Arg Phe Leu Leu Leu Pro Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95
```

-continued

```
Gln Arg Ser Asp Val Tyr Ser Asp Leu Asn Thr Gln Arg Pro Tyr Tyr
                100                 105                 110

Lys Val Glu Gly Gly Glu Gly Arg Gly Ser Leu Leu Thr Cys Gly
        115                 120                 125

Asp Val Glu Glu Asn Pro Gly Pro Arg Met Ala Leu Pro Val Thr Ala
    130                 135                 140

Leu Leu Leu Pro Leu Ala Leu Leu Leu His Ala Ala Arg Pro Gly Ser
145                 150                 155                 160

Lys Lys Val Val Leu Gly Lys Lys Gly Asp Thr Val Glu Leu Thr Cys
                165                 170                 175

Thr Ala Ser Gln Lys Lys Ser Ile Gln Phe His Trp Lys Asn Ser Asn
                180                 185                 190

Gln Ile Lys Ile Leu Gly Asn Gln Gly Ser Phe Leu Thr Lys Gly Pro
                195                 200                 205

Ser Lys Leu Asn Asp Arg Ala Asp Ser Arg Arg Ser Leu Trp Asp Gln
210                 215                 220

Gly Asn Phe Pro Leu Ile Ile Lys Asn Leu Lys Ile Glu Asp Ser Asp
225                 230                 235                 240

Thr Tyr Ile Cys Glu Val Glu Asp Gln Lys Glu Glu Val Gln Leu Leu
                245                 250                 255

Val Phe Gly Leu Thr Ala Asn Ser Asp Thr His Leu Leu Gln Gly Gln
                260                 265                 270

Ser Leu Thr Leu Thr Leu Glu Ser Pro Pro Gly Ser Ser Pro Ser Val
                275                 280                 285

Gln Cys Arg Ser Pro Arg Gly Lys Asn Ile Gln Gly Gly Lys Thr Leu
    290                 295                 300

Ser Val Ser Gln Leu Glu Leu Gln Asp Ser Gly Thr Trp Thr Cys Thr
305                 310                 315                 320

Val Leu Gln Asn Gln Lys Lys Val Glu Phe Lys Ile Asp Ile Val Val
                325                 330                 335

Leu Ala Phe Gln Lys Ala Ser Ser Ile Val Tyr Lys Lys Glu Gly Glu
                340                 345                 350

Gln Val Glu Phe Ser Phe Pro Leu Ala Phe Thr Val Glu Lys Leu Thr
                355                 360                 365

Gly Ser Gly Glu Leu Trp Trp Gln Ala Glu Arg Ala Ser Ser Ser Lys
    370                 375                 380

Ser Trp Ile Thr Phe Asp Leu Lys Asn Lys Glu Val Ser Val Lys Arg
385                 390                 395                 400

Val Thr Gln Asp Pro Lys Leu Gln Met Gly Lys Lys Leu Pro Leu His
                405                 410                 415

Leu Thr Leu Pro Gln Ala Leu Pro Gln Tyr Ala Gly Ser Gly Asn Leu
                420                 425                 430

Thr Leu Ala Leu Glu Ala Lys Thr Gly Lys Leu His Gln Glu Val Asn
    435                 440                 445

Leu Val Val Met Arg Ala Thr Gln Leu Gln Lys Asn Leu Thr Cys Glu
    450                 455                 460

Val Trp Gly Pro Thr Ser Pro Lys Leu Met Leu Ser Leu Lys Leu Glu
465                 470                 475                 480

Asn Lys Glu Ala Lys Val Ser Lys Arg Glu Lys Ala Val Trp Val Leu
                485                 490                 495

Asn Pro Glu Ala Gly Met Trp Gln Cys Leu Leu Ser Asp Ser Gly Gln
                500                 505                 510
```

```
Val Leu Leu Glu Ser Asn Ile Lys Val Leu Pro Thr Trp Ser Thr Pro
            515                 520                 525
Val Gln Pro Ala Ser Gly Gly Gly Ser Gly Gly Gly Ser Ser
    530                 535                 540
Pro Thr Glu Pro Ser Ser Lys Thr Gly Asn Pro Arg His Leu His Val
545                 550                 555                 560
Leu Ile Gly Thr Ser Val Val Lys Ile Pro Phe Thr Ile Leu Leu Phe
                565                 570                 575
Phe Leu Leu His Arg Trp Cys Ser Asn Lys Lys Asn Ala Ala Val Met
            580                 585                 590
Asp Gln Glu Pro Ala Gly Asn Arg Thr Val Asn Ser Glu Asp Ser Asp
        595                 600                 605
Glu Gln Asp His Gln Glu Val Ser Tyr Ala Glx
    610                 615

<210> SEQ ID NO 34
<211> LENGTH: 1923
<212> TYPE: DNA
<213> ORGANISM: Artificial Sequence
<220> FEATURE:
<223> OTHER INFORMATION: Artificially Synthesized

<400> SEQUENCE: 34
atggctctgc ctgtgacagc tctgctgctg cctctggccc tgctgctgca tgctgccaga      60
cctggatccg agatcgtgct gacacagagc cctggcaccc tgagcctgtc tccaggcgag     120
acagccatca tcagctgccg gacaagccag tacggcagcc tggcctggta tcagcagagg     180
cctggacagg ccccagact cgtgatctac agcggcagca agagccgc cggaatcccc        240
gatagattca gcggctctag atggggccct gactacaacc tgaccatcag caacctggaa     300
agcggcgact cggcgtgta ctactgccag cagtacgagt tcttcggcca gggcaccaag      360
gtgcaggtgg acatcaagag aggcggcagc tccagaagct ccagctctgg cggcggagga     420
tctggcggag gcggacaggt gcagctggtg cagtctggcg ccagatgaa gaaacccggc      480
gagagcatgc ggatcagctg cagagcctcc ggctacgagt tcatcgactg cacccttgaac    540
tggattcggc tggcccctgg caaaagaccc gagtggatgg gctggctgaa gcccagaggc     600
ggagccgtga attacgccag acctctgcag gcagagtga ccatgacccg ggacgtgtac      660
agcgataccg ccttcctgga actgcggagc ctgaccgtgg atgataccgc cgtgtacttc     720
tgcacccggg gcaagaactg cgactacaac tgggacttcg agcactgggg cagaggcacc     780
cctgtgatcg tgtctagcgc tagcgagagc aagtacggcc ctccctgccc cccttgccct     840
gcccccgagt tctgggcgg acccagcgtg ttcctgttcc ccccaagcc caaggacacc       900
ctgatgatca gccggacccc cgaggtgacc tgtgtggtgg tggacgtgtc ccaggaggac     960
cccgaggtcc agttcaactg gtacgtggac ggcgtggagg tgcacaacgc caagaccaag    1020
ccccggggagg agcagttcaa tagcacctac cgggtggtgt ccgtgctgac cgtgctgcac    1080
caggactggc tgaacggcaa ggaatacaag tgtaaggtgt ccaacaaggg cctgcccagc    1140
agcatcgaga aaaccatcag caaggccaag ggccagcctc gggagcccca ggtgtacacc    1200
ctgccccccta gccaagagga gatgaccaag aaccaggtgt ccctgacctg cctggtgaag    1260
ggcttctacc ccagcgacat cgccgtggag tgggagagca acggccagcc cgagaacaac    1320
tacaagacca cccccctgt gctggacagc gacggcagct cttcctgta cagccggctg    1380
accgtggaca agagccggtg gcaggagggc aacgtcttta gctgctccgt gatgcacgag    1440
```

```
gccctgcaca accactacac ccagaagagc ctgagcctgt ccctgggcaa gatgtccgga    1500
atctacatct gggcgccctt ggccgggact tgtggggtcc ttctcctgtc actggttatc    1560 acccttact gcaaacgggg cagaaagaaa ctcctgtata tattcaaaca accatttatg     1620
agaccagtac aaactactca agaggaagat ggctgtagct gccgatttcc agaagaagaa    1680
gaaggaggat gtgaactgcg tggccgggac cctgagatgg ggggaaagcc gagaaggaag    1740
aaccctcagg aaggcctgta caatgaactg cagaaagata agatggcgga ggcctacagt    1800
gagattggga tgaaaggcga gcgccggagg ggcaaggggc acgatggcct ttaccagggt    1860
ctcagtacag ccaccaagga cacctacgac gccttcaca tgcaggccct gcccctcgc     1920 taa                                                                  1923
```

<210> SEQ ID NO 35
<211> LENGTH: 679
<212> TYPE: PRT
<213> ORGANISM: Artificial Sequence
<220> FEATURE:
<223> OTHER INFORMATION: Artificially Synthesized

<400> SEQUENCE: 35

```
Met Ala Leu Pro Val Thr Ala Leu Leu Leu Pro Leu Ala Leu Leu Leu
1               5                   10                  15

His Ala Ala Arg Pro Gly Ser Glu Ile Val Leu Thr Gln Ser Pro Gly
            20                  25                  30

Thr Leu Ser Leu Ser Pro Gly Glu Thr Ala Ile Ile Ser Cys Arg Thr
        35                  40                  45

Ser Gln Tyr Gly Ser Leu Ala Trp Tyr Gln Gln Arg Pro Gly Gln Ala
    50                  55                  60

Pro Arg Leu Val Ile Tyr Ser Gly Ser Thr Arg Ala Ala Gly Ile Pro
65                  70                  75                  80

Asp Arg Phe Ser Gly Ser Arg Trp Gly Pro Asp Tyr Asn Leu Thr Ile
                85                  90                  95

Ser Asn Leu Glu Ser Gly Asp Phe Gly Val Tyr Tyr Cys Gln Gln Tyr
            100                 105                 110

Glu Phe Phe Gly Gln Gly Thr Lys Val Gln Val Asp Ile Lys Arg Gly
        115                 120                 125

Gly Ser Ser Arg Ser Ser Ser Gly Gly Gly Ser Gly Gly Gly
    130                 135                 140

Gly Gln Val Gln Leu Val Gln Ser Gly Gly Gln Met Lys Lys Pro Gly
145                 150                 155                 160

Glu Ser Met Arg Ile Ser Cys Arg Ala Ser Gly Tyr Glu Phe Ile Asp
                165                 170                 175

Cys Thr Leu Asn Trp Ile Arg Leu Ala Pro Gly Lys Arg Pro Glu Trp
            180                 185                 190

Met Gly Trp Leu Lys Pro Arg Gly Gly Ala Val Asn Tyr Ala Arg Pro
        195                 200                 205

Leu Gln Gly Arg Val Thr Met Thr Arg Asp Val Tyr Ser Asp Thr Ala
    210                 215                 220

Phe Leu Glu Leu Arg Ser Leu Thr Val Asp Asp Thr Ala Val Tyr Phe
225                 230                 235                 240

Cys Thr Arg Gly Lys Asn Cys Asp Tyr Asn Trp Asp Phe Glu His Trp
                245                 250                 255

Gly Arg Gly Thr Pro Val Ile Val Ser Ser Ala Ser Glu Ser Lys Tyr
            260                 265                 270
```

```
Gly Pro Pro Cys Pro Pro Cys Pro Ala Pro Glu Phe Leu Gly Gly Pro
            275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Asn Ser Thr Tyr Arg Val
            340                 345                 350

Val Ser Val Leu Thr Val Leu His Gln Asp Trp Leu Asn Gly Lys Glu
    355                 360                 365

Tyr Lys Cys Lys Val Ser Asn Lys Gly Leu Pro Ser Ser Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
    435                 440                 445

Asp Ser Asp Gly Ser Phe Phe Leu Tyr Ser Arg Leu Thr Val Asp Lys
    450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
                485                 490                 495

Lys Met Ser Gly Ile Tyr Ile Trp Ala Pro Leu Ala Gly Thr Cys Gly
            500                 505                 510

Val Leu Leu Leu Ser Leu Val Ile Thr Leu Tyr Cys Lys Arg Gly Arg
    515                 520                 525

Lys Lys Leu Leu Tyr Ile Phe Lys Gln Pro Phe Met Arg Pro Val Gln
    530                 535                 540

Thr Thr Gln Glu Glu Asp Gly Cys Ser Cys Arg Phe Pro Glu Glu Glu
545                 550                 555                 560

Glu Gly Gly Cys Glu Leu Arg Val Lys Phe Ser Arg Ser Ala Asp Ala
                565                 570                 575

Pro Ala Tyr Lys Gln Gly Gln Asn Gln Leu Tyr Asn Glu Leu Asn Leu
            580                 585                 590

Gly Arg Arg Glu Glu Tyr Asp Val Leu Asp Lys Arg Arg Gly Arg Asp
    595                 600                 605

Pro Glu Met Gly Gly Lys Pro Arg Arg Lys Asn Pro Gln Glu Gly Leu
    610                 615                 620

Tyr Asn Glu Leu Gln Lys Asp Lys Met Ala Glu Ala Tyr Ser Glu Ile
625                 630                 635                 640

Gly Met Lys Gly Glu Arg Arg Arg Gly Lys Gly His Asp Gly Leu Tyr
                645                 650                 655

Gln Gly Leu Ser Thr Ala Thr Lys Asp Thr Tyr Asp Ala Leu His Met
            660                 665                 670

Gln Ala Leu Pro Pro Arg Glx
            675
```

<210> SEQ ID NO 36
<211> LENGTH: 32
<212> TYPE: PRT
<213> ORGANISM: Artificial Sequence
<220> FEATURE:
<223> OTHER INFORMATION: Artificially Synthesized

<400> SEQUENCE: 36

Thr Thr Ala Ala Thr Gly Gly Gly Ala Thr Cys Cys Ala Thr Gly Ala
1               5                   10                  15

Ala Cys Cys Gly Gly Gly Gly Ala Gly Thr Cys Cys Cys Thr Thr Thr
            20                  25                  30

<210> SEQ ID NO 37
<211> LENGTH: 36
<212> TYPE: DNA
<213> ORGANISM: Artificial Sequence
<220> FEATURE:
<223> OTHER INFORMATION: Artificially Synthesized

<400> SEQUENCE: 37
aaggacttcc ggatggctgc accggggtgg accatg                              36

<210> SEQ ID NO 38
<211> LENGTH: 33
<212> TYPE: DNA
<213> ORGANISM: Artificial Sequence
<220> FEATURE:
<223> OTHER INFORMATION: Artificially Synthesized

<400> SEQUENCE: 38
gggacactcc ggaaccacga cgccagcgcc gcg                                 33

<210> SEQ ID NO 39
<211> LENGTH: 27
<212> TYPE: DNA
<213> ORGANISM: Artificial Sequence
<220> FEATURE:
<223> OTHER INFORMATION: Artificially Synthesized

<400> SEQUENCE: 39
gggacacgtc gacttagcga gggggca                                        27

<210> SEQ ID NO 40
<211> LENGTH: 20
<212> TYPE: DNA
<213> ORGANISM: Artificial Sequence
<220> FEATURE:
<223> OTHER INFORMATION: Artificially Synthesized

<400> SEQUENCE: 40
gtatcgatca cgagactagc                                                20

<210> SEQ ID NO 41
<211> LENGTH: 30
<212> TYPE: DNA
<213> ORGANISM: Artificial Sequence
<220> FEATURE:
<223> OTHER INFORMATION: Artificially Synthesized

<400> SEQUENCE: 41
ttaaaccggt gtctggcctt tgagtggtga                                     30

```
<210> SEQ ID NO 42
<211> LENGTH: 11
<212> TYPE: PRT
<213> ORGANISM: Artificial Sequence
<220> FEATURE:
<223> OTHER INFORMATION: Artificially Synthesized

<400> SEQUENCE: 42

Lys Ala Phe Ser Pro Glu Val Ile Pro Met Phe
1               5                   10

<210> SEQ ID NO 43
<211> LENGTH: 18
<212> TYPE: PRT
<213> ORGANISM: Artificial Sequence
<220> FEATURE:
<223> OTHER INFORMATION: Artificially Synthesized

<400> SEQUENCE: 43

Gly Gly Ser Ser Arg Ser Ser Ser Gly Gly Gly Ser Gly Gly
1               5                   10                  15

Gly Gly

<210> SEQ ID NO 44
<211> LENGTH: 625
<212> TYPE: PRT
<213> ORGANISM: Artificial Sequence
<220> FEATURE:
<223> OTHER INFORMATION: Artificially Synthesized

<400> SEQUENCE: 44

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220
```

-continued

```
Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
        290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
            355                 360                 365

Gln Cys Leu Leu Ser Asp Ser Gly Gln Val Leu Leu Glu Ser Asn Ile
        370                 375                 380

Lys Val Leu Pro Thr Trp Ser Thr Pro Val Gln Pro Ser Gly Thr Thr
385                 390                 395                 400

Thr Pro Ala Pro Arg Pro Pro Thr Pro Ala Pro Thr Ile Ala Ser Gln
                405                 410                 415

Pro Leu Ser Leu Arg Pro Glu Ala Cys Arg Pro Ala Ala Gly Gly Ala
            420                 425                 430

Val His Thr Arg Gly Leu Asp Phe Ala Cys Asp Phe Trp Val Leu Val
            435                 440                 445

Val Val Gly Gly Val Leu Ala Cys Tyr Ser Leu Leu Val Thr Val Ala
        450                 455                 460

Phe Ile Ile Phe Trp Val Arg Ser Lys Arg Ser Arg Leu Leu His Ser
465                 470                 475                 480

Asp Tyr Met Asn Met Thr Pro Arg Arg Pro Gly Pro Thr Arg Lys His
                485                 490                 495

Tyr Gln Pro Tyr Ala Pro Pro Arg Asp Phe Ala Ala Tyr Arg Ser Ile
            500                 505                 510

Asp Arg Val Lys Phe Ser Arg Ser Ala Asp Ala Pro Ala Tyr Gln Gln
            515                 520                 525

Gly Gln Asn Gln Leu Tyr Asn Glu Leu Asn Leu Gly Arg Arg Glu Glu
        530                 535                 540

Tyr Asp Val Leu Asp Lys Arg Arg Gly Arg Asp Pro Glu Met Gly Gly
545                 550                 555                 560

Lys Pro Arg Arg Lys Asn Pro Gln Glu Gly Leu Tyr Asn Glu Leu Gln
                565                 570                 575

Lys Asp Lys Met Ala Glu Ala Tyr Ser Glu Ile Gly Met Lys Gly Glu
            580                 585                 590

Arg Arg Arg Gly Lys Gly His Asp Gly Leu Tyr Gln Gly Leu Ser Thr
            595                 600                 605

Ala Thr Lys Asp Thr Tyr Asp Ala Leu His Met Gln Ala Leu Pro Pro
        610                 615                 620

Arg
625
```

<210> SEQ ID NO 45
<211> LENGTH: 621
<212> TYPE: PRT
<213> ORGANISM: Artificial Sequence
<220> FEATURE:
<223> OTHER INFORMATION: Artificially Synthesized

<400> SEQUENCE: 45

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365
```

```
Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Ser Gly Thr Thr
385                 390                 395                 400

Thr Pro Ala Pro Arg Pro Pro Thr Pro Ala Pro Thr Ile Ala Ser Gln
            405                 410                 415

Pro Leu Ser Leu Arg Pro Glu Ala Cys Arg Pro Ala Ala Gly Gly Ala
            420                 425                 430

Val His Thr Arg Gly Leu Asp Phe Ala Cys Asp Ile Tyr Ile Trp Ala
            435                 440                 445

Pro Leu Ala Gly Thr Cys Gly Val Leu Leu Leu Ser Leu Val Ile Thr
    450                 455                 460

Leu Tyr Cys Lys Arg Gly Arg Lys Lys Leu Leu Tyr Ile Phe Lys Gln
465                 470                 475                 480

Pro Phe Met Arg Pro Val Gln Thr Thr Gln Glu Asp Gly Cys Ser
            485                 490                 495

Cys Arg Phe Pro Glu Glu Glu Glu Gly Gly Cys Glu Leu Arg Val Lys
                500                 505                 510

Phe Ser Arg Ser Ala Asp Ala Pro Ala Tyr Gln Gln Gly Gln Asn Gln
    515                 520                 525

Leu Tyr Asn Glu Leu Asn Leu Gly Arg Arg Glu Glu Tyr Asp Val Leu
    530                 535                 540

Asp Lys Arg Arg Gly Arg Asp Pro Glu Met Gly Gly Lys Pro Arg Arg
545                 550                 555                 560

Lys Asn Pro Gln Glu Gly Leu Tyr Asn Glu Leu Gln Lys Asp Lys Met
                565                 570                 575

Ala Glu Ala Tyr Ser Glu Ile Gly Met Lys Gly Glu Arg Arg Arg Gly
            580                 585                 590

Lys Gly His Asp Gly Leu Tyr Gln Gly Leu Ser Thr Ala Thr Lys Asp
    595                 600                 605

Thr Tyr Asp Ala Leu His Met Gln Ala Leu Pro Pro Arg
    610                 615                 620

<210> SEQ ID NO 46
<211> LENGTH: 396
<212> TYPE: PRT
<213> ORGANISM: Artificial Sequence
<220> FEATURE:
<223> OTHER INFORMATION: Artificially Synthesized

<400> SEQUENCE: 46

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110
```

```
Asp Gln Lys Glu Glu Val Gln Leu Val Phe Gly Leu Thr Ala Asn
            115                 120                 125
Ser Asp Thr His Leu Leu Gln Gly Gln Ser Leu Thr Leu Thr Leu Glu
130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Val Leu Ala Phe Gln Lys Ala Ser
        195                 200                 205
Ser Ile Val Tyr Lys Lys Glu Gly Glu Gln Val Glu Phe Ser Phe Pro
    210                 215                 220
Leu Ala Phe Thr Val Glu Lys Leu Thr Gly Ser Gly Glu Leu Trp Trp
225                 230                 235                 240
Gln Ala Glu Arg Ala Ser Ser Ser Lys Ser Trp Ile Thr Phe Asp Leu
                245                 250                 255
Lys Asn Lys Glu Val Ser Val Lys Arg Val Thr Gln Asp Pro Lys Leu
            260                 265                 270
Gln Met Gly Lys Lys Leu Pro Leu His Leu Thr Leu Pro Gln Ala Leu
        275                 280                 285
Pro Gln Tyr Ala Gly Ser Gly Asn Leu Thr Leu Ala Leu Glu Ala Lys
    290                 295                 300
Thr Gly Lys Leu His Gln Glu Val Asn Leu Val Val Met Arg Ala Thr
305                 310                 315                 320
Gln Leu Gln Lys Asn Leu Thr Cys Glu Val Trp Gly Pro Thr Ser Pro
                325                 330                 335
Lys Leu Met Leu Ser Leu Lys Leu Glu Asn Lys Glu Ala Lys Val Ser
            340                 345                 350
Lys Arg Glu Lys Ala Val Trp Val Leu Asn Pro Glu Ala Gly Met Trp
        355                 360                 365
Gln Cys Leu Leu Ser Asp Ser Gly Gln Val Leu Leu Glu Ser Asn Ile
    370                 375                 380
Lys Val Leu Pro Thr Trp Ser Thr Pro Val Gln Pro
385                 390                 395

<210> SEQ ID NO 47
<211> LENGTH: 45
<212> TYPE: PRT
<213> ORGANISM: Artificial Sequence
<220> FEATURE:
<223> OTHER INFORMATION: Artificially Synthesized

<400> SEQUENCE: 47

Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp
        35                  40                  45

<210> SEQ ID NO 48
<211> LENGTH: 24
<212> TYPE: PRT
<213> ORGANISM: Artificial Sequence
```

```
<220> FEATURE:
<223> OTHER INFORMATION: Artificially Synthesized

<400> SEQUENCE: 48

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 49
<211> LENGTH: 68
<212> TYPE: PRT
<213> ORGANISM: Artificial Sequence
<220> FEATURE:
<223> OTHER INFORMATION: Artificially Synthesized

<400> SEQUENCE: 49

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 50
<211> LENGTH: 42
<212> TYPE: PRT
<213> ORGANISM: Artificial Sequence
<220> FEATURE:
<223> OTHER INFORMATION: Artificially Synthesized

<400> SEQUENCE: 50

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 51
<211> LENGTH: 112
<212> TYPE: PRT
<213> ORGANISM: Artificial Sequence
<220> FEATURE:
<223> OTHER INFORMATION: Artificially Synthesized

<400> SEQUENCE: 51

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
        100                 105                 110

<210> SEQ ID NO 52
<211> LENGTH: 444
<212> TYPE: PRT
<213> ORGANISM: Artificial Sequence
<220> FEATURE:
<223> OTHER INFORMATION: Artificially Synthesized

<400> SEQUENCE: 52

Gln Arg Leu Val Glu Ser Gly Gly Gly Val Val Gln Pro Gly Ser Ser
1               5                   10                  15

Leu Arg Leu Ser Cys Ala Ala Ser Gly Phe Asp Phe Ser Arg Gln Gly
            20                  25                  30

Met His Trp Val Arg Gln Ala Pro Gly Gln Gly Leu Glu Trp Val Ala
        35                  40                  45

Phe Ile Lys Tyr Asp Gly Ser Glu Lys Tyr His Ala Asp Ser Val Trp
    50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
        115                 120                 125

Gly Thr Thr Val Thr Val Ser Ser Gly Gly Gly Ser Gly Gly Gly
        130                 135                 140

Gly Ser Gly Gly Gly Ser Gln Ser Ala Leu Thr Gln Pro Ala Ser
145                 150                 155                 160

Val Ser Gly Ser Pro Gly Gln Ser Ile Thr Ile Ser Cys Asn Gly Thr
                165                 170                 175

Ser Asn Asp Val Gly Gly Tyr Glu Ser Val Ser Trp Tyr Gln Gln His
            180                 185                 190

Pro Gly Lys Ala Pro Lys Val Val Ile Tyr Asp Val Ser Lys Arg Pro
        195                 200                 205

Ser Gly Val Ser Asn Arg Phe Ser Gly Ser Lys Ser Gly Asn Thr Ala
    210                 215                 220

Ser Leu Thr Ile Ser Gly Leu Gln Ala Glu Asp Glu Gly Asp Tyr Tyr
225                 230                 235                 240

Cys Lys Ser Leu Thr Ser Arg Arg Val Phe Gly Thr Gly Thr
                245                 250                 255

Lys Leu Thr Val Leu Ser Gly Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Val Lys Phe
                325                 330                 335

```
Ser Arg Ser Ala Asp Ala Pro Ala Tyr Gln Gln Gly Gln Asn Gln Leu
            340                 345                 350

Tyr Asn Glu Leu Asn Leu Gly Arg Arg Glu Tyr Asp Val Leu Asp
        355                 360                 365

Lys Arg Arg Gly Arg Asp Pro Glu Met Gly Gly Lys Pro Arg Arg Lys
        370                 375                 380

Asn Pro Gln Glu Gly Leu Tyr Asn Glu Leu Gln Lys Asp Lys Met Ala
385                 390                 395                 400

Glu Ala Tyr Ser Glu Ile Gly Met Lys Gly Glu Arg Arg Arg Gly Lys
                405                 410                 415

Gly His Asp Gly Leu Tyr Gln Gly Leu Ser Thr Ala Thr Lys Asp Thr
            420                 425                 430

Tyr Asp Ala Leu His Met Gln Ala Leu Pro Pro Arg
        435                 440

<210> SEQ ID NO 53
<211> LENGTH: 442
<212> TYPE: PRT
<213> ORGANISM: Artificial Sequence
<220> FEATURE:
<223> OTHER INFORMATION: Artificially Synthesized

<400> SEQUENCE: 53

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln His Ala Gly Lys Ala Pro Lys Leu Val Ile Tyr Asp Val
        35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

Ala Val Tyr Tyr Cys Gly Ser Leu Val Gly Asn Trp Asp Val Ile Phe
                85                  90                  95

Gly Gly Gly Thr Lys Leu Thr Val Leu Gly Ser Ser Arg Ser Ser
            100                 105                 110

Ser Ser Gly Gly Gly Gly Ser Gly Gly Gly Gly Gln Pro Gln Leu Gln
        115                 120                 125

Glu Ser Gly Pro Thr Leu Val Glu Ala Ser Glu Thr Leu Ser Leu Thr
    130                 135                 140

Cys Ala Val Ser Gly Asp Ser Thr Ala Ala Cys Asn Ser Phe Trp Gly
145                 150                 155                 160

Trp Val Arg Gln Pro Pro Gly Lys Gly Leu Glu Trp Val Gly Ser Leu
                165                 170                 175

Ser His Cys Ala Ser Tyr Trp Asn Arg Gly Trp Thr Tyr His Asn Pro
            180                 185                 190

Ser Leu Lys Ser Arg Leu Thr Leu Ala Leu Asp Thr Pro Lys Asn Leu
        195                 200                 205

Val Phe Leu Lys Leu Asn Ser Val Thr Ala Ala Asp Thr Ala Thr Tyr
    210                 215                 220

Tyr Cys Ala Arg Phe Gly Gly Glu Val Leu Arg Tyr Thr Asp Trp Pro
225                 230                 235                 240

Lys Pro Ala Trp Val Asp Leu Trp Gly Arg Gly Thr Leu Val Thr Val
                245                 250                 255
```

```
Ser Ser Ser Gly Thr Thr Thr Pro Ala Pro Arg Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Arg Val Lys Phe Ser Arg Ser
                325                 330                 335

Ala Asp Ala Pro Ala Tyr Gln Gln Gly Gln Asn Gln Leu Tyr Asn Glu
            340                 345                 350

Leu Asn Leu Gly Arg Arg Glu Glu Tyr Asp Val Leu Asp Lys Arg Arg
            355                 360                 365

Gly Arg Asp Pro Glu Met Gly Gly Lys Pro Arg Arg Lys Asn Pro Gln
            370                 375                 380

Glu Gly Leu Tyr Asn Glu Leu Gln Lys Asp Lys Met Ala Glu Ala Tyr
385                 390                 395                 400

Ser Glu Ile Gly Met Lys Gly Glu Arg Arg Arg Gly Lys Gly His Asp
                405                 410                 415

Gly Leu Tyr Gln Gly Leu Ser Thr Ala Thr Lys Asp Thr Tyr Asp Ala
            420                 425                 430

Leu His Met Gln Ala Leu Pro Pro Arg Arg
            435                 440

<210> SEQ ID NO 54
<211> LENGTH: 426
<212> TYPE: PRT
<213> ORGANISM: Artificial Sequence
<220> FEATURE:
<223> OTHER INFORMATION: Artificially Synthesized

<400> SEQUENCE: 54

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg Gly Gly Ser Ser Arg Ser Ser Ser
            100                 105                 110

Ser Gly Gly Gly Gly Ser Gly Gly Gly Gln Val Gln Leu Val Gln
        115                 120                 125

Ser Gly Gly Gln Met Lys Lys Pro Gly Glu Ser Met Arg Ile Ser Cys
    130                 135                 140

Arg Ala Ser Gly Tyr Glu Phe Ile Asp Cys Thr Leu Asn Trp Ile Arg
145                 150                 155                 160

Leu Ala Pro Gly Lys Arg Pro Glu Trp Met Gly Trp Leu Lys Pro Arg
                165                 170                 175
```

Gly Gly Ala Val Asn Tyr Ala Arg Pro Leu Gln Gly Arg Val Thr Met
            180                 185                 190

Thr Arg Asp Val Tyr Ser Asp Thr Ala Phe Leu Glu Leu Arg Ser Leu
        195                 200                 205

Thr Val Asp Asp Thr Ala Val Tyr Phe Cys Thr Arg Gly Lys Asn Cys
    210                 215                 220

Asp Tyr Asn Trp Asp Phe Glu His Trp Gly Arg Gly Thr Pro Val Ile
225                 230                 235                 240

Val Ser Ser Ser Gly Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
        260                 265                 270

Arg Pro Ala Ala Gly Gly Ala Val His Thr Arg Gly Leu Asp Phe Ala
    275                 280                 285

Cys Asp Ile Tyr Ile Trp Ala Pro Leu Ala Gly Thr Cys Gly Val Leu
290                 295                 300

Leu Leu Ser Leu Val Ile Thr Leu Tyr Cys Arg Val Lys Phe Ser Arg
305                 310                 315                 320

Ser Ala Asp Ala Pro Ala Tyr Gln Gln Gly Gln Asn Gln Leu Tyr Asn
                325                 330                 335

Glu Leu Asn Leu Gly Arg Arg Glu Glu Tyr Asp Val Leu Asp Lys Arg
        340                 345                 350

Arg Gly Arg Asp Pro Glu Met Gly Gly Lys Pro Arg Arg Lys Asn Pro
    355                 360                 365

Gln Glu Gly Leu Tyr Asn Glu Leu Gln Lys Asp Lys Met Ala Glu Ala
370                 375                 380

Tyr Ser Glu Ile Gly Met Lys Gly Glu Arg Arg Arg Gly Lys Gly His
385                 390                 395                 400

Asp Gly Leu Tyr Gln Gly Leu Ser Thr Ala Thr Lys Asp Thr Tyr Asp
                405                 410                 415

Ala Leu His Met Gln Ala Leu Pro Pro Arg
            420                 425

<210> SEQ ID NO 55
<211> LENGTH: 423
<212> TYPE: PRT
<213> ORGANISM: Artificial Sequence
<220> FEATURE:
<223> OTHER INFORMATION: Artificially Synthesized

<400> SEQUENCE: 55

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ala Arg Phe Ser Gly Arg Arg Trp Gly
    50                  55                  60

Gln Glu Tyr Asn Leu Thr Ile Asn Asn Leu Gln Pro Glu Asp Val Ala
65                  70                  75                  80

Thr Tyr Phe Cys Gln Val Tyr Glu Phe Ile Val Pro Gly Thr Arg Leu
                85                  90                  95

Asp Leu Lys Gly Gly Ser Ser Arg Ser Ser Ser Gly Gly Gly Gly Gly
            100                 105                 110

```
Ser Gly Gly Gly Gln Val His Leu Ser Gln Ser Gly Ala Ala Val
            115                 120                 125

Thr Lys Pro Gly Ala Ser Val Arg Val Ser Cys Glu Ala Ser Gly Tyr
    130                 135                 140

Lys Ile Ser Asp His Phe Ile His Trp Trp Arg Gln Ala Pro Gly Gln
145                 150                 155                 160

Gly Leu Gln Trp Val Gly Trp Ile Asn Pro Lys Thr Gly Gln Pro Asn
                165                 170                 175

Asn Pro Arg Gln Phe Gln Gly Arg Val Ser Leu Thr Arg Gln Ala Ser
            180                 185                 190

Trp Asp Phe Asp Thr Tyr Ser Phe Tyr Met Asp Leu Lys Ala Val Arg
        195                 200                 205

Ser Asp Asp Thr Ala Ile Tyr Phe Cys Ala Arg Gln Arg Ser Asp Phe
    210                 215                 220

Trp Asp Phe Asp Val Trp Gly Ser Gly Thr Gln Val Thr Val Ser Ser
225                 230                 235                 240

Ser Gly Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Arg Val Lys Phe Ser Arg Ser Ala Asp
305                 310                 315                 320

Ala Pro Ala Tyr Gln Gln Gly Gln Asn Gln Leu Tyr Asn Glu Leu Asn
                325                 330                 335

Leu Gly Arg Arg Glu Glu Tyr Asp Val Leu Asp Lys Arg Arg Gly Arg
            340                 345                 350

Asp Pro Glu Met Gly Gly Lys Pro Arg Arg Lys Asn Pro Gln Glu Gly
        355                 360                 365

Leu Tyr Asn Glu Leu Gln Lys Asp Lys Met Ala Glu Ala Tyr Ser Glu
    370                 375                 380

Ile Gly Met Lys Gly Glu Arg Arg Arg Gly Lys Gly His Asp Gly Leu
385                 390                 395                 400

Tyr Gln Gly Leu Ser Thr Ala Thr Lys Asp Thr Tyr Asp Ala Leu His
                405                 410                 415

Met Gln Ala Leu Pro Pro Arg
            420

<210> SEQ ID NO 56
<211> LENGTH: 454
<212> TYPE: PRT
<213> ORGANISM: Artificial Sequence
<220> FEATURE:
<223> OTHER INFORMATION: Artificially Synthesized

<400> SEQUENCE: 56

Asp Phe Val Leu Thr Gln Ser Pro His Ser Leu Ser Val Thr Pro Gly
1               5                   10                  15

Glu Ser Ala Ser Ile Ser Cys Lys Ser His Ser Leu Ile His Gly
                20                  25                  30

Asp Arg Asn Asn Tyr Leu Ala Trp Tyr Val Gln Lys Pro Gly Arg Ser
            35                  40                  45
```

```
Pro Gln Leu Leu Ile Tyr Leu Ala Ser Ser Arg Ala Ser Gly Val Pro
 50                  55                  60
Asp Arg Phe Ser Gly Ser Gly Ser Asp Lys Asp Phe Thr Leu Lys Ile
 65                  70                  75                  80
Ser Arg Val Glu Thr Glu Asp Val Gly Thr Tyr Tyr Cys Met Gln Gly
                 85                  90                  95
Arg Glu Ser Pro Trp Thr Phe Gly Gln Gly Thr Lys Val Asp Ile Lys
            100                 105                 110
Gly Gly Ser Ser Arg Ser Ser Ser Gly Gly Gly Ser Gly Gly
        115                 120                 125
Gly Gly Gln Ala Gln Leu Val Gln Ser Gly Pro Glu Val Arg Lys Pro
130                 135                 140
Gly Thr Ser Val Lys Val Ser Cys Lys Ala Pro Gly Asn Thr Leu Lys
145                 150                 155                 160
Thr Tyr Asp Leu His Trp Val Arg Ser Val Pro Gly Gln Gly Leu Gln
                165                 170                 175
Trp Met Gly Trp Ile Ser His Glu Gly Asp Lys Lys Val Ile Val Glu
            180                 185                 190
Arg Phe Lys Ala Lys Val Thr Ile Asp Trp Asp Arg Ser Thr Asn Thr
        195                 200                 205
Ala Tyr Leu Gln Leu Ser Gly Leu Thr Ser Gly Asp Thr Ala Val Tyr
210                 215                 220
Tyr Cys Ala Lys Gly Ser Lys His Arg Leu Arg Asp Tyr Ala Leu Tyr
225                 230                 235                 240
Asp Asp Asp Gly Ala Leu Asn Trp Ala Val Asp Val Asp Tyr Leu Ser
                245                 250                 255
Asn Leu Glu Phe Trp Gly Gln Gly Thr Ala Val Thr Val Ser Ser Ser
            260                 265                 270
Gly Thr Thr Thr Pro Ala Pro Arg Pro Pro Thr Pro Ala Pro Thr Ile
        275                 280                 285
Ala Ser Gln Pro Leu Ser Leu Arg Pro Glu Ala Cys Arg Pro Ala Ala
290                 295                 300
Gly Gly Ala Val His Thr Arg Gly Leu Asp Phe Ala Cys Asp Ile Tyr
305                 310                 315                 320
Ile Trp Ala Pro Leu Ala Gly Thr Cys Gly Val Leu Leu Leu Ser Leu
                325                 330                 335
Val Ile Thr Leu Tyr Cys Arg Val Lys Phe Ser Arg Ser Ala Asp Ala
            340                 345                 350
Pro Ala Tyr Gln Gln Gly Gln Asn Gln Leu Tyr Asn Glu Leu Asn Leu
        355                 360                 365
Gly Arg Arg Glu Glu Tyr Asp Val Leu Asp Lys Arg Arg Gly Arg Asp
370                 375                 380
Pro Glu Met Gly Gly Lys Pro Arg Arg Lys Asn Pro Gln Glu Gly Leu
385                 390                 395                 400
Tyr Asn Glu Leu Gln Lys Asp Lys Met Ala Glu Ala Tyr Ser Glu Ile
                405                 410                 415
Gly Met Lys Gly Glu Arg Arg Arg Gly Lys Gly His Asp Gly Leu Tyr
            420                 425                 430
Gln Gly Leu Ser Thr Ala Thr Lys Asp Thr Tyr Asp Ala Leu His Met
        435                 440                 445
Gln Ala Leu Pro Pro Arg
        450
```

```
<210> SEQ ID NO 57
<211> LENGTH: 261
<212> TYPE: PRT
<213> ORGANISM: Artificial Sequence
<220> FEATURE:
<223> OTHER INFORMATION: Artificially Synthesized

<400> SEQUENCE: 57

Gln Arg Leu Val Glu Ser Gly Gly Val Val Gln Pro Gly Ser Ser
1               5                   10                  15

Leu Arg Leu Ser Cys Ala Ala Ser Phe Asp Phe Ser Arg Gln Gly
                20                  25                  30

Met His Trp Val Arg Gln Ala Pro Gly Gln Gly Leu Glu Trp Val Ala
            35                  40                  45

Phe Ile Lys Tyr Asp Gly Ser Glu Lys Tyr His Ala Asp Ser Val Trp
        50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
        115                 120                 125

Gly Thr Thr Val Thr Val Ser Ser Gly Gly Gly Ser Gly Gly Gly
            130                 135                 140

Gly Ser Gly Gly Gly Ser Gln Ser Ala Leu Thr Gln Pro Ala Ser
145                 150                 155                 160

Val Ser Gly Ser Pro Gly Gln Ser Ile Thr Ile Ser Cys Asn Gly Thr
                165                 170                 175

Ser Asn Asp Val Gly Gly Tyr Glu Ser Val Ser Trp Tyr Gln Gln His
            180                 185                 190

Pro Gly Lys Ala Pro Lys Val Val Ile Tyr Asp Val Ser Lys Arg Pro
        195                 200                 205

Ser Gly Val Ser Asn Arg Phe Ser Gly Ser Lys Ser Gly Asn Thr Ala
    210                 215                 220

Ser Leu Thr Ile Ser Gly Leu Gln Ala Glu Asp Glu Gly Asp Tyr Tyr
225                 230                 235                 240

Cys Lys Ser Leu Thr Ser Thr Arg Arg Arg Val Phe Gly Thr Gly Thr
                245                 250                 255

Lys Leu Thr Val Leu
            260

<210> SEQ ID NO 58
<211> LENGTH: 258
<212> TYPE: PRT
<213> ORGANISM: Artificial Sequence
<220> FEATURE:
<223> OTHER INFORMATION: Artificially Synthesized

<400> SEQUENCE: 58

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
                20                  25                  30

Tyr Gln Gln His Ala Gly Lys Ala Pro Lys Leu Val Ile Tyr Asp Val
            35                  40                  45
```

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
 65                 70                  75                  80

Ala Val Tyr Tyr Cys Gly Ser Leu Val Gly Asn Trp Asp Val Ile Phe
                85                  90                  95

Gly Gly Gly Thr Lys Leu Thr Val Leu Gly Gly Ser Ser Arg Ser Ser
            100                 105                 110

Ser Ser Gly Gly Gly Gly Ser Gly Gly Gly Gln Pro Gln Leu Gln
        115                 120                 125

Glu Ser Gly Pro Thr Leu Val Glu Ala Ser Glu Thr Leu Ser Leu Thr
130                 135                 140

Cys Ala Val Ser Gly Asp Ser Thr Ala Ala Cys Asn Ser Phe Trp Gly
145                 150                 155                 160

Trp Val Arg Gln Pro Pro Gly Lys Gly Leu Glu Trp Val Gly Ser Leu
                165                 170                 175

Ser His Cys Ala Ser Tyr Trp Asn Arg Gly Trp Thr Tyr His Asn Pro
            180                 185                 190

Ser Leu Lys Ser Arg Leu Thr Leu Ala Leu Asp Thr Pro Lys Asn Leu
            195                 200                 205

Val Phe Leu Lys Leu Asn Ser Val Thr Ala Ala Asp Thr Ala Thr Tyr
    210                 215                 220

Tyr Cys Ala Arg Phe Gly Gly Glu Val Leu Arg Tyr Thr Asp Trp Pro
225                 230                 235                 240

Lys Pro Ala Trp Val Asp Leu Trp Gly Arg Gly Thr Leu Val Thr Val
                245                 250                 255

Ser Ser

<210> SEQ ID NO 59
<211> LENGTH: 243
<212> TYPE: PRT
<213> ORGANISM: Artificial Sequence
<220> FEATURE:
<223> OTHER INFORMATION: Artificially Synthesized

<400> SEQUENCE: 59

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
 65                 70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg Gly Gly Ser Ser Arg Ser Ser Ser
            100                 105                 110

Ser Gly Gly Gly Gly Ser Gly Gly Gly Gly Gln Val Gln Leu Val Gln
        115                 120                 125

Ser Gly Gly Gln Met Lys Lys Pro Gly Glu Ser Met Arg Ile Ser Cys
    130                 135                 140

```
Arg Ala Ser Gly Tyr Glu Phe Ile Asp Cys Thr Leu Asn Trp Ile Arg
145                 150                 155                 160

Leu Ala Pro Gly Lys Arg Pro Glu Trp Met Gly Trp Leu Lys Pro Arg
                165                 170                 175

Gly Gly Ala Val Asn Tyr Ala Arg Pro Leu Gln Gly Arg Val Thr Met
            180                 185                 190

Thr Arg Asp Val Tyr Ser Asp Thr Ala Phe Leu Glu Leu Arg Ser Leu
            195                 200                 205

Thr Val Asp Asp Thr Ala Val Tyr Phe Cys Thr Arg Gly Lys Asn Cys
        210                 215                 220

Asp Tyr Asn Trp Asp Phe Glu His Trp Gly Arg Gly Thr Pro Val Ile
225                 230                 235                 240

Val Ser Ser

<210> SEQ ID NO 60
<211> LENGTH: 240
<212> TYPE: PRT
<213> ORGANISM: Artificial Sequence
<220> FEATURE:
<223> OTHER INFORMATION: Artificially Synthesized

<400> SEQUENCE: 60

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ala Arg Phe Ser Gly Arg Arg Trp Gly
    50                  55                  60

Gln Glu Tyr Asn Leu Thr Ile Asn Asn Leu Gln Pro Glu Asp Val Ala
65                  70                  75                  80

Thr Tyr Phe Cys Gln Val Tyr Glu Phe Ile Val Pro Gly Thr Arg Leu
                85                  90                  95

Asp Leu Lys Gly Gly Ser Ser Arg Ser Ser Ser Gly Gly Gly Gly
            100                 105                 110

Ser Gly Gly Gly Gly Gln Val His Leu Ser Gln Ser Gly Ala Ala Val
        115                 120                 125

Thr Lys Pro Gly Ala Ser Val Arg Val Ser Cys Glu Ala Ser Gly Tyr
    130                 135                 140

Lys Ile Ser Asp His Phe Ile His Trp Trp Arg Gln Ala Pro Gly Gln
145                 150                 155                 160

Gly Leu Gln Trp Val Gly Trp Ile Asn Pro Lys Thr Gly Gln Pro Asn
                165                 170                 175

Asn Pro Arg Gln Phe Gln Gly Arg Val Ser Leu Thr Arg Gln Ala Ser
            180                 185                 190

Trp Asp Phe Asp Thr Tyr Ser Phe Tyr Met Asp Leu Lys Ala Val Arg
        195                 200                 205

Ser Asp Asp Thr Ala Ile Tyr Phe Cys Ala Arg Gln Arg Ser Asp Phe
    210                 215                 220

Trp Asp Phe Asp Val Trp Gly Ser Gly Thr Gln Val Thr Val Ser Ser
225                 230                 235                 240
```

-continued

<210> SEQ ID NO 61
<211> LENGTH: 271
<212> TYPE: PRT
<213> ORGANISM: Artificial Sequence
<220> FEATURE:
<223> OTHER INFORMATION: Artificially Synthesized

<400> SEQUENCE: 61

```
Asp Phe Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

Gly Gly Ser Ser Arg Ser Ser Ser Gly Gly Gly Ser Gly Gly
        115                 120                 125

Gly Gly Gln Ala Gln Leu Val Gln Ser Gly Pro Glu Val Arg Lys Pro
130                 135                 140

Gly Thr Ser Val Lys Val Ser Cys Lys Ala Pro Gly Asn Thr Leu Lys
145                 150                 155                 160

Thr Tyr Asp Leu His Trp Val Arg Ser Val Pro Gly Gln Gly Leu Gln
                165                 170                 175

Trp Met Gly Trp Ile Ser His Glu Gly Asp Lys Lys Val Ile Val Glu
            180                 185                 190

Arg Phe Lys Ala Lys Val Thr Ile Asp Trp Asp Arg Ser Thr Asn Thr
        195                 200                 205

Ala Tyr Leu Gln Leu Ser Gly Leu Thr Ser Gly Asp Thr Ala Val Tyr
    210                 215                 220

Tyr Cys Ala Lys Gly Ser Lys His Arg Leu Arg Asp Tyr Ala Leu Tyr
225                 230                 235                 240

Asp Asp Asp Gly Ala Leu Asn Trp Ala Val Asp Val Asp Tyr Leu Ser
                245                 250                 255

Asn Leu Glu Phe Trp Gly Gln Gly Thr Ala Val Thr Val Ser Ser
            260                 265                 270
```

<210> SEQ ID NO 62
<211> LENGTH: 1863
<212> TYPE: DNA
<213> ORGANISM: Artificial Sequence
<220> FEATURE:
<223> OTHER INFORMATION: Artificially Synthesized

<400> SEQUENCE: 62
atgaaccggg gagtcccttt taggcacttg cttctggtgc tgcaactggc gctcctccca     60
gcagccactc agggaaagaa agtggtgctg ggcaaaaaag gggatacagt ggaactgacc    120
tgtacagctt cccagaagaa gagcatacaa ttccactgga aaaactccaa ccagataaag    180
attctgggaa atcagggctc cttcttaact aaaggtccat ccaagctgaa tgatcgcgct    240
gactcaagaa gaagcctttg gaccaagga aacttccccc tgatcatcaa gaatcttaag    300

| | |
|---|---|
| atagaagact cagatactta catctgtgaa gtggaggacc agaaggagga ggtgcaattg | 360 |
| ctagtgttcg gattgactgc caactctgac acccacctgc ttcagggca gagcctgacc | 420 |
| ctgaccttgg agagcccccc tggtagtagc ccctcagtgc aatgtaggag tccaaggggt | 480 |
| aaaaacatac aggggggaa gaccctctcc gtgtctcagc tggagctcca ggatagtggc | 540 |
| acctggacat gcactgtctt gcagaaccag aagaaggtgg agttcaaaat agacatcgtg | 600 |
| gtgctagctt tccagaaggc ctccagcata gtctataaga agaggggga acaggtggag | 660 |
| ttctccttcc cactcgcctt tacagttgaa aagctgacgg gcagtggcga gctgtggtgg | 720 |
| caggcggaga gggcttcctc ctccaagtct tggatcacct ttgacctgaa gaacaaggaa | 780 |
| gtgtctgtaa acgggttac ccaggaccct aagctccaga tgggcaagaa gctcccgctc | 840 |
| cacctcaccc tgccccaggc cttgcctcag tatgctggct ctggaaacct caccctggcc | 900 |
| cttgaagcga aaacaggaaa gttgcatcag gaagtgaacc tggtggtgat gagagccact | 960 |
| cagctccaga aaaatttgac ctgtgaggtg tggggaccca cctcccctaa gctgatgctg | 1020 |
| agcttgaaac tggagaacaa ggaggcaaag gtctcgaagc gggagaaggc ggtgtgggtg | 1080 |
| ctgaaccctg aggcggggat gtggcagtgt ctgctgagtg actcgggaca ggtcctgctg | 1140 |
| gaatccaaca tcaaggttct gcccacatgg tccaccccgg tgcagccaac cacgacgcca | 1200 |
| gcgccgcgac caccaacacc ggcgcccacc atcgcgtcgc agcccctgtc cctgcgccca | 1260 |
| gaggcgtgcc ggccagcggc ggggggcgca gtgcacacga gggggctgga cttcgcctgt | 1320 |
| gattttggg tgctggtggt ggttggtgga gtcctggctt gctatagctt gctagtaaca | 1380 |
| gtggccttta ttattttctg ggtgaggagt aagaggagca ggctcctgca cagtgactac | 1440 |
| atgaacatga ctccccgccg ccccgggccc accgcaagc attaccagcc ctatgcccca | 1500 |
| ccacgcgact tcgcagccta tcgctccaga gtgaagttca gcaggagcgc agacgccccc | 1560 |
| gcgtaccagc agggccagaa ccagctctat aacgagctca atctaggacg aagagaggag | 1620 |
| tacgatgttt tggacaagag acgtggccgg gaccctgaga tgggggaaa gccgagaagg | 1680 |
| aagaaccctc aggaaggcct gtacaatgaa ctgcagaaag ataagatggc ggaggcctac | 1740 |
| agtgagattg ggatgaaagg cgagcgccgg aggggcaagg ggcacgatgg cctttaccag | 1800 |
| ggtctcagta cagccaccaa ggacacctac gacgcccttc acatgcaggc cctgccccct | 1860 |
| cgc | 1863 |

<210> SEQ ID NO 63
<211> LENGTH: 1857
<212> TYPE: DNA
<213> ORGANISM: Artificial Sequence
<220> FEATURE:
<223> OTHER INFORMATION: Artificially Synthesized

<400> SEQUENCE: 63

| | |
|---|---|
| atgaaccggg gagtcccttt taggcacttg cttctggtgc tgcaactggc gctcctccca | 60 |
| gcagccactc agggaaagaa agtggtgctg gcaaaaaag gggatacagt ggaactgacc | 120 |
| tgtacagctt cccagaagaa gagcatacaa ttccactgga aaaactccaa ccagataaag | 180 |
| attctgggaa atcagggctc cttcttaact aaaggtccat ccaagctgaa tgatcgcgct | 240 |
| gactcaagaa gaagcctttg ggaccaagga aacttccccc tgatcatcaa gaatcttaag | 300 |
| atagaagact cagatactta catctgtgaa gtggaggacc agaaggagga ggtgcaattg | 360 |
| ctagtgttcg gattgactgc caactctgac acccacctgc ttcagggca gagcctgacc | 420 |
| ctgaccttgg agagcccccc tggtagtagc ccctcagtgc aatgtaggag tccaaggggt | 480 |

| | |
|---|---|
| aaaaacatac agggggggaa gaccctctcc gtgtctcagc tggagctcca ggatagtggc | 540 |
| acctggacat gcactgtctt gcagaaccag aagaaggtgg agttcaaaat agacatcgtg | 600 |
| gtgctagctt tccagaaggc ctccagcata gtctataaga aagaggggga acaggtggag | 660 |
| ttctccttcc cactcgcctt tacagttgaa aagctgacgg gcagtggcga gctgtggtgg | 720 |
| caggcggaga gggcttcctc ctccaagtct tggatcacct ttgacctgaa gaacaaggaa | 780 |
| gtgtctgtaa acgggttac ccaggaccct aagctccaga tgggcaagaa gctcccgctc | 840 |
| caccctcaccc tgccccaggc cttgcctcag tatgctggct ctggaaacct caccctggcc | 900 |
| cttgaagcga aaacaggaaa gttgcatcag gaagtgaacc tggtggtgat gagagccact | 960 |
| cagctccaga aaatttgac ctgtgaggtg tggggaccca cctcccctaa gctgatgctg | 1020 |
| agcttgaaac tggagaacaa ggaggcaaag gtctcgaagc gggagaaggc ggtgtgggtg | 1080 |
| ctgaaccctg aggcggggat gtggcagtgt ctgctgagtg actcgggaca ggtcctgctg | 1140 |
| gaatccaaca tcaaggttct gcccacatgg tccaccccgg tgcagccaac cacgacgcca | 1200 |
| gcgccgcgac caccaacacc ggcgcccacc atcgcgtcgc agccctgtc cctgcgccca | 1260 |
| gaggcgtgcc ggccagcggc gggggcgca gtgcacacga gggggctgga cttcgcctgt | 1320 |
| gatatctaca tctgggcgcc cttggccggg acttgtgggg tccttctcct gtcactggtt | 1380 |
| atcaccctttt actgcaaacg gggcagaaag aaactcctgt atatattcaa acaaccattt | 1440 |
| atgagaccag tacaaactac tcaagaggaa gatggctgta gctgccgatt tccagaagaa | 1500 |
| gaagaaggag gatgtgaact gagagtgaag ttcagcagga gcgcagacgc ccccgcgtac | 1560 |
| cagcagggcc agaaccagct ctataacgag ctcaatctag gacgaagaga ggagtacgat | 1620 |
| gttttggaca gagacgtgg ccgggaccct gagatggggg gaaagccgag aaggaagaac | 1680 |
| cctcaggaag gcctgtacaa tgaactgcag aaagataaga tggcggaggc ctacagtgag | 1740 |
| attgggatga aaggcgagcg ccggaggggc aaggggcacg atggcctttta ccagggtctc | 1800 |
| agtacagcca ccaaggacac ctacgacgcc cttcacatgc aggccctgcc ccctcgc | 1857 |

<210> SEQ ID NO 64
<211> LENGTH: 1188
<212> TYPE: DNA
<213> ORGANISM: Artificial Sequence
<220> FEATURE:
<223> OTHER INFORMATION: Artificially Synthesized

<400> SEQUENCE: 64

| | |
|---|---|
| atgaaccggg gagtcccttt taggcacttg cttctggtgc tgcaactggc gctcctccca | 60 |
| gcagccactc agggaaagaa agtggtgctg ggcaaaaaag gggatacagt ggaactgacc | 120 |
| tgtacagctt cccagaagaa gagcatacaa ttccactgga aaaactccaa ccagataaag | 180 |
| attctgggaa atcagggctc cttcttaact aaaggtccat ccaagctgaa tgatcgcgct | 240 |
| gactcaagaa gaagcttttg ggaccaagga aacttccccc tgatcatcaa gaatcttaag | 300 |
| atagaagact cagatactta catctgtgaa gtggaggacc agaaggagga ggtgcaattg | 360 |
| ctagtgttcg gattgactgc caactctgac acccacctgc ttcagggca gagcctgacc | 420 |
| ctgaccttgg agagccccc tggtagtagc ccctcagtgc aatgtaggag tccaagggt | 480 |
| aaaaacatac agggggggaa gaccctctcc gtgtctcagc tggagctcca ggatagtggc | 540 |
| acctggacat gcactgtctt gcagaaccag aagaaggtgg agttcaaaat agacatcgtg | 600 |
| gtgctagctt tccagaaggc ctccagcata gtctataaga aagaggggga acaggtggag | 660 |
| ttctccttcc cactcgcctt tacagttgaa aagctgacgg gcagtggcga gctgtggtgg | 720 |

```
caggcggaga gggcttcctc ctccaagtct tggatcacct ttgacctgaa gaacaaggaa      780
gtgtctgtaa acgggttac ccaggaccct aagctccaga tgggcaagaa gctcccgctc       840
cacctcaccc tgccccaggc cttgcctcag tatgctggct ctggaaacct caccctggcc      900
cttgaagcga aaacaggaaa gttgcatcag gaagtgaacc tggtggtgat gagagccact      960
cagctccaga aaatttgac ctgtgaggtg tggggaccca cctcccctaa gctgatgctg       1020
agcttgaaac tggagaacaa ggaggcaaag gtctcgaagc gggagaaggc ggtgtgggtg      1080
ctgaaccctg aggcggggat gtggcagtgt ctgctgagtg actcgggaca ggtcctgctg      1140
gaatccaaca tcaaggttct gcccacatgg tccaccccgg tgcagcca                  1188
```

<210> SEQ ID NO 65
<211> LENGTH: 135
<212> TYPE: DNA
<213> ORGANISM: Artificial Sequence
<220> FEATURE:
<223> OTHER INFORMATION: Artificially Synthesized

<400> SEQUENCE: 65

```
accacgacgc cagcgccgcg accaccaaca ccggcgccca ccatcgcgtc gcagcccctg      60
tccctgcgcc cagaggcgtg ccggccagcg gcgggggggcg cagtgcacac gagggggctg     120
gacttcgcct gtgat                                                     135
```

<210> SEQ ID NO 66
<211> LENGTH: 72
<212> TYPE: DNA
<213> ORGANISM: Artificial Sequence
<220> FEATURE:
<223> OTHER INFORMATION: Artificially Synthesized

<400> SEQUENCE: 66

```
atctacatct gggcgccctt ggccgggact tgtgggtcc ttctcctgtc actggttatc       60 acccttact gc                                                          72
```

<210> SEQ ID NO 67
<211> LENGTH: 204
<212> TYPE: DNA
<213> ORGANISM: Artificial Sequence
<220> FEATURE:
<223> OTHER INFORMATION: Artificially Synthesized

<400> SEQUENCE: 67

```
ttttgggtgc tggtggtggt tggtggagtc ctggcttgct atagcttgct agtaacagtg      60
gcctttatta ttttctgggt gaggagtaag aggagcaggc tcctgcacag tgactacatg      120
aacatgactc cccgccgccc cgggcccacc cgcaagcatt accagcccta tgccccacca      180
cgcgacttcg cagcctatcg ctcc                                            204
```

<210> SEQ ID NO 68
<211> LENGTH: 126
<212> TYPE: DNA
<213> ORGANISM: Artificial Sequence
<220> FEATURE:
<223> OTHER INFORMATION: Artificially Synthesized

<400> SEQUENCE: 68

```
aaacggggca gaaagaaact cctgtatata ttcaaacaac catttatgag accagtacaa      60
actactcaag aggaagatgg ctgtagctgc cgatttccag aagaagaaga aggaggatgt      120
gaactg                                                                126
```

<210> SEQ ID NO 69
<211> LENGTH: 336
<212> TYPE: DNA
<213> ORGANISM: Artificial Sequence
<220> FEATURE:
<223> OTHER INFORMATION: Artificially Synthesized

<400> SEQUENCE: 69

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggagggca aggggcacga tggcctttac cagggtctca gtacagccac caaggacacc   300
tacgacgccc ttcacatgca ggccctgccc cctcgc                             336
```

<210> SEQ ID NO 70
<211> LENGTH: 1325
<212> TYPE: DNA
<213> ORGANISM: Artificial Sequence
<220> FEATURE:
<223> OTHER INFORMATION: Artificially Synthesized

<400> SEQUENCE: 70

```
cagagactgg tggaaagcgg tggaggcgtg gtgcagcctg gcagcagcct gagactgagc    60
tgcgccgctt ccggcttcga cttcagccgg cagggcatgc attgggtgcg ccaggctcca   120
ggacagggac tggaatgggt ggccttcatc aagtacgacg gcagcgagaa gtaccacgcc   180
gacagcgtgt ggggtagact gtctatcagc cgggacaaca gcaaggacac cctgtacctg   240
cagatgaaca gcctgcgggt ggaggacacc gccacatact tttgcgtgcg ggaggctggt   300
ggacctgact accggaacgg ctacaactac tacgacttct acgacggcta ctacaactac   360
cactacatgg atgtgtgggg caagggcacc accgtgaccg tgtctagcgg aggcggagga   420
tctggcggcg gaggaagtgg aggcggcgga agccagtctg ccctgaccca gcctgcctct   480
gtgtctggca gccctggcca gagcatcacc atcagctgca acggaccagc aacgacgtg   540
ggcggctacg agagcgtgtc ctggtatcag cagcaccccg gcaaggcccc caaggtggtg   600
atctacgacg tgtccaagag gcccagcggc gtgagcaacc ggttcagcgg cagcaagagc   660
ggcaataccg ccagcctgac catctctggg ctgcaggccg aggacgaggg cgactactac   720
tgcaagagcc tgaccagcac caggcggaga gtgttcggca ccggcaccaa gctgaccgtg   780
ctgaccacga cgccagcgcc gcgaccacca acaccggcgc ccaccatcgc gtcgcagccc   840
ctgtccctgc gcccagaggc gtgccggcca gcggcggggg gcgcagtgca cacgaggggg   900
ctggacttcg cctgtgatat ctacatctgg gcgcccttgg ccgggacttg tggggtcctt   960
ctcctgtcac tggttatcac cctttactgc gagtgaagtt cagcaggagc gcagacgccc  1020
ccgcgtacaa gcagggccag aaccagctct ataacgagct caatctagga cgaagagagg  1080
agtacgatgt tttggacaag agacgtggcc gggaccctga gatgggggga aagccgagaa  1140
ggaagaaccc tcaggaaggc ctgtacaatg aactgcagaa agataagatg gcggaggcct  1200
acagtgagat tgggatgaaa ggcgagcgcc ggaggggcaa ggggcacgat ggcctttacc  1260
agggtctcag tacagccacc aaggacacct acgacgccct tcacatgcag gccctgcccc  1320
ctcgc                                                              1325
```

<210> SEQ ID NO 71
<211> LENGTH: 1328
<212> TYPE: DNA
<213> ORGANISM: Artificial Sequence
<220> FEATURE:
<223> OTHER INFORMATION: Artificially Synthesized

<400> SEQUENCE: 71

| | | |
|---|---|---|
| ggatcccaga gcgccctgac acagcctcct agcgcctctg gatctcccgg ccagagcatc | 60 |
| accatcagct gtaccggcac cagcaacaac ttcgtgtcct ggtatcagca gcacgccggc | 120 |
| aaggccccca agctcgtgat ctacgacgtg aacaagcggc ccagcggcgt gcccgataga | 180 |
| ttcagcggca gcaagagcgg caacaccgcc agcctgacag tgtctggcct gcagaccgat | 240 |
| gacgaggccg tgtactactg cggcagcctc gtgggcaact gggacgtgat ctttggcgga | 300 |
| ggcaccaagc tgaccgtgct gggcggaagc agcagaagct ctagttctgg cggcggagga | 360 |
| agcggaggcg gaggacagcc tcagctgcag gaatctggcc ccacactggt ggaagccagc | 420 |
| gagacactga gcctgacctg tgccgtgtcc ggcgattcta ccgccgcctg caatagcttc | 480 |
| tggggctggg tgcgccagcc tcctggaaag ggactggaat gggtgggaag cctgagccac | 540 |
| tgcgccagct attggaaccg ggctggacc taccacaacc ccagcctgaa gtccagactg | 600 |
| accctggccc tggacacccc caagaacctg tgttcctga agctgaacag cgtgacagcc | 660 |
| gccgacaccg ccacctacta ctgtgccaga tttggcggcg aggtgctgcg gtacaccgac | 720 |
| tggcctaaac tgcctgggt ggacctgtgg ggcagaggaa cactcgtgac cgtgtctagc | 780 |
| tccggaacca cgacgccagc gccgcgacca ccaacaccgg cgcccaccat cgcgtcgcag | 840 |
| cccctgtccc tgcgcccaga ggcgtgccgg ccagcggcgg ggggcgcagt gcacacgagg | 900 |
| gggctggact cgcctgtga tatctacatc tgggcgccct tggccgggac ttgtggggtc | 960 |
| cttctcctgt cactggttat caccctttac tgcgagtgaa gttcagcagg agcgcagacg | 1020 |
| cccccgcgta caagcagggc cagaaccagc tctataacga gctcaatcta ggacgaagag | 1080 |
| aggagtacga tgttttggac aagagacgtg gccgggaccc tgagatgggg ggaaagccga | 1140 |
| gaaggaagaa ccctcaggaa ggcctgtaca tgaactgca gaaagataag atggcggagg | 1200 |
| cctacagtga gattgggatg aaaggcgagc gccgagggg caaggggcac gatggccttt | 1260 |
| accagggtct cagtacagcc accaaggaca cctacgacgc ccttcacatg caggccctgc | 1320 |
| cccctcgc | 1328 |

<210> SEQ ID NO 72
<211> LENGTH: 1283
<212> TYPE: DNA
<213> ORGANISM: Artificial Sequence
<220> FEATURE:
<223> OTHER INFORMATION: Artificially Synthesized

<400> SEQUENCE: 72

| | | |
|---|---|---|
| ggatccgaga tcgtgctgac acagagccct ggcaccctga gcctgtctcc aggcgagaca | 60 |
| gccatcatca gctgccggac aagccagtac ggcagcctgg cctggtatca gcagaggcct | 120 |
| ggacaggccc ccagactcgt gatctacagc ggcagcacaa gagccgccgg aatcccgat | 180 |
| agattcagcg gctctagatg gggccctgac tacaacctga ccatcagcaa cctggaaagc | 240 |
| ggcgacttcg cgtgtacta ctgccagcag tacgagttct tcggccaggg caccaaggtg | 300 |
| caggtgaca tcaagagagg cggcagctcc agaagctcca gctctggcgg cggaggatct | 360 |
| ggcggaggcg gacaggtgca gctggtgcag tctggcggcc agatgaagaa accggcgag | 420 |

| | |
|---|---|
| agcatgcgga tcagctgcag agcctccggc tacgagttca tcgactgcac cctgaactgg | 480 |
| attcggctgg cccctggcaa aagacccgag tggatgggct ggctgaagcc cagaggcgga | 540 |
| gccgtgaatt acgccagacc tctgcagggc agagtgacca tgacccggga cgtgtacagc | 600 |
| gataccgcct tcctggaact gcggagcctg accgtggatg ataccgccgt gtacttctgc | 660 |
| acccggggca agaactgcga ctacaactgg gacttcgagc actggggcag aggcacccct | 720 |
| gtgatcgtgt ctagctccgg aaccacgacg ccagcgccgc gaccaccaac accggcgccc | 780 |
| accatcgcgt cgcagcccct gtccctgcgc ccagaggcgt gccggccagc ggcgggggc | 840 |
| gcagtgcaca cgagggggct ggacttcgcc tgtgatatct acatctgggc gcccttggcc | 900 |
| gggacttgtg gggtccttct cctgtcactg gttatcaccc tttactgcga gtgaagttca | 960 |
| gcaggagcgc agacgccccc gcgtacaagc agggccagaa ccagctctat aacgagctca | 1020 |
| atctaggacg aagagaggag tacgatgttt tggacaagag acgtggccgg accctgaga | 1080 |
| tgggggggaaa gccgagaagg aagaaccctc aggaaggcct gtacaatgaa ctgcagaaag | 1140 |
| ataagatggc ggaggcctac agtgagattg ggatgaaagg cgagcgccgg aggggcaagg | 1200 |
| ggcacgatgg cctttaccag ggtctcagta cagccaccaa ggacacctac gacgcccttc | 1260 |
| acatgcaggc cctgcccct cgc | 1283 |

<210> SEQ ID NO 73
<211> LENGTH: 1262
<212> TYPE: DNA
<213> ORGANISM: Artificial Sequence
<220> FEATURE:
<223> OTHER INFORMATION: Artificially Synthesized

<400> SEQUENCE: 73

| | |
|---|---|
| gacatccaga tgacccagag ccccagcagc ctgtctgcca gagtgggcga caccgtgacc | 60 |
| atcacctgtc aggccaacgg ctacctgaac tggtatcagc agcggagagg caaggccccc | 120 |
| aagctgctga tctacgacgg cagcaagctg gaaagaggcg tgcccgccag attcagcggc | 180 |
| agaagatggg gccaggagta caacctgacc atcaacaacc tgcagcccga ggacgtggcc | 240 |
| acatactttt gccaggtgta cgagttcatc gtgcccggca cccggctgga tctgaagggc | 300 |
| ggaagcagca gaagcagctc tagcggcgga ggcggatctg gcggaggggg acaggtgcac | 360 |
| ctgagtcagt ctggcgccgc tgtgacaaag ccaggcgctt ctgtgcgggt gtcctgtgaa | 420 |
| gccagcggct acaagatcag cgaccacttc atccactggt ggcggcaggc tccaggacag | 480 |
| ggactgcagt gggtgggatg gatcaacccc aagaccggcc agcccaacaa ccccagacag | 540 |
| ttccagggca gagtgtccct gaccagacag gccagctggg acttcgacac ctacagcttc | 600 |
| tacatggacc tgaaggccgt gcggagcgac gacaccgcca tctactttg cgccagacag | 660 |
| agaagcgact tctgggattt cgacgtgtgg ggcagcggca cccaagtgac cgtgtcatct | 720 |
| accacgacgc cagcgccgcg accaccaaca ccggcgccca ccatcgcgtc gcagcccctg | 780 |
| tccctgcgcc cagaggcgtg ccggccagcg gcggggggcg cagtgcacac gagggggctg | 840 |
| gacttcgcct gtgatatcta catctgggcg cccttggccg ggacttgtgg ggtccttctc | 900 |
| ctgtcactgg ttatcaccct ttactgcgag tgaagttcag caggagcgca gacgcccccg | 960 |
| cgtacaagca gggccagaac cagctctata cgagctcaa tctaggacga agagaggagt | 1020 |
| acgatgtttt ggacaagaga cgtggccggg accctgagat ggggggaaag ccgagaagga | 1080 |
| agaaccctca ggaaggcctg tacaatgaac tgcagaaaga taagatgcg gaggcctaca | 1140 |
| gtgagattgg gatgaaaggc gagcgccgga ggggcaaggg gcacgatggc ctttaccagg | 1200 |

| | |
|---|---|
| gtctcagtac agccaccaag gacacctacg acgcccttca catgcaggcc ctgcccctc | 1260 |
| gc | 1262 |

<210> SEQ ID NO 74
<211> LENGTH: 1355
<212> TYPE: DNA
<213> ORGANISM: Artificial Sequence
<220> FEATURE:
<223> OTHER INFORMATION: Artificially Synthesized

<400> SEQUENCE: 74

| | |
|---|---|
| gacttcgtgc tgacccagag ccctcacagc ctgagcgtga cacctggcga gagcgccagc | 60 |
| atcagctgca agagcagcca ctccctgatc cacggcgacc ggaacaacta cctggcttgg | 120 |
| tacgtgcaga gcccggcag atcccccag ctgctgatct acctggccag cagcagagcc | 180 |
| agcggcgtgc ccgatagatt ttctggcagc ggcagcgaca aggacttcac cctgaagatc | 240 |
| agccgggtgg aaaccgagga cgtgggcacc tactactgta tgcagggcag agagagcccc | 300 |
| tggacctttg gccagggcac caaggtggac atcaagggcg gcagctccag aagcagctct | 360 |
| agcggaggcg gaggatctgg cggcggagga caggctcagc tggtgcagtc tggacccgaa | 420 |
| gtgcggaagc ctggcaccag cgtgaaggtg tcctgtaaag cccctggcaa caccctgaaa | 480 |
| acctacgacc tgcactgggt gcgcagcgtg ccaggacagg gactgcagtg gatgggctgg | 540 |
| atcagccacg agggcgacaa gaaagtgatc gtggaacggt tcaaggccaa agtgaccatc | 600 |
| gactgggaca gaagcaccaa caccgcctac ctgcagctga gcggcctgac ctctggcgat | 660 |
| accgccgtgt actactgcgc caagggcagc aagcaccggc tgagagacta cgccctgtac | 720 |
| gacgatgacg gcgccctgaa ctgggccgtg gatgtggact acctgagcaa cctggaattc | 780 |
| tggggccagg gaaccgccgt gaccgtgtca tctaccacga cgccagcgcc gcgaccacca | 840 |
| acaccggcgc ccaccatcgc gtcgcagccc ctgtccctgc gcccagaggc gtgccggcca | 900 |
| gcggcggggg gcgcagtgca cacgagggg ctggacttcg cctgtgatat ctacatctgg | 960 |
| gcgcccttgg ccgggacttg tggggtcctt ctcctgtcac tggttatcac cctttactgc | 1020 |
| gagtgaagtt cagcaggagc gcagacgccc ccgcgtacaa gcagggccag aaccagctct | 1080 |
| ataacgagct caatctagga cgaagagagg agtacgatgt tttggacaag acgtggcc | 1140 |
| gggaccctga gatgggggga aagccgagaa ggaagaaccc tcaggaaggc ctgtacaatg | 1200 |
| aactgcagaa agataagatg gcggaggcct acagtgagat tgggatgaaa ggcgagcgcc | 1260 |
| ggagggggcaa ggggcacgat ggcctttacc agggtctcag tacagccacc aaggacacct | 1320 |
| acgacgccct tcacatgcag gccctgcccc ctcgc | 1355 |

<210> SEQ ID NO 75
<211> LENGTH: 783
<212> TYPE: DNA
<213> ORGANISM: Artificial Sequence
<220> FEATURE:
<223> OTHER INFORMATION: Artificially Synthesized

<400> SEQUENCE: 75

| | |
|---|---|
| cagagactgg tggaaagcgg tggaggcgtg gtgcagcctg gcagcagcct gagactgagc | 60 |
| tgcgccgctt ccggcttcga cttcagccgg cagggcatgc attgggtgcg ccaggctcca | 120 |
| ggacagggac tggaatgggt ggccttcatc aagtacgacg gcagcgagaa gtaccacgcc | 180 |
| gacagcgtgt ggggtagact gtctatcagc cgggacaaca gcaaggacac cctgtacctg | 240 |
| cagatgaaca gcctgcgggt ggaggacacc gccacatact tttgcgtgcg ggaggctggt | 300 |

| | |
|---|---:|
| ggacctgact accggaacgg ctacaactac tacgacttct acgacggcta ctacaactac | 360 |
| cactacatgg atgtgtgggg caagggcacc accgtgaccg tgtctagcgg aggcggagga | 420 |
| tctggcggcg gaggaagtgg aggcggcgga agccagtctg ccctgaccca gcctgcctct | 480 |
| gtgtctggca gccctggcca gagcatcacc atcagctgca acggaccag caacgacgtg | 540 |
| ggcggctacg agagcgtgtc ctggtatcag cagcaccccg gcaaggcccc caaggtggtg | 600 |
| atctacgacg tgtccaagag gcccagcggc gtgagcaacc ggttcagcgg cagcaagagc | 660 |
| ggcaataccg ccagcctgac catctctggg ctgcaggccg aggacgaggg cgactactac | 720 |
| tgcaagagcc tgaccagcac caggcggaga gtgttcggca ccggcaccaa gctgaccgtg | 780 |
| ctg | 783 |

<210> SEQ ID NO 76
<211> LENGTH: 786
<212> TYPE: DNA
<213> ORGANISM: Artificial Sequence
<220> FEATURE:
<223> OTHER INFORMATION: Artificially Synthesized

<400> SEQUENCE: 76

| | |
|---|---:|
| ggatcccaga gcgccctgac acagcctcct agcgcctctg gatctcccgg ccagagcatc | 60 |
| accatcagct gtaccggcac cagcaacaac ttcgtgtcct ggtatcagca gcacgccggc | 120 |
| aaggccccca gctcgtgat ctacgacgtg aacaagcggc cagcggcgt gcccgataga | 180 |
| ttcagcggca gcaagagcgg caacaccgcc agcctgacag tgtctggcct gcagaccgat | 240 |
| gacgaggccg tgtactactg cggcagcctc gtgggcaact gggacgtgat ctttggcgga | 300 |
| ggcaccaagc tgaccgtgct gggcggaagc agcagaagct ctagttctgg cggcggagga | 360 |
| agcggaggcg gaggacagcc tcagctgcag gaatctggcc ccacactggt ggaagccagc | 420 |
| gagacactga gcctgacctg tgccgtgtcc ggcgattcta ccgccgcctg caatagcttc | 480 |
| tggggctggg tgcgccagcc tcctggaaag ggactggaat gggtgggaag cctgagccac | 540 |
| tgcgccagct attggaaccg gggctggacc taccacaacc ccagcctgaa gtccagactg | 600 |
| accctggccc tggacacccc caagaacctg gtgttcctga gctgaacag cgtgacagcc | 660 |
| gccgacaccg ccacctacta ctgtgccaga tttggcggcg aggtgctgcg gtacaccgac | 720 |
| tggcctaaac tgcctgggt ggacctgtgg ggcagaggaa cactcgtgac cgtgtctagc | 780 |
| tccgga | 786 |

<210> SEQ ID NO 77
<211> LENGTH: 741
<212> TYPE: DNA
<213> ORGANISM: Artificial Sequence
<220> FEATURE:
<223> OTHER INFORMATION: Artificially Synthesized

<400> SEQUENCE: 77

| | |
|---|---:|
| ggatccgaga tcgtgctgac acagagccct ggcaccctga gcctgtctcc aggcgagaca | 60 |
| gccatcatca gctgccggac aagccagtac ggcagcctgg cctggtatca gcagaggcct | 120 |
| ggacaggccc ccagactcgt gatctacagc ggcagcacaa gagccgccgg aatcccgat | 180 |
| agattcagcg gctctagatg gggccctgac tacaacctga ccatcagcaa cctggaaagc | 240 |
| ggcgacttcg cgtgtacta ctgccagcag tacgagttct tcggccaggg caccaaggtg | 300 |
| caggtggaca tcaagagagg cggcagctcc agaagctcca gctctggcgg cggaggatct | 360 |
| ggcggaggcg gacaggtgca gctggtgcag tctggcggcc agatgaagaa acccggcgag | 420 |

```
agcatgcgga tcagctgcag agcctccggc tacgagttca tcgactgcac cctgaactgg    480
attcggctgg cccctggcaa aagacccgag tggatgggct ggctgaagcc cagaggcgga    540
gccgtgaatt acgccagacc tctgcagggc agagtgacca tgacccggga cgtgtacagc    600
gataccgcct tcctggaact gcggagcctg accgtggatg ataccgccgt gtacttctgc    660
acccggggca agaactgcga ctacaactgg gacttcgagc actggggcag aggcacccct    720
gtgatcgtgt ctagctccgg a                                              741
```

```
<210> SEQ ID NO 78
<211> LENGTH: 720
<212> TYPE: DNA
<213> ORGANISM: Artificial Sequence
<220> FEATURE:
<223> OTHER INFORMATION: Artificially Synthesized

<400> SEQUENCE: 78
gacatccaga tgacccagag ccccagcagc ctgtctgcca gagtgggcga caccgtgacc     60
atcacctgtc aggccaacgg ctacctgaac tggtatcagc agcggagagg caaggccccc    120
aagctgctga tctacgacgg cagcaagctg aaagaggcg tgcccgccag attcagcggc     180
agaagatggg gccaggagta caacctgacc atcaacaacc tgcagcccga ggacgtggcc    240
acatactttt gccaggtgta cgagttcatc gtgcccggca cccggctgga tctgaagggc    300
ggaagcagca aagcagctc tagcggcgga ggcggatctg gcggaggggg acaggtgcac    360
ctgagtcagt ctggcgccgc tgtgacaaag ccaggcgctt ctgtgcgggt gtcctgtgaa    420
gccagcggct acaagatcag cgaccacttc atccactggt ggcggcaggc tccaggacag    480
ggactgcagt gggtgggatg gatcaacccc aagaccggcc agcccaacaa ccccagacag    540
ttccagggca gagtgtccct gaccagacag gccagctggg acttcgacac ctacagcttc    600
tacatggacc tgaaggccgt gcggagcgac gacaccgcca tctactttg cgccagacag    660 agaagcgact ctgggattt cgacgtgtgg ggcagcggca cccaagtgac cgtgtcatct    720
```

```
<210> SEQ ID NO 79
<211> LENGTH: 813
<212> TYPE: DNA
<213> ORGANISM: Artificial Sequence
<220> FEATURE:
<223> OTHER INFORMATION: Artificially Synthesized

<400> SEQUENCE: 79
gacttcgtgc tgacccagag ccctcacagc ctgagcgtga cacctggcga gagcgccagc     60
atcagctgca gagagcagcca ctccctgatc cacggcgacc ggaacaacta cctggcttgg    120
tacgtgcaga agcccggcag atcccccag ctgctgatct acctggccag cagcagagcc    180
agcggcgtgc ccgatagatt ttctggcagc ggcagcgaca aggacttcac cctgaagatc    240
agccgggtgg aaaccgagga cgtgggcacc tactactgta tgcagggcag agagagcccc    300 tggaccttg gccagggcac caaggtggac atcaagggcg gcagctccag aagcagctct    360
agcggaggcg gaggatctgg cggcggagga caggctcagc tggtgcagtc tggacccgaa    420
gtgcggaagc ctggcaccag cgtgaaggtg tcctgtaaag cccctggcaa caccctgaaa    480
acctacgacc tgcactgggt gcgcagcgtg ccaggacagg gactgcagtg gatgggctgg    540
atcagccacg agggcgacaa gaaagtgatc gtggaacggt tcaaggccaa agtgaccatc    600
gactgggaca gaagcaccaa caccgcctac ctgcagctga gcggcctgac ctctggcgat    660
accgccgtgt actactgcgc caagggcagc aagcaccggc tgagagacta cgccctgtac    720
```

```
gacgatgacg gcgccctgaa ctgggccgtg gatgtggact acctgagcaa cctggaattc      780
tggggccagg gaaccgccgt gaccgtgtca tct                                   813

<210> SEQ ID NO 80
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 80
ctgtgcttca aggtccttgt ctgc                                             24

<210> SEQ ID NO 81
<211> LENGTH: 24
<212> TYPE: DNA
<213> ORGANISM: Artificial Sequence
<220> FEATURE:
<223> OTHER INFORMATION: Artificially Synthesized

<400> SEQUENCE: 81
ctctgtctcc ttctacagcc aagc                                             24

<210> SEQ ID NO 82
<211> LENGTH: 46
<212> TYPE: DNA
<213> ORGANISM: Artificial Sequence
<220> FEATURE:
<223> OTHER INFORMATION: Artificially Synthesized
<220> FEATURE:
<221> NAME/KEY: misc_feature
<222> LOCATION: (21)..(25)
<223> OTHER INFORMATION: n is a, c, g, or t

<400> SEQUENCE: 82
acacgacgct cttccgatct nnnnngccag gttgagcagg tagatg                     46

<210> SEQ ID NO 83
<211> LENGTH: 45
<212> TYPE: DNA
<213> ORGANISM: Artificial Sequence
<220> FEATURE:
<223> OTHER INFORMATION: Artificially Synthesized

<400> SEQUENCE: 83
gacgtgtgct cttccgatct gctctactca ctggtgttca tcttt                      45
```

US 10,738,099 B2

METHOD OF REDIRECTING T CELLS TO TREAT HIV INFECTION

CROSS-REFERENCE TO RELATED APPLICATIONS

The present application is a 35 U.S.C. § 371 national phase application from, and claims priority to International Application No. PCT/US2016/053097, filed Sep. 22, 2016, which claims priority under 35 U.S.C. § 119(e) to U.S. Provisional Patent Application No. 62/222,132, filed Sep. 22, 2015 and U.S. Provisional Patent Application No. 62/253,790, filed Nov. 11, 2015, which are incorporated herein by reference in their entireties.

STATEMENT REGARDING FEDERALLY SPONSORED RESEARCH OR DEVELOPMENT

This invention was made with government support under Grant Nos AI104280, AI117950, and AR064220 awarded by the National Institutes of Health. The government has certain rights in the invention.

BACKGROUND OF THE INVENTION

Despite the ability of antiretroviral therapy to minimize human immunodeficiency virus type (HIV) replication and increase the duration and quality of patients' lives, the health consequences and financial burden associated with the lifelong treatment regimen render a permanent cure highly attractive. Although T cells play an important role in controlling virus replication, they are themselves targets of HIV-mediated destruction.

Restoration of CD4 T cell activity, whether by immune augmentation or by protection from deletion, is a critical factor to enable long-term control of HIV replication in the absence of highly active antiretroviral therapy (HAART). Attempts to manufacture T cells as therapeutic agents to treat HW have been ongoing for over two decades. T cells can be engineered to express a synthetic immunoreceptor comprised of an extracellular targeted antibody and intracellular signaling domain, known as chimeric antigen receptor (CAR). This new area of research, referred to as adoptive T cell therapy, has recently undergone many technological advances. Importantly, T-cell therapy approaches have the potential to protect helper CD4 T cells and equip them with direct antiviral functions, which may be critical for improving HIV-specific cytotoxicity and achieving control over HIV replication in the absence of antiretroviral therapy. While major advances have already been made in the field of T cell engineering for adoptive therapy, including demonstrations of safety and feasibility, no clinical trial has resulted in durable and consistent control over HIV-replication in the absence of HAART.

In contrast to a vaccine approach, which relies on the production and priming of HIV-specific lymphocytes within a patient's own body, adoptive T-cell therapy provides an opportunity to customize the therapeutic T cells prior to administration. Thus, despite the unsuccessful therapeutic attempts using direct genetic manipulation of T cells, it is clear that adoptive cellular therapies could facilitate a functional cure by generating HIV-resistant cells, redirecting HIV-specific immune responses, or a combination of the two strategies. However, at present, it is unclear how to best engineer T cells so that sustained control over HIV replication can be achieved in the absence of antiretroviral therapy.

There is a great need in the art for more effective T-cell gene-engineering and gene-editing strategies that inhibit HIV replication and provide a gene therapy-mediated functional cure. This invention addresses this need.

SUMMARY OF THE INVENTION

As described herein, the present invention relates to compositions and methods for treating of a HIV infected mammal using a CD4 membrane-bound chimeric receptor or a HIV specific single chain variable fragments (scFvs) CARs.

In one aspect, the invention includes an isolated nucleic acid sequence encoding a membrane-bound chimeric receptor. The isolated nucleic acid sequence comprises a CD4 extracellular domain, a transmembrane domain, and a signaling domain, wherein the CD4 extracellular domain is capable of recognizing and binding a HIV infected cell.

In another aspect, the invention includes an isolated amino acid sequence encoding a membrane-bound chimeric receptor. The isolated amino acid sequence comprises a CD4 extracellular domain, a transmembrane domain, and a signaling domain, wherein the CD4 extracellular domain is capable of recognizing and binding a HIV infected cell.

In some embodiments, the CD4 extracellular domain is encoded by a nucleic acid sequence comprising SEQ ID NO: 3 or 64. In some embodiments, the CD4 extracellular domain comprises the amino acid sequence SEQ ID NO: 46. In some other embodiments, the CD4 extracellular domain specifically binds to the HIV envelope (Env) glycoprotein.

In some embodiments, the transmembrane domain comprises a CD8alpha hinge encoded by nucleic acid sequence SEQ ID NO: 4 or 65 and a transmembrane domain comprising at least one domain encoded by a nucleic acid sequence comprising one selected from the group consisting of SEQ ID NOs: 5 and 8. In other embodiments, the transmembrane domain comprises the transmembrane domain comprises a CD8alpha hinge of SEQ ID NO: 47, and a transmembrane domain comprising at least one amino acid sequence selected from the group consisting of SEQ ID NOs: 48 and 49.

In other embodiments, the signaling domain comprises a CD3zeta signaling domain encoded by a nucleic acid sequence comprising SEQ ID NO: 6 or 68. In other embodiments, the signaling domain comprises a CD3zeta signaling domain comprising SEQ ID NO: 51.

In yet other embodiments, the isolated nucleic acid or amino acid sequence of the invention further comprises a costimulatory signaling region.

In various embodiments of the above aspects or any other aspect of the invention delineated herein, the costimulatory signaling region comprises an intracellular domain of a costimulatory molecule selected from the group consisting of alpha, beta or zeta chain of a TCR zeta, FcR gamma, FcR beta, CD3 gamma, CD3 delta, CD3 epsilon, CD5, CD22, CD79a, CD79b, or CD66d, a costimulatory signaling region from CD27, CD28, 4-1BB (CD137), DAP12, OX9, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof. In some embodiments, the costimulatory signaling region is CD28 and is encoded by a nucleic acid sequence comprising SEQ ID NO: 9 or 67. In other embodiments, the costimulatory signaling region is CD28 and comprises SEQ ID NO: 49.

In one aspect, the invention includes a vector comprising an isolated nucleic acid sequence encoding a membrane-bound chimeric receptor. The isolated nucleic acid sequence of the vector comprises a CD4 extracellular domain, a transmembrane domain, and a signaling domain, wherein the CD4 extracellular domain is capable of recognizing and binding a HIV infected cell. In some embodiments the nucleic acid sequence of the vector comprises at least one from the group consisting of SEQ ID NOs: 1, 7, 62 and 63.

In another aspect, the invention includes a vector comprising a membrane-bound chimeric receptor. The membrane-bound chimeric receptor of the vector comprises a CD4 extracellular domain, a transmembrane domain, and a signaling domain, wherein the CD4 extracellular domain is capable of recognizing and binding a HIV infected cell, wherein the vector comprises at least one amino acid sequence selected from the group consisting of SEQ ID NOs: 44 and 45. In some embodiments, the vector comprises an EFu promoter.

In yet another aspect, the invention includes an isolated nucleic acid sequence encoding a chimeric antigen receptor (CAR). The isolated nucleic acid sequence encoding the CAR of the invention comprises a HIV-specific binding domain, a transmembrane domain, a costimulatory signaling region, and a signaling domain, wherein the HIV binding domain comprises an anti-HIV antibody or a fragment thereof.

In some embodiments, the HIV-specific binding domain comprises a heavy and light chain. In other embodiments, the HIV-specific binding domain is a human antibody, a humanized antibody, and a fragment thereof. In other embodiments, the antibody or a fragment thereof is selected from the group consisting of a Fab fragment, a F(ab')$_2$ fragment, a Fv fragment, and a single chain Fv (scFv). In yet other embodiments, the scFv comprises an amino acid sequence selected from the group consisting of SEQ ID NOs: 13, 17, 21, 25, 29, 57-60 and 61. In further embodiments, the scFv is encoded by a nucleic acid sequence selected from the group consisting of SEQ ID NOs: 12, 16, 20, 24, 28, 75-78 and 79. In still further embodiments, the HIV-specific binding domain specifically binds to the surface of HIV infected cells, or HIV virions.

In some embodiments, the costimulatory signaling region of the CAR of the invention comprises an intracellular domain of a costimulatory molecule selected from the group consisting of TCR, CD3 zeta, CD3 gamma, CD3 delta, CD3 epsilon, CD86, common FcR gamma, FcR beta (Fc Epsilon Rib), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, and any combination thereof.

In some embodiments, the signaling domain of the CAR of the invention comprises a CD3zeta signaling domain encoded by nucleic acid sequence SEQ ID NO: 6 or 68.

In some embodiments, the CAR is encoded by a nucleic acid sequence selected from the group consisting of SEQ ID NOs: 10, 14, 18, 22, 26, 34, 70-73, and 74. In other embodiments, the CAR has an amino acid sequence selected from the group consisting of SEQ ID NOs: 11, 15, 19, 23, 27, 35, 52-55, and 56.

In one aspect, the invention includes a modified cell comprising either an isolated nucleic acid sequence that comprises a CD4 extracellular domain, a transmembrane domain, and a signaling domain, wherein the CD4 extracellular domain is capable of recognizing and binding a HIV infected cell; or an isolated nucleic acid sequence encoding a CAR that comprises a HIV-specific binding domain, a transmembrane domain, a costimulatory signaling region, and a signaling domain, wherein the HIV binding domain comprises an anti-HIV antibody or a fragment thereof.

In some embodiments, the modified cell of this invention cell is selected from the group consisting of a T cell, a natural killer (NK) cell, a cytotoxic T lymphocyte (CTL), and a regulatory T cell. In other embodiments, the nucleic acid sequence of the modified cell is selected from the group consisting of a DNA and an mRNA. In yet other embodiments, the nucleic acid sequence is introduced into the cell by at least one procedure selected from the group consisting of electroporation, usage of a lentivirus, usage of a retrovirus and a chemical-based transfection.

In another aspect, the invention includes a composition comprising the modified cell of the invention as listed above herein.

In another aspect, the invention includes the use of the modified cell of this invention in the manufacture of a medicament for the treatment of HIV infection in a subject in need thereof.

In yet another aspect, the invention includes a pharmaceutical composition comprising the modified cell of the invention and a pharmaceutically acceptable carrier.

In a further aspect, the invention includes a method for stimulating a cellular immune response in a HIV infected mammal. The method comprises administering to the mammal an effective amount of the modified cell of the invention as listed above herein.

In yet a further aspect, the invention includes a method of treating a HIV infected mammal. The method comprises administering to the mammal the modified cell of the invention as listed above herein. In some embodiments, the modified cell is autologous to the mammal. In other embodiments, the method of the invention further comprises administering antiretroviral therapy (HAART) the mammal. In yet other embodiments, the modified cell and the HAART are co-administered to the mammal.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments, which are presently preferred. It should be understood, however, that the invention is not limited to the precise arrangements and instrumentalities of the embodiments shown in the drawings.

FIG. 1A: CD4 and CD8 T cells were obtained from an HLA-B57+ normal donor. CD4 T cells were infected with HIV Bal and, 24 hours later, non-transduced CD8 T cells (NTD), CD8 T cells expressing a HLA-B57 restricted TCR specific for KAFSPEVIPMF-B57-KF11 (KF11), or CD8 T cells expressing an EF1α-CD8αTM CD4 CAR construct (CD4z), both expressed under the EF1a promoter, were mixed in at the indicated effector to target ratios. Transduction efficiencies were normalized to 40% prior to co-culture. After 6 days of co-culture, Gag p24 and CD4 staining is shown for CD8 negative T cells. CD4 membrane-bound chimeric receptor (also referred to as CD4 zeta or CD4 zeta construct) controls NL4-3 HIV-1 replication better than the HLA-B*57 restricted KF11 elite controller TCR. The KF11 TCR is associated with better control over HIV-1 replication in patients and is one of the most potent patient-derived TCRs against HIV-1. This represents the best control over HIV-1 that can be achieved with a TCR-based strategy. In contrast to KF11 TCR, the CD4 zeta was able to completely control HIV-1 replication at all Effector Cell to Target Cell (E:T) ratios shown. FIG. 1B: Summary data for a single experiment performed in triplicate, gating on the CD8 negative cells. Error bars indicate standard error of the mean (SEM). These data are representative of 3 independent experiments.

FIG. 2A: schematic of the new, improved CD4 membrane-bound chimeric receptor construct (top) with the CD8α transmembrane (TM) and EF1α promoter compared to the construct that entered clinical trials (bottom) that contained the PGK promoter and the CD4 TM domains. FIG. 2B: Surface expression of the CD4 zeta in transduced CD8s. Compared to the retroviral vector-based construct that entered clinical trials (far right), the same construct was expressed at a higher level when a lentiviral vector was used (second from left). This expression was increased further when the EF1α promoter was substituted into the lentiviral vector (second from left). FIG. 2C: Experimental timeline for all of the data shown in the presentation. Healthy donor CD4 and CD8 T lymphocytes were stimulated with αCD3/CD28 coated beads and 100-300 IU/ml IL-2. After 24 hours the CD8s were transduced with lentivirus, or on days 3 and 5 transduced with retrovirus. After 5 days the beads were removed, and 48 hours later the CD4 T cells were infected. 24 hours after infecting the CD4 T cells, the CD8s were co-cultured in varying E:T ratios. The cultures were fed with media and IL-2 and stained for CD4, CD8, and intracellular p24 every other day until HIV-1 replication reached maximum replication capacity in the NTD wells (typically around days 10-12). FIGS. 2D-2E: Intracellular p24 stain 8 days following infection of the CD4 T cells with HIV-1 Bal. FIG. 2D, gating on the CD4 T cells and FIG. 2E, gating on the CD8 T cells. The new, improved CD4 zeta construct with the lentiviral vector, EF1α promoter, and CD8α transmembrane domain controlled HIV-1 at much lower E:T ratios (until roughly 1:100) than the constructs with the PGK promoter and CD4 transmembrane domains (loss of control at 1:5 and 1:10). Although a higher expression of the lentivirus PGK CD4 TM construct was observed when compared to the retrovirus PGK CD4 TM construct, a small benefit was seen in terms of control over HIV-1 replication. Importantly, higher expression of the EF1α CD8 TM construct did not promote higher rates of infection, as the CD8s remained uninfected until approximately the 1:100 ratio whereas the PGK CD4 TM+ CD8s became infected at lower E:T ratios. FIG. 2F: Summary data for a single experiment performed in triplicate, gating on the CD8 negative cells. Error bars indicate standard error of the mean (SEM). FIG. 2G: Measurement of levels of intracellular p24 in CD8 negative T cells over the time course of an experiment. Each graph represents a different E:T ratio. These data are representative of three independent experiments.

FIG. 3A: schematic of the four lentiviral vector chimeric receptor constructs that were generated to compare how changing the promoter and transmembrane components each individually impacted control over HIV-1 replication. Top construct refers to what was used in clinical trials but is now inserted into a lentiviral vector.

FIG. 3B: CD4 CAR expression on CD8 T cells 8 days after activation. Primary human CD8 T cells were activated with αCD3/αCD28 coated beads and were either left non-transduced (NTD) or transduced with the indicated lentiviral vectors. After 8 days of culture, CAR expression was measured by CD4 staining. Median fluorescence intensity (MFI) of each construct is indicated on each graph. FIG. 3C: Intracellular p24 stain 8 days following infection of the CD4 T cells with HIV-1 Bal. Left set of columns was gated on the CD4 T cells and right set of columns was gated on the CD8 T cells. As seen previously, the EF1α CD8TM construct controlled HIV-1 at the lowest E:T ratios. Simply increasing expression of the CD4 TM with the EF1α promoter (middle column) improved control over HIV-1 replication, but the combination of increased expression with the EF1α promoter and CD8α transmembrane substitution produced the best control over HIV-1. CD8α TM appeared to reduce infection of the CD8 T cells engineered with a chimeric receptor (right set of columns), particularly at the 1:50 ratio for the EF1α constructs and the 1:25 ratio for the PGK constructs. FIG. 3D: Summary data for a single experiment performed in triplicate, gating on the CD8 negative cells. Error bars indicate standard error of the mean (SEM). FIG. 3E: The levels of intracellular p24 in CD8 negative T cells over the time course of an experiment. Each graph represents a different E:T ratio. These data are representative of three independent experiments.

FIG. 4A: A panel of single-chain variable fragment (scFv) CARs adapted from HIV-1 specific bnAbs was generated under the hypothesis that these potent and broadly neutralizing HIV-specific antibodies would provide an alternate means of targeting HIV-infected cells. A panel of scFvs (see table in FIG. 4A) that ranged in their HIV-1 binding breadth and neutralization potency were cloned into the same EF1α-CD8α TM-zeta construct backbone as the CD4 membrane-bound chimeric receptor and assessed for their ability to control HIV-1 replication. Two weeks following activation, these T cells were mixed with Cr51 labeled K562 target cells expressing HIV-1 YU2 GP160 at the indicated effector to target ratios. Specific lysis of the targets is plotted. Data plotted shows the average of three independent experiments. Cr51 release killing assay from a 4 hour co-culture showed that CD8 T cells expressing any of the scFv CARs or the CD4 membrane-bound chimeric receptor, but not non-transduced (NTD) T cells, lysed Env-expressing target cells. This indicates the scFv CARs were expressed with proper folding/conformation and able to bind Env. FIG. 4B: Primary human CD8 T cells were activated with αCD3/αCD28 coated beads and were either left non-transduced (NTD) or transduced with EF1α-CD8α TM lentiviral vectors encoding HIV-specific CARs derived from the VRC01, 3BNC60, PG9, PGT128, or PGDM1400 antibodies, or the CD4 CAR. Two weeks post activation, the CD8 T cells were co-cultured for 6 hours at a 1:1 ratio with K562 cells expressing HIV-1 YU2 GP160 and intracellular IFNγ and MIP-1β production was measured. Transduction efficiencies were normalized to 60% prior to co-culture. FIG. 4C: Using the experimental design summarized in FIG. 2C, the HIV-specific CARs were tested for their ability to control HIV-1 replication in primary human CD4 T cells. Transduction efficiencies were normalized to 70% prior to co-culture. Intracellular Gag p24 and CD4 stain 9 days following infection of the CD4 T cells with HIV-1 Bal, CD4 T cells are shown. Both the CD4 membrane-bound chimeric receptor and the scFv CARs demonstrated lysis of Env target cells relative to NTD controls up to a E:T ratio of 1:50-1:200, which is superior to the activity of the KF11 TCR shown in FIG. 1A, which demonstrates efficacy up to a 1:25 E:T ratio. Error bars indicate standard error of the mean (SEM). Data are representative of three independent experiments.

FIGS. 5A-5B are series of graphs showing that CD28 costimulation promotes control over HIV-1 Bal and that CD28 and 4-1BB costimulation have opposing effects on the control of HIV-1 replication in vitro. FIG. 5A: Intracellular p24 stain 10 days following infection of the CD4 T cells with HIV-1 Bal, CD4 T cells is shown. A panel of costimulatory domains that have been utilized in common CAR designs was cloned into the CD4 membrane-bound chimeric receptor backbone to determine the effects of costimulation on control over HIV-1 in vitro. The only membrane-bound chimeric receptor that consistently controlled HIV-1 as well or better than CD4 zeta construct was the CD4 CD28 zeta construct. In contrast, the addition of 4-1BB, ICOS, and CD27 impaired control over HIV-1, and OX40 and a CD28-4-1BBzeta combination appeared to have little effect. FIG. 5B: Summary data for a single experiment performed in triplicate, gated on the CD8 negative T cells. Error bars indicate standard error of the mean (SEM). Data are representative of three independent experiments.

FIG. 6 is the nucleotide sequence of CD4 membrane-bound chimeric receptor (CD4 zeta construct; SEQ ID NO: 1). This sequence has been annotated in red for the section related to the EF1α promoter (SEQ ID NO: 2), in yellow for the CD4 extracellular domain (SEQ ID NO: 3), in green for the CD8α extracellular hinge (SEQ ID NO: 4), in Turquoise for the CD8α transmembrane domain (SEQ ID NO: 5) and in pink for the CD3 zeta (SEQ ID NO: 6).

FIG. 7 is the nucleotide sequence of CD4 CD28 membrane-bound chimeric receptor (CD4 CD28 zeta construct; SEQ ID NO: 7). This sequence has been annotated in red for the section related to the EF1α promoter, in yellow for the CD4 extracellular domain, in green for the CD8α extracellular hinge, in Turquoise for the CD28 transmembrane domain (SEQ ID NO: 8), in blue for the CD28 costimulatory domain (SEQ ID NO: 9) and in pink for the CD3 zeta.

FIG. 8 is the listing of the nucleotide and amino acid (aa) sequences of five antibody based CAR constructs: PGDM1400 killer cell immunoglobulin-like receptor (KIR) nucleotide and aa sequences (SEQ ID NOs: 10 and 11, respectively), PGDM1400 scFv nucleotide and aa sequences (SEQ ID NOs: 12 and 13, respectively), PGT128 KIR nucleotide and aa sequences (SEQ ID NOs: 14 and 15, respectively), PGT128 scFv nucleotide and aa sequences (SEQ ID NOs: 16 and 17, respectively), VRC01 KIR nucleotide and aa sequences (SEQ ID NOs: 18 and 19, respectively), VRC01 scFv nucleotide and aa sequences (SEQ ID NOs: 20 and 21, respectively), 3BNC60-KIR nucleotide and aa sequences (SEQ ID NOs: 22 and 23, respectively), 3BNC60 scFv nucleotide and aa sequences (SEQ ID NOs: 24 and 25, respectively), VRC01 c-mut-KIR nucleotide and aa sequences (SEQ ID NOs: 26 and 27, respectively), VRC01 c-mut scFv nucleotide and aa sequences (SEQ ID NOs: 28 and 29, respectively), CD4 Dap12-KIRS2 nucleotide and aa sequences (SEQ ID NOs: 30 and 31, respectively), CD4-KIR nucleotide and aa sequences (SEQ ID NOs: 32 and 33, respectively), and VRC01 IgG4 bbz nucleotide and aa sequences (SEQ ID NOs: 34 and 35, respectively).

FIG. 11A: Primary human CD8 T cells were activated with αCD3/αCD28 coated beads and were either left non-transduced (NTD) or transduced with EF1α-CD8α TM lentiviral vectors encoding CD4 CARs expressing the CD3-zeta signaling domain, alone or in combination with CD28 or 4-1BB costimulatory domains. Two weeks post activation, the CD8 T cells were co-cultured for 6 hours at a 1:1 ratio with unmodified K562 cells, K562 cells expressing high levels of HLA-DR (see FIG. 14), or K562 cells expressing HIV-1 YU2 GP160. Intracellular IFNγ and MIP-1β expression is shown on the left, and intracellular IL-2 expression and CD107a surface mobilization is shown on the right. FIG. 11B: A co-culture assay was designed to demonstrate that CD4 CAR+ CD8 T cells do not kill MHC class II-expressing target cells. Briefly, NTD or CD4 28z CAR transduced CD8 T cells from FIG. 6A were co-cultured with K562 cells expressing HLA-A2 and GFP as well as K562 expressing HLA-DR*0401 and mCherry at a 1:1:1 ratio. Flow cytometry measuring GFP and mCherry expression was performed immediately after mixing (0 hr) and after 3 days of co-culture (72 hr). FIG. 11C: Summary data for a single experiment performed in triplicate, measuring the ratio of HLA-A2/GFP-expressing cells to HLA-DR*0401/mCherry-expressing cells after 24, 48, and 72 hours of culture. Error bars indicate standard error of the mean (SEM). Data are representative of three independent experiments.

(FIG. 12E) Seven and (FIG. 12F) eighteen days post infection the copies of plasma HIV RNA were measured. Mann Whitney Test was used to determine statistical significance (p values: ns>0.05, *<0.05, <0.01, *<0.0001).

FIG. 13A: After 22 days of HIV infection, splenic CD8 T cells were isolated from HIV-infected mice and analyzed for CCR5 disruption frequency. FIG. 13B: The ratio of CD4 CAR-expressing CD8 T cells to nontransduced CD8 T cells was determined by staining for human CD4 and CD8 and performing flow cytometry on peripheral blood isolated 22 days post HIV or mock infection. Flow cytometry plots are shown in FIG. 15. FIG. 13C: Eighteen days post infection, the copies of plasma HIV RNA were measured in HIV-infected mice, as in FIG. 12F, but with the four ZFN-treated groups incorporated. Significance was detected using a Mann Whitney Test (p values: ns>0.05, *<0.05, <0.01, *<0.0001).

FIG. 15 is a series of graphs depicting that 4-1BB costimulatory domain results in greater T cell persistence in the absence of antigen. After 22 days of mock infection, peripheral blood cells or splenic cells from BBz or 28z transduced, ZFN-treated mice cohorts were stained for CAR expression with αCD4 and αCD8 antibodies. The top panel shows peripheral blood and the bottom panel shows splenic cells. One representative flow plot is shown in all cases from an HIV-infected mouse.

FIG. 16A: Endpoint peripheral blood CD4 T cell counts were collected 22 days post HIV infection, as shown in FIG. 12B, but now includes data from mice that received CCR5 ZFN modified CD8 T cells as well. (B) Endpoint peripheral blood CAR+ CD8 T cell counts were enumerated 22 days post infection in all cohorts. Significance was detected using a Mann Whitney Test (p values: ns>0.05, *<0.05, <0.01, *<0.0001).

FIGS. 17A-17D are series of tables and graphs summarizing the improvements made in this invention to the original clinical trial vector. FIG. 17A: Table and schematic depicting the complete list of modifications explored to improve the original clinical trial, MMLV-based construct. FIG. 17B: Using the experimental design summarized in FIG. 2C, primary human CD8 T cells were activated with αCD3/αCD28 coated beads and were either left non-transduced (NTD), transduced with the original MMLV-based CD4 based CAR driven by the PGK promoter (clinical trial CAR), or transduced the optimized EF1α-CD8α TM CAR, placed in a HIV-based lentiviral vector. Transduction efficiencies were normalized to 60% prior to co-culture. After 7 days of co-culture with HIV Bal-infected CD4 T cells, the expression of surface CD4 and intracellular Gag p24 was measured by flow cytometry, gating on CD8 negative T cells. FIG. 17C: Shows gating on the CD8 positive cells. FIG. 17D: Summary data for a single experiment performed in triplicate, gating on the CD8 negative cells. Error bars indicate standard error of the mean (SEM). This data is representative of three independent experiments.

FIG. 18 is a list of annotated amino acid sequences for some of the optimized HIV CD4 CARs and HIV antibody based CARs (SEQ ID NOs: 44-61) of this invention.

FIG. 19 is a list of annotated nucleic acid sequences for some of the optimized HIV CD4 CARs and HIV antibody based CARs (SEQ ID NOs: 63-79) of this invention.

DETAILED DESCRIPTION

Definitions

Figure 1A:
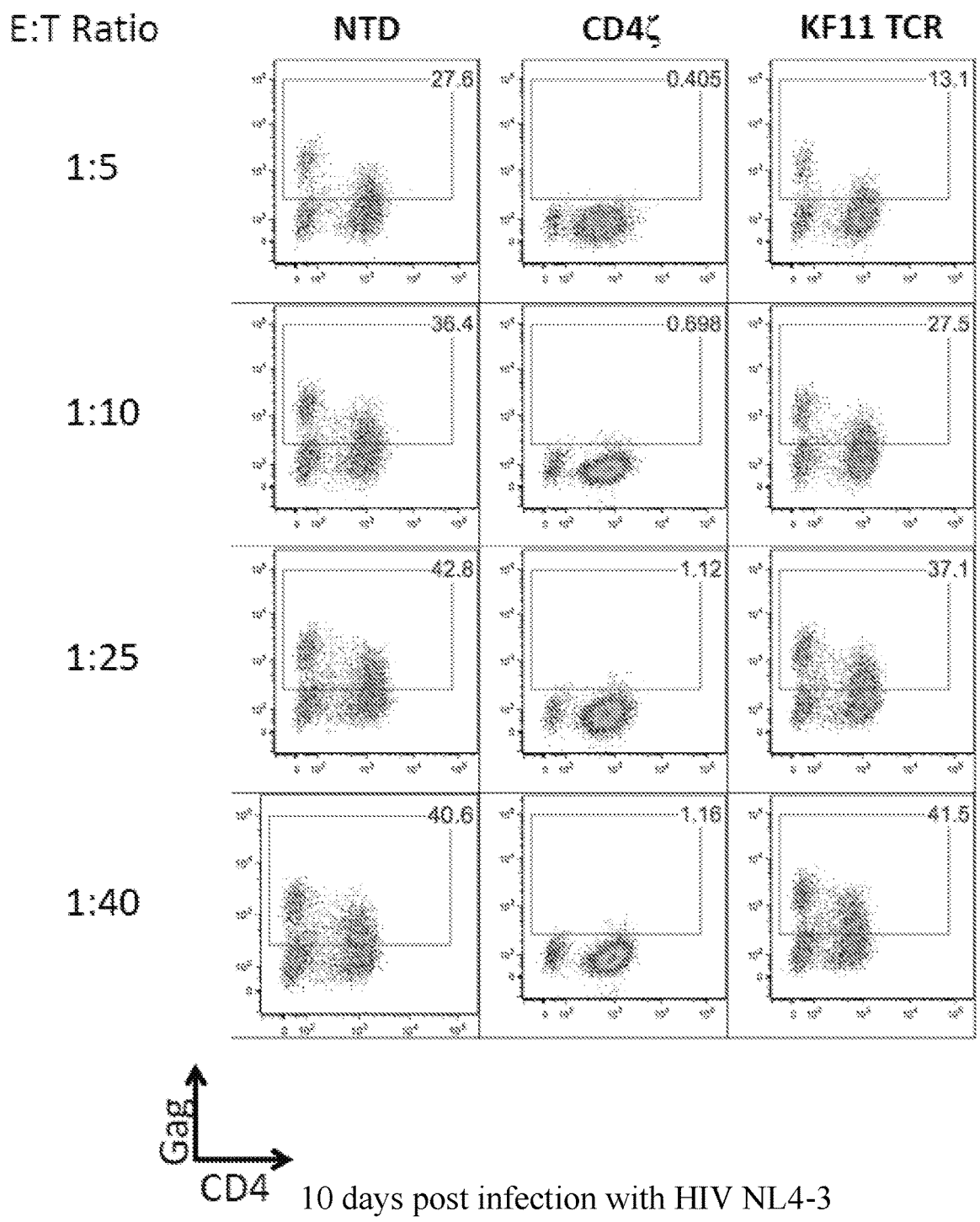
FIGS. 1A-1B are series of graphs demonstrating that CD4 CAR is over 100-fold more potent than HIV-specific elite controller TCR in vitro.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.10% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, the term "adaptor molecule" refers to a polypeptide with a sequence that permits interaction with two or more molecules, and in certain embodiments, promotes activation or inactivation of a cytotoxic cell.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. $\alpha$ and $\beta$ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), epididymitis, glomerulonephritis, Graves' disease, Guillain-Barre syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "broadly neutralizing antibody (bnAb)" refers to an antibody that defends a cell from multiple strains of a particular virus by neutralizing its effect. In some embodiments, broadly neutralizing HIV-1 Antibodies (bnAbs) are neutralizing antibody which neutralize multiple HIV-1 viral strain.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

By the term "CD4" as used herein is meant any amino acid sequence specifying CD4 from any source, including an amino acid sequence of CD4 that has been generated through codon optimization of the nucleic acid sequence encoding CD4. Codon optimization may be accomplished using any available technology and algorithms designed to optimize codons in an amino acid sequence.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs have been expressed with specificity to a tumor associated antigen, for example. CARs may also comprise an intracellular activation domain, a transmembrane domain and an extracellular domain comprising a tumor associated antigen binding region. In some aspects, CARs comprise fusions of single-chain variable fragments (scFv) derived monoclonal antibodies, fused to transmembrane and intracellular domain. The specificity of CAR designs may be derived from ligands of receptors (e.g., peptides). In some embodiments, a CAR can target HIV infected cells by redirecting the specificity of a T cell expressing the CAR specific for HIV associated antigens.

The term "chimeric intracellular signaling molecule" refers to recombinant receptor comprising one or more intracellular domains of one or more co-stimulatory molecules. The chimeric intracellular signaling molecule substantially lacks an extracellular domain. In some embodiments, the chimeric intracellular signaling molecule comprises additional domains, such as a transmembrane domain, a detectable tag, and a spacer domain.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to TCR, CD3 zeta, CD3 gamma, CD3 delta, CD3 epsilon, CD86, common FcR gamma, FcR beta (Fc Epsilon Rib), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

A "co-stimulatory signal", as used herein, refers to a signal, which in combination with a primary signal, such as TCR/CD3 ligation, leads to T cell proliferation and/or upregulation or downregulation of key molecules.

The term "cytotoxic" or "cytotoxicity" refers to killing or damaging cells. In one embodiment, cytotoxicity of the modified cells is improved, e.g. increased cytolytic activity of T cells.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

By the terms "Human Immunodeficiency Virus" or HIV" as used herein is meant any HIV strain or variant that is known in the art or that is heretofore unknown, including without limitation, HIV-1 and HIV-2.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. As applied to the nucleic acid or protein, "homologous" as used herein refers to a sequence that has about 50% sequence identity. More preferably, the homologous sequence has about 75% sequence identity, even more preferably, has at least about 80%, 85%, 90%, 91%, 92%, 93%, 94%, 95%, 96%, 97%, 98%, 99% sequence identity.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The guide nucleic acid sequence may be complementary to one strand (nucleotide sequence) of a double stranded DNA target site. The percentage of complementation between the guide nucleic acid sequence and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The guide nucleic acid sequence can be at least 10, 11, 12, 13, 14, 15, 16, 17, 18, 19, 20, 21, 22, 23, 24, 25, 26, 27, 28, 29, 30, 31, 32, 33, 34, 35 or more nucleotides in length. In some embodiments, the guide nucleic acid sequence comprises a contiguous stretch of 10 to 40 nucleotides. The variable targeting domain can be composed of a DNA sequence, a RNA sequence, a modified DNA sequence, a modified RNA sequence (see for example modifications described herein), or any combination thereof.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"KIR" means killer cell immunoglobulin-like receptor, KIRs have been characterized in humans and non-human primates, and are polymorphic type 1 trans-membrane molecules present on certain subsets of lymphocytes, including NK cells and some T cells. KIRs regulate the killing function of NK cells by interacting with determinants in the alpha 1 and 2 domains of the MHC class I molecules. This interaction allows them to detect virus infected cells or tumor cells.

Most KIRs are inhibitory, meaning that their recognition of MHC suppresses the cytotoxic activity of the NK cell that expresses them. Only a limited number of KIRs have the ability to activate cells. The KIR gene family has at least 15 gene loci (KIR2DL1, KIR2DL2/L3, KIR2DL4, KIR2DL5A, KIR2DL5B, KIR2DS1, KIR2DS2, KIR2DS3, KIR2DS4, KIR2DS5, KIR3DL1/S1, KIR3DL2, KIR3DL3) and two pseudogenes (KIR2DP1 and KIR3DP1) encoded within a 100-200 Kb region of the Leukocyte Receptor Complex (LRC) located on chromosome 19 (19q13.4). The LRC constitutes a large, 1 Mb, and dense cluster of rapidly evolving immune genes which contains genes encoding other cell surface molecules with distinctive Ig-like extracellular domains. In addition, the extended LRC contains genes encoding the transmembrane adaptor molecules DAP10 and DAP12.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "resistance to immunosuppression" refers to lack of suppression or reduced suppression of an immune system activity or activation.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the term "substantially lacks an extracellular domain" refers to a molecule that is essentially free of a domain that extrudes extracellularly. In one embodiment, the chimeric intracellular signaling molecule lacks any function performed by an extracellular domain, such as antigen binding. In another embodiment, the chimeric intracellular signaling molecule includes a transmembrane domain but lacks a functional extracellular domain.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the ICR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The term "tumor" as used herein, refers to an abnormal growth of tissue that may be benign, pre-cancerous, malignant, or metastatic.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes compositions and methods for the treatment of HIV infection using a CD4 membrane-bound chimeric receptor or HIV specific scFV chimeric antigen receptors (CARs). According to the invention, T cells are modified for adoptive T cell therapy by expressing a fragment of CD4 or scFVs capable of specifically recognizing and binding HIV-infected cells. The modified T cells of this invention are specific for HIV infected cells and have improved cytotoxicity and efficacy against HIV infection.

HIV Specific CD4 Membrane-Bound Chimeric Receptor

The present invention includes a membrane-bound chimeric receptor comprising a CD4 domain, particularly a CD4 extracellular domain that specifically binds to HIV virions or HIV infected cells. In certain embodiments, the CD4 membrane-bound chimeric receptor of the invention comprises particular structural features such as particular amino acid sequences or peptides as disclosed herein. The invention also includes methods of making such a receptor.

The membrane-bound chimeric receptor of the invention can be incorporated into a pharmaceutical composition for use in treating a subject, for example for use as an immunotherapy. Accordingly, the present invention provides compositions and methods for treating HIV infection or HIV related diseases.

In one aspect the invention includes an isolated nucleic acid sequence encoding a membrane-bound chimeric receptor comprising a CD4 extracellular domain, a transmembrane domain, and a signaling domain, wherein the CD4 extracellular domain is capable of recognizing and binding a HIV infected cell. In another aspect, the invention includes an isolated amino acid sequence encoding a membrane-bound chimeric receptor comprising a CD4 extracellular domain, a transmembrane domain, and a signaling domain, wherein the CD4 extracellular domain is capable of recognizing and binding a HIV infected cell.

In one embodiment, the CD4 extracellular domain comprises SEQ ID NO: 3, 46 or 64, the transmembrane domain comprises a CD8alpha hinge (SEQ ID NO: 4, 47 or 65) and a transmembrane domain comprising at least one domain selected from the group consisting of CD8alpha transmembrane domain (SEQ ID NO: 5, 48 or 66) and CD28 transmembrane domain (SEQ ID NO: 8, 49 or 67). In another embodiment, the signaling domain comprises a CD3zeta signaling domain (SEQ ID NO: 6, 51 or 68). In yet another embodiment, the costimulatory signaling region comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof. In yet another embodiment, the costimulatory signaling region CD28 (SEQ ID NO: 9, 49 or 67) is present in the construct. In a further embodiment, CD4 extracellular domain specifically binds to the HIV envelope (Env) glycoprotein.

In one aspect, the invention includes a vector comprising a eukaryotic elongation factor (EF1 alpha) promoter, a CD4 extracellular domain, a CD8alpha hinge, a CD8alpha transmembrane domain and CD3zeta signaling domain (SEQ ID NO: 1). In another aspect, the invention includes a vector comprising an EF1α promoter, a CD4 extracellular domain, a CD8alpha hinge, a CD28 transmembrane domain, a CD28 costimulatory domain and CD3zeta signaling domain (SEQ ID NO: 7). In yet another aspect, the invention includes a vector comprising a membrane-bound chimeric receptor comprising a CD4 extracellular domain, a transmembrane domain, and a signaling domain, wherein the CD4 extracellular domain is capable of recognizing and binding a HIV infected cell, wherein the vector comprises at least one amino acid sequence selected from the group consisting of SEQ ID NOs: 44, 45, 62 and 63.

In one embodiment, the membrane-bound chimeric receptor is encoded by the nucleic acid sequence of SEQ ID NO: 30, 32 or 64. In another embodiment, the membrane-bound chimeric receptor has an amino acid sequence of SEQ ID NO: 31, 33 or 46.

CD4 Extracellular Domain

CD4 is a member of the immunoglobulin superfamily and includes four extracellular immunoglobulin domains (D1 to D4). D1 and D3 are similar to immunoglobulin variable domains and D2 and D4 are similar to immunoglobulin constant domains. D1 includes the region of CD4 that interacts with beta2-microglobulin of the major histocompatibility complex class II molecules.

In one embodiment, the membrane-bound chimeric receptor comprises an extracellular domain of CD4 or a fragment thereof. In another embodiment, the membrane-bound chimeric receptor comprises at least one immunoglobulin domain of CD4. In another embodiment, the CD4 extracellular domain comprises SEQ ID NO: 3 or 64.

The CD4 extracellular domain described herein, such as at least one immunoglobulin domain of CD4 or the CD4 extracellular domain comprising SEQ ID NO: 3 or 64, can be combined with any of the transmembrane domains described herein, any of the signaling domains described herein, or any of the other domains described herein that may be included in the membrane-bound chimeric receptor.

Transmembrane Domain

In one embodiment, the transmembrane domain is associated with one of the domains in the CD4 chimeric antigen receptor construct. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge. In one embodiment, the transmembrane domain comprises a CD8alpha hinge and transmembrane domain.

In one embodiment, the transmembrane domain comprises a CD8alpha transmembrane domain (SEQ ID NO: 5 or 66). In another embodiment, the transmembrane domain comprises a CD28 transmembrane domain (SEQ ID NO: 8 or 67). In yet another embodiment, the transmembrane domain comprises a hinge domain, such as a CD8alpha hinge (SEQ ID NO: 4 or 65). The transmembrane domain may be combined with any hinge domain and/or may comprise one or more transmembrane domains described herein.

The transmembrane domains described herein, such as at least a transmembrane region(s) of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, or CD154, can be combined with any of the CD4 extracellular domain described herein, any of the signaling domains described herein, or any of the other domains described herein that may be included in the membrane-bound chimeric receptor.

In another embodiment, the transmembrane domain may be synthetic, in which case it comprises predominantly hydrophobic residues such as leucine and valine. Preferably a triplet of phenylalanine, tryptophan and valine is present at each end of a synthetic transmembrane domain. Optionally, a short oligo- or polypeptide linker, preferably between 2 and 10 amino acids in length may form the linkage between the transmembrane domain and the cytoplasmic signaling domain. A glycine-serine doublet provides a particularly suitable linker.

Signaling Domain

The signaling domain or intracellular signaling domain is responsible for activation of at least one of the normal effector functions of the immune cell in which the CD4 chimeric antigen receptor construct is expressed. The term "effector function" refers to a specialized function of a cell. Effector function of a T cell, for example, may be cytolytic activity or helper activity including the secretion of cytokines. Thus the term "intracellular signaling domain" or "signaling domain" refers to the portion of a protein which transduces the effector function signal and directs the cell to perform a specialized function. While usually the entire signaling domain can be employed, in many cases it is not necessary to use the entire molecule. To the extent that a truncated portion of the signaling domain is used, such truncated portion may be used in place of the intact chain as long as it transduces the effector function signal. The term signaling domain is thus meant to include any truncated portion of the signaling domain sufficient to transduce the effector function signal.

Examples of signaling domains for use in this invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the immunoreceptor of the invention comprises a cytoplasmic signaling sequence derived from CD3-zeta.

In a preferred embodiment, the signaling domain of the CD4 chimeric antigen receptor construct can be designed to comprise the CD3-zeta signaling domain by itself or combined with any other desired signaling domain(s) useful in the context of the immunoreceptor. For example, the signaling domain of the immunoreceptor can comprise a CD3 zeta chain portion and a costimulatory signaling region. The costimulatory signaling region refers to a portion of the immunoreceptor comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), DAP12, OX9, OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 as the co-stimulatory signaling element, other costimulatory elements are within the scope of the invention.

In one embodiment, the signaling domain comprises a CD3zeta signaling domain (SEQ ID NO: 6, 51 or 68). In another embodiment, the signaling domain comprises a CD4 CD28 zeta (SEQ ID NO:7 or 62). In another embodiment, the signaling domain comprises a CD28 costimulatory domain (SEQ ID NO:9 or 67). In yet another embodiment, the signaling domain comprises a CD4 4-1BB costimulatory domain (SEQ ID NO: 63). In yet another embodiment, the signaling domain comprises a 4-1BB (CD137) costimulatory domain (SEQ ID NO:69). The signaling domain may be comprise one or more signaling domains described herein.

The signaling domains described herein, such as cytoplasmic signaling sequences of the alpha, beta or zeta chain of the TCR zeta, FcR gamma, FcR beta, CD3 gamma, CD3 delta, CD3 epsilon, CD5, CD22, CD79a, CD79b, or CD66d or a costimulatory signaling region from CD27, CD28, 4-1BB (CD137), DAP12, OX9, OX40, CD30, CD40, PD-1, ICOS, lymphocyte function-associated antigen-1 (LFA-1), CD2, CD7, LIGHT, NKG2C, B7-H3, or a ligand that specifically binds with CD83, can be combined with any of the CD4 extracellular domain described herein, any of the transmembrane domains described herein, or any of the other domains described herein that may be included in the membrane-bound chimeric receptor.

Chimeric Antigen Receptor (CAR)

Without wishing to be bound by theory, it is understood that use of a CAR that targets HIV, wherein the CAR comprises an anti-HIV scFv will be beneficial for treatment of subjects that have reservoir populations of HIV-infected cells. The invention therefore includes such a CAR for such use in one aspect of the invention.

Thus, in one aspect of the invention, a T cell is generated by expressing a CAR therein. Thus, the present invention encompasses a CAR and a nucleic acid construct encoding a CAR, wherein the CAR includes an antigen binding domain (e.g., an scFv encoding an anti-HIV antibody), a transmembrane domain and an intracellular domain.

In one aspect, the invention includes a modified cell comprising a chimeric antigen receptor (CAR), wherein the CAR comprises an antigen binding domain, a transmembrane domain and an intracellular domain of a co-stimulatory molecule, and wherein the cell is a T cell that possesses targeted effector activity. In another aspect, the invention includes a modified cell comprising a nucleic acid sequence encoding a chimeric antigen receptor (CAR), wherein nucleic acid sequence comprises a nucleic acid sequence encoding an antigen binding domain, a nucleic acid sequence encoding a transmembrane domain and a nucleic acid sequence encoding an intracellular domain of a co-stimulatory molecule, and wherein the cell is a T cell that expresses the CAR and possesses targeted effector activity (e.g. targeted cellular cytotoxicity and antigen presentation). In one embodiment, the targeted effector activity is directed against an antigen on a target cell that specifically binds the antigen binding domain of the CAR. In one aspect, the target antigen is a HIV specific antigen and the CAR comprises a HIV specific binding domain comprising an anti-HIV antibody or fragment thereof.

In one embodiment, the CAR is encoded by a nucleic acid sequence selected from SEQ ID NO:10, 14, 18, 22, 26, 34, 70-73 and 74. In another embodiment, the CAR has an amino acid sequence of SEQ ID NO:11, 15, 19, 23, 27, 35, 52-55, or 56.

Antigen Binding Domain

In one embodiment, the antigen binding domain of the invention comprises a HIV specific binding domain that binds to HIV virions, such as HIV envelope glycoprotein (Env) (e.g. gp120), and/or HIV infected cell. Examples of other cell surface markers that may act as an antigen include those associated with viral, bacterial and parasitic infections, autoimmune disease, and cancer cells. In another embodiment, the antigen binding domain of the invention comprises an antibody or fragment thereof that binds to a HIV protein, such as a scFv antibody. Preferably, the antigen binding domain is scFv antibody that binds to a HIV protein, for example, HIV Env. Specific scFvs that are useful are those shown in FIG. 4A, FIG. 8, FIG. 18 and FIG. 19 (SEQ ID NO:11, 12, 16, 17, 20, 21, 24, 25, 28, 29, 57-61, 75-78, or 79).

The choice of antigen binding domain depends upon the type and number of antigens that are present on the surface of a target cell. For example, the antigen binding domain may be chosen to recognize an antigen that acts as a cell surface marker on a target cell associated with a particular disease state.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof. In another embodiment, the antigen binding domain of the CAR is selected from the group consisting of an anti-HIV antibody and a fragment thereof.

In some instances, it is beneficial for the antigen binding domain to be derived from the same species in which the CAR will ultimately be used in. For example, for use in humans, it may be beneficial for the antigen binding domain of the CAR to comprise a human antibody, as described elsewhere herein, or a fragment thereof.

It is also beneficial that the antigen binding domain is operably linked to another domain of the CAR, such as the transmembrane domain or the intracellular domain, both described elsewhere herein, for expression in the cell. In one embodiment, a nucleic acid encoding the antigen binding domain is operably linked to a nucleic acid encoding a transmembrane domain and a nucleic acid encoding an intracellular domain.

The antigen binding domains described herein, such as the antibody or fragment thereof that binds to a HIV protein, can be combined with any of the transmembrane domains described herein, any of the intracellular domains or cytoplasmic domains described herein, or any of the other domains described herein that may be included in the CAR.

Transmembrane Domain

With respect to the transmembrane domain, the CAR (or the membrane-bound chimeric receptor construct) can be designed to comprise a transmembrane domain that connects the antigen binding domain of the CAR to the intracellular domain. In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, Toll-like receptor 1 (TLR1), TLR2, TLR3, TLR4, TLR5, TLR6, TLR7, TLR8, and TLR9. In some instances, a variety of hinges can be employed as well including the Ig (immunoglobulin) hinge.

In one embodiment, the transmembrane domain comprises a CD8alpha transmembrane domain (SEQ ID NOs: 5, 48, 66). In another embodiment, the transmembrane domain comprises a CD28 transmembrane domain (SEQ ID NOs: 8, 49 and 67). In yet another embodiment, the transmembrane domain comprises a hinge domain, such as a CD8alpha hinge (SEQ ID NO: 4, 47 and 65). The transmembrane domain may be combined with any hinge domain and/or may comprise one or more transmembrane domains described herein.

The transmembrane domains described herein, such as a transmembrane region of alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, Toll-like receptor 1 (TLR1), TLR2, TLR3, TLR4, TLR5, TLR6, TLR7, TLR8, and TLR9, can be combined with any of the antigen binding domains described herein, any of the intracellular domains or cytoplasmic domains described herein, or any of the other domains described herein that may be included in the CAR.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Intracellular Domain

The intracellular domain or otherwise the cytoplasmic domain of the CAR (or the membrane-bound chimeric receptor construct) includes a similar or the same intracellular domain as the chimeric intracellular signaling molecule described elsewhere herein, and is responsible for activation of the cell in which the CAR is expressed.

In one embodiment, the intracellular domain of the CAR includes a domain responsible for signal activation and/or transduction.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160

(BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

In one embodiment, the intracellular domain of the CAR includes any portion of one or more co-stimulatory molecules, such as at least one signaling domain from CD3, CD8, CD27, CD28, ICOS, 4-1BB, PD-1, any derivative or variant thereof, any synthetic sequence thereof that has the same functional capability, and any combination thereof.

In one embodiment, the intracellular domain comprises a CD3zeta signaling domain (SEQ ID NO: 6, 51 or 68). In another embodiment, the intracellular domain comprises a CD4 CD28 zeta, (SEQ ID NO:7, or 62). In another embodiment, the intracellular domain comprises a CD28 costimulatory domain (SEQ ID NO: 9 or 67). In yet another embodiment, the signaling domain comprises a CD4 4-1BB costimulatory domain (SEQ ID NO:63). In still another embodiment, the signaling domain comprises a 4-1BB (CD137) costimulatory domain (SEQ ID NO:69). In another embodiment, the intracellular domain comprises a DAP12 domain. In yet another embodiment, the intracellular domain comprises a KIR domain. The intracellular domain may comprise one or more intracellular domains described herein described herein.

The intracellular domains described herein, such as a fragment or domain from TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, or other co-stimulatory molecules, can be combined with any of the antigen binding domains described herein, any of the transmembrane domains described herein, or any of the other domains described herein that may be included in the CAR.

Between the antigen binding domain and the transmembrane domain of the CAR, or between the intracellular domain and the transmembrane domain of the CAR, a spacer domain may be incorporated. As used herein, the term "spacer domain" generally means any oligo- or polypeptide that functions to link the transmembrane domain to, either the antigen binding domain or, the intracellular domain in the polypeptide chain. In one embodiment, the spacer domain may comprise up to 300 amino acids, preferably 10 to 100 amino acids and most preferably 25 to 50 amino acids. In another embodiment, a short oligo- or polypeptide linker, preferably between 2 and 10 amino acids in length may form the linkage between the transmembrane domain and the intracellular domain of the CAR. An example of a linker includes a glycine-serine doublet.

Human Antibodies

It may be preferable to use human antibodies or fragments thereof when using the antigen binding domains of a CAR. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

Vectors

A vector may be used to introduce the chimeric intracellular signaling molecule or the CAR into a T cell as described elsewhere herein. In one aspect, the invention includes a vector comprising a nucleic acid sequence encoding a chimeric intracellular signaling. In another aspect, the invention includes a vector comprising a nucleic acid sequence encoding a CAR. In one embodiment, the vector comprises a plasmid vector, viral vector, retrotransposon (e.g. piggyback, sleeping beauty), site directed insertion vector (e.g. CRISPR, zn finger nucleases, TALEN), or suicide expression vector, or other known vector in the art.

All constructs mentioned above are capable of use with 3rd generation lentiviral vector plasmids, other viral vectors, or RNA approved for use in human cells. In one embodiment, the vector is a viral vector, such as a lentiviral vector. In another embodiment, the vector is a RNA vector.

The production of any of the molecules described herein can be verified by sequencing. Expression of the full length proteins may be verified using immunoblot, immunohistochemistry, flow cytometry or other technology well known and available in the art.

The present invention also provides a vector in which DNA of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

The expression of natural or synthetic nucleic acids is typically achieved by operably linking a nucleic acid or portions thereof to a promoter, and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the EF-1 alpha promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Introduction of Nucleic Acids

Methods of introducing and expressing genes, such as the chimeric intracellular signaling molecule or the CAR, into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). Nucleic acids can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). Nucleic acids can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. RNA vectors include vectors having a RNA promoter and/other relevant domains for production of a RNA transcript. Viral vectors, and especially retroviral vectors, have become the most widely used method for inserting genes into mammalian, e.g., human cells. Other viral vectors may be derived from lentivirus, poxviruses, herpes simplex virus, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the molecules described herein, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, one or more of the nucleic acid sequences described elsewhere herein are introduced by a method selected from the group consisting of transducing the population of cells, transfecting the population of cells, and electroporating the population of cells. In one embodiment, a population of cells comprises one or more of the nucleic acid sequences described herein.

In one embodiment, the nucleic acids introduced into the cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric intracellular signaling molecule.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

Some in vitro-transcribed RNA (IVT-RNA) vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In one aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Alternatively, in another aspect, the invention includes a method for generating a modified T cell comprising electroporating a population of T cells with a nucleic acid sequence encoding a chimeric intracellular signaling molecule, wherein the nucleic acid sequence comprises a nucleic acid sequence of an intracellular domain of a co-stimulatory molecule and substantially lacks an extracellular domain. In one embodiment, the nucleic acid sequence encoding a chimeric intracellular signaling molecule is electroporated into a cell. In yet another embodiment, a nucleic acid sequence encoding a CAR or a membrane-bound chimeric receptor is further electroporated into the cell.

Sources of T Cells

The modified T cells may be generated from any source of T cells. In one embodiment, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PER- COLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11 b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, a population of cells comprise the T cells of the present invention. Examples of a population of cells include, but are not limited to, peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Expansion of T Cells

T cells generated by any method described herein may be expanded ex vivo. In one embodiment, T cells or a population of cells comprising T cells are cultured for expansion. Generally, T cells are expanded by contact with a surface having attached thereto an agent that stimulates a CD3/TCR complex associated signal and a ligand that stimulates a co-stimulatory molecule on the surface of the T cells.

Methods for expanding T cells are described herein. For example, the T cells can be expanded by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

The T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing one or more of the molecules described elsewhere herein into the T cells.

The culturing step as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

In one embodiment, the T cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The T cell culturing medium may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

Therapy

In one aspect, the invention includes a method of treating a disease or condition associated with HIV infection in a subject comprising administering to the subject a therapeutically effective amount of a pharmaceutical composition comprising the modified T cell described herein.

The modified T cells as described herein can be administered to an animal, preferably a mammal, even more preferably a human, to treat HIV infection. In addition, the modified T cells of the present invention can be used for the treatment of any condition in which a diminished or otherwise inhibited immune response, especially a cell-mediated immune response, is desirable to treat or alleviate the disease.

The administration of the modified T cells of the invention may be carried out in any convenient manner known to those of skill in the art. The modified T cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the modified T cells of the invention are injected directly into a site of inflammation in the subject, a local disease site in the subject, a lymph node, an organ, a tumor, and the like.

Pharmaceutical Compositions

Pharmaceutical compositions of the present invention may comprise the modified T cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-immune response effective amount", "an immune response-inhibiting effective amount", or "therapeutic amount" is indicated, the precise amount of the compositions of the present invention to be administered can be determined by a physician with consideration of individual differences in age, weight, immune response, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer the modified T cells to a subject and then subsequently redraw blood (or have an apheresis performed), metabolically enhance T cells therefrom according to the present invention, and reinfuse the patient with these modified T cells. This process can be carried out multiple times every few weeks. In certain embodiments, T cells can be obtained from blood draws from about 10 ml to about 400 ml. In certain embodiments, modified T cells are obtained from blood draws of about 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

In certain embodiments of the present invention, T cells are modified using the methods described herein, and stimulated, activated or expanded using the methods described herein or other methods known in the art where T cells are expanded to therapeutic levels, are administered to a patient in conjunction with (e.g., before, simultaneously or following) any number of relevant treatment modalities, including but not limited to any available anti-HIV therapy.

The dosage of the above treatments to be administered to a patient will vary with the precise nature of the condition being treated and the recipient of the treatment. It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Single Chain Variable Fragment (scFv) Based CAR Constructs:

scFvs were synthesized as a single transcript in a 2nd generation CAR using the CD137 and CD3zeta signal transduction domains or as an artificial NK cell receptor by means of KIRS2 together with DAP12. All constructs were codon-optimized for expression in humans as one transcript following a proprietary codon adaptation index (Geneart, Life Techn.).

The following constructs have been created and tested in this invention:

"PGDM1400" targeting V1/V2 glycans (SEQ ID NOs: 10-13), "PGT128" targeting V3/V4 glycans (SEQ ID NOs: 14-17), "VRC01" targeting CD4 binding site (SEQ ID NOs: 18-21 and 34-35), "VRC01 c-mut" (mutation of non-canonic disulfide bond between HCDR1 and HCDR3) targeting CD4 binding site (SEQ ID NOs: 26-29), "3BNC60" targeting CD4 binding site (SEQ ID NOs: 22-25), and CD4 Dap12-KIRS2 (SEQ ID NOs: 30-31).

Vector Construction:

pRT43.2 GFP, the backbone of the original clinical trial vector, was obtained (Liu and Eiden. Retrovirology 9, 51 (2012)) and a restriction site linker was inserted into the PstI and SalI sites, removing the CMV promoter region. The CD4 zeta sequence expressed under the PGK promoter was amplified from plasmid pRRL.PGK.F3 with oligos 5' GTATCGATCACGAGACTAGC (SEQ ID NO: 40) and 5'TTAAACCGGTGTCTGGCCTTTGAGTGGTGA (SEQ ID NO: 41) and inserted into XhoI and AgeI sites in the linker within pRT43.2. pTRPE CD4 zeta was created by amplifying. The CD4 extracellular domain was amplified by PCR from the pRRL.PGK.F3 retroviral backbone containing the original clinical trial CD4-CD3 construct with the following primers:

```
Primer-1 Sense (SEQ ID NO: 36):
5'-TTAATGGGATCCATGAACCGGGGAGTCCCTTT-3'

Primer-2 Antisense (SEQ ID NO: 37):
5'-AAGGACTTCCGGATGGCTGCACCGGGGTGGACCATG-3'
```

PCR product was then inserted into the BamHI and BspE1 restriction sites in the pELNS lentiviral backbone which contained the CD8α extracellular hinge and transmembrane domains and the 4-1BB and CD3 zeta intracellular costimulatory domains (ICD). pELNS lentiviral vectors containing the CD8α hinge-CD8αTM-CD3ζ or containing the CD8α hinge-CD28TM-CD28-CD3ζ ICD were obtained and used as template to PCR amplify the hinge-TM-and ICD region with the following primers:

```
Primer-3 Sense (SEQ ID NO: 38):
5'-GGGACACTCCGGAACCACGACGCCAGCGCCGCG-3'

Primer-4 Antisense (SEQ ID NO: 39):
5'-GGGACACGTCGACTTAGCGAGGGGCA-3'
```

This PCR template was then inserted into the BspE1 and Sal1 sites in the recently generated pELNS CD4 4-1BB zeta construct to replace the region containing the CD8α hinge-4-1BB-CD3ζ region. Plasmid was then electroporated into and propagated in the Top10 strain of *E. coli*.

A lentiviral vector that expressed B57 restricted TCR capable of recognizing HIV p24Gag epitope KAFSPE-VIPMF (SEQ ID NO: 42, pTRPE B57-KF11) was generated by synthesizing the TCRα and TCRβ gene sequence (IDT)). The TCRα and TCRβ gene sequence was separated by the T2A which allows coordinate expression of both TCR genes as previously described (Varela-Rohena et al., Nature medicine 14, 1390-1395 (2008)). VRC01, 3BNC60, PGT128, and PGDM1400 scFv CARs were generated from the published parental antibody sequences, with a light-linker-heavy chain configuration. The linker sequence is as follows: GGSSRSSSSGGGGSGGGG (SEQ ID NO: 43). Amino acid sequences were codon-optimized (Geneart) and synthesized as double-stranded DNA fragments (IDT or Geneart), flanked with suitable restriction sites and then cloned into pTRPE expression plasmid with the BamHI and BspE1 restriction sites. The PG9 scFv was cloned into the pTRPE expression plasmid with the BamHI and BspE1 restriction sites. Some of the sequences of optimized HIV CARs used in this study are listed in FIG. 18 (SEQ ID NOs: 44-61, amino acids) and in FIG. 19 (SEQ ID NOs: 62-79, nucleic acids).

Construction of VRC01, VRC01c-, and 3BNC60 scFv-Based KIR and IgG4-41BB-Zeta CARs.

VRC01, VRC01c-, 3BNC60 scFvs were cloned into a 3$^{rd}$ generation lentiviral expression vector under control of an EF1α promoter after digestion with BamHI and NheI, so that the scFv is in frame with a 9 amino acid GS-linker which is followed by the KIRS2 transmembrane and signaling domain. DAP-12 is located 5' of the scFv leader sequence, from which it is separated by a T2A ribosomal skipping site. A similar strategy was applied to clone the scFv coding sequences into a vector that allows expression of the scFvs in frame with an IgG4 hinge, followed by a CD8 transmembrane domain and 41BB co-stimulatory and CD3zeta signaling domain.

Construction of VRC01, 3BNC60, PGT128, PGDA1400 and PG9 scFv-Based CD3zeta CARs.

VRC01, 3BNC60, PGT128, PGDM1400 and PG9 scFv coding sequences were PCR amplified with primers encoding a 5' flanking BamHI and a 3' flanking BspEI site, which allowed digestion and cloning into the aforementioned pELNS CD8α hinge-CD8αTM-CD3ζ between leader sequence and CD8α hinge. All constructs were sequence verified.

TABLE 1

| SEQ ID Number | Listing of Sequences | |
|---|---|---|
| | Description | |
| 1 | CD4 zeta | Nucleic acid |
| 2 | EF1α promoter | Nucleic acid |
| 3 | CD4 extracellular domain | Nucleic acid |
| 4 | CD8α extracellular hinge | Nucleic acid |

TABLE 1-continued

Listing of Sequences

| SEQ ID Number | Description | |
|---|---|---|
| 5 | CD8α transmembrane domain | Nucleic acid |
| 6 | CD3 zeta | Nucleic acid |
| 7 | CD4 CD28 zeta | Nucleic acid |
| 8 | CD28 transmembrane domain | Nucleic acid |
| 9 | CD28 costimulatory domain | Nucleic acid |
| 10 | PGDM1400-KIR | Nucleic acid |
| 11 | PGDM1400-KIR | Amino acid |
| 12 | PGDM1400 scFv | Nucleic acid |
| 13 | PGDM1400 scFv | Amino acid |
| 14 | PGT128-KIR | Nucleic acid |
| 15 | PGT128-KIR | Amino acid |
| 16 | PGT128 scFv | Nucleic acid |
| 17 | PGT128 scFv | Amino acid |
| 18 | VRC01-KIR | Nucleic acid |
| 19 | VRC01-KIR | Amino acid |
| 20 | VRC01 scFv | Nucleic acid |
| 21 | VRC01 scFv | Amino acid |
| 22 | 3BNC60-KIR | Nucleic acid |
| 23 | 3BNC60-KIR | Amino acid |
| 24 | 3BNC60 scFv | Nucleic acid |
| 25 | 3BNC60 scFv | Amino acid |
| 26 | VRC01c-KIR | Nucleic acid |
| 27 | VRC01c-KIR | Amino acid |
| 28 | VRC01-c scFv | Nucleic acid |
| 29 | VRC01-c scFv | Amino acid |
| 30 | CD4 Dap12-KIRS2 | Nucleic acid |
| 31 | CD4 Dap12-KIRS2 | Amino acid |
| 32 | CD4KIR | Nucleic acid |
| 33 | CD4KIR | Amino acid |
| 34 | VRC01 IgG4 bbz | Nucleic acid |
| 35 | VRC01 IgG4 bbz | Amino acid |
| 44 | Optimized CD4-CD28 zeta | Amino acid |
| 45 | Optimized CD4 4-1BB zeta | Amino acid |
| 46 | Optimized CD4 extracellular domain | Amino acid |
| 47 | Optimized CD8α extracellular hinge | Amino acid |
| 48 | Optimized CD8α TM | Amino acid |
| 49 | Optimized CD28 TM and ICD | Amino acid |
| 50 | Optimized 4-1BB | Amino acid |
| 51 | Optimized CD3 zeta | Amino acid |
| 52 | Optimized PG9 CD3zeta | Amino acid |
| 53 | Optimized PGT128 CD3zeta | Amino acid |
| 54 | Optimized VRC01 CD3zeta | Amino acid |
| 55 | Optimized 3BNC60 CD3zeta | Amino acid |
| 56 | Optimized PGDM1400 CD3zeta | Amino acid |
| 57 | Optimized PG9 | Amino acid |
| 58 | Optimized PGT128 | Amino acid |
| 59 | Optimized VRC01 | Amino acid |
| 60 | Optimized 3BNC60 | Amino acid |
| 61 | Optimized PGDM1400 | Amino acid |
| 62 | Optimized CD4-CD28 zeta | Nucleic acid |
| 63 | Optimized CD4 4-1BB zeta | Nucleic acid |
| 64 | Optimized CD4 extracellular domain | Nucleic acid |
| 65 | Optimized CD8α extracellular hinge | Nucleic acid |
| 66 | Optimized CD8α TM | Nucleic acid |
| 67 | Optimized CD28 TM and ICD | Nucleic acid |
| 68 | Optimized 4-1BB | Nucleic acid |
| 69 | Optimized CD3 zeta | Nucleic acid |
| 70 | Optimized PG9 CD3zeta | Nucleic acid |
| 71 | Optimized PGT128 CD3zeta | Nucleic acid |
| 72 | Optimized VRC01 CD3zeta | Nucleic acid |
| 73 | Optimized 3BNC60 CD3zeta | Nucleic acid |
| 74 | Optimized PGDM1400 CD3zeta | Nucleic acid |
| 75 | Optimized PG9 | Nucleic acid |
| 76 | Optimized PGT128 | Nucleic acid |
| 77 | Optimized VRC01 | Nucleic acid |
| 78 | Optimized 3BNC60 | Nucleic acid |
| 79 | Optimized PGDM1400 | Nucleic acid |

Lentivirus Harvesting, Concentration, and Transduction of Primary CD8 T Cells:

Plasmid preparations were combined with commercially available lentiviral packaging plasmids expressing VSV glycoprotein, HIV-1 Gag and Pol, and Rev (pRSV.REV, pMDLg/p.RRE, pVSV-G) and transfected onto HEK293T cells with pTRPE transfer vectors using the Lipofectamine 2000 transfection reagent (Invitrogen, Life Technologies). The same process was completed with the RD114 Env and MMLV gag/pol plasmids (pMSCV RD114 and pNGLV3g/p) to generate the retrovirus. 30 ml aliquots of supernatant were collected at 24 and 48 hour time points and concentrated by ultracentrifugation overnight at 8,500RPM at 4° C.. Supernatant was aspirated and cell pellet was resuspended in 1.2 ml total volume, flash frozen on dry ice, and transferred to −80° C. for storage.

Cell Culture—Experimental Protocol:

Healthy donor CD8 and CD4 T lymphocytes were obtained and activated with Dynabeads—αCD3/αCD28 coated T-expander beads. T cells were purified by negative selection using the RosetteSep Human CD4+ or CD8+ T Cell Enrichment Cocktails according to the manufacturer's protocols (StemCell Technologies). T cells were cultured at $1 \times 10^6$ per mL in RPMI 1640 (Life Technologies) supplemented (ThermoFisher Scientific) with 10% fetal calf serum (Seradigm), 1% Penn Strep (Life Technologies), 2 mM GlutaMax (Life Technologies), and 25 mM HEPES buffer (Life Technologies). T cells were stimulated with anti-CD3/CD28 coated Dynabeads (Life Technologies) at a 3:1 bead to cell ratio and 100-300 international units per milliliter of recombinant human interleukin 2 for 5 days and then beads were removed. 1 day after stimulation, 200 ul of lentivirus supernatant was added to $0.5 \times 10^6$ cells. MMLV vector transduction was performed on days 3 and 5, with 1 ml virus supernatant added to a Retronectin (Takara) coated 24 well plate and spinoculated according to the manufacturer's instructions. Medium was doubled on day 3 and changed completely on day 5, and then added every other day throughout cell culture, or as necessary based on cell counts.

Hiv-1 Infections.

Two days after removing the anti-CD3/CD28 beads, CD4 T cells were infected with CCR5-tropic HIV strain Bal, and 24 hours later were co-cultured at varying effector to target (E:T) ratios with CAR+ CD8 T cells. The CCR5-tropic HIV-1 Bal viral stock (280 ng/ml p24) was prepared by harvesting the cell free supernatant from anti CD3/CD28 activated CD4 T cells. Activated CD4 T cells were infected by adding approximately 1ml of supernatant per 20 million cells 2-3 days after removing beads. The following day CD4 and CD8 T cells were co-cultured at varying E:T ratios and HIV spread was monitored by intracellular p24 staining was detected with the KC57 anti-Gag-RD1 antibody (Beckman Coulter) and the Invitrogen Fix and Perm buffers, according the manufacturers' instructions.

In Vitro Cytotoxicity and Cytokine Assays

In vitro killing of K562 cells expressing HIV-1 gp120/41 envelope (YU-2) was tested with a $^{51}$Cr-release assay. $5 \times 10^5$ target cells were loaded with 50 μCi of $Na_{251}CrO_4$ (Perkin Elmer) for 90-120 minutes, washed twice and resuspended in phenol red-free medium with 5% FBS. CAR or mock transduced T cells (8-10 days after initial activation) were co-incubated with loaded target cells for 4 hours at various effector:target (E:T) ratios, and chromium release into the supernatant was measured with a MicroBeta2 plate counter (Perkin Elmer). Intracellular cytokine production was measured after co-culturing $5 \times 10^5$ NTD, CD4 CAR, or scFv CAR transduced T cells at a 1:1 E:T ratio with parental K562s, HLA-DR*0401 transduced K562s, or HIV YU2 Env transduced K562s for 6 hours. Cytokine production was detected as previously described (86) using rat anti human IL-2 APC (BD biosciences), mouse anti human MIP-1β PerCP Cy5.5 (BD biosciences), mouse anti human IFN-γ FITC (BD biosciences), and mouse anti human CD107a PE (BD biosciences), along with Invitrogen Fix and Perm buffers. Spontaneous release by target cells (without effector cells) was analyzed in the same volume, and maximum release was assessed by treating target cells with SDS at a final concentration of 5%. Percent specific lysis=[(Experimental Release−Spontaneous Release)/(Maximum Release−Spontaneous Release)]*100. All experiments were performed with at least 3 replicates, and with primary human T cells from 3 distinct donors. Interferonγ production was quantified by ELISA (R&D) according to the manufacturer's recommendations in duplicate culture supernatants after co-culture of $3 \times 10^5$ effector cells and $10^5$ target cells in 400 ul for 24 h.

CCR5 ZFN Disruption.

Previously described CCR5 specific ZFNs were cloned into a RNA expression vector (Beatty et al., Cancer immunology research 2, 112-120 (2014)). The mMessage mMachine T7 Transcription Kit (Ambion, Thermo Fisher Scientific) was utilized to generate capped, in vitro transcribed RNA, which was subsequently purified with the RNeasy Mini Kit (Qiagen) and eluted in RNase-free water at 1 mg/ml. Normal donor CD8 T cells were washed three times with OPTI-MEM medium and re-suspended at a final concentration of $1 \times 10^8$/ml prior to electroporation. 10E6 T cells in 0.1 ml were mixed with 30 g of RNA encoding for each ZFN, electroporated in a 2 mm cuvette (Harvard Apparatus BTX) using an ECM830 Electro Square Wave Porator (Harvard Apparatus BTX), and incubated at 30° C. for 48 hours prior to activation with αCD3/αCD28 coated Dynabeads (Life Technologies).

To measure efficiency of genome modification by CCR5 ZFNs, genomic DNA was purified from T cells and used to prepare samples for Illumina deep sequencing (Wang et al., Nucleic Acids Res 44, e30 (2016). Briefly, the CCR5 target region was amplified and MiSeq adaptor was added using a nested PCR method with the following 2 CCR5-specific primer pairs. CCR5 Out-Outl primers: CTGTGCTTCAAGGTCCTTGTCTGC (SEQ ID NO: 80) and CTCTGTCTCCTTCTACAGCCAAGC (SEQ ID NO: 81); CCR5 MiSeq adaptor primers: ACACGACGCTCTTCCGATCTNNNNNGCCAGGTTGAGCAGGTAGATG (SEQ ID NO: 82) and GACGTGTGCTCTTCCGATCTGCTCTACTCACTGGTGTTCATCTTT (SEQ ID NO: 83). Sequence barcodes were then added in the subsequent PCR reaction using the barcode primer pairs. For analysis of gene modification levels, a custom-written computer script was used to merge paired-end 150 bp sequences, and adapter trimmed via SeqPrep (John St. John, https://github.com/jstjohn/SeqPrep). Reads were aligned to the wild-type template sequence. Merged reads were filtered using the following criteria: the 5' and 3' ends (23 bp) must match the expected amplicon exactly, the read must not map to a different locus in the target genome as determined by Bowtie2 (Yu et al., Journal of virology 81, 1619-1631 (2007)) with default settings, and deletions must be <70% of the amplicon size or <70 bp long. Indel events in aligned sequences were defined as described previously (Gabriel et al., Nat Biotech 29, 816-823 (2011)), with the exceptions that indels of lbp in length were also considered true indels to avoid undercounting real events, and true indels must include deletions occurring within the sequence spanning between the penultimate bases (adjacent to the gap) of the binding site for each partner ZFN.

Humanized Mouse Model.

6 week old NSG (NOD-scid IL2Rgnull) mice were obtained from The Jackson Laboratory (JAX) and at 7 weeks treated with 30 mg/kg Busulfan mixed 1:1 with PBS. 24 hours later mice were injected via tail vein with $10 \times 10^6$ human lymphocytes in 100 ul 0.5% human serum albumin in PBS. Three weeks later mice were infected with 15 ng of the CCR5-tropic Bal strain of HIV mixed 1:1 with PBS via tail vein injection. Peripheral blood was obtained by retro-orbital bleeding, and human CD4 and CAR+ CD8 lymphocyte counts were enumerated using BD lysis buffer and BD TruCount tubes as previously described (Richardson et al., Molecular therapy: the journal of the American Society of Gene Therapy 22, 1084-1095 (2014)), staining with mouse anti human CD45 PerCp Cy5.5 (BD Biosciences), mouse anti human CD4 BV421 (Biolegend), and mouse anti human CD8α BV711 (Biolegend).

HIV Viral Load Assay.

RNA was extracted from 10-30 μl of plasma depending on availability using methods as described in (Cillo et al., J Clin Microbiol 52, 3944-3951 (2014)) and reconstituted in a final volume of 15 ul. Prior to extraction, a uniform quantity of Replication Competent Avian Sarcoma (RCAS) virus spiked into each plasma sample and amplified separately to verify virus/RNA recovery and absence of PCR inhibition (Palmer et al., J Clin Microbiol 41, 4531-4536 (2003)). RNA was reverse transcribed using random hexamers and quantified by Q-PCR using the LightCycler 480 Probes Master (Roche; Indianapolis, Ind.) on an ABI 7500FAST real-time thermocycler using an in vitro transcribed RNA standard. For each sample, the Q-RT-PCR reaction was run in duplicate on 5 ul RNA; no-reverse transcriptase reaction and RCAS amplification were run on one well per sample using 2.5 ul RNA. The HIV-1 primer/probe targets the pol gene and detects all group M clades as described in (Cillo et al., J Clin Microbiol 52, 3944-3951 (2014)), and RCAS amplification used primer/probe as described in (Palmer et al., J Clin Microbiol 41, 4531-4536 (2003). HIV-1 quantification was normalized to equivalent volumes of starting plasma.

The results of the experiments are now described.

Example 1: Lentiviral Backbone Augments CD4 CAR Expression and Control Over HIV Replication Preclinical studies testing the CD4 CAR used in the previous clinical trials showed that T cells expressing this construct had equivalent antiviral activity to naturally generated HIV-specific T cells. The hypothesis of the failure of these clinical trials to demonstrate durable clinical responses is that the T cells used in these clinical trials were not any more potent than the endogenous HIV-specific T cell response. The present invention optimizes each component of the CAR in a step-by-step manner to augment the potency by which T cells control HIV replication.

Primary human CD8 T cells were transduced with the original murine retroviral vector (MMLV) clinical trial construct and with analogous third generation lentiviral vector construct that also used the PGK promoter to drive CD4 CAR expression. Lentiviral transduction of primary human CD8 T cells consistently resulted in a ~10-fold higher median fluorescence intensity (MFI) of CAR expression compared to murine retrovirus.

Figures 2A, 2B, 2C:
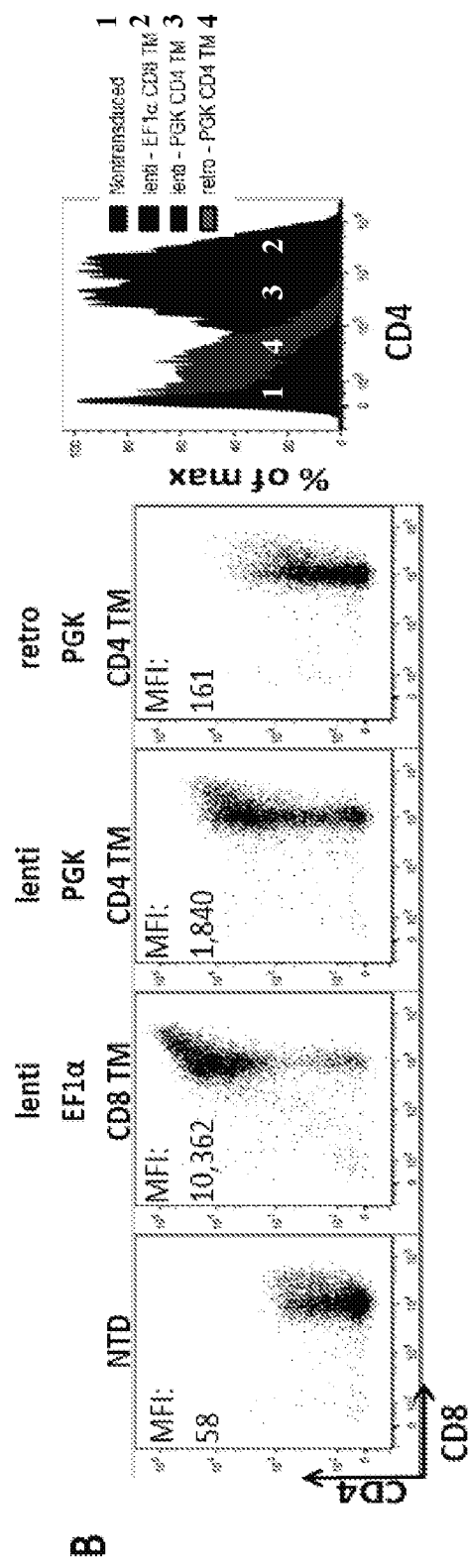
FIGS. 2A-2G are series of schematic representations and graphs depicting that promoter and transmembrane changes improve CD4 membrane-bound chimeric receptor efficacy and increase control over HIV-1.
Figure 2D:
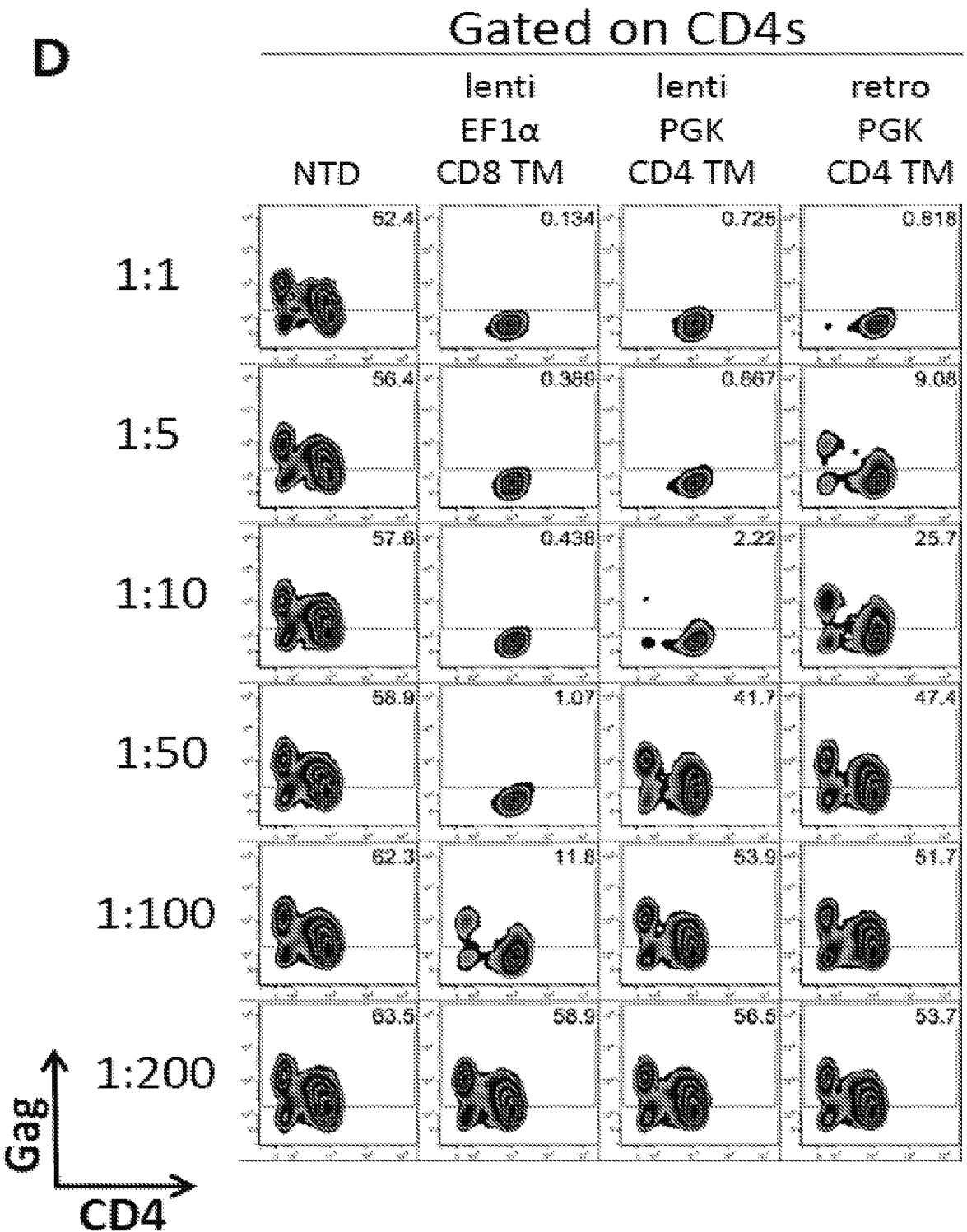
Figure 2E:
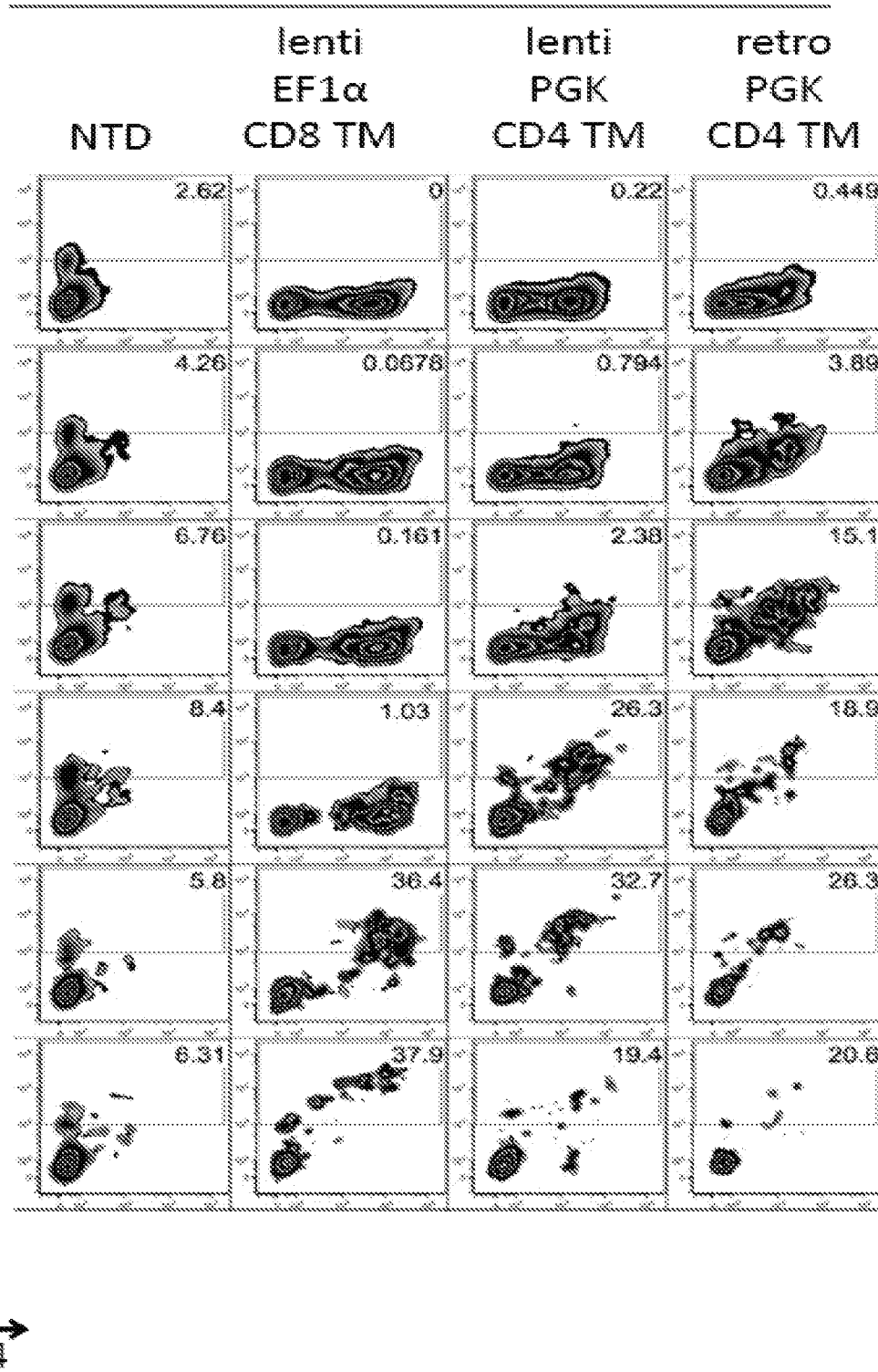
Figures 2F, 2G:
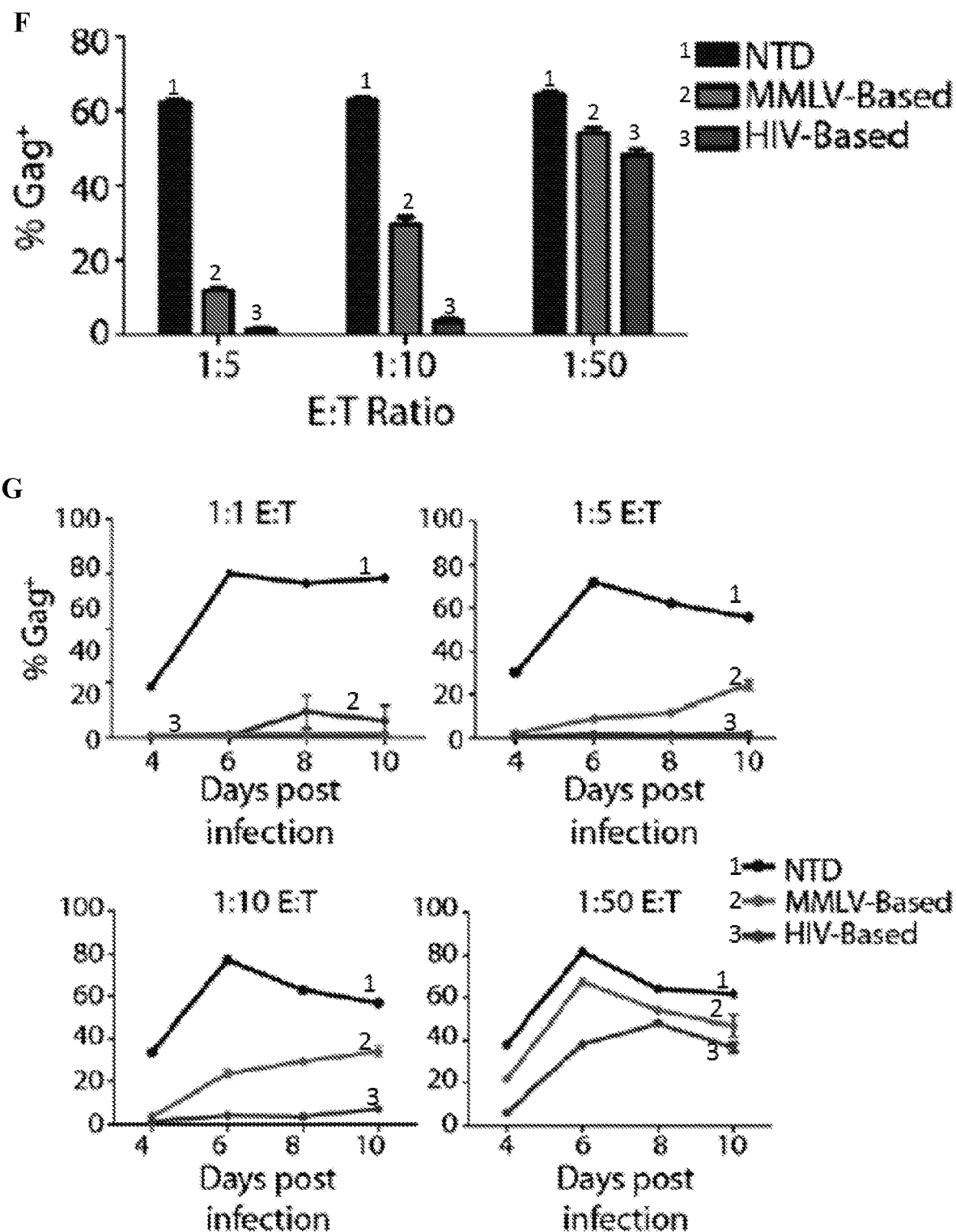

The present new, improved CD4 membrane-bound chimeric receptor (CD4 zeta construct) with the lentiviral vector, EF1α promoter, and CD8α transmembrane domain controlled HIV-1 at much lower E:T ratios (until roughly 1:100) than the constructs with the PGK promoter and CD4 transmembrane domains (lose control at 1:5 and 1:10). Even in view of higher expression of the lentivirus PGK CD4 TM CAR compared to the retrovirus PGK CD4 TM CAR, a small benefit was seen in terms of control over HIV-1 replication. Importantly, higher expression of the EF1α CD8 TM construct did not promote higher rates of infection, as the CD8s remaining uninfected until approximately the 1:100 ratio whereas the PGK CD4 TM engineered CD8 cells became infected at lower E:T ratios (FIGS. 2A-2D). Upon diluting the CD4 CAR transduced CD8 T cells to lower E:T ratios, T cells transduced with the lentiviral vector were superior at controlling HIV replication compared to T cells transduced with the retroviral vector (FIGS. 2F-2G). Ultimately neither population of transduced CD8 T cells could control HIV spread at a 1:50 E: T ratio. Thus the promoter and transmembrane changes of the present invention improved the CD4 membrane-bound chimeric receptor efficacy and provided an increased control over HIV-1 infection.

In contrast to recent reports that CD4 CAR transduced CD8 T cells are susceptible to infection by cell free virus (Liu et al., Journal of virology 89, 6685-6694 (2015); Zhen et al., Molecular therapy: the journal of the American Society of Gene Therapy 23, 1358-1367 (2015)), the present results only show detection intracellular gag in CAR CD8 T cells after diluting to low E: T ratios with HIV-infected CD4 T cells (FIG. 2E). Relative to non-transduced CD8 T cells, high levels of intracellular gag were shown to be present in CAR-transduced CD8 T cells, indicating the CD4 CAR renders these cells susceptible to infection (FIG. 2E). Importantly, the higher expression of CD4 on the lentivirus transduced CD8 T cells did not promote greater levels of infection of these cells or infection at higher E:T ratios. This data demonstrated that lentiviral vectors are the preferred method of introducing constructs that re-direct T cells to target HIV.

Example 2: EF1α Promoter and CD8α Transmembrane Domains Improve CAR Expression and Control Over HIV-1

Figure 3A:
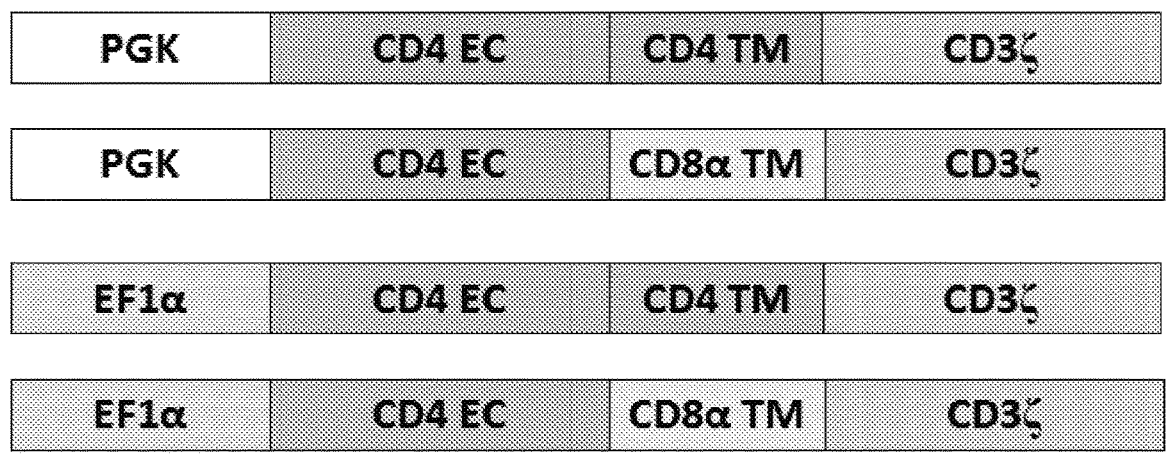
FIGS. 3A-3E are series of schematic representations and graphs depicting that EF1α promoter and CD8α transmembrane change is a critical modification to improve CAR expression and control of HIV-1 replication.

The EF1α CD8TM construct was shown to control HIV-1 replication at the lowest E:T ratios. Simply increasing expression of the CD4 TM with the EF1 a promoter (FIGS. 3A-3B, middle column) improved control over HIV-1 replication, but the combination of increased expression with the EF1α promoter and CD8α transmembrane substitution produced the best control over HIV-1. Furthermore, CD8α TM appeared to reduce infection of the CD4 membrane-bound chimeric receptor CD8 cells (FIGS. 3A-3B right set of columns), particularly at the 1:50 ratio for the EF1α constructs and the 1:25 ratio for the PGK constructs.

Figure 3B:
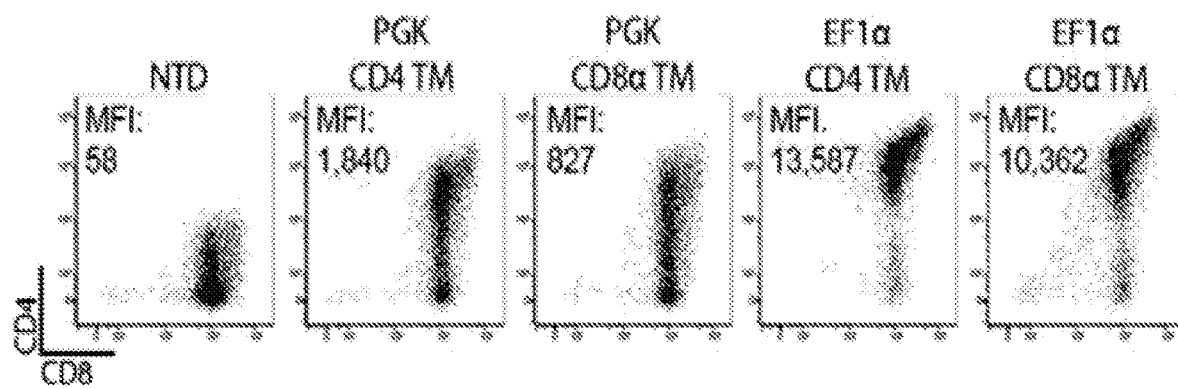
Figure 3C:
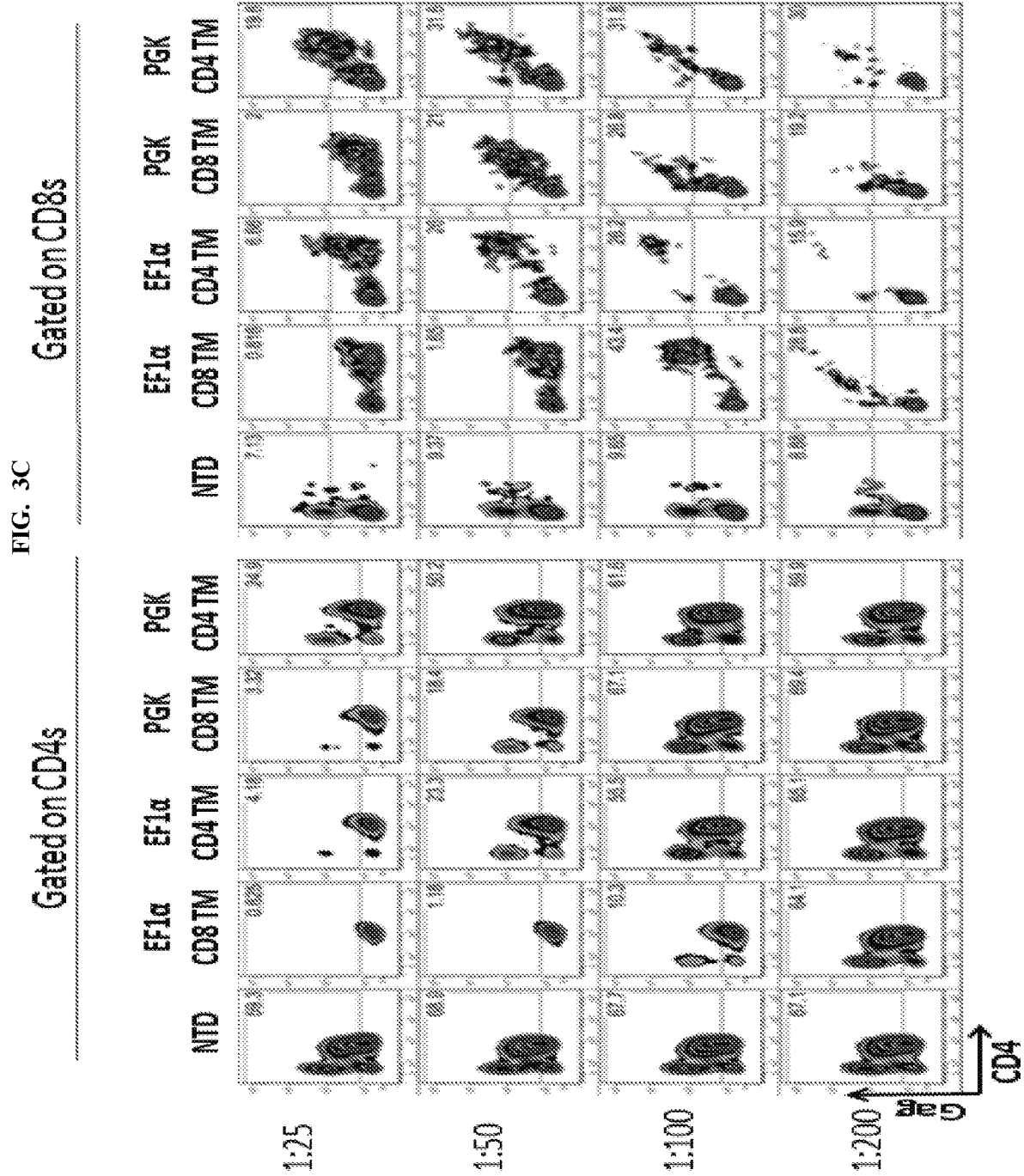
Figure 3D:
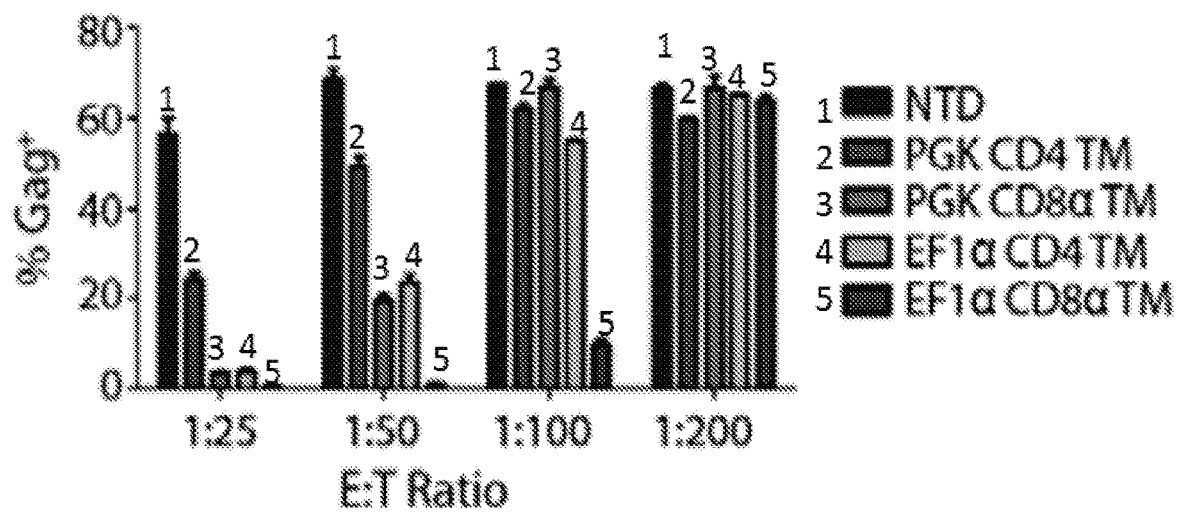
Figure 3E:
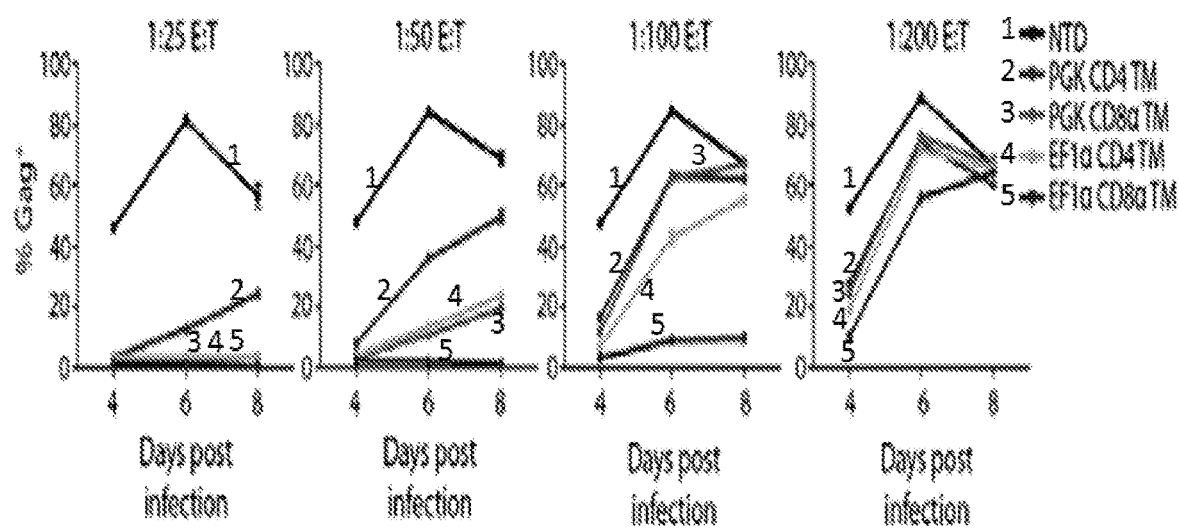

Substitution of the CD8α TM domain decreased infection of CAR+ CD8 T cells regardless of the promoter used at the 1:25 and 1:50 E:T ratios (FIG. 3B). However, as seen in FIGS. 2A-2G, the CAR+ CD8 T cells can be diluted to the point where they no longer can control HIV infection and succumb to infection themselves. Thus, altering the viral vector, promoter, and transmembrane domains afforded a 50-fold increase in potency over the clinical trial retrovirus, resulting in complete control over HIV replication at a 1:50 E: T ratio in vitro (FIGS. 3C-3D).

Thus, the CD8α transmembrane change was a critical modification to improve control of HIV-1 replication.

Example 3: Broadly Neutralizing Antibody Based CARs can Control HIV-1

Figure 1B:
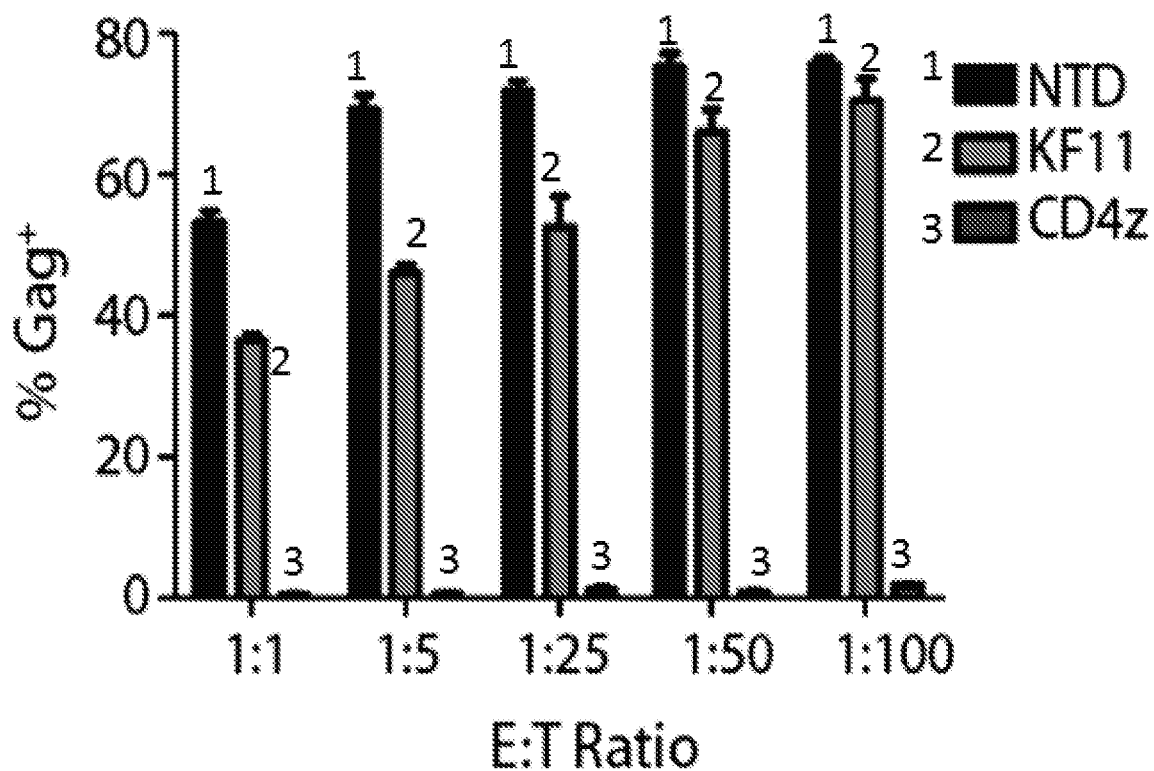
Figure 4A:
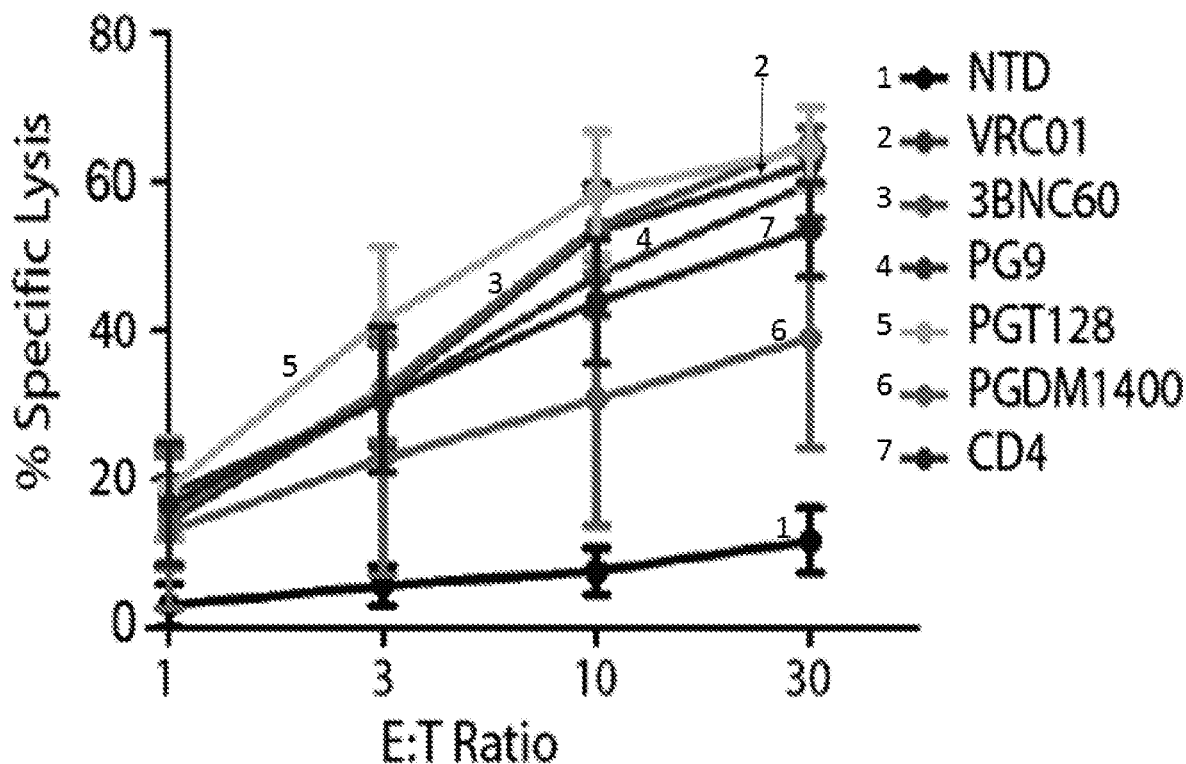
FIGS. 4A-4C are a series of table and graphs demonstrating that both single chain variable fragment (scFv) broadly neutralizing antibody (bnAb)-based CARs and CD4 membrane-bound chimeric receptor can control HIV-1 infection.
Figure 4B:
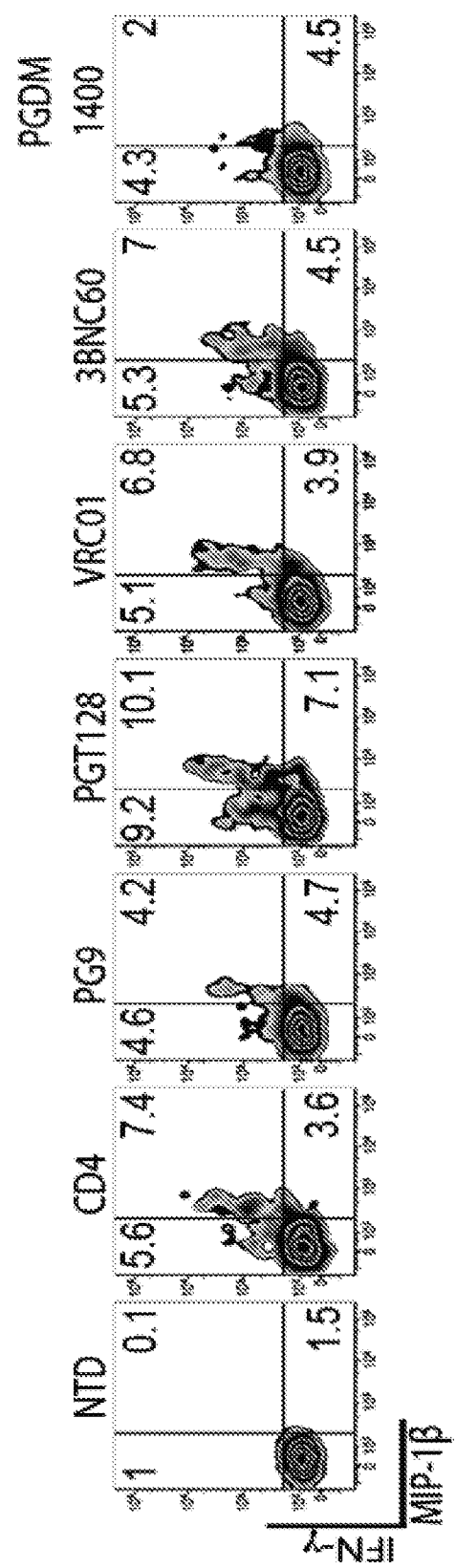
Figure 4C:
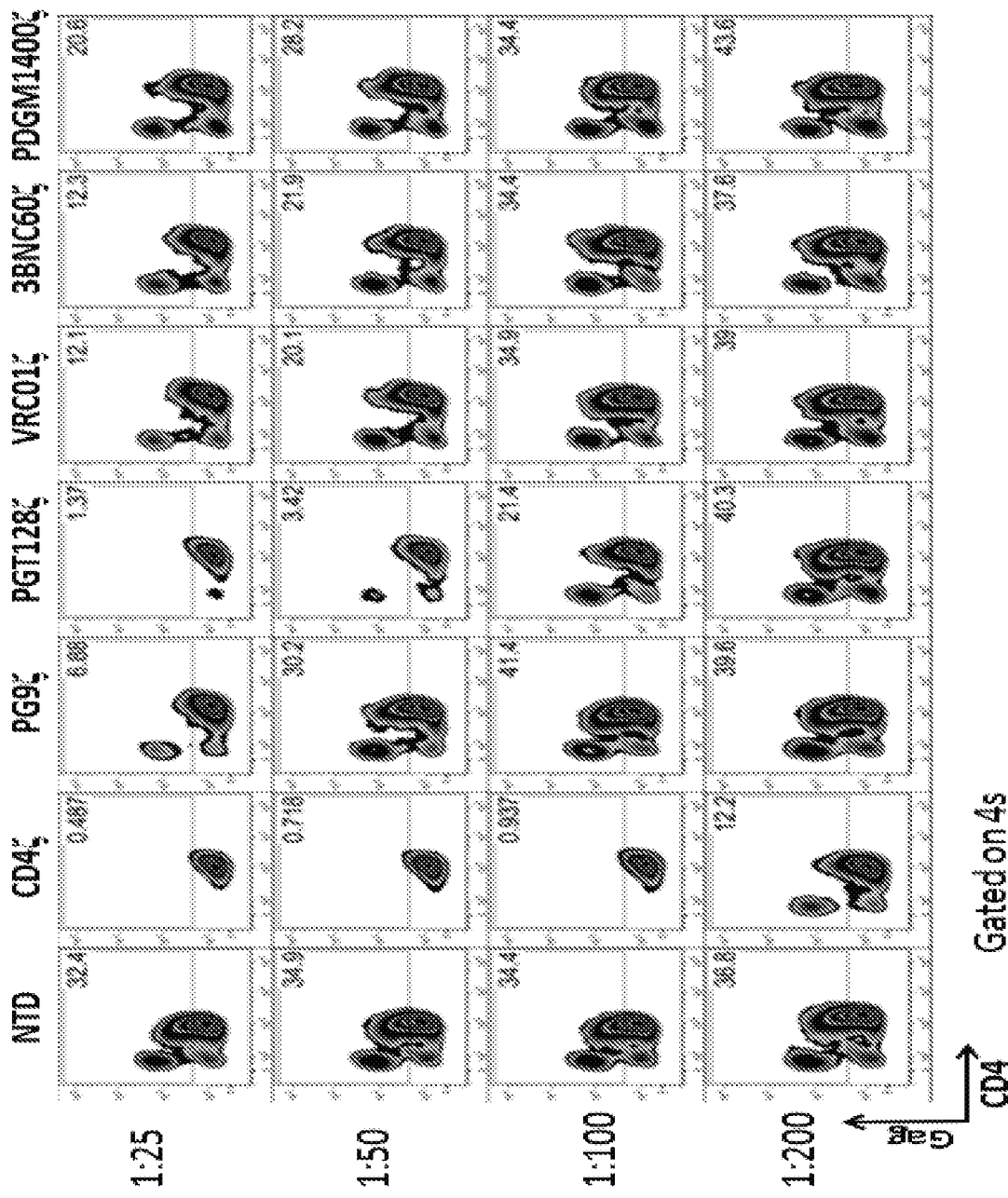

As seen in FIGS. 4A-4B, both single chain variable fragment (scFv) broadly neutralizing antibody (bnAb)-based CARs and CD4 membrane-bound chimeric receptor can control HIV-1 infection. A panel of scFvs (see table in FIG. 4A) that ranged in their HIV-1 binding breadth and neutralization potency were cloned into the same EF1α-CD8α TM-zeta construct backbone as the CD4 membrane-bound chimeric receptor and assessed for their ability to control HIV-1 replication. Cr51 release killing assay from a 4 hour co-culture showed that CD8 T cells expressing any of the scFv CARs or the CD4 membrane-bound chimeric receptor, but not non-transduced (NTD) T cells, lysed Env-expressing target cells. This indicates the scFv CARs were expressed with proper folding/conformation and able to bind Env (FIG. 4B). Many of the scFv CARs consistently produced high levels of intracellular cytokines in response to Env-expressing targets. Both the CD4 membrane-bound chimeric receptor and the scFv CARs demonstrated lysis of Env target cells relative to NTD controls up to a E:T ratio of 1:50-1:200 (FIG. 4C), which was superior to the activity of the KF11 TCR shown in FIG. 1, which demonstrated efficacy up to a 1:25 E:T ratio.

Without wishing to be bound by theory, it is understood that use of a CAR that targets HIV, wherein the CAR comprises an anti-HIV scFv will be beneficial for treatment of subjects that have reservoir populations of HIV-infected cells. The invention therefore includes such a CAR for such use in one aspect of the invention.

Example 4: CD4 CAR is Over 100-Fold More Potent than HIV-Specific Elite Controller TCR In Vitro Elite controllers (ECs) are rare individuals who are able to control HIV replication in the absence of ART. Certain HLA alleles, such as HLA-B57, are overrepresented in elite controller cohorts, suggesting that T cell responses play a key role in controlling HIV replication in these individuals (Walker et al., Nature reviews. Immunology 13, 487-498 (2013)). HIV-specific T cells isolated from ECs have higher cytolytic potential than HIV-specific T cells isolated from HIV progressors (Migueles et al., PNAS 97, 2709-2714 (2000); Saez-Cirion et al., PNAS 104, 6776-6781 (2007)). Therefore, to determine whether T cells expressing a CD4 CAR are able to control HIV replication better than T cells expressing a HLA-B57 restricted TCR isolated from an elite controller that is associated with better control over HIV replication in patients, HLA-B57 expressing primary human CD8 T cells were transduced with a TCR specific for KF11 (HIV p24Gag epitope KAFSPEVIPMF, SEQ ID NO: 42) that was also expressed under the EF1α promoter, and their ability to limit HIV spread was determined using CD4 T cells from the same donor. KF11 TCR is known in the art to be associated with better control over HIV-1 replication in patients and is one of the most potent patient-derived TCRs against HIV-1. While KF11 TCR-transduced CD8 T cells reduced HIV replication down to a 1:25 E:T ratio, complete control over HIV replication was never achieved (FIGS. 1A-1B and FIGS. 3A-3D). In contrast, the CD4 CAR of the present invention controlled HIV almost completely down to a 1:100 E: T ratio. These results revealed that CD4 zeta CAR controls NL4-3 HIV-1 replication better than the HLA-B*57 restricted KF11 elite controller TCR.

These data indicates that CD4 CAR of this invention has much greater potency than an endogenous HIV T cell response and suggests that T cells expressing optimized CD4 CAR will be able to control HIV replication after ART removal at an effector to target ratio that can be achieved by adoptive T cell therapy.

Figure 5B:
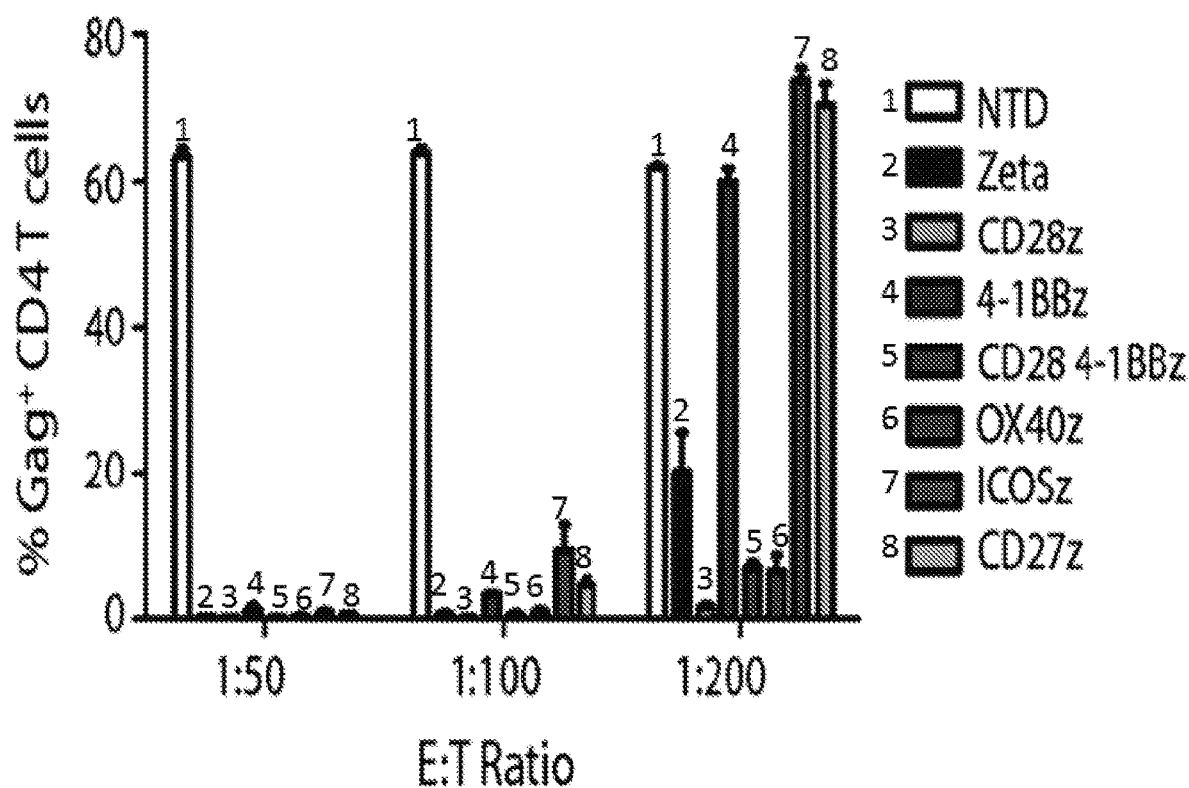

Additionally, FIGS. 5A-5B reveal that CD28 costimulation promoted control over HIV-1 Bal. Another membrane-bound chimeric receptor construct that consistently controlled HIV-1 as well or better than CD4 zeta construct was CD4 CD28 zeta construct.

Example 5: CD28 and 4-1BB Costimulation have Opposing Effects on the Control of HIV-1 Replication In Vitro T cells require costimulatory signals for proliferation, effector function, and long-term survival. Additional costimulatory domains, such as CD28 and 4-1BB, have been incorporated into more recent CAR designs, which have proven necessary for inducing durable CAR T cell responses in vivo (Van der Stegen et al., Nature reviews. Drug discovery 14, 499-509 (2015)). A panel of CD4 CARs that incorporated a variety of costimulatory domains were generated in conjunction with the CD3-zeta domain, including CD28, 4-1BB, CD28+4-1BB, OX40, ICOS, or CD27 and their ability to control HIV infection in vitro was tested. CD8 T cells expressing CARs that contained 4-1BB, CD27, or ICOS costimulation domains did not control HIV as effectively as T cells expressing CAR that only contained CD3-zeta signaling domain, suggesting that these costimulatory pathways interfered with T cell control of HIV replication (FIGS. 5A-5B). CARs containing OX40 or a combination of CD28 and 4-1BB controlled HIV to similar levels as CARs containing only CD3-zeta. In contrast, CD28 improved control in vitro, indicating that CD28 costimulation may be beneficial in HIV-specific CARs.

Figure 11A:
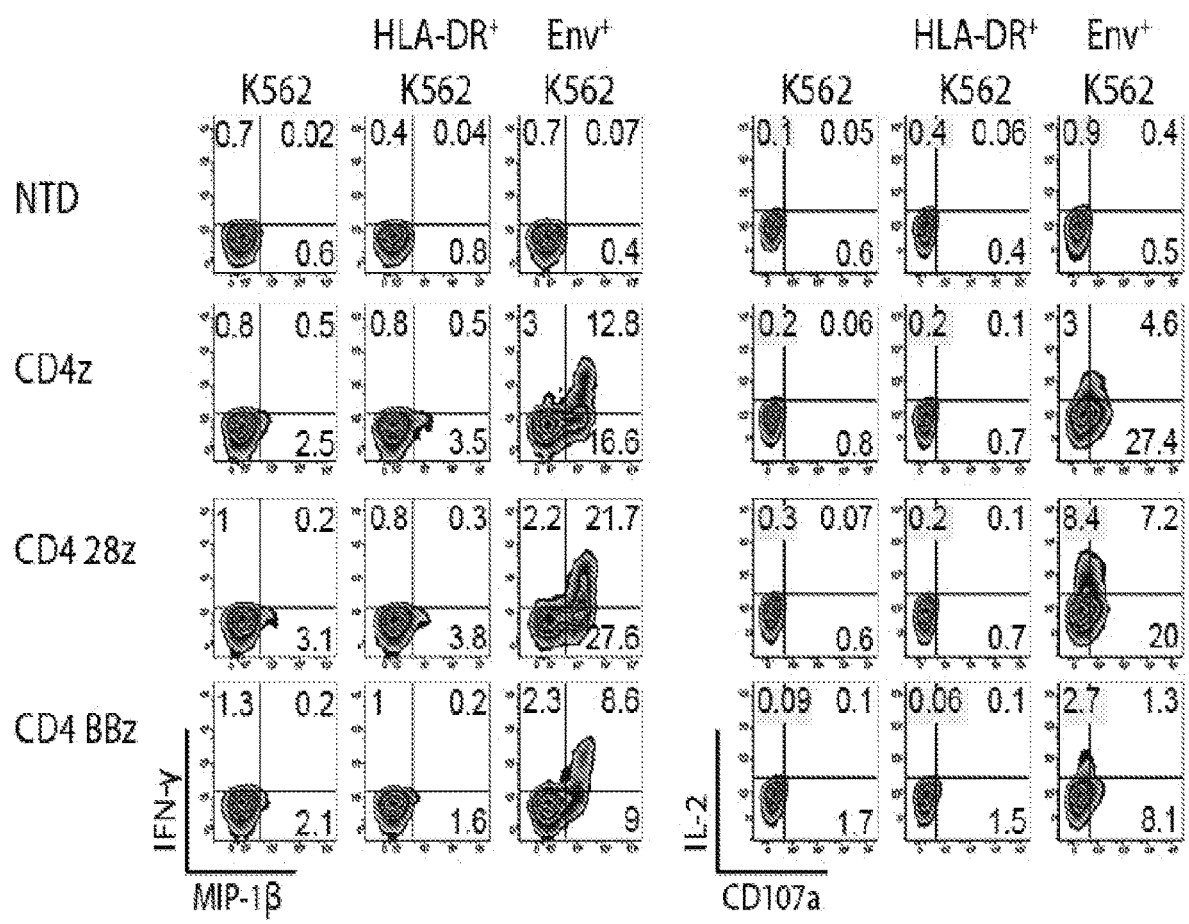
FIGS. 11A-11C are series of graph demonstrating that CD4 CARs specifically respond to Env+ cells and not MHC class II+ cells.
Figure 14:
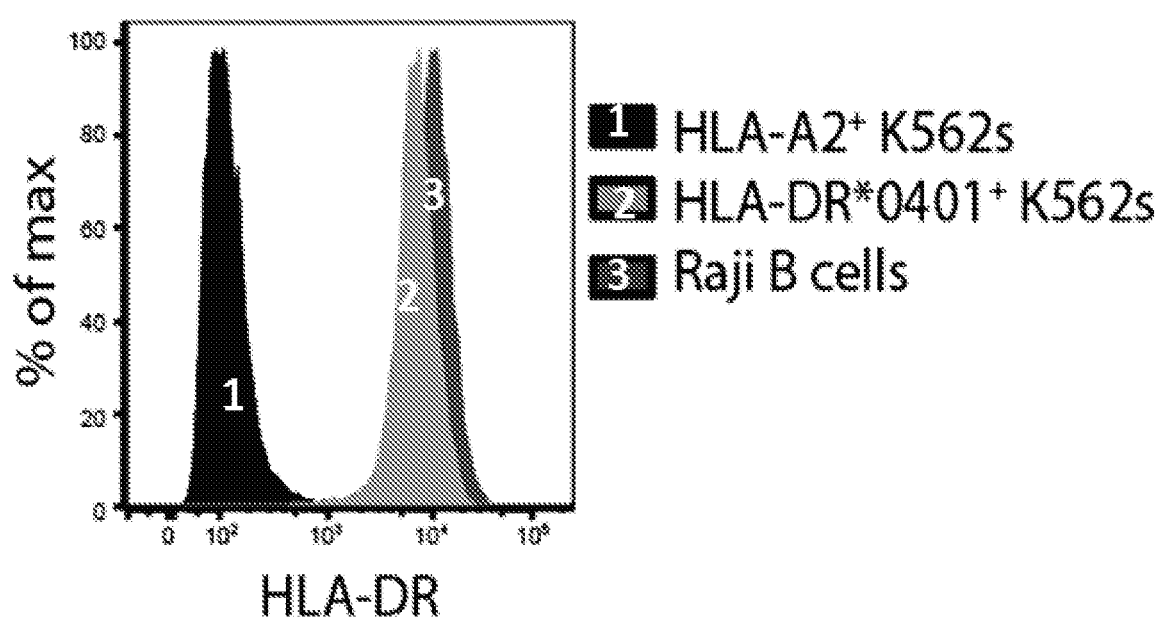
FIG. 14 is a graph depicting high levels of MHC class II expression on HLA-DR-transduced K562 cells. To confirm high expression of MHC class II on the HLA-DR*0401-transduced K562 cells, HLA-DR expression was measured by flow cytometry. As a gating control, K562 cells that had been transduced with HLA-A2 were stained, as well as the high MHC class II expressing Raji B cells. A histogram overlaying the three cell populations is depicted.

Example 5: CD4 CARs Specifically Respond to Env+ Cells and not MHC Class II+ Cells Preclinical data demonstrated that T cells expressing the clinical trial CD4 CAR did not kill Raji cells, which express high levels of MHC class II, the low affinity ligand of CD4 (Romeo et al., Cell 64, 1037-1046 (1991)). However, the long half-life of CD4 CAR T cells in patients was speculated to be a result of low affinity interactions with MHC class II or possibly the release of Env during viral blips (Scholler et al., Science translational medicine 4, 132ra153 (2012)). To determine if the previously described vector modifications facilitated off-target reactivity to MHC class II, CD4 CAR+ CD8 T cell responses were measured against a K562 cell line stably expressing high levels of the HLA-DR*0401 allele (see FIG. 14). CD8 T cells were transduced with optimized CD4 CARs containing CD3-zeta, 4-1BB-CD3-zeta, or CD28-CD3-zeta costimulatory domains and cultured with unmodified K562 target cells, HLA-DR*0401+ K562 cells, or HIV YU2 Env+K562 cells. CAR transduced CD8 T cells produced IL-2, CD107a, IFN-γ, and MIP-1β in response to HIV Env+ targets but not in response to HLA-DR+ or parental K562s, with the most robust production in CD28-containing CAR T cells (FIG. 11A). A small amount of MIP-1β signal was observed for all CARs when mixed with either parental or HLA-DR expressing targets that was not observed in nontransduced controls, likely due to some constitutive, non-antigen specific signaling observed in CAR expressing T cells. However, compared to CAR T cells cultured alone or with parental K562s, no additional cytokine or CD107a production was detected in response to MHC II expressing cells.

Figure 11B:
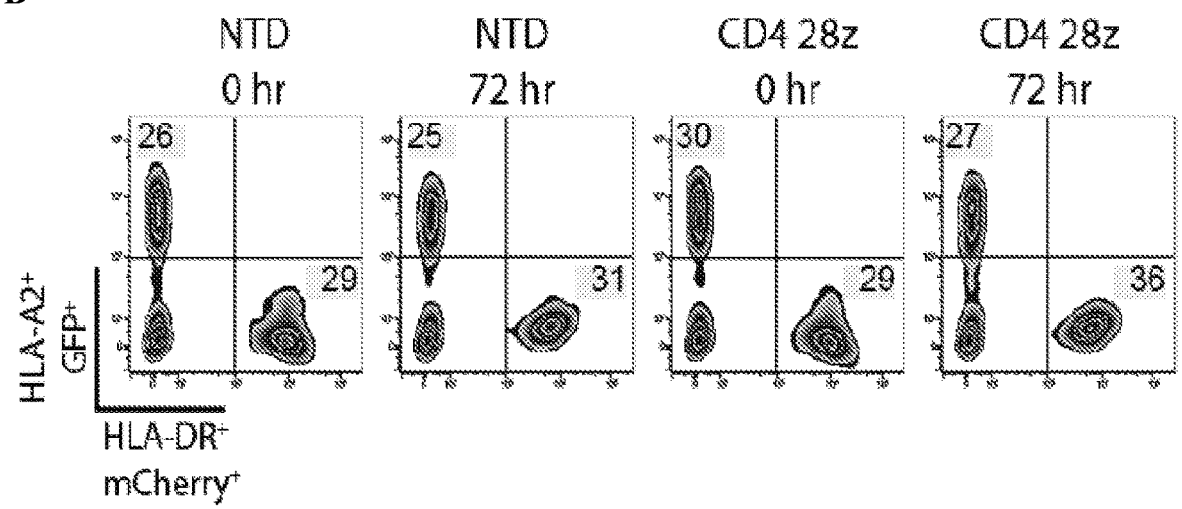
Figure 11C:
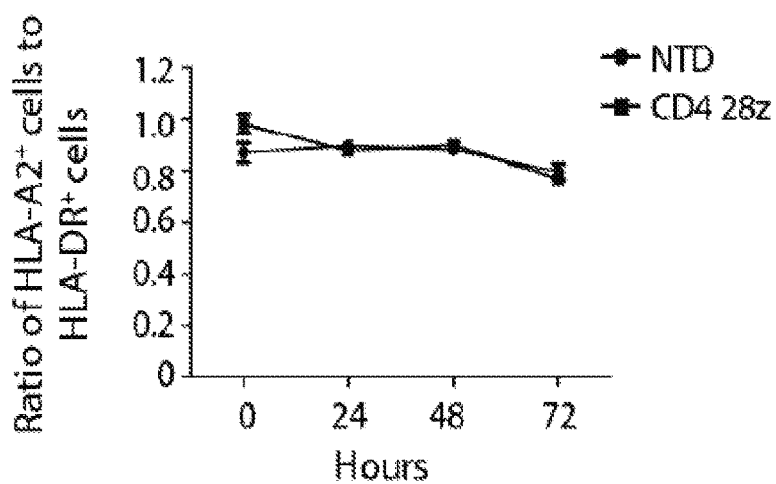

A co-culture assay was performed to determine if CAR+ CD8 T cells could kill MHC class II targets, despite the lack of cytokine production. CD4 CARs containing the CD28-CD3-zeta costimulatory domains were added to a 1:1 mixture of HLA-A*02+/GFP+ K562s and HLA-DR*0401+/mCherry+ K562s and the ratio of the two K562 cell types was measured over time. Prolonged culture over 72 hours did not result in a reduction of the proportion of HLA-DR*0401+K562s (FIGS. 11B-11C). These results suggest that use of the re-engineered CD4 CAR will be as safe to use in humans as the original CD4 CAR vector.

Example 6: T Cells Expressing Optimized CD4 CAR Control HIV-1 Replication and Expand to Much Greater Levels In Vivo than the First Generation CD4 CAR CD19-specific CARs containing the CD28 and CD3-zeta signaling domains had superior in vitro activity than those containing the 4-1BB and CD3-zeta signaling domains, but the 4-1BB containing CARs proved superior in humanized mouse models and ultimately in patients with B cell leukemias ((Porter et al., Science translational medicine 7, 303ra139 (2015); Milone et al., Molecular therapy: the journal of the American Society of Gene Therapy 17, 1453-1464 (2009); Brentjens et al., Blood 118, 4817-4828 (2011)). In order to determine whether the same was true for HIV-targeting CARs and if optimized CD4 CARs of this invention could control HIV better in vivo then the original CD4 CAR construct that was previously tested in the clinic, cohorts of mice were infused with 10 million human T cells, comprised of 8 million CD4 T cells and 2 million CD8 T cells. Four groups of mice were compared with different CD8 effector cell populations: nontransduced (NTD), transduced with the optimized lentiviral vector containing either CD28 (28z) or 4-1BB costimulatory domains (BBz), or transduced with the clinical trial MMLV-based vector (CD4z).

Figures 12A, 12B, 12C, 12D, 12E, 12F:
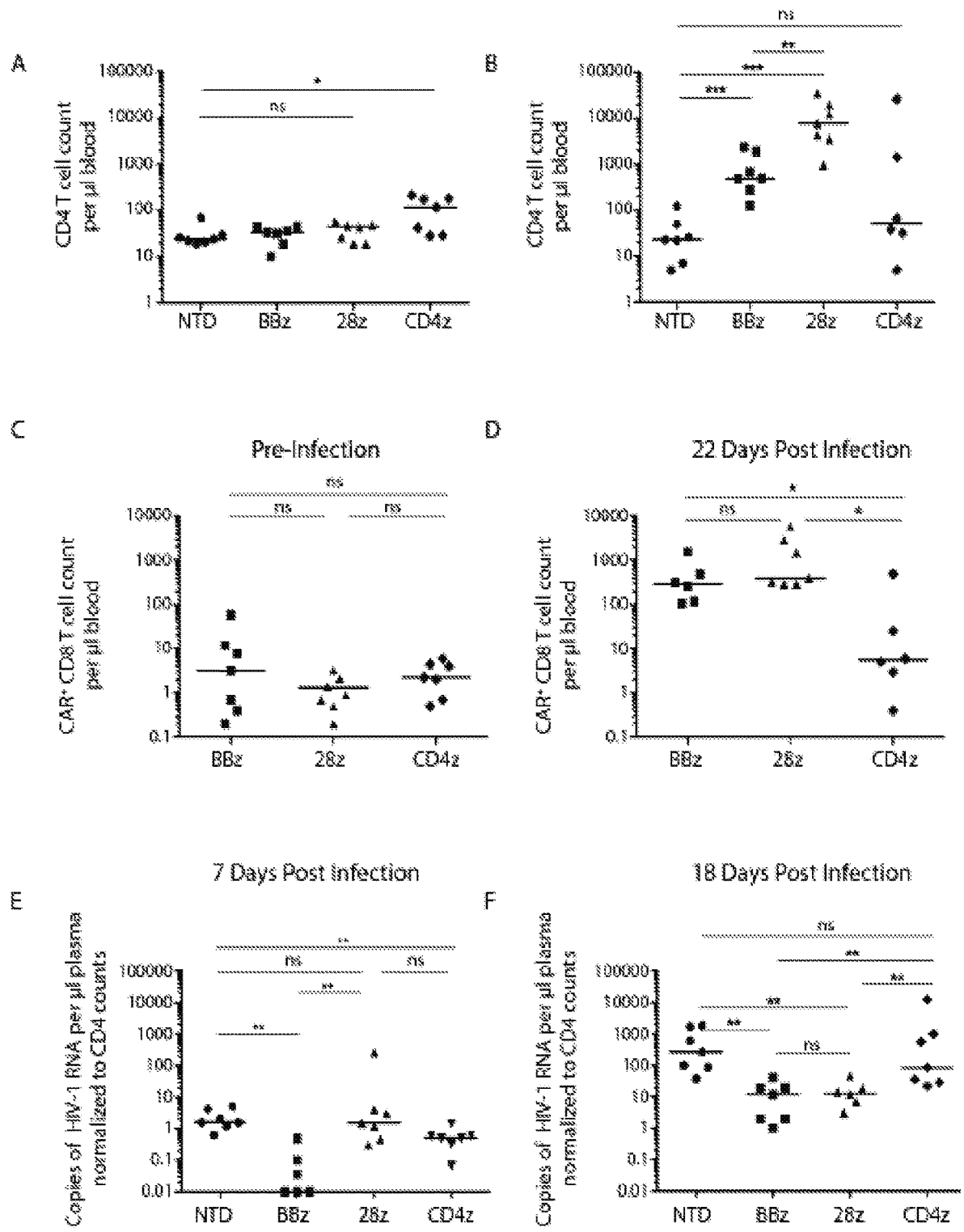
FIGS. 12A-12F are series of graphs depicting T cells expressing optimized CD4 CAR control HIV-1 replication and expanded to much greater levels in vivo than the original CD4 CAR. Cohorts of 7 NSG (NOD-scid IL2Rgnull) mice were infused with 8 million CD4 T cells and 2 million CD8 T cells. CD8 T cells were either left non-transduced (NTD), transduced with optimized (EF1α-CD8α TM, lentiviral vector) CD4-zeta CARs containing either 4-1BB or CD28 intracellular costimulatory domains, or the clinical trial (MMLV-based, PGK-CD4TM) CD4 CAR, denoted as NTD, BBz, 28z, and CD4z, respectively. CD8 T cell transduction efficiencies were normalized to 50% prior to injection into mice. Three weeks post injection, engraftment was measured to determine (FIG. 12A) baseline peripheral CD4 T cell counts and (FIG. 12C) CAR+ CD8 T cell counts. Two days later mice were infected with HIV-1 Bal via tail vein injection. 22 Days post infection, (FIG. 12B) endpoint peripheral CD4 T cell counts and (FIG. 12D) CAR+ CD8 T cell counts were obtained.

Pre-infection baseline CD4 T cell counts did not differ significantly between the NTD, BBz, or 28z groups, and were significantly higher for the CD4z treated mice (FIG. 12A). Mice were then infected with the CCR5-tropic HIV strain Bal, and after 22 days of infection, endpoint peripheral CD4 T cell counts were enumerated. Mice infused with T cells expressing the BBz or 28z construct showed a 17-fold and 177-fold expansion of the number of human CD4 T cells, respectively (FIG. 12B). In contrast, peripheral CD4 counts remained very low in mice treated with nontransduced CD8 T cells or CD4z T cells, presumably due to HIV-mediated depletion (FIG. 12B). Examination of the number of CD4 CAR+ CD8 T cells in the different mouse cohorts revealed 389-fold, 587-fold, and 2-fold expansions in the BBz, 28z, and CD4z T cells, respectively (FIGS. 12C-12D). The ability of the CD4 CAR T cells to control viral load were also examined in this model. Seven days following HIV infection, BBz CAR T cells exhibited the greatest control over virus replication, with mostly undetectable virus loads, whereas plasma from NTD, 28z, and CD4z treated animals contained approximately 1 copy of HIV RNA per μl (FIG. 12E). 18 days post infection, the median copy number of HIV RNA was reduced by more than 10 fold in BBz and 28z treated animals, compared to the mice that were treated with NTD T cells (FIG. 12F). However, CD4z treated mice did not statistically reduce HIV RNA compared to NTD treated mice. While either optimized CD4 CAR controlled HIV better than the clinical trial CAR, these results indicate that different costimulatory domains have disparate protective roles in HIV infection, with CD28 protecting CD4 T cells to the greatest extent and 4-1BB promoting early control over HIV replication.

Example 7: CCR5-ZFN Modified CD4 CAR CD8 T Cells are Enriched In Vivo

Despite increased control over HIV replication in vitro and in vivo, the in vitro data suggested that transduction of CD8 T cells with HIV-specific CARs rendered them susceptible to infection. To determine whether these CAR T cells become infected in vivo, CAR T cells resistant to infection enrich were tested in the presence of HIV in vivo. The survival benefits afforded by gene editing the CCR5 HIV co-receptor using zinc finger nucleases (ZFNs) has previously been demonstrated in primary human CD4 T cells (Perez et al., Nat Biotechnol 26, 808-816 (2008); Tebas et al., Nature reviews. Immunology 13, 693-701 (2013)). However, similar enrichment analyses on CD4 CAR+ CD8 T cells in the presence of HIV infection had not been explored. To determine if co-receptor editing promotes better enrichment of CAR+ CD8 T cells as a means to determine with CD4 CAR CD8 T cells are susceptible to infection in vivo, four additional groups were included in the experiment described in FIGS. 12A-12F in which the CD8 T cells were treated with CCR5 ZFNs and subsequently transduced with each of the CD4 CAR constructs.

Figures 13A, 13B, 13C:
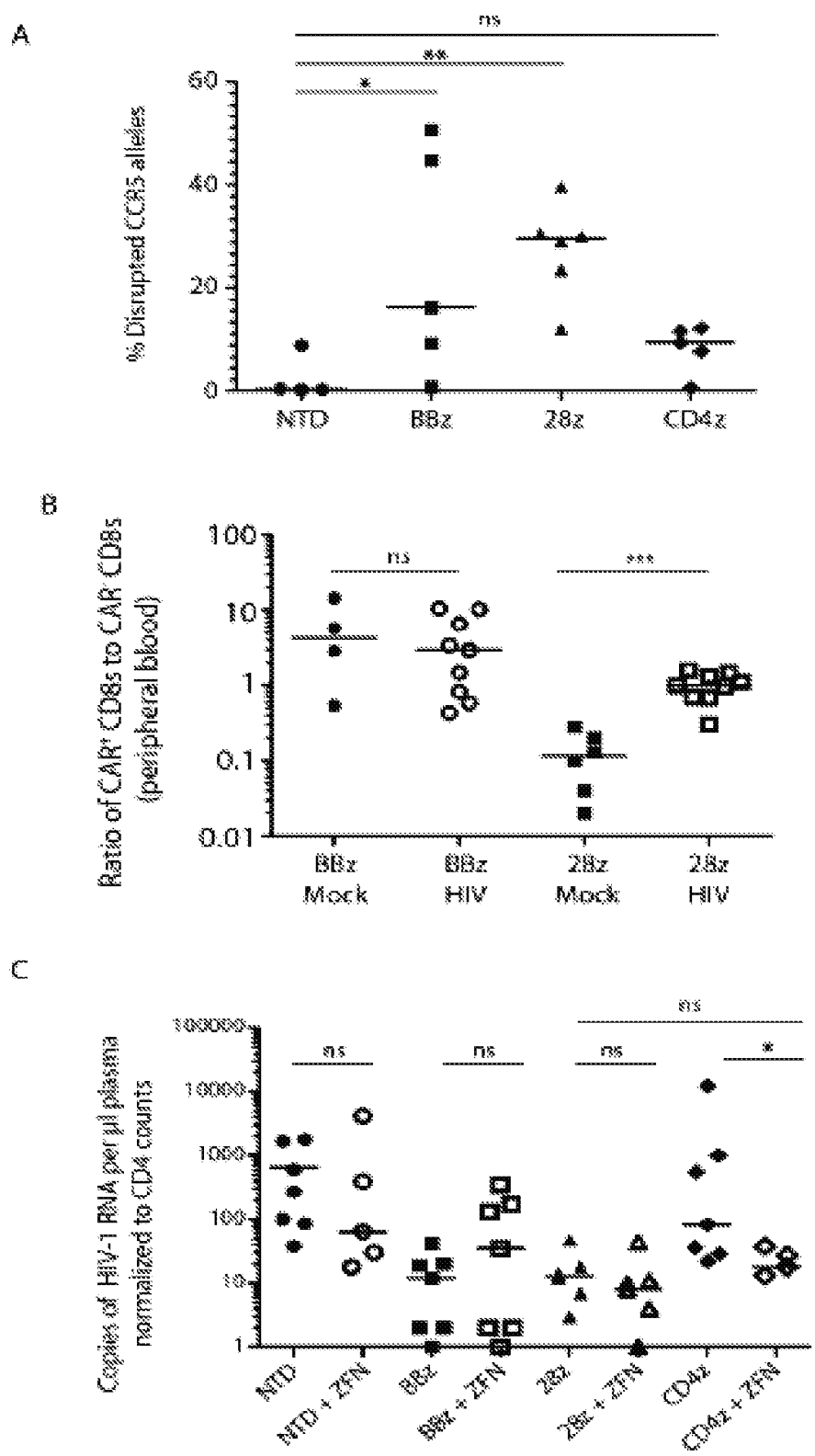
FIGS. 13A-13C are series of graphs showing that CCR5-ZFN modified CD4 CAR CD8 T cells are enriched in vivo. In the NSG mouse experimental design described in FIG. 7, four additional cohorts were added in which the CD8 T cells were electroporated with CCR5 ZFN RNA 48 hours before activation and CD4 CAR transduction, or left non-transduced (NTD).

CCR5 disrupted alleles were enriched in mice that were treated with CD4 CAR T cells and infected with HIV relative to non-transduced CD8 T cells (FIG. 13A). HIV-infected mice engrafted with non-transduced CD8 T cells had a median disruption frequency of 0.4%. As these CD8 T cells were not CD4 CAR transduced, they were not expected to enrich in the presence of HIV. Mice treated with BBz, 28z, or CD4z T cells had median disruption frequencies of 14.4%, 29.6%, and 9.5%, respectively, indicating that HIV-resistant, CD4 CAR-expressing CD8 T cells enrich in the presence of HIV infection. CCR5 disruption enrichment is influenced by the ability of CAR+ CD8 T cells to expand in the presence of HIV, as shown in FIG. 13B and FIG. 15, and thus greater antigen-specific expansion of 28z CAR T cells could be responsible for the greater CCR5 enrichment seen in FIG. 8A. This data also shows that BBz engineered T cells are able to persist better than 28z engineered T cells in the absence of antigen, which is consistent with findings using tumor specific CARs (Milone et al., Molecular therapy: the journal of the American Society of Gene Therapy 17, 1453-1464 (2009); Carpenito et al., PNAS 106, 3360-3365 (2009)). Together, this data suggest that HIV infection of HIV-specific CAR T cells does occur, and strategies that protect these cells from HIV infection will likely be necessary to ensure durable control of HIV infection.

Figure 16A:
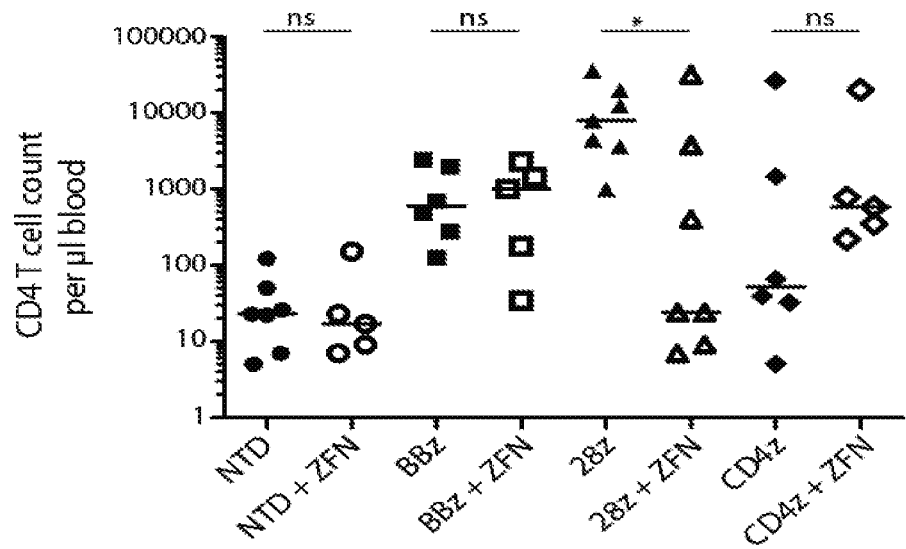
FIGS. 16A-16B are series of graphs demonstrating that CCR5 ZFN treatment does not improve the ability of CD4 CAR CD8 T cells to protect CD4 T cell in vivo or expand CAR+ CD8 T cell counts.
Figure 16B:
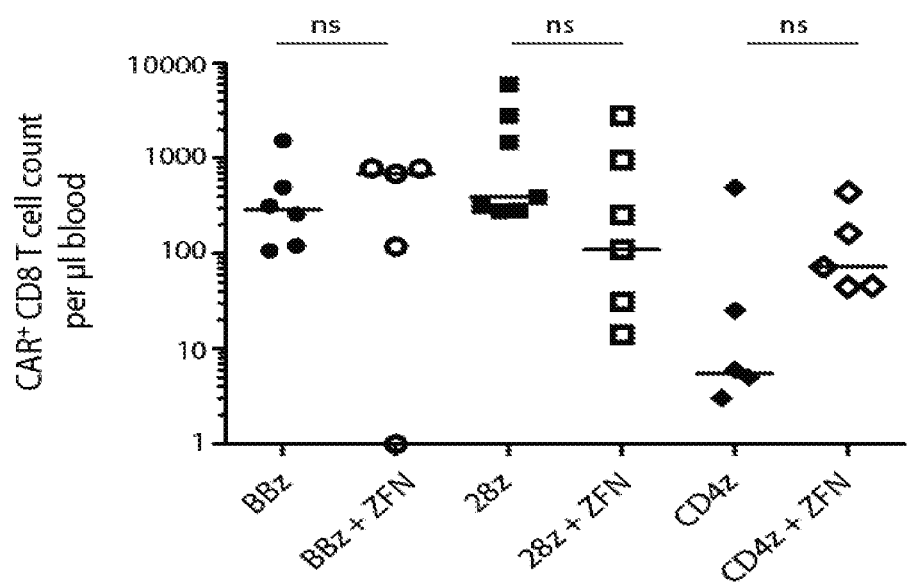

It was also examined whether rendering CD4 CAR CD8 T cells resistant to HIV infection enhanced their ability to control HIV-1 infection. After 22 days of infection, in general there were no significant differences in peripheral blood CD4 T cell counts or expansion of CAR+CD8 T cells in infected mice given ZFN-treated cells or non-ZFN treated cells, with the exception of lower endpoint CD4 T cell counts in 28z mice treated with ZFNs compared to non-ZFN treated (FIGS. 16A-16B). However, there was a trend for greater CD4 and CAR+ CD8 T cell expansions in ZFN-treated, CD4z mice (FIGS. 16A-16B). In 28z or BBz mice, which had low viral loads in the absence of ZFN treatment, no further decrease in viral RNA resulted from ZFN treatment (FIG. 13C). On the other hand, a significant decrease in plasma viral RNA was seen in mice given ZFN-treated CD4z T cells, to the point where plasma virus was no longer significantly higher than mice given the BBz or 28z CARs. As the viral loads were approximately a log-fold higher in the CD4z retrovirus treated mice without ZFNs compared to BBz or 28z treated mice without ZFNs, it is easier to detect a significant reduction in viral load in the context of poorly controlled virus replication resulting from ZFN treatment. Moreover, the short duration of the experiment could have precluded seeing full benefit of ZFN treatment on CAR T cells, including a detectable enrichment of transduced CD8 T cells, particularly in the CD4z treated mice in which they yielded the most antiviral benefit. In summary, in the absence of ZFN treatment, optimized CARs are superior to the clinical trial CD4z in vivo; however, if the T cells expressing the original CAR construct can be protected by CCR5 disruption, then control over HIV replication can be achieved within this relatively short in vivo assay.

Figures 17B, 17C, 17D:
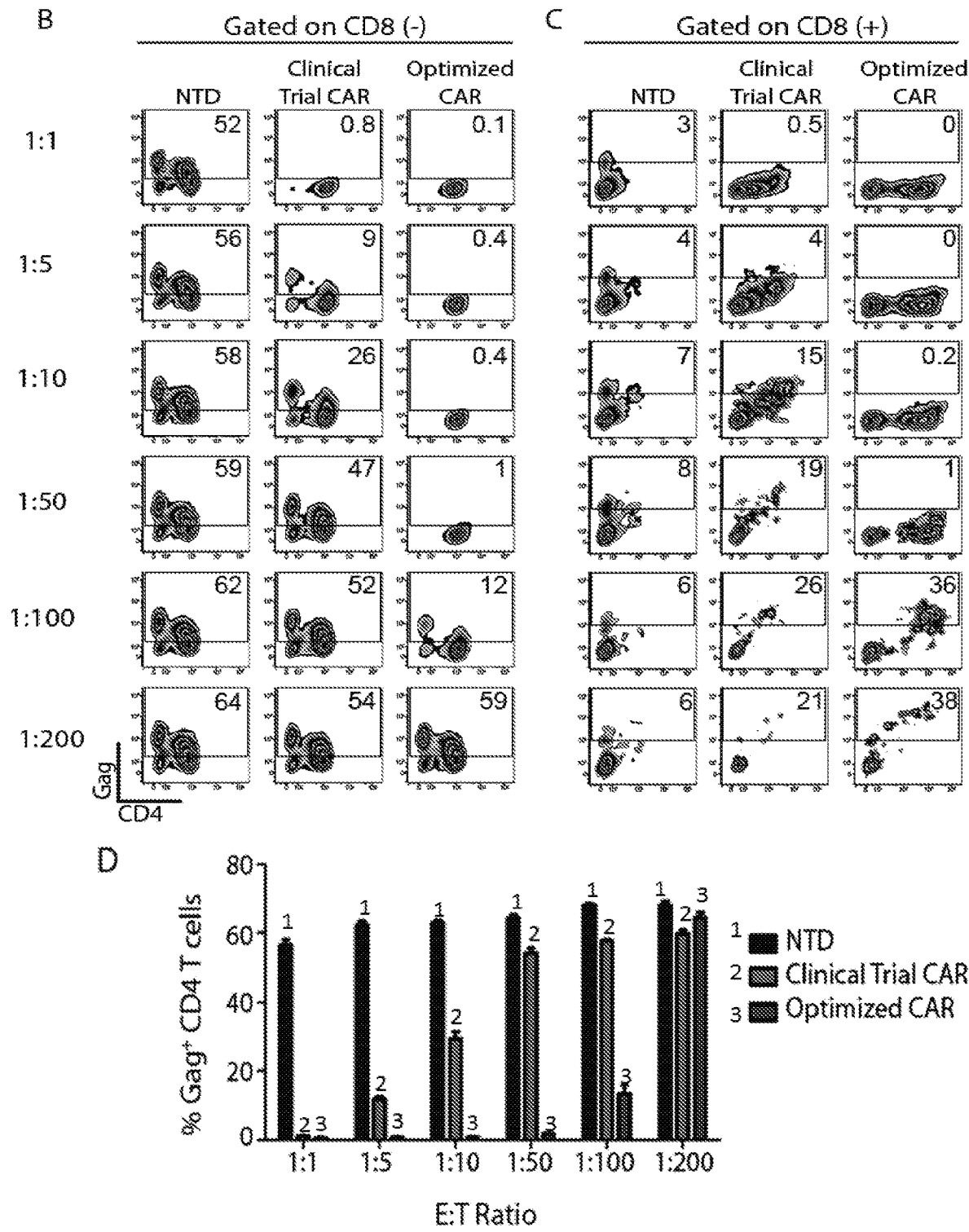

Overall, the improved control of HIV replication disclosed herein is impressive (FIGS. 17A-17C). This invention includes several improvements to the previously disclosed CD4 membrane-bound chimeric receptor that result in a 50-fold increase in the ability of killing HIV-1 infected cells. This increased efficacy, unlike the 1st generation CD4 membrane-bound chimeric receptor, titrates to effector:target (E:T) ratios that are physiologically relevant in in vitro assays, suggesting that these improved CD4 membrane-bound chimeric receptor constructs will likely be more effective in reducing viral loads in patients.

Figures 9A, 9B:
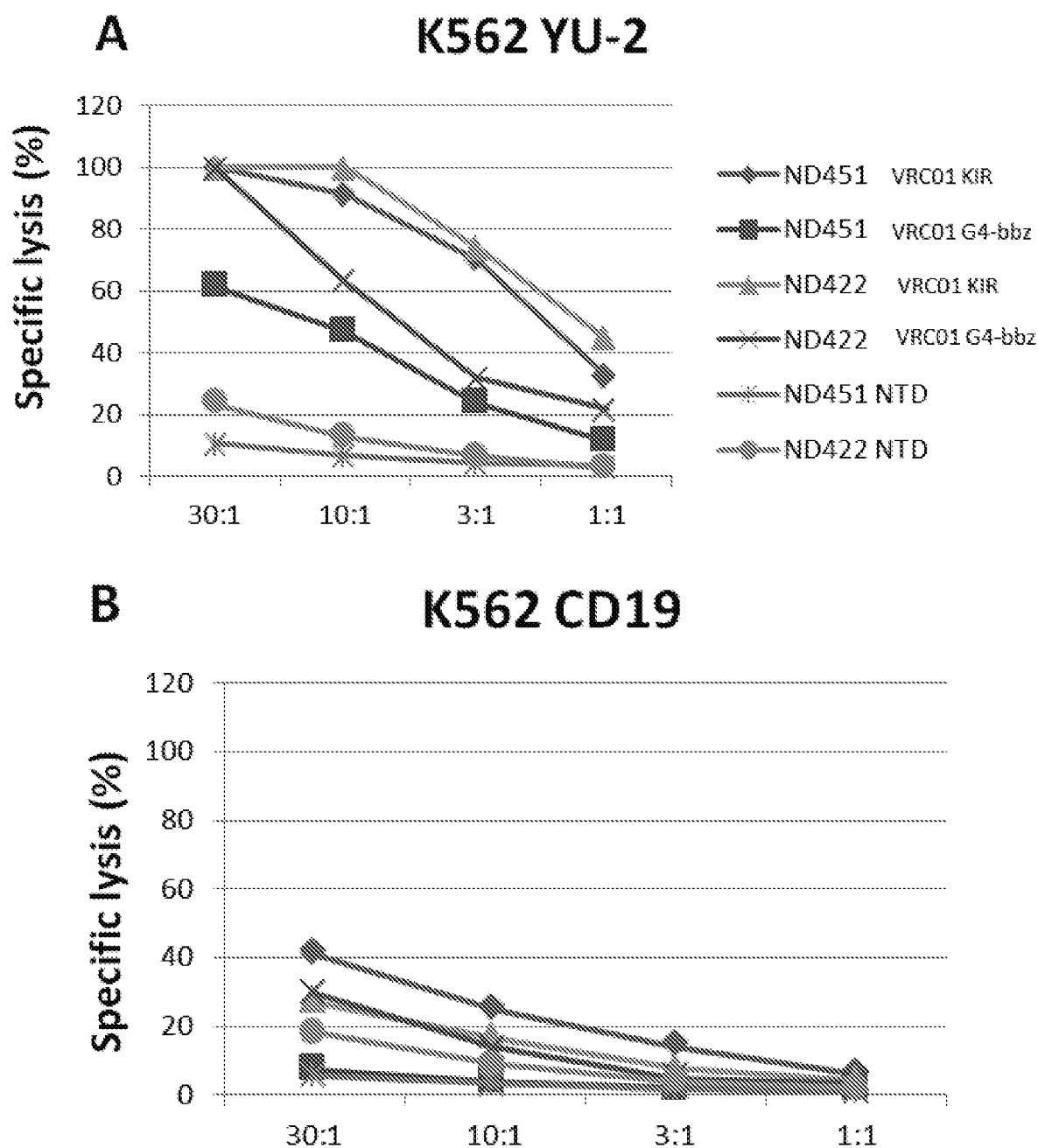
FIGS. 9A-9C are a series of graphs and histograms demonstrating that scFv based CAR's (scFv-CARs) cytotoxicity is specific and potent. VRC01 CARs showed specific cytotoxicity against target cells expressing HIV YU-2 strain (FIG. 9A) but not cells expressing CD19 (FIG. 9B); cytotoxicity can be increased by using a killer cell immunoglobulin-like receptor (KIR) cytoplasmic domain (FIG. 9A). Killing efficacy correlated with interferon gamma (IFNg) release by CAR T cells (FIG. 9C). The duration of the $^{51}$Cr release assay was 4 hours. The KIR construct consisted of DAP12 and the scFv linked to a KIRS2 transmembrane domain. The G4-bbz construct consisted of the scFv linked to an IgG4 hinge, a CD8 transmembrane domain and 4-1BB and CD3 zeta intracellular tail. bn01=VRC01; NTD=non-transduced control T cells.
Figure 9C:
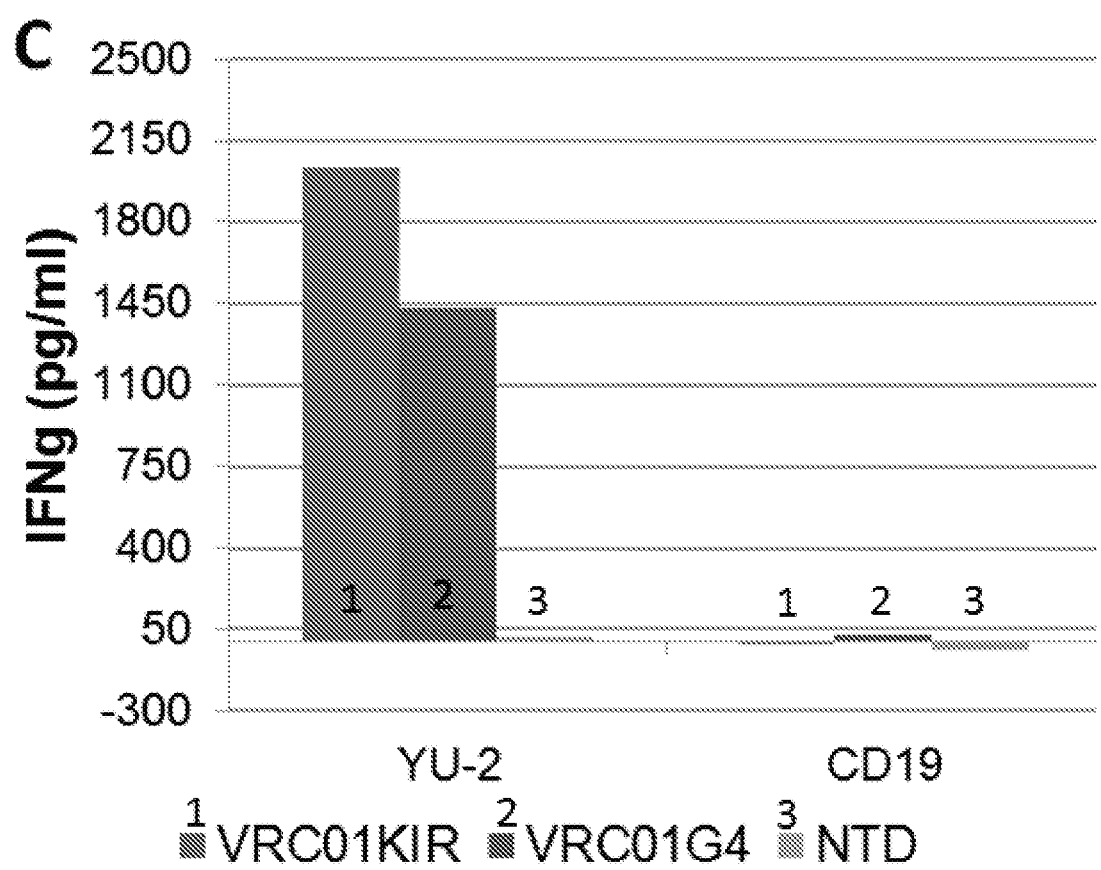
Figures 10A, 10B:
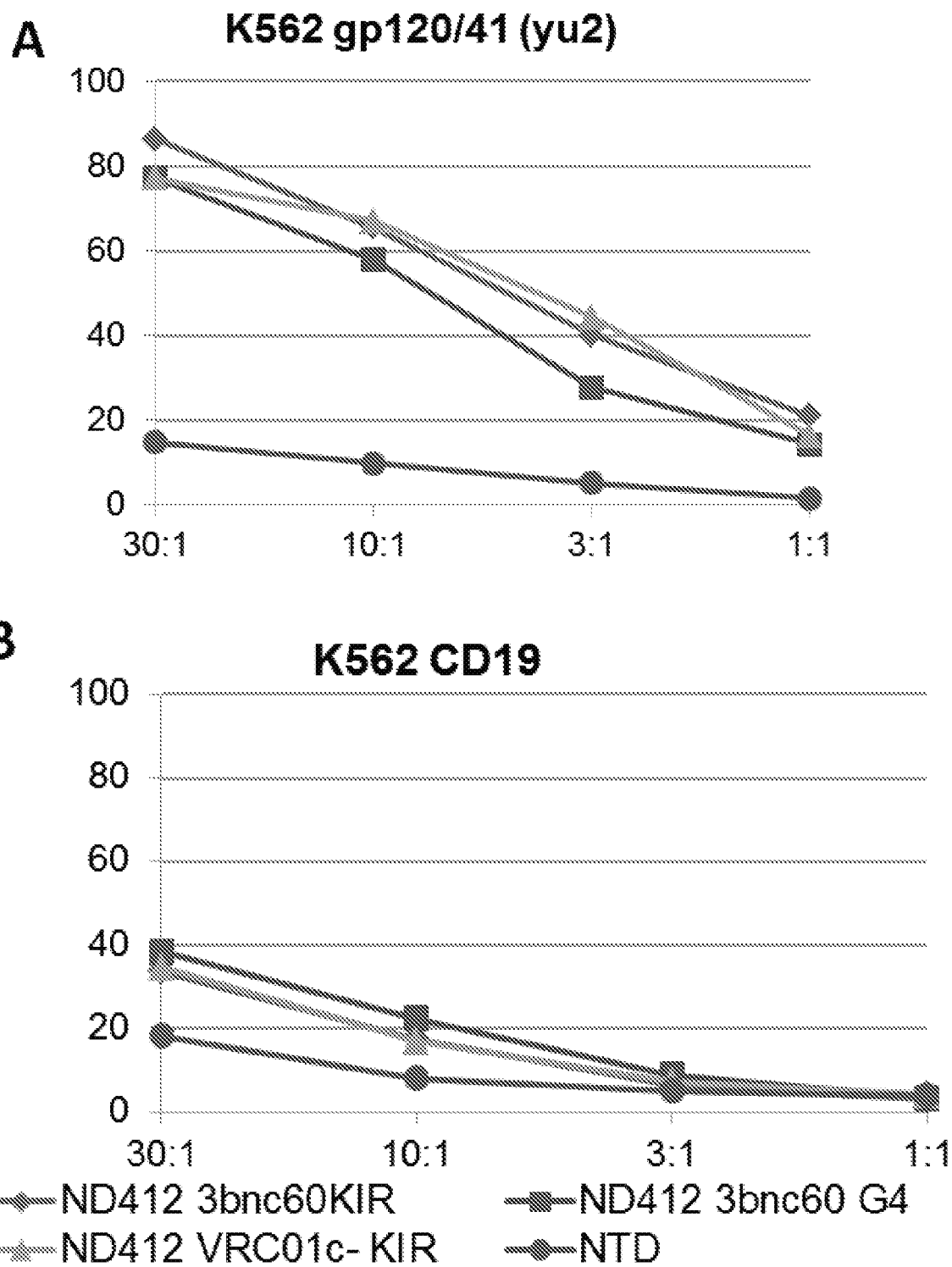
FIGS. 10A-10C are a series of graphs and histograms depicting another instance of cell specific cytotoxicity for scFv-CARs. 3BNC60 and VRC01c-CARs showed specific lysis of K562 cells expressing HIV-1 envelope gp120/41 (YU-2 isolate) (FIG. 10A), but not CD19 expressing K562 cells (FIG. 10B). As shown previously in FIG. 9C, specific IFNgamma production by CAR T cells correlated with killing efficacy (FIG. 10C). 3BNC60 relates to another CD4 binding site broadly neutralizing antibody. VRC01-c is a derivative of VRC01, which lacks a disulfide bond between HCDR3 and HCDR1 and may therefore show a greater percentage of correctly folded scFvs compared to the original VRC01 scFv that involves an additional, non-canonical disulfide-bond. For 3BNC60 and VRC01-c, there was no difference detectable in terms of killing between the KIR and the IgG4-bbz (also referred to as G4) construct.
Figure 10C:
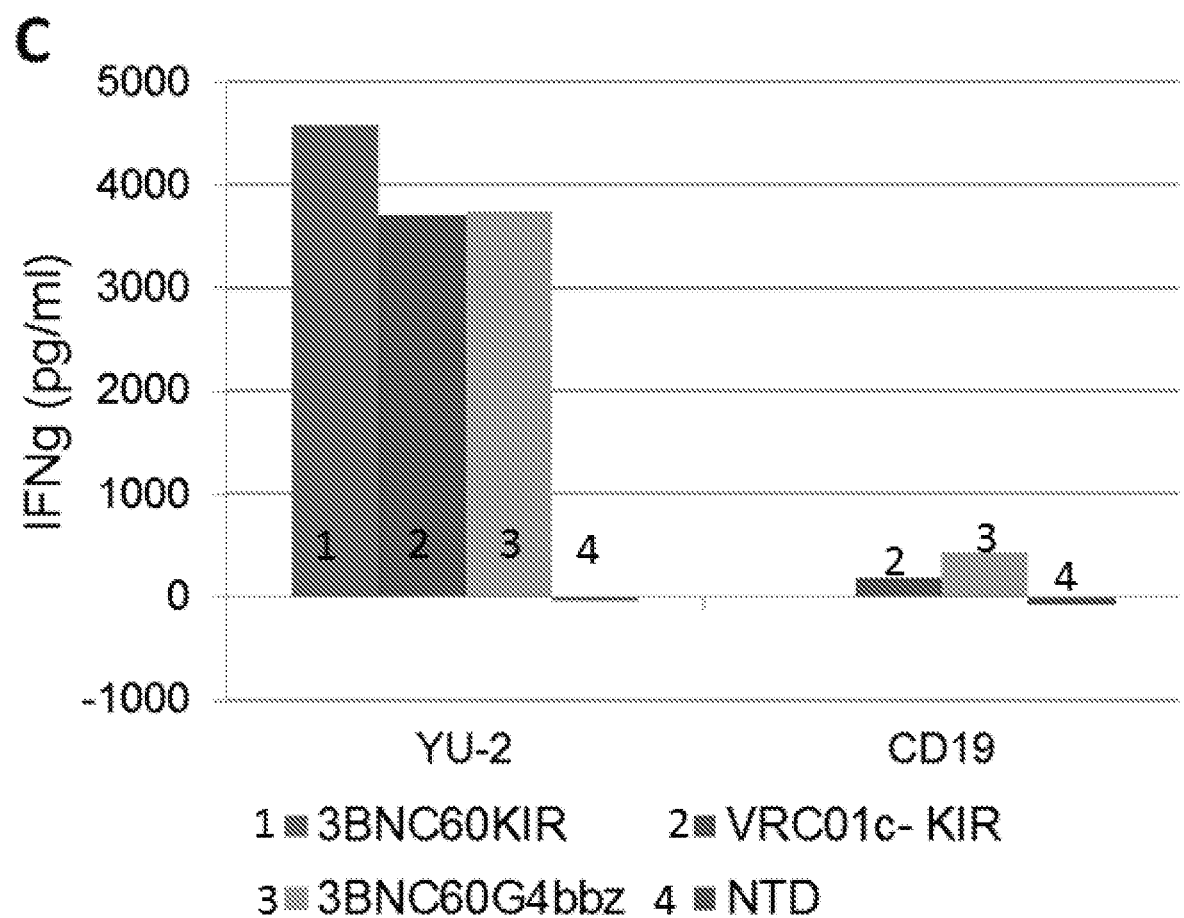

One of the major challenges for long-term control of HIV infection is the immune escape of some virus mutants. The scFv based CARs (scFv-CARs) of the present invention address this challenge and were shown to be beneficial for treatment of subjects that have reservoir populations of HIV-infected cells. The addition of T cells expressing scFv based CARs may further augment the ability of engineered T cells to provide durable control of HIV replication in the absence of ART. As seen in FIG. 9A and FIG. 10A, VRC01, VRC01c and 3BNC60-CARs showed specific lysis of K562 cells expressing HIV-1 envelope gp120/41 (YU-2 isolate) but not of K562 cells expressing CD19 which confirmed that scFv-CARs cytotoxicity is both potent and specific. Also, interferon gamma (IFNg) released by scFv-CAR T cells was tightly correlated with cells' killing efficacy (FIG. 9C and FIG. 10C). Additionally, scFv-CARs cytotoxicity was increased further by using a killer cell immunoglobulin-like receptor (KIR) cytoplasmic domain.

The present invention provides an enormous potential for improved HIV therapy. T cells isolated from HIV patients can be transduced with the scFv-CARs and/or CD4 membrane-bound chimeric receptors, expanded ex vivo and reinfused into the subject. The transduced T cells recognize gp120 expressing cells and become activated, resulting in killing of HIV harboring cells. This approach can be applied to any virus mediated disease in which a target antigen may shift or drift and therefore escape immunosurveillance by normal antibodies (e.g. hemagglutinin of influenza A). This therapy can be combined with other known antibody therapies, HAART or may be combined with viral inducers during or before CAR therapy.

Prophylactic application of the present invention is also possible in high risk populations, since the T cells should kill infected CD4 cells, which prevents establishment of a HIV repertoire.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid sequence encoding a membrane-bound chimeric receptor comprising a CD4 extracellular domain, a CD8alpha hinge, a CD8alpha transmembrane domain, and a signaling domain comprising a 4-1BB costimulatory signaling region, wherein the CD4 extracellular domain is encoded by a nucleic acid sequence comprising SEQ ID NO: 3 or 64 and is capable of recognizing and binding a HIV infected cell.

2. The isolated nucleic acid sequence of claim 1, wherein the CD8alpha hinge is encoded by a nucleic acid sequence comprising SEQ ID NO: 4 or 65.

3. The isolated nucleic acid sequence of claim 1, wherein the signaling domain further comprises a CD3zeta signaling domain encoded by a nucleic acid sequence comprising SEQ ID NO: 6 or 69.

4. The isolated nucleic acid sequence of claim 1, wherein the CD4 extracellular domain specifically binds to the HIV envelope (Env) glycoprotein.

5. A vector comprising the isolated nucleic acid sequence of claim 1.

6. The vector of claim 5, wherein the nucleic acid sequence comprises at least one from the group consisting of SEQ ID NOs: 3-6, 63-66, 68, and 69.

7. An isolated amino acid sequence encoding a membrane-bound chimeric receptor comprising a CD4 extracellular domain, a CD8alpha hinge, a CD8alpha transmembrane domain, and a signaling domain comprising a 4-1BB costimulatory signaling region, wherein the CD4 extracellular domain is encoded by a nucleic acid sequence comprising SEQ ID NO: 3 or 64 and is capable of recognizing and binding an HIV infected cell.

8. The isolated amino acid sequence of claim 7, wherein the CD4 extracellular domain comprises the amino acid sequence SEQ ID NO: 46.

9. The isolated amino acid sequence of claim 7, wherein the CD8alpha hinge comprises the amino acid sequence SEQ ID NO: 47, and the CD8alpha transmembrane domain comprises the amino acid sequence SEQ ID NO: 48.

10. The isolated amino acid sequence of claim 7, wherein the signaling domain further comprises a CD3zeta signaling domain comprising SEQ ID NO: 51.

11. The isolated amino acid sequence of claim 7, wherein the 4-1BB costimulatory signaling region comprises SEQ ID NO: 50.

12. The isolated amino acid sequence of claim 7, wherein the CD4 extracellular domain specifically binds to the HIV envelope (Env) glycoprotein.

13. A vector comprising a nucleic acid encoding a membrane-bound chimeric receptor comprising a CD4 extracellular domain, a CD8alpha hinge, a CD8alpha transmembrane domain, and a signaling domain comprising a 4-1BB costimulatory signaling region, wherein the CD4 extracellular domain is capable of recognizing and binding an HIV infected cell, wherein the nucleic acid sequence encodes the amino acid sequence SEQ ID NO: 45.

14. The vector of claim 13, wherein the vector comprises an EFa promoter.

15. A modified cell comprising the isolated nucleic acid sequence of claim 1.

16. The modified cell of claim 15, wherein the cell is selected from the group consisting of a T cell, a natural killer (NK) cell, a cytotoxic T lymphocyte (CTL), and a regulatory T cell.

17. The modified cell of claim 16, wherein the nucleic acid sequence is selected from the group consisting of a DNA and an mRNA.

18. The modified cell of claim 16, wherein the nucleic acid sequence is introduced into the cell by at least one procedure selected from the group consisting of electroporation, usage of a lentivirus, usage of a retrovirus and a chemical-based transfection.

19. A composition comprising the modified cell of claim 16.

20. A pharmaceutical composition comprising the modified cell of claim 16 and a pharmaceutically acceptable carrier.

21. A method for stimulating a cellular immune response in a HIV infected mammal, the method comprising administering to the mammal an effective amount of the modified cell of claim 16.

22. A method of treating a HIV infected mammal, the method comprising administering to the mammal the modified cell of claim 16.

23. The method of claim 22, wherein the modified cell is autologous to the mammal.

24. The method of claim 23, further comprising administering antiretroviral therapy (HAART) the mammal.

25. The method of claim 23, wherein the modified cell and the HAART are co-administered to the mammal.

26. The isolated nucleic acid sequence of claim 1, wherein the CD8alpha transmembrane domain is encoded by a nucleic acid sequence comprising SEQ ID NO: 5 or 66.

27. The isolated nucleic acid sequence of claim 1, wherein the 4-1BB costimulatory signaling region is encoded by a nucleic acid sequence comprising SEQ ID NO: 68.

* * * * *